US009046523B2

(12) United States Patent
Sutton et al.

(10) Patent No.: US 9,046,523 B2
(45) Date of Patent: Jun. 2, 2015

(54) RAPID BIOLUMINESCENCE DETECTION SYSTEM

(71) Applicant: The Secretary of State for Health, London (GB)

(72) Inventors: Mark J. Sutton, Salisbury (GB); Toryn Poolman, Salisbury (GB); Richard J. Hesp, Salisbury (GB)

(73) Assignee: THE SECRETARY OF STATE FOR HEALTH, London (GB)

( * ) Notice: Subject to any disclaimer, the term of this patent is extended or adjusted under 35 U.S.C. 154(b) by 28 days.

(21) Appl. No.: 13/958,335

(22) Filed: Aug. 2, 2013

(65) Prior Publication Data

US 2014/0030740 A1 Jan. 30, 2014

Related U.S. Application Data

(63) Continuation of application No. 13/143,722, filed as application No. PCT/GB2010/050018 on Jan. 7, 2010, now Pat. No. 8,512,970.

(30) Foreign Application Priority Data

Jan. 7, 2009 (GB) .................................. 0900151.2

(51) Int. Cl.
*G01N 33/58* (2006.01)
*C12Q 1/48* (2006.01)
*C12Q 1/66* (2006.01)

(52) U.S. Cl.
CPC .............. *G01N 33/581* (2013.01); *C12Q 1/485* (2013.01); *C12Q 1/66* (2013.01)

(58) Field of Classification Search
CPC .................................................. G01N 33/581
See application file for complete search history.

(56) References Cited

U.S. PATENT DOCUMENTS

| | | | |
|---|---|---|---|
| 5,246,834 A | 9/1993 | Tsuji et al. | |
| 6,811,990 B1 | 11/2004 | Corey et al. | |
| 8,512,970 B2 | 8/2013 | Sutton et al. | |
| 2011/0177539 A1* | 7/2011 | Sutton et al. ..................... | 435/8 |

FOREIGN PATENT DOCUMENTS

| | | |
|---|---|---|
| CN | 1946857 A | 4/2007 |
| GB | 2370113 A | 6/2002 |
| WO | 96/02666 A1 | 2/1996 |
| WO | 00/46357 A1 | 8/2000 |
| WO | 00/70082 A1 | 11/2000 |
| WO | 2004/090089 A1 | 10/2004 |
| WO | 2005/093085 A1 | 10/2005 |
| WO | 2009/104013 A1 | 8/2009 |

OTHER PUBLICATIONS

Chinese Office Action for Chinese Application No. 201080008250.X, mailed May 9, 2014, State Intellectual Property Office of People's Republic of China.
Translation of Chinese Office Action for Chinese Application No. 201080008250.X (NPL1).
Japanese Office Action for Japanese Patent Application No. 2011-544086, mailed Jul. 1, 2014, Japanese Patent Office.
English Language Translation of Japanese Office Action for Japanese Patent Application No. 2011-544086, mailed Jul. 1, 2014.
European Office Action for European Patent Application No. 10700590.2, mailed Sep. 26, 2014, European Patent Office.
Squirell et al., Rapid and specific detection of bacteria using bioluminescence, Analytica Chimica Acta, 457;109-114 (2002).
Office Action for Chinese Patent Application No. 201080008250.X, mailed Feb. 27, 2013.
English Translation of NPL2 (Office Action for Chinese Patent Application No. 201080008250.X)., 2010.
Murakami et al., Bioluminescent Enzyme Immunoassay Using Thermostable Mutant Luciferase and acetate kinase as a labelled enzyme, Analytica Chimica Acta, 361:19-26 (1998).
Maeda et al., Development of New Label Enzyme for Bioluminescent Enzyme Immunoassay, Analytical Letters, 28:383-394 (1995).
Maeda et al., New Label Enzymes for Bioluminescent Enzyme Immunoassay, Journal of Pharmaceutical and Biomedical Analysis, 30:1725-1734 (2003).
Ito et al., Highly Sensitive Simultaneous Bioluminescent Measurement of Acetate Kinase and Pyruvate Phosphate Dikinase Activities Using a Firefly Luciferase-Luciferin Reaction and Its Application to a Tandem Bioluminescent Enzyme Immunoassay, Analytical Sciences, 19:105-109 (2003).
Hesp et al., Thermostable adenylate kinase technology: a new process indicator and its use as a validation tool for the reprocessing of surgical instruments, Journal of Hospital Infection, 74:137-143 (2010).
Blasco et al., Specific assays for bacteria using phage mediated release of adenylate kinase, Journal of Applied Microbiology, 84:661-666 (1998).
International Preliminary Report on Patentability, Application No. PCT/GB2004/001517, International Bureau of WIPO, Switzerland, mailed Oct. 15, 2005.
Written Opinion of the International Searching Authority, Application No. PCT/GB2004/001517, European Patent Office, Germany, mailed Apr. 8, 2004.

* cited by examiner

*Primary Examiner* — Maryam Monshipouri
(74) *Attorney, Agent, or Firm* — Nevrivy Patent Law Group P.L.L.C.

(57) ABSTRACT

An assay is provided for detecting the activity of a reporter kinase comprising (i) adding said reporter kinase to an assay mixture wherein said reporter kinase is contacted with bioluminescent reagent no more than 5 minutes after being contacted with ADP, and wherein, prior to contacting the reporter kinase with ADP, the assay mixture is substantially free from kinase other than reporter kinase; and (ii) detecting light output from the assay mixture. Methods for detecting the presence of an analyte in a sample and methods for validating a treatment process using the above assay are also provided. Further provided are devices for conducting these assays and methods.

10 Claims, 12 Drawing Sheets

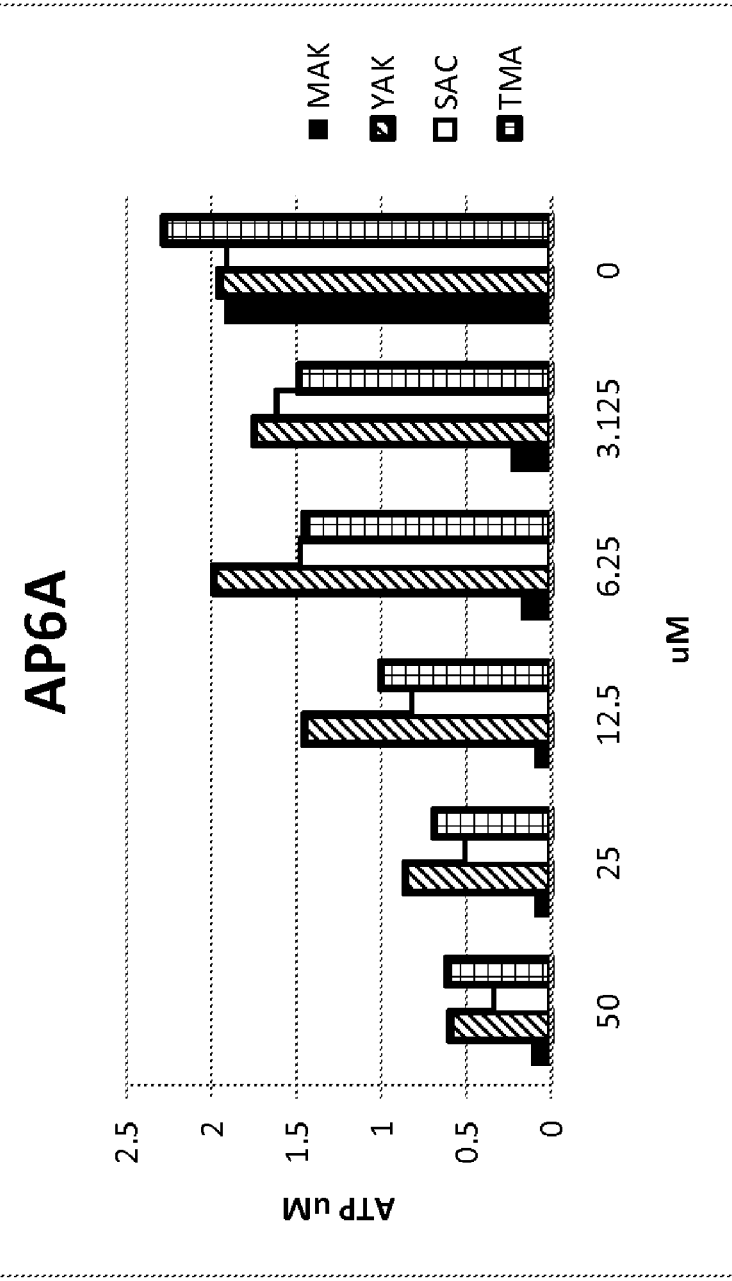

RAPID BIOLUMINESCENCE DETECTION SYSTEM

CROSS REFERENCE TO RELATED APPLICATIONS

This application is a continuation of U.S. application Ser. No. 13/143,722, which is the U.S. National Stage of International Application No.: PCT/GB10/50018, filed Jan. 7, 2010, the entire contents of which are hereby incorporated by reference herein.

REFERENCE TO A SEQUENCE LISTING SUBMITTED ELECTRONICALLY VIA EFS-WEB

The content of the sequence listing (Name: Sequence_listing.txt, Size: 180,647 bytes; and Date of Creation: Jul. 6, 2011) electronically submitted via EFS-Web is incorporated by reference in its entirety.

BACKGROUND OF THE INVENTION

The invention relates to the field of rapid bioluminescence detection systems, in particular to rapid and very sensitive bioluminescence detection systems for detecting the activity of reporter kinases. Bioluminescent assays, devices, and kits for detecting the activity of reporter kinases are also provided.

The use of kinases as reporter enzymes has been described in the art. By way of example, the present inventors have described the use of reporter kinases in diagnostic systems for detecting the presence of an analyte in a sample (see WO00/46357), and also in systems for validating the effectiveness of decontamination processes (see WO2005/093085). The activity of these reporter kinases is typically detected using an ATP bioluminescence system (e.g. luciferin-luciferase), which generates a light output signal. The light output generated is measured using a luminometer, and these measurements are then correlated with the amount of kinase activity.

A potential problem associated with reporter kinase systems is the length of time required to obtain the output signal. To date, the typical time required to obtain an output signal ranges from 30 minutes to several hours. There is thus a need in the art for a quicker and/or simplified reporter system.

BRIEF DESCRIPTION OF THE DRAWINGS

The invention is now described in specific embodiments in the following examples and with reference to the accompanying drawings in which.

DETAILED DESCRIPTION OF THE INVENTION

Figure 1A:
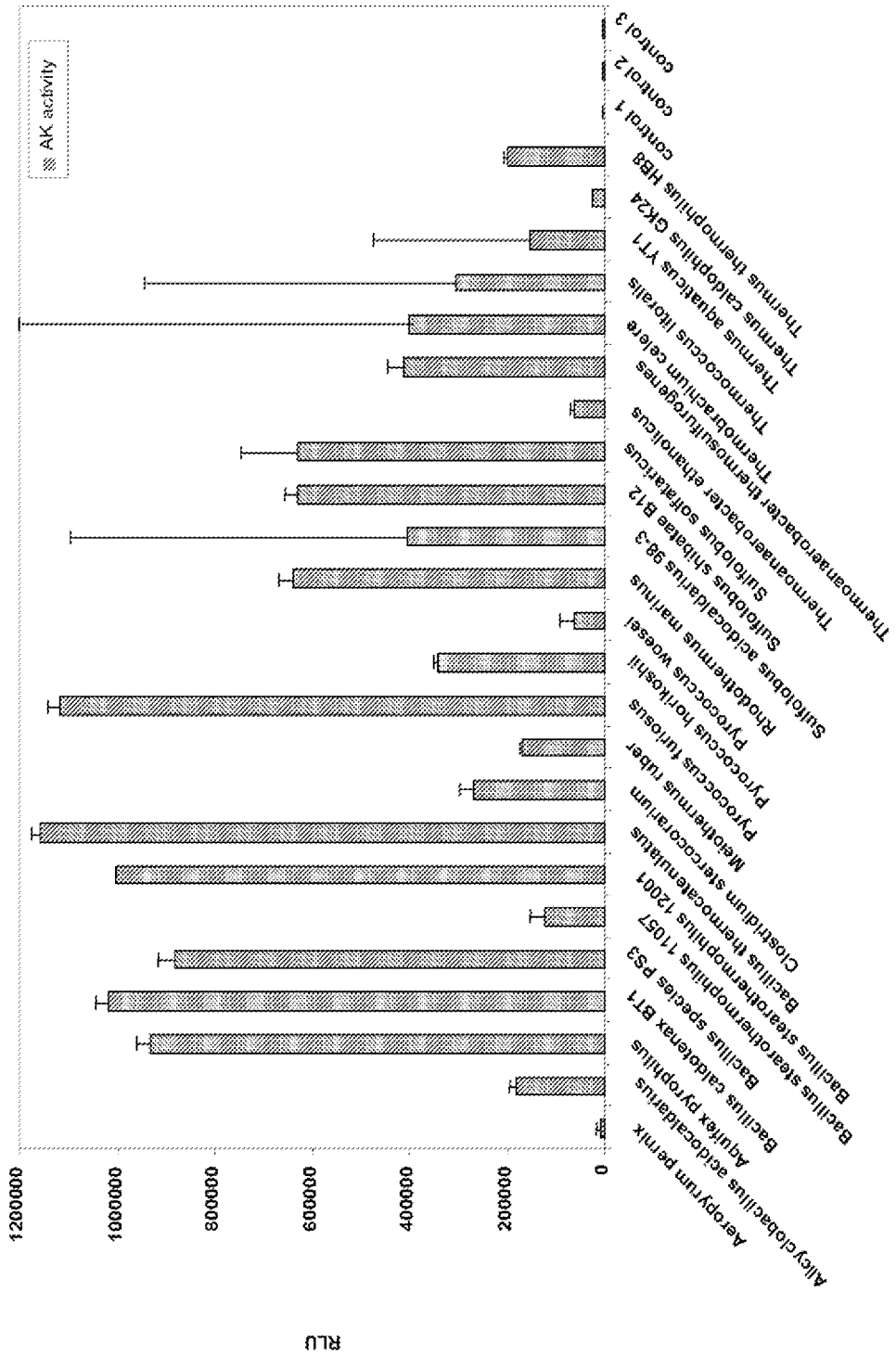
FIG. 1 shows activity of adenylate kinase (AK) enzymes after treatment at 70° C. (A), 80° C. (B) and 90° C. (C).

One or more of the above-mentioned problems is solved by the present invention, which, in a first aspect, provides an assay for detecting the activity of a reporter kinase, comprising:
(i) adding said reporter kinase to an assay mixture, wherein said reporter kinase is contacted with ADP, and, no more than 5 minutes after being contacted with ADP, said reporter kinase is contacted with a bioluminescent reagent,
wherein, prior to contacting the reporter kinase with ADP, the assay mixture is substantially free from non-reporter kinase (ie. kinase other than reporter kinase); and
(ii) detecting light output from the assay mixture.

In one embodiment of the invention, the method further comprises the step of recording the light output data obtained in step (ii) on a suitable data carrier.

In another embodiment of the invention, the reporter kinase is contacted with the bioluminescent reagent no more than 2 minutes, no more than 1 minute, no more than 30 seconds, or no more than 10 seconds, after being contacted with the ADP. In another embodiment, the reporter kinase is contacted simultaneously with the ADP and the bioluminescent reagent.

Thus, there is no significant incubation period (or only a very short incubation period) between contacting the reporter kinase with the ADP and contact with the bioluminescent reagent. The invention can therefore be said to employ a "one-step" bioluminescent detection process.

In contrast to the above rapid detection system, conventional reporter systems typically employ a "two-step" detection process:

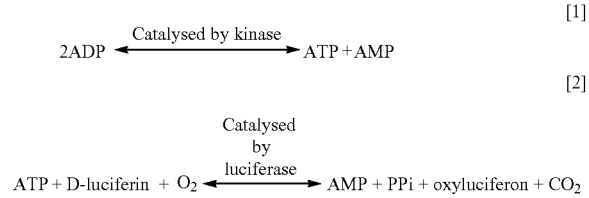

In the first step, the reporter kinases are exposed to a source of ADP substrate, and incubated for a sufficient time to allow the generation of ATP [1]. Then, in a second, separate, step, the luciferin/luciferase reagent is added to convert the ATP generated by the reporter kinase into light [2]. This "two-step" bioluminescent assay has been shown to provide accurate kinase detection. However, its "two-step" nature (i.e. the addition of ADP, incubation, and then separate addition of bioluminescent reagent) has proved cumbersome and slow when detection is carried out "in the field", and not in a laboratory setting.

To date, the two reaction steps (illustrated above) have been considered incompatible as AMP generated during step [2] drives the equilibrium of step [1] over to the left-hand side, thereby favoring the re-conversion of ATP generated in step [1] into ADP. Since the light signal output of the system is dependent on the presence of ATP, this makes the detection of kinase activity more difficult. Thus, to date, steps [1] and [2] have been separated either temporally (i.e. by including an incubation step as described above), or spatially (i.e. where the reactions are carried out in separate compartments).

Contrary to this dogma, the present inventors have found that reaction steps [1] and [2] can in fact be performed simultaneously, without any significant adverse effect on the sensitivity of the detection of the reporter kinases. The resulting "one-step" bioluminescent assay provides significant advantages in terms of speed and convenience, and is particularly advantageous in point-of-care diagnostic tests, and rapid process release indicators, i.e. for the detection of kinase activity in the field rather than in the laboratory.

In addition, in order to ensure a high sensitivity and accuracy of detection, the present inventors have found it advantageous to ensure that, prior to the addition of any ADP, the sample containing the reporter kinase is substantially free from any non-reporter (ie. contaminating) kinase activity, and/or any endogenous ATP. As will be clear from the reaction schemes above, the presence of either of these contaminants can significantly adversely affect the sensitivity/accuracy of the detection of kinase activity. By way of example, non-reporter kinases may convert ADP to ATP and thus generate a false (or increased) light output signal. Thus, it has been found advantageous to treat the sample containing the reporter kinase to remove or inactivate any non-reporter kinase and/or any endogenous ATP.

In one embodiment of the invention, non-reporter kinase is removed and/or inactivated using one or more of the treatment steps described below. In this regard, preferred non-reporter kinases that are inactivated or removed in accordance with the present invention are mammalian, fungal and/or plant kinases (eg. a mammalian, fungal or plant adenylate kinase). These treatments may be used in any number (preferably one or more, or at least two, or at least three) and/or in any combination. In all cases, however, the treatment leaves the reporter kinase substantially intact (eg. active in terms of kinase activity). Any one or more of the following treatment steps can be applied to any aspect of the invention.

In one embodiment, non-reporter kinase is inactivated by exposure to a temperature of between 50 to 120 C for a period of between 1 and 30 minutes, for example 90 C for 10 minutes, 90 C for 3 minutes, 90 C for 1 minute, 120 C for 3 minutes, or 120 C for 1 minute. The temperature and duration of the inactivation process denature non-reporter kinase whilst leaving the activity of the reporter kinase substantially intact.

In a further embodiment, non-reporter kinase is removed/inactivated using a chemical denaturation treatment. Examples of suitable treatments include exposure to a chaotrope such as urea (e.g. concentrations greater than 2M urea) or guanidine (e.g. concentrations greater than 1M guanidine), exposure to a detergent (e.g. greater than 0.5% SDS, sarkosyl or triton X-100) exposure to a free-radical generator (e.g. >1000 ppm active chlorine derived from sodium hypochlorite or equivalent reagents) or exposure to an oxidative treatment.

In another embodiment, non-reporter kinase is removed/inactivated using an enzymatic denaturation treatment. Examples of suitable enzymes include highly processive proteases, such as e.g. Prionzyme®, Properase®, proteinase-K, and thermolysin.

In a further embodiment, non-reporter kinase is removed/inactivated by exposure to a selected pH (e.g. below pH 4, or greater than pH 11 using buffers such as 50 mM CAPS pH 11), a selected salt concentration (e.g. >2M ammonium sulphate), EDTA, or combinations thereof.

In a further embodiment, non-reporter kinase is removed/inactivated by the addition of an inhibitor, which selectively or specifically inhibits the non-reporter kinase (i.e. the inhibitor inactivates the non-reporter kinase, whilst leaving the activity of the reporter kinase substantially intact). Examples of suitable inhibitors include: staurosporine; vanadate (eg. orthovanadate or decavanadate); glycerophosphate; Diadenosine phosphates such as Ap6A (Diadenosine hexaphosphate), Ap5A (Diadenosine pentaphosphate), Ap4A (Diadenosine tetraphosphate), and/or Ap3A (Diadenosine triphosphate); vitamin C; AMP-PCP; AMP-PNP; AMP-S; ATP-γS; and Ara-ATP. Competitive inhibitors of non-reporter kinases (eg. of non-reporter adenylate kinase) are preferred (eg. Diadenosine phosphate inhibitors such as Ap4A and/or Ap5A). In one embodiment, the inhibitor selectively or specifically inhibits mammalian and fungal (eg. yeast) and plant non-reporter kinases. In another embodiment, the inhibitor (eg. Ap5A) selectively or specifically inhibits mammalian and fungal (eg. yeast) non-reporter kinases. In a further embodiment, the inhibitor (eg. Ap4A and/or Ap6A) selectively or specifically inhibits mammalian non-reporter kinases.

Figure 4A:
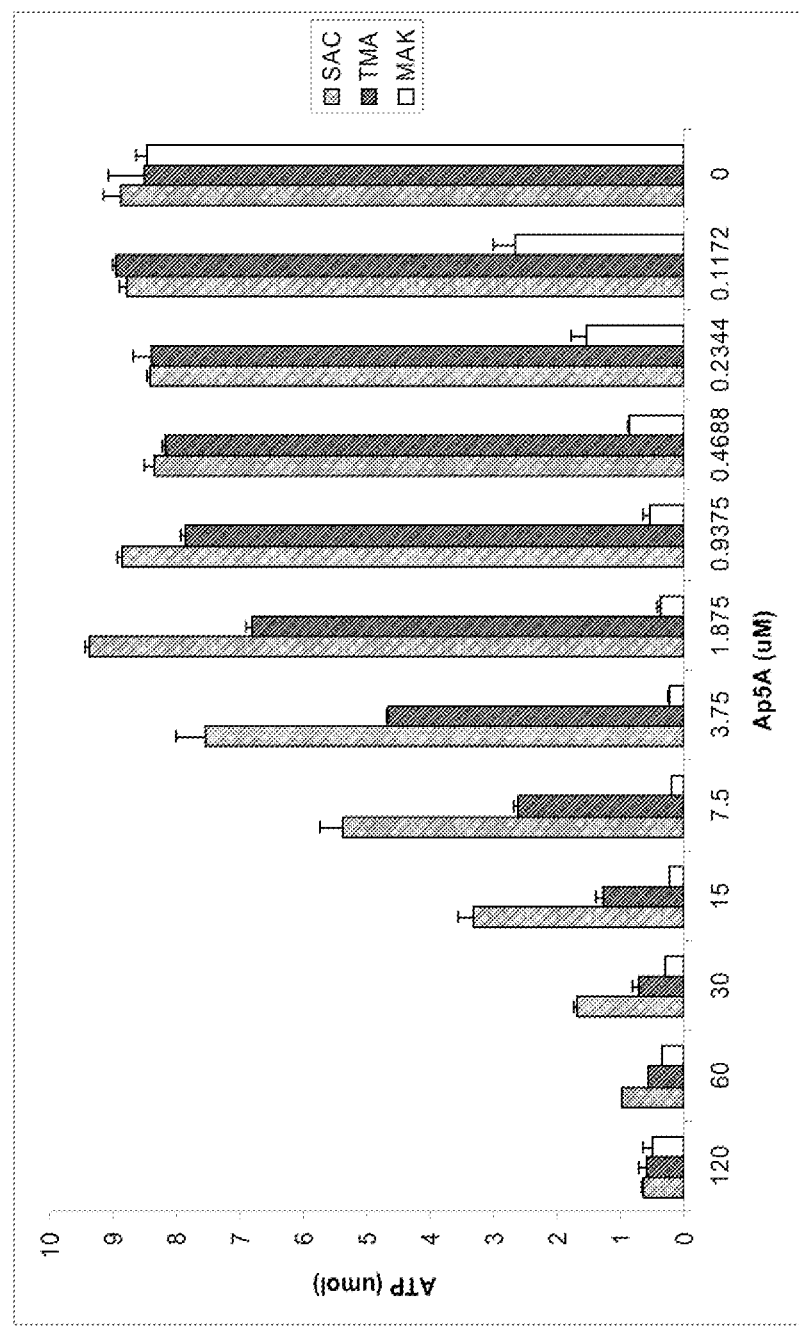
FIG. 4 shows the differential inhibition of reporter kinase and non-reporter (endogenous) tissue kinase using Ap5a (Diadenosine pentaphosphate pentasodium salt) (A) and the effect of Ap5a on luciferase (B). The reporter adenylate kinases from *S. acidocaldarius* or *T. maritima* were purified as described previously. Rabbit myokinase (muscle adenylate kinase) was obtained from Sigma. 100 ng of each enzyme was incubated with the inhibitor at the concentrations shown in reaction buffer (15 mM MgAc, 10 mM tris, 1 mM EDTA pH 7.75) for 5 minutes. ADP was added to a final concentration of 70 μM and the reaction incubated before addition of luciferin and luciferase. The RLUs generated following detection with luciferase/luciferin were converted to equivalent ATP units using a standard curve and the results are shown in (A). An $IC_{50}$ (the concentration of inhibitor which reduces the activity of the enzyme by 50%) was calculated and gives values of 10.4 μM (Sac), 4.3 μM (Tma) and 0.06 μM (Rabbit myokinase). The presence of Ap5A does not have a detrimental effect on the activity of the luciferase (see (B)).
Figure 4B:
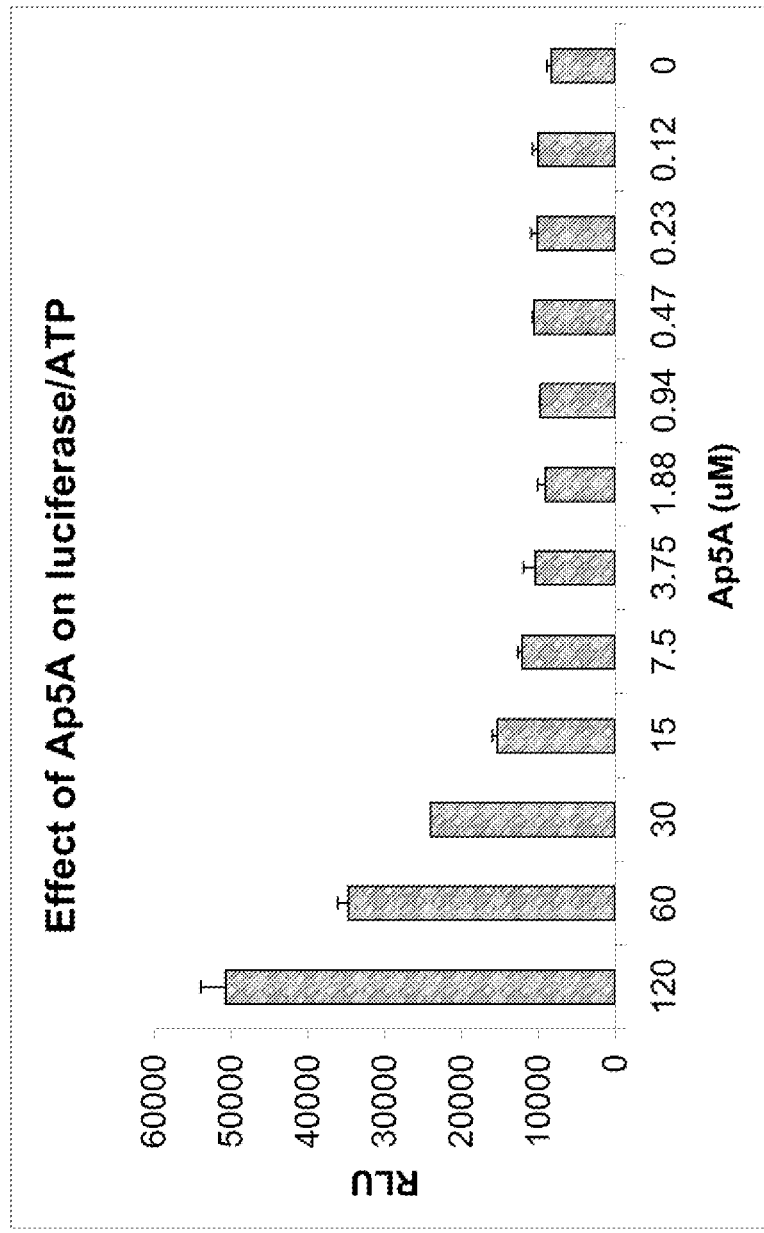
Figures 7B, 7C:
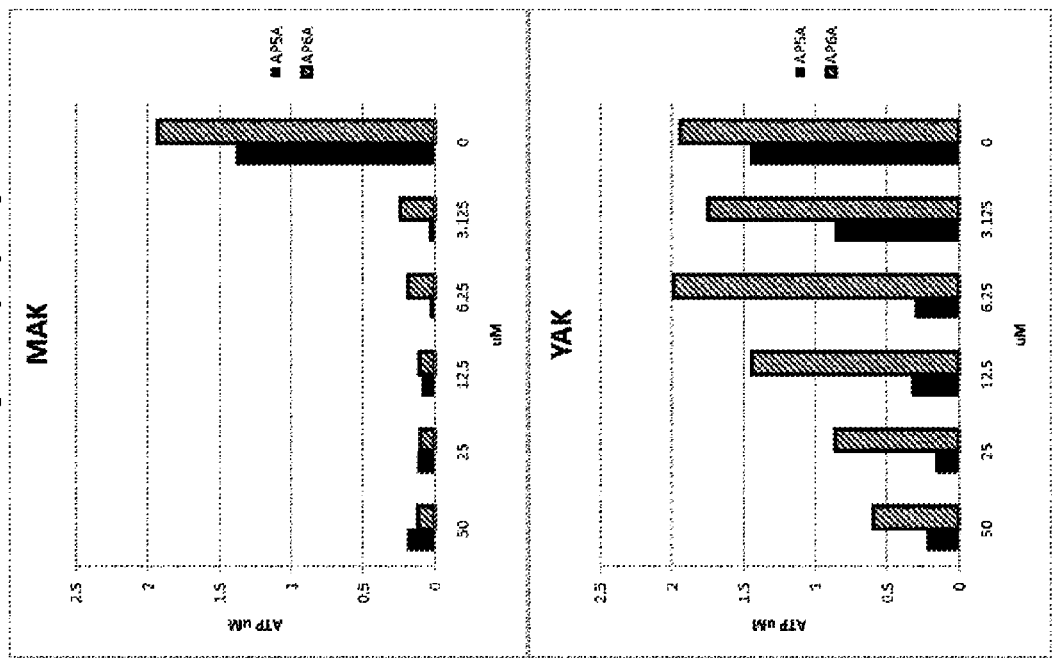
FIG. 7 shows the effects of further inhibitors on the background activity derived from mammalian tissues or samples and/or background from other sources (e.g. yeast contamination). Experiments were carried out essentially as described for FIG. 4. No adverse effect on the activity of luciferase was observed for any of the inhibitors examined (results not shown). Yeast adenylate kinase was obtained from Sigma. (A); comparison of inhibition of adenylate kinases by Ap6A, MAK=rabbit muscle AK (myokinase); YAK=yeast AK; SAC=*S. acidocladarius* AK; TMA=*T. maritima* AK. (B-C); comparison of Ap5A and Ap6A for inhibition of contaminating background adenylate kinase from either mammalian cells (MAK) (B) or yeast (YAK) (C). AP4A (not shown) and Ap6A gives similar profiles to Ap5A for differentiating between an example of a monomeric (bacterial) reporter adenylate kinases (from *Thermotoga maritima*) and an example of a trimeric (archaeal) adenylate kinase from *Sulfolobus acidocaldarius* when either is compared to a representative example of non-reporter mammalian tissue adenylate kinase (A). Ap4A (not shown) and Ap6A do not allow for an assay to distinguish between the bacterial and Archael enzymes and an enzyme of fungal origin (represented here by the AK from *Saccharomyces cerevisiae*) (B). In this case Ap5A can still be used to distinguish the reporter adenylate kinases from the yeast enzyme.

Inhibitors may be determined empirically, for example for different samples or matrices. For example a range of different inhibitors have been shown experimentally to provide discrimination between a reporter kinase (e.g. a kinase from *S. acidocaldarius, T. maritima*, or *Chlamydia pneumonae*) and a non-reporter kinase such as a mammalian tissue-derived kinase as represented by rabbit muscle adenylate kinase (FIG. 4 and FIG. 7). Thus, in one embodiment, the use of one or more inhibitor such as Ap4A, Ap5A and/or Ap6A substantially reduces the activity of non-reporter kinase (eg. endogenous tissue-derived kinase such as adenylate kinase)—the employed inhibitor concentrations are typically in the low micromolar range and have no significant effect on a reporter kinase. By way of further example, Ap5A discriminates reporter kinase from non-reporter kinase (eg. fungal adenylate kinase) represented here by the enzyme from *Saccharomyces cerevisiae*. On this basis inhibitor selection may be based on both the nature of the reporter kinase and the background (ie. non-reporter kinase) of the sample.

Examples of suitable reporter kinase applications of the present invention are illustrated in Table 1 (below)—also shown are examples of contaminating non-reporter kinases typically encountered in said applications. Table 1 also lists, purely by way of example, a selection of inhibitors that may be employed (eg. by addition to sample preparation buffers) in the context of the present invention.

TABLE 1

| Example of reporter kinase | Example of non-reporter kinase | Example of inhibitor | Utility |
|---|---|---|---|
| Bacterial kinase (eg. AK); e.g from *Chlamydia pneumonia* | Mammalian-derived tissue, cell or sample | Mammalian kinase inhibitor (eg. Ap4A, Ap5A and/or Ap6A) | Detection of bacterial infection in a patient |
| Bacterial kinase (eg. AK); e.g. from *Burkoldheria pseudomallei* | Mammalian-derived tissue, cell or sample | Mammalian kinase inhibitor (eg. Ap4A, Ap5A and/or Ap6A) | Detection of viable bacterial pathogens in a cell culture model |
| Archaeal kinase (eg. AK); e.g from *S. acidocaldarius* | Mammalian-derived tissue, cell or sample | Mammalian kinase inhibitor (eq. Ap4A, Ap5A and/or Ap6A) | Detection of an analyte in a patient sample |
| Bacterial kinase (eg. AK); e.g from *Thermotoga maritima* | Fungal-derived cell or culture | Fungal kinase inhibitor (eg. Ap5A) | Detection of bacterial contaminant in a brewing vessel |
| Fungal kinase (eg. AK); e.g. from *S. cerevisiae* | Mammalian-derived tissue, cell or sample | Mammalian kinase inhibitor (eg. Ap4A and/or Ap6A) | Detection of a fungal contaminant in a tissue culture |
| Bacterial kinase (eg. AK); e.g. from *Pseudomonas aeruginosa* | Plant-derived tissue, cell or sample | Plant kinase inhibitor (eg. Ap4A and/or Ap5A) | Detection of a bacterial contaminant in a plant cell culture |
| Fungal kinase (eg. AK); e.g. from *Phytophthora ramorum* | Plant-derived tissue, cell or sample | Plant kinase inhibitor (eg. Ap4A and/or Ap6A) | Detection of a fungal pathogen in a plant |
| Protozoan kinase (eg. AK); e.g. from *Plasmodium falciparum* | Mammalian-derived tissue, cell or sample | Mammalian kinase inhibitor (eg. Ap3A and/or Ap4A) | Detection of a malarial infection in a patient blood sample |

In another embodiment, non-reporter kinase may be separated from reporter kinase on the basis of size. By way of example, the sample containing the reporter kinase can be run on a filtration device, which separates the non-reporter kinase and the reporter kinase on the basis of size, with the reporter kinase being retained on a suitable filter whilst the non-reporter kinase passes through (see e.g. Example 14, and FIG. 6). This may be achieved by coupling the reporter kinase to a particle or within a vesicle which is preferentially retained by the filter. In either case the adherence of the reporter kinase to the filter does not result in the significant loss of the reporter kinase activity. Suitable filter matrices include: nitrocellulose, cellulose acetate or paper filters. Filter matrices typically employ a range of pore sizes, such as from 0.2 μm to 20 μm or larger depending on the nature of the particulate carrier employed.

Physical size may also be used as a basis for separation of non-reporter kinase from reporter kinase using gel filtration or size exclusion chromatography. In one embodiment, the reporter kinase has a lower molecular weight than the non-reporter kinase. In another embodiment, the reporter kinase has a higher molecular weight than the non-reporter kinase. By way of example, the reporter kinase may have a molecular weight of at least 40 to 80 kDa, whereas the non-reporter kinase may have a molecular weight of no more than 30 kDa. When run through a size exclusion resin or membrane, this provides very efficient separation with the larger protein (eg. the reporter kinase) running at or near the void volume of the matrix (hence running quickly) whilst the non-reporter kinase (eg. endogenous kinase such as mammalian tissue kinase) interacts with the pores of the matrix and elutes more slowly. Suitable "higher molecular weight" reporter kinases may be obtained from Archael sources (e.g. trimeric adenylate kinases enzymes from Aracheal sources), which are in the region of 60 kDa in size compared to the 21-22 kDa of contaminating non-reporter kinase (eg. endogenous kinase such as mammalian tissue kinase). In addition, the size differential between the reporter and non-reporter kinase may be enhanced by the addition of a protein or antibody fragment (e.g. a single chain antibody variable region (scFv), by either chemical conjugation or genetic fusion and recombinant expression) to the reporter kinase. For example, a trimeric adenylate kinase fused to a single chain antibody variable region (scFv) has a size in the order of 120 kDa (based on an scFv size of approximately 20 kDa, attached to each of the three subunits).

In a further embodiment, separation of non-reporter kinase from reporter kinase can be achieved by the use of surface charge. In one embodiment, the isoelectric point of the reporter kinase may be lower than that of the non-reporter kinase. In another embodiment, the isoelectric point of the reporter kinase may be higher than that of the non-reporter kinase. As such, the reporter kinase can be separated from the non-reporter kinases with selective binding of either the reporter kinase or the non-reporter kinase to a cation exchange matrix or anion exchange matrix at a suitable pH. The isoelectric point of reporter kinase is frequently in the high basic range; e.g. the tAK from S. acidocaldarius has a predicted pI of 9.03 (although the inventors have demonstrated that the actual pI is in excess of pH10—see Table 2). By contrast, the majority of non-reporter kinases that could interfere with the assay typically have a lower isoelectric point, e.g. a pI in the region of pH7. As such, the reporter kinase can be separated from the non-reporter kinases with selective binding of the reporter kinase, by the use of either a cation exchange resin, membrane or other solid matrix at a pH of at least 8, or using an anion exchange resin, membrane or other solid matrix above pH10. Many of the reporter kinases of the invention retain enzymatic activity in this pH range. Alternatively, non-reporter kinases can be selectively removed by binding them to suitable matrices, e.g. an anion exchange matrix up to pH9.

In another embodiment of the invention, non-reporter kinase can be separated from reporter kinase using a "hydrophobic capture" technique. Reporter kinases (eg. those from the Sulfolubus family, and related Sulfolobaceae families such as acidianus, metallosphaera, stygiolobus, and sulfurisphaera) show exceptionally tight binding to a variety of surfaces, even when such surfaces are pre-treated or pre-coated (termed "blocked") with other proteins or detergent-based blocking agents. In contrast, the "blocking" of surfaces substantially prevents the binding of non-reporter kinases (eg. mammalian, fungal and/or plant non-reporter kinases). This difference in physical binding properties allows for an effective separation of reporter kinase from contaminating non-reporter kinases by adherence onto a surface, with the measurement of the reporter kinase being made on that surface after capture. For example, use of a polypropylene of polycarbonate surface) coated with either of the commonly used blocking agents bovine serum albumen (eg. BSA; 3% w/v in neutral buffer) or skimmed milk (eg. 5% w/v in neutral buffer) will completely prevent the binding of non-reporter kinases (eg. endogenous kinases such as mammalian tissue kinases) but not reporter kinase. In this regard, the trimeric reporter kinases such as those derived from S. acidocaldarius, S. solfataricus and related genera are particularly adherent in these circumstances.

One or more of the above treatments for removing/inactivating non-reporter kinase can be combined to achieve or enhance the desired effect. This may mean that the relative concentrations of one or more of the chemical components may be reduced in the presence of second component. For example, the level of urea required to inactivate non-reporter kinase may be around 2M on its own but can be reduced to 1M in the presence of 0.5% SDS, as they both exert an effect on the target molecules.

Some of the above treatments may also have other beneficial effects in clarifying samples being processed and providing greater access to molecules to be detected. In this regard, a preferred application of the present invention is the detection of a microbial infection in a biological sample. Accordingly, the present application provides a sensitive and rapid point-of-care microbial assay. The invention is particularly suited to the rapid detection of bacterial, viral and/or fungal infections in biological samples, such as the microbial sources listed under 'reporter kinase' in Table 1. Additional microbial infections include those described in the Examples, such as hepatitis species, measles species, norovirus species, legionella species, chlamydia species, listeria species, salmonella species, and burkholderia species. The present invention facilitates the detection of microorganisms in stool samples (for example, by the addition of urea and SDS), both in terms of more uniform samples and in the release of the microbial antigens from clumps or aggregates. Similarly, the addition of sodium hypochlorite to a stool sample may simultaneously sterilise the sample (minimising the chance of infections) and reduce the activity of the non-reporter kinase.

The precise order/timing of the steps for removing non-reporter kinase is not critical, provided that these steps are carried out before the reporter kinase comes into contact with ADP. Thus, they can be carried out in the sample preparation phase, or during the assay before the reporter kinase comes into contact with ADP. In one embodiment, the treatment is instead of, or in addition to, a washing step.

TABLE 2

Summary of properties of reporter kinases (eg. AKs).

| Adenylate kinase (AK) origin | Structure | Mw | pI Predicted/ Actual (if known) |
|---|---|---|---|
| S. acidocaldarius | Trimer | 63330 (3x21110) | 9.03/>10 |
| S. solfataricus | Trimer | 63975 (3x21325) | 8.31 |
| P. furiosus | Trimer | 70602 (3x23534) | 910 |
| A. pernix | Trimer | 70149 (3x23383) | 9.31 |
| T. maritima | Monomer | 26458 | 6.44/~6.7 |
| P. abyssi | Monomer | 26793 | 8.70 |
| A. fulgidus | Monomer | 24703 | 5.74 |
| C. trachomatis | Monomer | 27784 | 4.63 |
| C. pneumoniae | Monomer | 23952 | 7.19 |
| C. difficile | Monomer | 23700 | 5.29 |
| B. pseudomallei | Monomer | 24169 | 8.03 |
| B. anthracis | Monomer | 23743 | 4.80 |
| S. aureus | Monomer | 23974 | 4.69 |
| M. tuberculosis | Monomer | 20124 | 4.91 |
| A. baumanii | Monomer | 24022 | 4.98 |
| R. prowazekii | Monomer | 24501 | 9.25 |
| Francisella tularensis | Monomer | 24361 | 8.06 |
| E. coli | monomer | 23589 | 5.56 |

As mentioned above, the presence of endogenous ATP may adversely affect the accuracy sensitivity of the assay of the present invention. Thus, in one embodiment, any ATP present prior to addition of ADP is optionally removed using one or more of the treatment steps described below. These treatments may be used in any number (preferably one or more, or at least two, or at least three) and/or in any combination. In all cases, however, the treatment leaves the reporter kinase substantially intact. The treatment steps can be applied to any aspect of the invention.

In one embodiment, the removal of endogenous ATP is achieved using an ATPase (e.g. apyrase). The ATPase may then be removed and/or inactivated before the contact with ADP, to avoid the presence of the ATPase adversely influencing the signal obtained using the reporter kinase. By way of example, an ATPase can be used to remove ATP and then the ATPase is itself destroyed by use of elevated temperature. Alternatively, the ATPase can be immobilised on a device (such as a lateral flow device or filtration device described elsewhere in this specification), such that when ATP flows over the ATPase, the ATP is inactivated. As above, this inactivation step must occur before the reporter kinase comes into contact with the ADP.

In a further embodiment, endogenous ATP can be removed by physical means. By way of example, a filtration device can be used, which separates out the ATP on the basis of size in a similar way to that described above for separation of the reporter kinase from non-reporter kinases. Advantageously, the removal of both the ATP and non-reporter kinase can be achieved simultaneously as they are both much smaller than the reporter kinase, either when the latter is on its own or when attached to an antibody, structure or other diagnostic reagent.

In another embodiment, endogenous ATP can be removed on the basis of surface charge as described above. The negative charge of the ATP at pH 5.5 allow it to bind to an anion exchange resin, along with non-reporter kinases, but not the reporter kinase. This again effectively separates the contaminating ATP and non-reporter kinase from the signal-generating reporter kinase in a single step.

The precise order/timing of the steps for removing endogenous ATP is not critical, provided that these steps are carried out before the reporter kinase comes into contact with ADP. Thus, they can be carried out in the sample preparation phase, or during the assay before the reporter kinase comes into contact with ADP. In one embodiment, the treatment is instead of, or in addition to, a washing step.

Figure 3A:
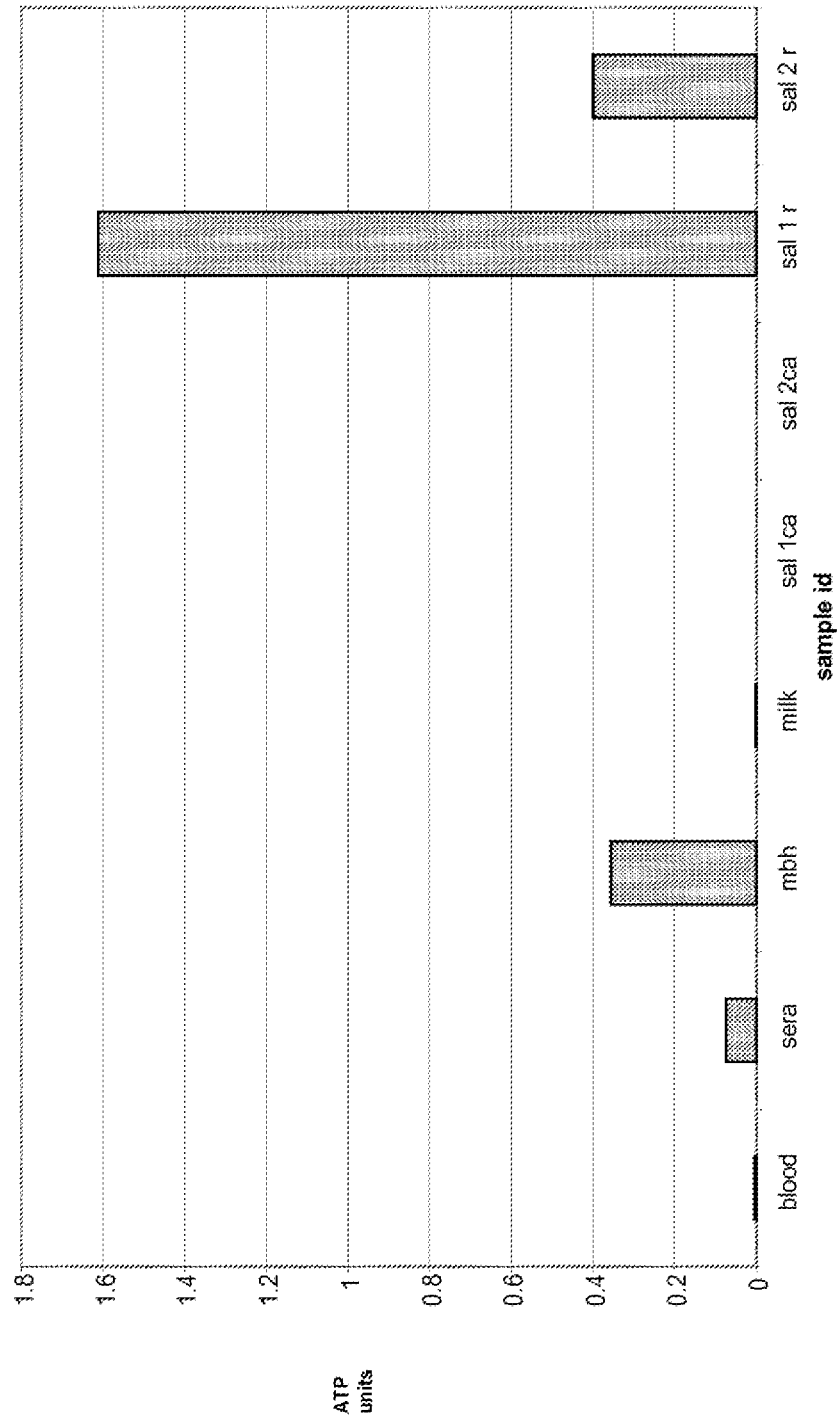
FIG. 3 shows the relative levels of non-reporter adenylate kinase activity (A) and ATP (B) in a variety of samples relevant to clinical diagnosis. Samples from healthy donors were assessed for the levels of ATP generated by non-reporter adenylate kinase (after addition of ADP as substrate; (A) or present naturally in the sample (B). This information can be used to assist in deciding which background reduction steps need to be included in assays for particular samples, although this information does not preclude their use in any assay type, particularly where infections can influence the background levels of either ATP or reporter kinase. Samples are whole blood and sera from sheep, mouse brain homogenate (MBH; representative of tissue biopsy samples), cows' milk, and two saliva samples (1 and 2) collected using either a citric acid ("ca") method or swab device ("r"). The relative light units generated from the raw assay are converted into ATP units based on a standard curve.
Figure 3B:
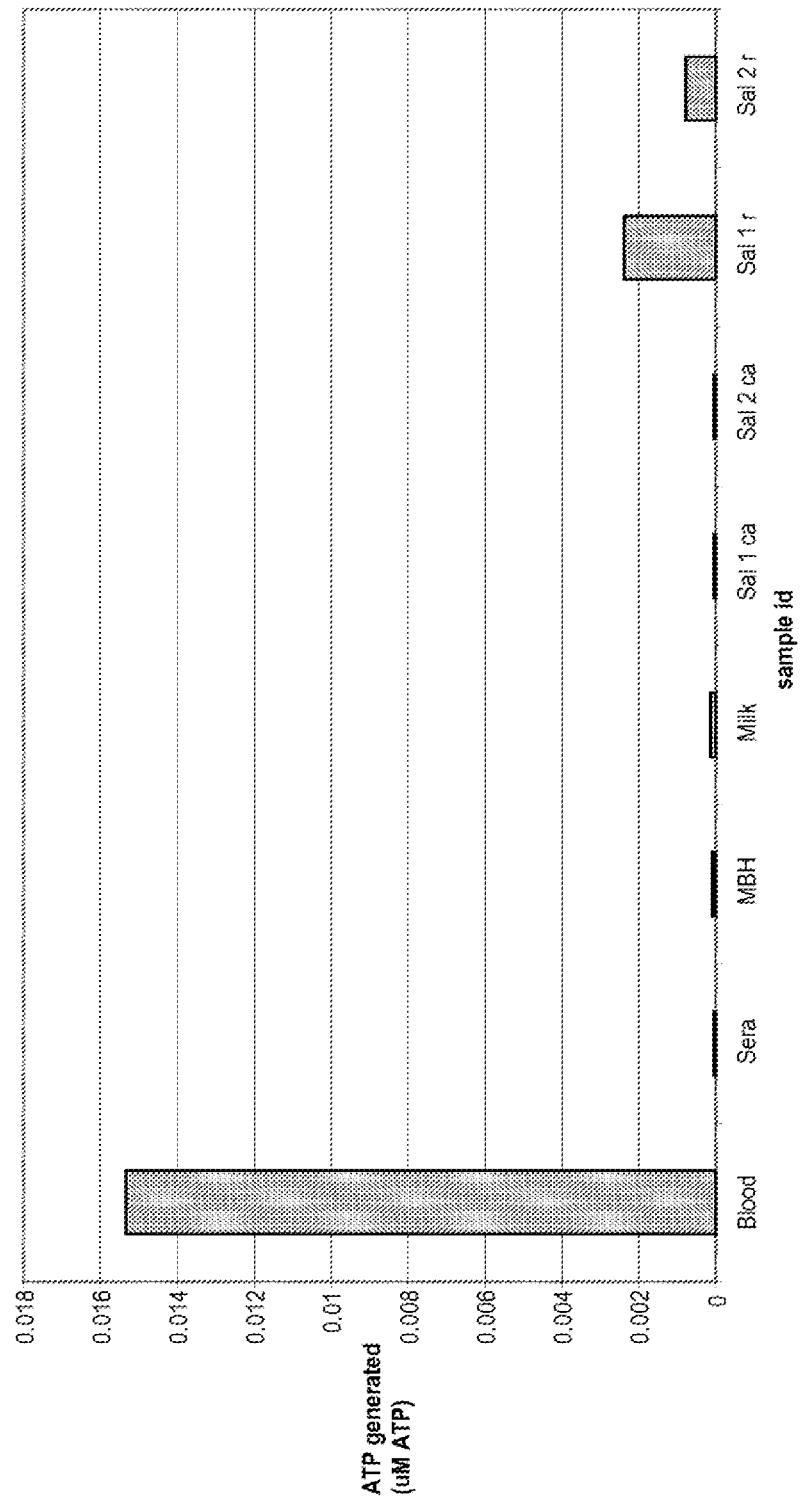

Data of the type presented in FIG. 3 are helpful when deciding on the type and/or number of background-reduction steps (i.e. removal or inactivation of non-reporter kinase and/or ATP) to use in the assay of a particular sample (although this information does not preclude the use of these steps in any assay type, particularly where infections can influence the background levels of either ATP or reporter kinase).

Any suitable kinase enzyme may be used as the reporter kinase in the present invention. In one embodiment, the reporter kinase is an adenylate kinase, acetate kinase or pyruvate kinase, or a combination thereof.

The reporter kinase used in the invention may have a trimeric or monomeric structure—these tertiary structures are associated with an improved stability of the kinase to conditions such as e.g. temperature, pH, chemical denaturants, or proteases.

In one embodiment, the reporter kinase is a non-mammalian, a non-fungal, and/or a non-plant kinase.

In one embodiment, the reporter kinase is a microbial kinase—suitable kinases include *Pyrococcus* species kinases such as *Pyrococcus furiousus* kinase, *P. abyssi* kinase, *P. furiosus* kinase, *P. horikoshii* kinase, *P. woesii* kinase; *Sulfolobus* species kinases such as *Sulfolobus solfataricus* kinase, *S. acidocaldarius* kinase, *S. shibatae* kinase; *Rhodothermus* species kinases such as *Rhodothermus marinus* kinase; *Thermococcus* species kinases such as *Thermococcus litoralis* kinase; *Thermotoga* species kinases such as *Thermatoga maritima* kinase, *Thermatoga neapolitana* kinase; and *Methanococcus* species kinases such as *M. ruber* kinase. In another embodiment, the kinase is an *Archeoglobus* species kinase such as *A. fulgidus* kinase; an *Aeropyrum* species kinase such as *A. pernix* kinase; an *Aquifex* species kinase such as *A. pyrophilus* kinase, an *Alicyclobacillus* kinase such as *A. acidocaldarius* kinase; a *Bacillus* species kinase such as *B. caldotenax* BT1 kinase, a *Bacillus* species PS3 kinase, *B. stearothermophilus* 11057 kinase, *B. stearothermophilus* 12001 kinase, *B. thermocatenulatus* kinase; a clostridial species kinase such as *C. stercocorarium* kinase; a *Thermoanaerobacter* species kinase such as *T. ethanolicus* kinase, *T. thermosulfurogenes* kinase, *T. celere* kinase, *T. aquaticus* YT1 kinase, *T. caldophilus* GK24 kinase, *T. thermophilus* HB8 kinase, In preferred embodiment, the kinase is a *T. litoralis* kinase, *T. maritima* kinase, or a *T. neapolitana* kinase.

In one embodiment, the reporter kinase is thermostable. As well as being resistant to high temperatures, thermostable kinases are also found to be resistant to other biochemical and physical processes that routinely damage or destroy proteins or render them inactive, such as exposure to certain chemicals e.g. chaotropes, free-radical damage, detergents, extremes of pH, exposure to proteases, protein cross-linking, encapsulation within non-permeable or semi-permeable membranes or polymers, or irreversible immobilisation onto surfaces. (See for example: Daniel R M, Cowan D A, Morgan H W, Curran M P, "A correlation between protein thermostability and resistance to proteolysis", Biochem J. 1982 207:641-4; Rees D C, Robertson A D, "Some thermodynamic implications for the thermostability of proteins", Protein Sci. 2001 10:1187-94; Burdette D S, Tchemajencko V V, Zeikus J G. "Effect of thermal and chemical denaturants on *Thermoanaerobacter ethanolicus* secondary-alcohol dehydrogenase stability and activity", Enzyme Microb Technol. 2000 27:11-18; Scandurra R, Consalvi V, Chiaraluce R, Politi L, Engel P C., "Protein thermostability in extremophiles", Biochimie. 1998 November; 80(11):933-41; and Liao H H., "Thermostable mutants of kanamycin nucleotidyltransferase are also more stable to proteinase K, urea, detergents, and water-miscible organic solvents", Enzyme Microb Technol. 1993 April; 15(4):286-92, all of which are hereby incorporated by reference in their entirety).

In another embodiment, the reporter kinase may be an *E. coli* kinase, *Clostridium difficile* kinase, *Bacillus anthracis* kinase, *Acinetobacter baumanii* kinase, *Burkholderia pseudomallei* kinase, *Chlamydia trachomatis* kinase, *Chlamydia pneumonia* kinase, *Staphylococcus aureus* kinase, *Klebsiella pneumonia* kinase, *Rickettsia prowazekii* kinase, *Mycobacterium tuberculosis* kinase, *Saccharomyces cerevisiae* kinase, *Leishmania donovanii* kinase, *Trypanosoma cruzii* kinase, *Shigella flexneri* kinase, *Listeria monocytogenes* kinase, *Plasmodium falciparum* kinase, *Mycobacterium marinum* kinase, *Cryptococcus neoformans* kinase, *Francisella tulraensis* kinase, *Salmonella* spp. kinase, *Coxiella bumetii* kinase, and/or *Brucella abortus* kinase, In several of the embodiments, the kinase derived from these organisms is non-thermostable, but can be distinguished from non-reporter kinase by the use of different sample treatment, extraction or separation techniques. Many of these reporter kinases, in combination with the method to distinguish their activity from non-reporter kinases, may be used in rapid assays to detect the presence/absence, viability or destruction of the organism from which they originate. Such methods are suitable for assessing the presence of an infection within a patient sample, tissue or cell population and the effectiveness of different therapeutic regimes or drugs.

Examples of specific kinases that have been sequenced and that are suitable for use in the invention are SEQ ID NOs 1-25, 31-36, 38, 40, 42, 44, 46, 48, 50, 52, 54, 56, 58, and 61-84. In one embodiment, the kinases used in the invention have at least 70%, 80%, 85%, 90%, 95%, 99% or 100% identity to SEQ ID Nos: 1-25, 31-36, 38, 40, 42, 44, 46, 48, 50, 52, 54, 56, 58, and 61-84.

Other examples of suitable reporter kinases may be found in WO00/46357 and WO2005/093085, which are hereby incorporated by reference in their entirety.

The stability of the reporter kinases may be increased using a variety of methods well-known to those familiar with the art.

By way of example, stabilising agents (such as sorbitol up to a concentration of 4M, or other polyols such as ethylene glycol, glycerol, or mannitol at a concentration of up to 2M) may improve the stability of the kinase. Other additives such as xylan, trehalose, gelatin may also provide additional stabilisation effects either individually or in combination. Addition of a range of divalent metal ions, most notably $Ca^{2+}$, $Mg^{2+}$ or $Mn^{2+}$ may also improve stability of the kinase.

Chemical modification of the kinases can also be used to improve their stability. Reductive alkylation of surface exposed amino groups by glyoxylic acid (e.g Melik-Nubarov (1987) Biotech letts 9:725-730), addition of carbohydrates to the protein surface (e.g. Klibanov (1979) Anal. Biochem. 93:1-25) and amidation (e.g. Klibanov (1983) Adv. Appl. Microbiol. 29:1-28) may all increase the stability of the kinase. Further methods including the use of chemical cross-linking agents and the use of various polymeric supports for enzyme immobilisation are also relevant methods for increasing the stability of enzymes (reviewed in Gupta (1991) Biotech. Appl. Biochem. 14:1-11).

Formulation of the kinase in a solution containing up to around 10 mg/ml of a suitable carrier protein such as casein or albumin, or the addition of free amino acids such as glycine, tyrosine, tryptophan or dipeptides to the formulation, may increase the stability of the kinase to protease treatments.

The genetic modification of enzymes has been shown to provide significant increases in thermal stability and by analogy such mutations are also likely to significantly enhance the stability of the enzymes to other conditions such as protease treatment or gaseous phase "sterilisation". The comparison of the thermostability of the kinase enzymes taken with the defined 3-D structure of the trimeric (archaeal) AKs (Vonrhein et al (1998) J. Mol. Biol. 282:167-179 and Criswell et al (2003) J. Mol. Biol. 330:1087-1099) has identified amino acids that influence the stability of the enzyme.

Genetically engineered variants of kinases showing improved stability can be generated in a number of ways. Essentially these involve the specific site-directed mutagenesis of amino acids believed to form part of the central core packing region of the trimeric molecule and random "directed evolution" methods where the whole molecule is subjected to subsequent rounds of mutagenesis and selection/screening of molecules with improved properties. Specific modified enzymes are set out in SEQ ID NOs: 17-19 (several variants are embraced by each reference). These modifications outlined are based on a hybrid approach using a consensus based approach to define regions likely to influence the thermostability of the enzymes based on observed differences between structurally related molecules. This is followed by either defined changes to incorporate the amino acids that correlate with the best thermostability or a random replacement to incorporate every available amino acid at the positions defined as being essential for thermostability.

In one embodiment of the invention, the reporter kinases may be bound onto a solid support.

Suitable solid supports include a plastic (e.g. polycarbonate, polystyrene or polypropylene) surface, a ceramic surface, a latex surface, a magnetic surface, a steel or other metallic surface, a flow matrix (as described elsewhere in this specification), a filter membrane, or other polymer surface. The solid support can take the form of e.g. strips, dipsticks, microtitre plates, beads.

Binding of the reporter kinase to the solid support may be achieved using any of a wide variety of methods known in the art.

In one embodiment, the reporter kinase is bound onto the solid support via standard protein adsorption methods, such as outlined below.

Binding of the reporter kinase onto the solid support may be achieved by methods routinely used to link protein to surfaces, e.g. incubation of protein in 0.1M sodium bicarbonate buffer at about pH 9.6 at room temperature for about 1 hour. Alternatively the protein is covalently coupled to the surface using any of a wide range of coupling chemistries known to those familiar with the art. For example an adenylate kinase fusion protein (e.g. to Sup35) derivatised with SPDP (Pierce chemicals; using manufacturer's instructions), reduced with DTT to provide free sulfhydryl groups for cross-linking, is covalently attached to a polystyrene support with a maleimide surface. Plastic surfaces with such sulfhydryl-binding surfaces are well described in the literature. The reporter kinases described in this application have the property that their activity is retained upon derivatisation and cross-linking to such supports.

Alternatively an amine reactive surface on a polystyrene or polycarbonate support is used, with a bifunctional cross-linking agent such as monomeric glutaraldehyde, to provide direct non-cleavable cross-linking of the kinase via free amine groups on the protein. UV treatment can also be used to directly link the indicator to a suitable support. Steel surfaces can be treated in a similar way to plastic surfaces to mediate covalent attachment of the kinase.

A wide variety of protein cross-linking reagents is available from companies such as Pierce chemical company (Perbio). Reagents reactive to sulfhydryl, amino, hydroxyl and carboxyl groups are designed for coupling proteins but they can equally be used for cross-linking proteins to either naturally reactive or coated solid supports such as plastics, other polymers, glass and metals. Reactive chemistries are also available for cross-linking the enzymes to carbohydrates. For example, the reagents BMPH ((N-[β-Maleimidopropionic acid]hydrazide.TFA), KMUH ((N-[k-Maleimidoundecanoic acid]hydrazide), and MPBH (4-(4-N-Maleimidophenyl)butyric acid hydrazide hydrochloride) can be used to cross link the indicator containing either a free sulfhydryl in the form of a cysteine residue or a chemically derivatised protein reduced to generate a sulfhydryl reactive group, to carbohydrates. This may be particularly important for a solid support which is either a complex carbohydrate (e.g. paper, cellulose-based membranes, gels or resins) or can be coated or treated with a carbohydrate solution to generate a suitably reactive surface.

For each type of support the reporter kinase may be formulated in a solution that enhances binding and/or stabilises the bound protein. Such formulations include solutions containing up to 10% (w/v) sucrose, sorbitol, mannitol, cellulose, or polyethylene glycol (PEG). In addition the kinase can be formulated as part of a gel that is applied to the surface or lumen of a suitable support. Examples include alginate, agar or polyacrylamide matrices.

In another embodiment, the reporter kinase may be attached to a solid support via a linker that comprises a binding agent specific for an analyte. Details of suitable methods for achieving this attachment are given elsewhere in this specification.

The assay described in the first aspect of the invention is particularly suitable for detecting kinase activity in kinase-based analyte detection assays such as those described in the applicant's earlier filing, WO00/46357, the entirety of which is hereby incorporated by reference.

Thus, in a second aspect of the invention, there is provided a method for determining the presence of an analyte in a sample, comprising:
(i) exposing the sample to a reporter kinase coupled to a binding agent specific for the analyte, so that a complex is formed between the reporter kinase and any analyte present in the sample;
(ii) separating complexed reporter kinase from uncomplexed reporter kinase; and
(iii) measuring the activity of the complexed reporter kinase using an assay according to the first aspect of the invention.

The binding agent used in this method (and in any other method described in this specification) is typically an antibody (or a fragment thereof) that binds specifically to the analyte under investigation. The antibody may be obtained using conventional techniques for identification and isolation of specific antibodies, and the assay is thus of application to substantially all analytes against which an antibody can be raised. Alternatively, the binding agent may be selected from the group consisting of lectins, growth factors, DNA/RNA aptamers, phage or other species that bind specifically to the analyte under investigation. Where a first and second binding agent are involved, these binding agents may be the same or different.

The reporter kinase may be coupled to the specific binding agent by conventional techniques. For example, there are numerous ways of labelling immunoreactive biomolecules with enzymes (conjugation). Antibodies, the majority of antigens, and enzymes are all proteins and, therefore, general methods of protein covalent cross-linking can be adapted to the production of immunoassay reagents. The preparation of antibody-enzyme conjugates requires mild conditions to ensure the retention of both the immunological properties of the antibody and the catalytic properties of the enzyme. Common methods include, glutaraldehyde coupling, the use of periodate oxidation of glycoproteins to generate dialdehydes capable of forming Schiff-base linkages with free amino groups on other protein molecules, and the use of heterobifunctional reagents, for example, succinimidyl-4-(N-maleimidomethyl)cyclohexane-1-carboxylate (SMCC).

In one embodiment of the invention, the above method is a performed as a "capture assay", such as a sandwich assay (sometimes referred to as a two antibody capture assay), an antigen capture assay, or an antibody capture assay. In an example of an antibody capture assay, an analyte is first bound to a solid support, by e.g. non-specific binding. The analyte is then exposed to a reporter kinase linked to a binding agent (e.g. an antibody) specific for the analyte. A complex is thus formed between the analyte and the reporter kinase. Any uncomplexed reporter kinase is removed by one or more routine washing steps. ADP and luciferin/luciferase are then added to the solid support where the ADP is converted to ATP by the reporter kinase complex. The luciferin/luciferase converts the ATP to a light output, which can then be measured and correlated to the amount of analyte present on the solid support.

In one embodiment, at any point prior to step (iii), the sample is treated to remove/inactivate non-reporter kinase and/or ATP. Suitable treatments that may be employed in this regard are described earlier in this specification.

In one embodiment, the method described in this aspect of the invention is completed within less than 15 minutes, less than 10 minutes, less than 5 minutes, or less than 2 minutes.

Example 10 describes the use of a method according this aspect of the invention to detect the presence of Hepatitis C in an oral swab sample. An oral swab sample is taken from the mouth of a patient and dried in an oven at 90 C for 1 minute to remove any non-reporter kinase (eg. endogenous kinase such as mammalian tissue kinase). The swab is then exposed to a conjugate comprising a reporter kinase coupled to an antibody for Hepatitis C antigen. The reporter kinase conjugate forms a complex with any Hepatitis C antigen present on the swab sample. The swab is then rinsed to remove any uncomplexed reporter kinase conjugate, and is inserted into a reagent tube containing ADP and luciferin and luciferase. The reagent tube is transferred to a hand-held luminometer and the light output is measured. The light output can then be correlated with the amount of analyte present in the sample.

In a third aspect, the invention provides a method for determining the presence of an analyte in a sample, comprising:
(i) providing a solid support comprising a reporter kinase, wherein the reporter kinase is attached to the solid support via a linker that comprises a binding agent specific for the analyte;
(ii) applying the sample to the solid support, whereby any analyte present in the sample displaces reporter kinase from the solid support; and
(iii) measuring the activity of the displaced reporter kinase using an assay according to the first aspect of the invention.

In one embodiment, the method described in this aspect of the invention is completed within less than 15 minutes, less than 10 minutes, less than 5 minutes, or less than 2 minutes.

By way of example, a clinical sample is provided that is suspected to contain a bacterial toxin. A solid support is also provided, which comprises a reporter kinase linked to the solid support by a binding agent (e.g. an antibody) that is specific for the bacterial toxin. When the sample is applied to the solid support, any bacterial toxin present will competitively interfere with the binding of the antibody to the solid support and will thereby displace the reporter kinase from the solid support. The amount of displaced reporter kinase can then be measured using an assay according to the first aspect of the invention and correlated with the amount of bacterial toxin present in the sample.

Example 13 describes the use of this method to detect the presence of norovirus in a clinical sample. In this example, the solid support is coated with an antibody to norovirus (i.e. a binding agent specific for the analyte). A reporter kinase conjugate is formed comprising a reporter kinase conjugated to a VP1 norovirus protein (i.e. the analyte). By virtue of the interaction between the VP1 and the antibody, the reporter kinase is attached to the solid support. The clinical sample is then applied to the solid support. Any norovirus (i.e. analyte) present in the sample displaces the reporter kinase conjugate from the solid support. The activity of this displaced reporter kinase is then measured and correlated with the amount of norovirus present in the sample.

In one embodiment, the solid support is a flow matrix. The term "flow matrix" is used throughout this specification to mean any liquid-transport solid material that allows for liquid flow therethrough, including materials such as nitrocellulose, nylon, rayon, cellulose, paper, glass fibre, silica, a gel matrix, or any other porous or fibrous materials. In one embodiment, the flow matrix is configured as a substantially planar elongate strip. The flow matrix material can be pre-treated or modified as required.

Suitable methods for attaching the reporter kinase to the solid support are described below. The binding agent is as defined above in relation to the second aspect of the invention.

An analyte is coupled directly to the surface of the solid support.

The reporter kinase is linked to a binding agent specific for the analyte (e.g. an antibody) and thereby associates with the analyte on the surface. The reporter kinase remains attached to the surface until displaced by the presence of either antibody or analyte in the sample.

An analyte is bound to the solid support via a first binding agent specific for the analyte.

The reporter kinase is conjugated to a second binding agent specific for the analyte and thereby associates with the analyte on the surface. The reporter kinase remains attached to the surface (in a sandwich-type arrangement) until displaced by the presence of either antibody or analyte in the sample.

A binding agent specific to the analyte is used to coat the solid support.

The reporter kinase is conjugated or genetically fused to the target analyte and thereby associates with the binding agent on the surface. The reporter kinase-analyte conjugate is released from the solid support by competing analyte or antibody in the test sample.

The reporter kinase is therefore indirectly attached to the solid support by a linker that comprises a binding agent specific for the analyte. The linker may also comprise the analyte (or a fragment thereof).

In one embodiment, at any point prior to step (iii), the sample is treated to remove/inactivate non-reporter kinase and/or ATP. Suitable treatments are described elsewhere in this specification.

In a fourth aspect, the invention provides a method for determining the presence of an analyte in a sample, comprising:
(i) providing a solid support on which is attached a first binding agent specific for the analyte;
(ii) exposing the solid support to the sample so that any analyte present in the sample becomes attached to the solid support via said first binding agent;
(iii) exposing the solid support to a reporter kinase coupled to a second binding agent specific for the analyte, so that the reporter kinase becomes attached to the solid support via the interaction between the second binding agent and the already-bound analyte;
(iv) applying the mixture obtained in step (iii) to a filter membrane, wherein the solid support is retained on the filter membrane; and
(v) measuring the activity of the retained reporter kinase using an assay according to the first aspect of the invention.

In one embodiment, the method described above is completed within less than 15 minutes, less than 10 minutes, less than 5 minutes, or less than 2 minutes.

In one embodiment, the solid support is a latex support, or a magnetic support, e.g. a latex bead or a magnetic bead. When the solid support is magnetic, step (iv) may be replaced by exposing the mixture obtained in step (iii) to a magnet, so that the solid support is retained on the magnet.

Example 14 describes the use of this method for detecting the presence of *legionella* in a water sample. Antibodies specific for *legionella* are attached to a solid support (a latex bead). The latex beads are then exposed to (i) the sample to be tested (potentially containing *legionella*) and (ii) a reporter kinase coupled to a second antibody specific for *legionella*. Any *legionella* present in the sample binds to the antibody on the latex bead. Subsequently, the reporter kinase-antibody conjugate binds to the latex bead via the already-bound *legionella*. The mixture thus obtained is applied to a filter membrane, which retains the latex beads. The other components of the mixture (e.g. unbound reporter kinase conjugate, ATP, non-reporter kinase (eg. mammalian tissue kinase, plant and/or fungal kinase endogenous to the test sample etc.) pass through the filter membrane. The reporter kinase retained on the filter membrane is then exposed to ADP and a mixture luciferin/luciferase, and the light output measured using a luminometer. Optionally, the filter membrane can be treated using any of the treatment steps described above for removing any remaining ATP or non-reporter kinase.

Suitable filter membranes for use in this aspect of the invention include: nitrocellulose, cellulose acetate or paper filters. Filter matrices typically employ a range of pore sizes from 0.2 μm to 20 μm or larger depending on the nature of any particulate carrier used.

Example 17 describes the use of this method for detecting the presence of *Salmonella* in a food sample. The method is essentially as described for Example 14 above, except that a magnetic bead is used as the solid support instead of a latex bead, and the mixture obtained in step (iii) is exposed to a magnet rather than a filter membrane.

In one embodiment, at any point prior to step (v), the sample is treated to remove or inactivate non-reporter kinase and/or ATP. Suitable treatments are described elsewhere in this specification.

The assay described in the first aspect of the invention is also suitable for detecting kinase activity in kinase-based biological indicator systems such as those described in the applicant's earlier filing, WO2005/093085, which is hereby incorporated by reference in its entirety.

A typical biological indicator is prepared by adsorbing a reporter kinase onto a solid support such as an indicator strip or dipstick. The indicator is then included with a sample (containing a contaminant) to be treated, and the indicator plus sample are subjected to a treatment process. The reduction in activity of the indicator kinase by the treatment is then correlated with the reduction in amount or activity of the contaminant. When a level of activity is determined that is known to correlate with an acceptable reduction in the contaminant, the treatment is then regarded as validated.

It has also been found that the performance of these kinase-based indicators can be improved by covalently cross-linking the kinase to a biological component, wherein the biological component is a mimetic/surrogate of the contaminant. This allows the indicator to more accurately reflect the reaction of the contaminant to the treatment process, which in turn leads to improved indicator accuracy/sensitivity, and thus fewer "false" process validations.

Thus, in a fifth aspect of the invention, there is provided a method of validating a treatment process for reducing the amount or activity of a contaminating biological agent in a sample, comprising the steps of:
(i) providing a sample that contains, or is suspected to contain, a contaminating biological agent;
(ii) subjecting the sample to a treatment process in the presence of a defined amount of a reporter kinase, wherein the reporter kinase and the contaminating biological agent are both exposed to the treatment process;

(iii) measuring the residual activity of the reporter kinase using an assay according to the first aspect of the invention; and (iv) comparing said residual activity to a predetermined kinase activity, wherein the pre-determined kinase activity corresponds to a confirmed reduction in the amount or activity of the contaminating biological agent under the same conditions.

In one embodiment, steps (i) to (iv) are completed in less than 15 minutes, less than 10 minutes, less than 5 minutes, less than 2 minutes.

In one embodiment, at any point prior to step (iii), the sample is treated to remove/inactivate non-reporter kinase and/or ATP. Suitable treatments are described elsewhere in this specification.

The term "treatment" or "treatment process" encompasses any process that is designed to reduce the amount or activity of a contaminant in a sample. Suitable treatments include one or more of: a selected pH, temperature or pressure, exposing the sample to a protease or other lytic enzyme, exposing the sample to a detergent, a chemical sterilant, radiation, free radicals, or a gas-phase sterilant. In one embodiment, the treatment is designed to reduce the infectious activity (also known as the infectivity) of an infectious biological contaminant, such as TSE. The term "treatment" or "treatment process" also encompasses cleaning and inactivation processes such as high temperature autoclaving with wet or dry steam, ozone sterilisation, $H_2O_2$ sterilisation, rendering or other method designed to eliminate or inactivate the contaminant. In one embodiment of the invention, both the reporter kinase and the contaminant are directly exposed to the treatment process, i.e. there is no seal or barrier between the reporter kinase/contaminant and the treatment process. The reporter kinase and the contaminant are therefore both in direct contact with the treatment process, and are subject to the same treatment conditions.

In one embodiment, the contaminating biological agent is selected from the group consisting of bacteria, viruses, spores, toxins, prions, proteins and peptides. In a further embodiment, the reporter kinase is bound onto a solid support using any of the methods described in relation to the first aspect of the invention.

In another embodiment of the invention, the reporter kinase is covalently linked to a biological component.

The biological component is advantageously a mimetic or surrogate of the contaminant, and therefore reacts to the treatment process in substantially the same way as the contaminant. In one embodiment, the biological component may be the same as, but physically distinct from, the contaminant in the sample that is to be subjected to the treatment process, e.g. if the contaminant is a protein, then the biological component is also a protein; if the contaminant is a blood protein, the biological component is also blood protein; if the contaminant is a DNA molecule, then the biological component is also a DNA molecule; if the contaminant is an RNA molecule then the biological component is also an RNA molecule, etc. for each of the contaminants and biological components disclosed in this specification.

Examples of biological components that can be used in the invention include proteins, nucleic acids, carbohydrates and lipids.

In one embodiment, the biological component comprises a protein selected from the group consisting of a blood protein, a bacterial protein, a viral protein, a fungal protein, and a self-aggregating or amyloid forming protein.

In a further embodiment, the blood protein is selected from the group consisting of blood clotting proteins (e.g. fibrinogen, fibrin peptides, fibrin, transglutaminase substrates, thrombin), serum proteins (e.g. albumin and globulin), platelet proteins, blood cell glycoproteins, and haemoglobin.

In another embodiment, the bacterial protein is selected from the group consisting of a bacterial fimbrial protein (e.g CgsA from *E. coli* and AgfA from *Salmonella*), a bacterial toxin protein (e.g. toxins from *Bacillus anthracis, Corynebacterium diphtheriae, Clostridium botulinum*), a bacterial cell surface protein (e.g. peptidoglycan, lipoproteins), and a bacterial spore protein (e.g. from Gram positive bacteria and having a similar sequence or overall structure to the proteins forming ribbon appendages in *Clostridium taeniosporum*, chaplin proteins, rodlin proteins).

In yet another embodiment, the viral protein is selected from the group consisting of a viral envelope protein, a viral capsid protein, and a viral core protein. Preferably, the viral proteins are from a bacteriophage virus (e.g. the MS2 and PP7 proteins), norwalk virus (e.g. capsid protein), rotavirus (e.g. VP2, VP6 and VP7 proteins), coronavirus (e.g. SARS S, E and M proteins), bluetongue virus (e.g. VP2 protein), human papillomavirus (e.g. viral major structural protein, L1), hepatitis B (e.g. small envelope protein HBsAg), Hepatitis C virus (e.g. core, E1 and E2 proteins), influenza virus (e.g. neuraminidase and haemagglutinin and matrix proteins), poliovirus (e.g. capsid VP0, 1 and 3 proteins), HIV (e.g. Pr55gag, envelope proteins) and dengue B virus (e.g. envelope (e) and pre-membrane/membrane (prM/M).

In a further embodiment, the fungal protein is selected from the group consisting of hydrophobin proteins (e.g. SC3 from *Schizophyllum commune*, RodA/B from *Aspergillus fumigates*, and equivalent proteins from yeast), fungal spore proteins, hyphal proteins, mycotoxins, and fungal prions (e.g. Sup35, Het S, URE 2, Rnq1, New 1).

In yet a further embodiment, the self-aggregating protein is selected from the group consisting of prions (e.g. PrP$^{Sc}$ and PrP$^c$, Sup35, Het S, Ure 2, Rnq1, New 1), prion mimetic proteins, amyloid fibrils, cell surface adhesins from floc forming and filamentous bacteria in activated sludge, beta amyloid protein, tau protein, polyadenine binding protein, herpes simplex virus glycoprotein B, lung surfactant protein C, CsgA protein from *E. coli*, AgfA protein from *Salmonella* species, bacterial fimbrial proteins, apolipoproteins (e.g. apolipoprotein A1), hydrophobins from fungal species (e.g. SC3 from *Schizophyllum commune*, RodA/B from *Aspergillus fumigates*), chaplins (e.g. Chps A-H from *streptomyces* spp), rodlins (e.g. Rd1A and Rd1B from *streptomyces* spp), gram positive spore coat proteins (e.g. P29a, P29b, GP85 and a SpoVM analogue), and barnacle cement-like proteins (e.g. the 19 kDa protein from *Balanus albicostatus*, and the kDa protein from *Megabalanus rosa*, and the novel calcite-dependent cement-like protein from *Balanus albicostatus*).

In a further embodiment, the nucleic acid is selected from a DNA molecule and an RNA molecule. Preferably, the nucleic acid is derived from neurological tissue.

In a further embodiment, the carbohydrate is selected from the group consisting of exopolysaccharide, lipopolysaccharide (EPS/LPS, sometimes known as endotoxin) (e.g. from *Legionella, E. coli, Staphylococcus* species, *Streptococcus* species, *Pseudomonas* species, *Acinetobacter* species, *Campylobactor* species, and *Bacillus* species), peptidoglycan, cell wall components of plants, fungi and yeast (e.g. chitin, lignin, glucan), mucin preparations, glycolipids (especially brain derived glycolipids), glycoproteins (e.g. cell surface glycoproteins, Eap1p), spore extracts (e.g. from *Bacillus* spp, Clostridial spp and other spore-formers), polysaccharides from yeast capsules, and invertebrate secretions (e.g. from molluscan gels).

In another embodiment, the lipid is selected from the group consisting of glycolipids (e.g. brain-derived glycolipids), gangliosides (e.g. neuronal cell gangliosides such as $GT_{1b}$, $GT_{1a}$ and gangliosides of more general cell origin such as $GM_1$), and plant oils and lipids.

Advantageously, the biological component is part of a biological matrix. The biological matrix may be a mimetic of the sample that is to be treated. In one embodiment, the biological matrix comprises one or more components selected from the group consisting of proteins, lipids, nucleic acids, and carbohydrates, or fragments or derivatives thereof. In another embodiment, the biological matrix may comprise a mixture of proteins. In a further embodiment, the biological matrix may comprise one or more components selected from the group consisting of blood, serum, albumin, mucus, egg, neurological tissue, food, culled animal material, and a commercially available test soil. In a further embodiment of the invention, the biological matrix comprises one or more components selected from the group consisting of fibrinogen, thrombin, factor VIII, $CaCl_2$, and, optionally, albumin and/or haemoglobin. Examples of reporter kinases linked to biological components are described in SEQ ID NOs: 34-38, 40, 42, 48, 50, 52, 54, 61, 67, 72, and 73.

The biological indicator may be prepared by covalently linking a reporter kinase to an appropriate biological component. Any suitable method of covalent attachment known in the art may be used. In one embodiment, the kinase is genetically or chemically cross-linked to the biological component.

Chemical cross-linking may be achieved using a range of homo- and hetero-bifunctional reagents commonly used for cross-linking of proteins for the generation of enzyme conjugates or other related purposes. For example, in an indicator comprising fibrin as the biological component, the fibrin and the reporter kinase may be derivatised with the addition of SPDP (Perbio) to primary amine groups. The reporter kinase can then be reduced to generate a reactive thiol group and this is then mixed with the fibrin to produce covalent fibrin-kinase linkages.

The reporter kinases can also be chemically cross-linked to carbohydrates, lipids or other glycoconjugates using heterobifunctional agents following treatment of the target carbohydrate with meta-periodate.

Alternatively, the indicator may be prepared as a fusion protein. This is achieved by fusing a synthetic gene encoding an appropriate kinase (e.g. the gene encoding AK from *Sulfolobus acidocaldarius* or *Thermatoga neopolitana*) to a gene encoding an appropriate biological component.

Methods according to this aspect of the invention are illustrated in Examples 18-21.

In a sixth aspect of the invention, there is provided a device for detecting the activity of a reporter kinase in a sample, comprising:
an elongate flow matrix, wherein said flow matrix comprises:
(i) a sample-receiving zone; and
(ii) a detection zone, located downstream of the sample-receiving zone, comprising a mixture of ADP and a bioluminescent reagent;
wherein, in use, a sample is applied to the sample-receiving zone and is drawn along the flow matrix to the detection zone.

In use, the sample is applied to the sample-receiving zone of the device and is allowed to migrate to the detection zone where it comes into contact with the mixture of ADP and bioluminescent reagent. Here, any reporter kinase present in the sample acts on the ADP to generate ATP, which in turn reacts with the bioluminescent reagent to produce light. The light output from the detection zone can be readily measured using a luminometer, preferably a hand-held luminometer. In one embodiment, the detection zone of the device is snapped off and placed in a luminometer. The amount of light produced can then be correlated with the amount of reporter kinase activity.

In one embodiment, the device comprises a backing strip on which the elongate flow matrix is positioned. The backing strip may be made from any suitable non-absorbing material, such as a plastic-adhesive backing card. In another embodiment, the flow matrix is at least partially sandwiched between a top and a bottom laminate. The top laminate may include a sample-application window, which provides access to the sample-receiving zone of the flow matrix, and may also include a detection window, which provides access to the detection zone of the flow matrix. The laminates may be made from any suitable non-absorbing material, e.g. a transparent or translucent adhesive plastic film.

In one embodiment, the device is a lateral flow device. Lateral flow devices and methods for their construction are well known in the art, being best known as the standard pregnancy test kit.

In a further embodiment, the device may comprise a background-reduction zone, situated between the sample-receiving zone and the detection zone. This zone functions to remove/inactivate any non-reporter kinase and/or ATP that may be present in the sample before the sample reaches the detection zone. Thus, these contaminants are prevented from interfering with the sensitivity or accuracy of the assay.

In one embodiment, the background-reduction removal zone comprises a substance that selectively (or specifically) inhibits non-reporter kinase, whilst leaving the reporter kinase substantially unaffected. Suitable inhibitors are described elsewhere in this specification. In another embodiment, the background-reduction zone comprises a protease that selectively destroys non-reporter kinase, whilst leaving the reporter kinase substantially unaffected. Suitable proteases are described elsewhere in this specification. In a further embodiment, the background-reduction zone may be arranged so as to physically capture out non-reporter kinases on the basis of their size, charge, or binding properties as described elsewhere in this specification. The captured non-reporter kinases are thus prevented from reaching the detection zone.

In another embodiment, the background-reduction zone comprises an immobilised ATPase, e.g. apyrase. In another embodiment, the background-reduction zone may be arranged so as to physically capture out ATP on the basis of its size or charge as described elsewhere in this specification. The captured ATP is thus prevented from reaching the detection zone.

In one embodiment, the ADP in the detection zone of the device is high purity ADP, and the bioluminescent reagent is a mixture of luciferin and luciferase. In another embodiment, the ADP and luciferin/luciferase are immobilised in the detection zone using conventional immobilisation methods.

In a further embodiment, the device is portable.

In a further embodiment, the detection zone may include a cationic membrane that retains and concentrates the reporter kinase conjugate for enhanced detection.

In another embodiment, the sample-receiving zone may include a suitable dye which also migrates to the detection zone, acting as a control for the proper flow of the sample through the device. This positive internal control may also exploit the use of a cation-binding membrane within the detection zone to help retain the dye to provide a clear visual signal.

In a seventh aspect of the invention, there is provided a lateral flow device for use in an assay for detecting the presence of an analyte in a sample, comprising:
a backing strip on which is positioned an elongate flow matrix, wherein said flow matrix comprises:
(i) a sample-receiving zone comprising a reporter kinase attached to the flow matrix via a linker comprising a binding agent specific for the analyte; and
(ii) a detection zone, located downstream of the sample-receiving zone;
wherein, in use, a sample is applied to the sample-receiving zone and any analyte present in the sample displaces the reporter kinase from the flow matrix and thereby allows the reporter kinase to migrate to the detection zone.

In use, the sample is applied to the sample-receiving zone, and any analyte present in the sample displaces the reporter kinase attached to the sample-receiving zone. Any reporter kinase that is not displaced remains attached to the sample-receiving zone, and this is the case for a sample negative for the presence of the analyte. Thus, only the displaced reporter kinase proceeds to the detection zone where it can be detected and correlated with the amount of analyte present in the sample.

The backing strip of the device may be made from any suitable non-absorbing material, such as a plastic-adhesive backing card. In one embodiment, the flow matrix is at least partially sandwiched between a top and a bottom laminate. The top laminate may include a sample-application window, which provides access to the sample-receiving zone of the flow matrix, and may also include a detection window, which provides access to the detection zone of the flow matrix. The laminates may be made from any suitable non-absorbing material, e.g. a transparent or translucent adhesive plastic film. In a further embodiment, the detection zone comprises a mixture of ADP and a bioluminescent reagent.

The reporter kinase is attached to the flow matrix by a linker comprising a binding agent specific for the analyte. Binding agents and methods for attaching the reporter kinase to the flow matrix are as described in relation to the second aspect of the invention.

In one embodiment, the device may further comprise a background-reduction zone, situated between the sample-receiving zone and the detection zone. This zone functions to remove/inactivate any non-reporter kinase and/or ATP that may be present in the sample before the sample reaches the detection zone. Thus, these contaminants are prevented from interfering with the sensitivity or accuracy of the assay.

In one embodiment, the background-reduction removal zone comprises a substance that selectively (or specifically) inhibits non-reporter kinase, whilst leaving the reporter kinase substantially unaffected. Suitable inhibitors are described elsewhere in this specification. In another embodiment, the background-reduction removal zone comprises a protease that selectively destroys non-reporter kinase, whilst leaving the reporter kinase substantially unaffected. Suitable proteases are described elsewhere in this specification. In a further embodiment, the background-reduction zone may be arranged so as to physically capture out non-reporter kinases on the basis of their size, charge, or binding properties as described elsewhere in this specification. The captured non-reporter kinases are thus prevented from reaching the detection zone.

In another embodiment, the background-reduction zone comprises an immobilised ATPase, e.g. apyrase. In another embodiment, the background-reduction zone may be arranged so as to physically capture out ATP on the basis of its size or charge as described elsewhere in this specification. The captured ATP is thus prevented from reaching the detection zone.

In one embodiment, the ADP in the detection zone of the device is high purity ADP, and the bioluminescent reagent is a mixture of luciferin and luciferase. In another embodiment, the ADP and luciferin/luciferase are immobilised in the detection zone using conventional immobilisation methods.

In another embodiment, the device is portable.

In a further embodiment, the detection zone may include a cationic membrane that retains and concentrates the reporter kinase conjugate for enhanced detection.

In another embodiment, the sample-receiving zone may include a suitable dye which also migrates to the detection zone, acting as a control for the proper flow of the sample through the device. This positive internal control may also exploit the use of a cation-binding membrane within the detection zone to help retain the dye to provide a clear visual signal.

In an eighth aspect, the invention provides a method for detecting the activity of a reporter kinase in a sample, wherein the method is conducted using a device according to the sixth aspect of the invention, comprising the steps of:
(i) applying the sample to the sample-receiving zone of the device;
(ii) allowing the sample to flow through to the detection zone of the device; and
(iii) detecting the light output from the detection zone.

In one embodiment, after step (i), the method further comprises allowing the sample to flow through a background-reduction zone as described in relation to the sixth aspect of the invention.

In another embodiment, step (iii) is carried out by snapping off the detection zone of the device, and then placing the detection zone into a luminometer.

In a further embodiment, the method comprises the step of recording the light output data obtained on a suitable data carrier.

In a ninth aspect of the invention there is provided a method for detecting the presence of an analyte in a sample using the device described in relation to the seventh aspect of the invention comprising:
(i) applying the sample to the sample-receiving zone of the device;
(ii) allowing any reporter kinase displaced from the sample-receiving zone to migrate to the detection zone; and
(iii) detecting the light output from the detection zone.

In one embodiment, after step (i), the method further comprises allowing the sample to flow through a background-reduction zone described in relation to the seventh aspect of the invention.

In another embodiment, step (iii) is carried out by snapping off the detection zone of the device, exposing the detection zone to ADP and a bioluminescent reagent, wherein the detection zone is exposed to the bioluminescent reagent no more than 5 minutes (or no more than 2 minutes, 1 minute, 30 seconds, or 10 seconds) after having been exposed to the ADP, and then placing the detection zone into a luminometer. In one embodiment, the detection zone is exposed to the ADP and bioluminescent reagent simultaneously.

In a further embodiment, the method comprises the step of recording the light output data obtained on a suitable data carrier.

In a tenth aspect, the invention provides a kit comprising a device according to the sixth or seventh aspect of the invention, and a luminometer. In one embodiment, the luminometer is a hand-held (i.e. portable) luminometer.

DEFINITIONS SECTION

The term "light output" means the light that is emitted by the reaction of ATP with the bioluminescent reagent. This light output can be detected using entirely conventional technology, such as a standard luminometer (e.g. a Berthold Orion 96-well microplate luminometer, or a hand-held luminometer).

The term "flow matrix" refers to any liquid-transport solid material that allows for liquid flow therethrough, and includes materials such as nitrocellulose, nylon, rayon, cellulose, paper, glass fibre, silica, gel matrices, or any other porous or fibrous materials. In one embodiment, the flow matrix is configured as a substantially planar elongate strip. The flow matrix material can be pre-treated or modified as required.

The term "reporter kinase" refers to a kinase enzyme that is not a mammalian, plant and/or fungal kinase. Thus, in the context of a biological sample to be tested, a reporter kinase is a kinase that is not normally present (to any significant degree) in a sample taken from a healthy individual. Put another way, a reporter kinase of the present invention is a kinase that is not normally inherent or endogenous (to any significant degree) in a sample taken from a healthy individual. Reporter kinase may be added to the sample as a separate (ie. exogenous) reagent, e.g as an isolated kinase. Reporter kinases are preferably thermostable.

The term "non-reporter kinase" refers to kinase enzyme that is not a reporter kinase as defined above. Non-reporter kinases may also be referred to as endogenous kinases, contaminating kinases, or background kinases. Non-reporter kinases are typically present in a sample taken from a healthy individual. Non-reporter kinase activity can also be defined as activity that is not associated with the reporter kinase. Many non-reporter kinases are derived from mesophilic organisms, i.e. organisms that grow best at moderate temperatures (e.g. 25-40 C). Examples of non-reporter kinases include mammalian, plant and/or fungal kinases—in particular, any of the range of 7 human adenylate kinase isoforms found in varying amounts in clinical samples, equivalent proteins in animal species or food derived from them, or kinases (e.g. adenylate kinases) from common commensal organisms in humans or animals.

The term "thermostable kinase" refers to a kinase that retains activity after exposure to heat, i.e. that is relatively unaffected by high temperatures. Preferred thermostable kinases retain at least 70% activity (or 80% activity, 90% activity, 95% activity, or 100% activity) after exposure to a temperature of between 50-120 C. Particularly preferred thermostable kinases retain at least 70% activity (or 80% activity, 90% activity, 95% activity, or 100% activity) after exposure to 50 C for 30 minutes, or after exposure to 60 C for 30 minutes, or after exposure to 70 C for 30 minutes, or after exposure to 80 C for 20 minutes, or after exposure to 90 C for 3 minutes, or after exposure to 120 C for 3 minutes. Thermostable kinases may also be more resistant than non-thermostable kinases to a range of other biochemical and physical processes that routinely damage or destroy proteins or render them inactive, such as exposure to certain chemicals e.g. chaotropes, free-radical damage, detergents, extremes of pH, exposure to proteases, protein cross-linking, encapsulation within non-permeable or semi-permeable membranes or polymers, or irreversible immobilisation onto surfaces. In a particular embodiment, thermostable kinases may retain at least 70% activity (or 80% activity, 90% activity, 95% activity, or 100% activity) after exposure to one or more of the biochemical and physical processes described above. In all cases, this "retained activity" can be readily confirmed using conventional tests. In brief, the kinase is incubated with ADP under the given treatment conditions for a given amount of time, and then analysed for residual activity by detecting the generation of ATP using luciferin/luciferase and a luminometer. From this, the % of kinase activity retained after the treatment can be determined.

The terms "kinase" and "kinase activity" are used interchangeably throughout this specification.

The term "sample" encompasses any item, instrument, surface, fluid or material. Examples include, but are not limited to clinical samples (such as whole blood, serum, oral samples such as saliva, pus, vaginal samples, stool samples, vomitus), environmental samples (such a water, soil, air samples), surgical and medical instruments, microtitre plates, dipsticks, lateral flow devices, hospital gowns, bedclothes, bulk liquids, culled animal material, pharmaceuticals, workbenches, walls and floors, biological matrices, and biological indicators.

The terms "substantially free from non-reporter kinase", "free from non-reporter kinase", "substantially free from kinase other than reporter kinase", and "free from kinase other than reporter kinase" are considered synonymous, and are used interchangably throughout the specification to mean that the level of non-reporter kinase is sufficiently low or absent and does not interfere to any significant degree with the sensitivity or accuracy of the assay. In terms of assay read-out, the impact of the non-reporter kinase is usually defined in terms of the signal-to-noise ratio. As such, the term "substantially free" can also be defined as meaning that the non-reporter kinase does not account for more than 10% (preferably not more than 5% or 2%) of the total kinase signal at the limit of detection of the assay.

The terms "substantially free from ATP" and "free from ATP" are considered synonymous and are used interchangably throughout the specification to mean that the level of endogenous ATP is sufficiently low or absent and does not interfere to any significant degree with the sensitivity or accuracy of the assay. Endogenous ATP may have an impact on the assay in terms of signal: noise—thus, the "substantially free" term means that any endogenous ATP accounts for not more than 10% (preferably not more than 5% or 2%) of the total signal at the limit of detection of the assay.

The term "simultaneously" means at the same time. In the context of the first aspect of the invention where, in one embodiment, the reporter kinase is contacted with ADP and bioluminescent reagent simultaneously, this means that there is no (or substantially no) separate incubation period between contacting the kinase with ADP and contacting the kinase with the bioluminescent reagent.

The term "bioluminescent reagent" refers to any substance or mixture of substances able to react with ATP to generate light. A preferred reagent is a mixture of luciferin and luciferase.

The term "RLU" means Relative Light Unit. Relative Light Units are a relative, not absolute, measurement. The figures given in the specification relate to measurements taken using a Berthold Orion 96-well microplate luminometer with injector system using a "flash" method of light measurement for 2 seconds immediately after the addition of the luciferase/luciferin reagents (technical specification photomultiplier measuring light emitted at a wavelength of 300-650 nm). To address this issue, manufacturers have generated data for RLU "factors", which allow the data generated by a given luminometer to be normalised to a calibrated standard. Thus, comparisons can be made between different instruments. The RLU factor for the Berthold Orion 96-well microplate luminometer is 1. Accordingly, the RLU values given in the specification can be regarded as standardised/normalised RLU values.

In terms of absolute values, an RLU value can be related to the concentration of ATP required to give said value with the reagents as described in the method. As an approximate conversion, and given the linear relationship between RLU values and ATP concentration, the following values can be used:

| RLU | Approximate concentration of ATP/µM |
|---|---|
| 12,000,000 | 1000 |
| 1,200,000 | 100 |
| 120,000 | 10 |
| 12,000 | 1 |
| 1,200 | 0.1 |
| 120 | 0.01 |

All references cited in this application are hereby incorporated by reference in their entirety.

SEQ ID NOs

SEQ ID 1 Protein sequence of Adenylate kinase from *Sulfolobus solfataricus*
SEQ ID 2 Protein sequence of Adenylate kinase from *Sulfolobus acidocaldarius*
SEQ ID 3 Protein sequence of Adenylate kinase from *Sulfolobus tokodaii*
SEQ ID 4 Protein sequence of Adenylate kinase from *Pyrococcus furiosus*
SEQ ID 5 Protein sequence of Adenylate kinase from *Pyrococcus horikoshii*
SEQ ID 6 Protein sequence of Adenylate kinase from *Pyrococcus abyssi*
SEQ ID 7 Protein sequence of Adenylate kinase from *Methanococcus thermolithotrophicus*
SEQ ID 8 Protein sequence of Adenylate kinase from *Methanococcus voltae*
SEQ ID 9 Protein sequence of Adenylate kinase from *Methanococcus jannaschii*
SEQ ID 10 Protein sequence of Adenylate kinase from *Methanopyrus kandleni*
SEQ ID 11 Protein sequence of Adenylate kinase from *Methanotorris igneus*
SEQ ID 12 Protein sequence of Adenylate kinase from *Pyrobaculum aerophilum*
SEQ ID 13 Protein sequence of Adenylate kinase from *Thermotoga maritima*
SEQ ID 14 Protein sequence of Adenylate kinase from *Aeropyrum pernix*
SEQ ID 15 Protein sequence of Adenylate kinase from *Archaeoglobus fulgidus*
SEQ ID 16 Protein sequence of Adenylate kinase from *Pyrococcus abyssi* (monomeric adenylate kinase (AdkE))
SEQ ID 17 Protein sequence of Adenylate kinase from *Pyrococcus furiosus* genetically engineered to provide improved stability
SEQ ID 18 Protein sequence of Adenylate kinase from *Pyrococcus horikoshii* genetically engineered to provide improved stability
SEQ ID 19 Protein sequence of Adenylate kinase from *Sulfolobus acidocaldarius* genetically engineered to provide improved stability
SEQ ID 20 Protein sequence of Acetate kinase from *Thermatoga maritima*
SEQ ID 21 Protein sequence of Pyruvate kinase from *Pyrococcus horikoshii*
SEQ ID 22 Protein sequence of Pyruvate kinase from *Sulfolobus solfataricus*
SEQ ID 23 Protein sequence of Pyruvate kinase from *Thermotoga maritima*
SEQ ID 24 Protein sequence of Pyruvate kinase from *Pyrococcus furiosus*
SEQ ID 25 Protein sequence of Acetate kinase from *Methanosarcina thermophila*
SEQ ID 26 DNA sequence encoding the Adenylate kinase from *Sulfolobus acidocaldarius*
SEQ ID 27 DNA sequence encoding the Adenylate kinase from *Sulfolobus acidocaldarius*, wherein codon usage has been optimised for expression of the gene in E-coli.
SEQ ID 28 DNA sequence encoding the Adenylate kinase from *Thermotoga maritima*
SEQ ID 29 DNA sequence encoding the Adenylate kinase from, *Thermotoga maritima*, wherein codon usage has been optimised for expression of the gene in E-coli.
SEQ ID 30 DNA sequence encoding the Adenylate kinase from *Archaeoglobus fulgidus*, wherein codon usage has been optimised for expression of the gene in E-coli.
SEQ ID 31 Protein sequence of Adenylate kinase from *Sulfolobus acidocaldarius*, wherein codon usage has been optimised for expression of the gene in E-coli (SEQ ID 27).
SEQ ID 32 Protein sequence of Adenylate kinase from *Thermotoga maritima*, wherein codon usage has been optimised for expression of the gene in E-coli (SEQ ID 29).
SEQ ID 33 Protein sequence of transglutaminase substrate
SEQ ID 34 Protein sequence of Adenylate Kinase from *Sulfolobus acidcaldarius* fused at the N-terminus with a transglutaminase (Factor XIII) substrate sequence
SEQ ID 35 Protein sequence of Adenylate Kinase from *Sulfolobus acidcaldarius* fused at the C-terminus with a transglutaminase (Factor XIII) substrate sequence
SEQ ID 36 Protein sequence of Adenylate Kinase from *Sulfolobus acidcaldarius* fused at the N-terminus and C-terminus with a transglutaminase (Factor XIII) substrate sequence
SEQ ID 37 DNA sequence of transglutaminase (Factor XIII) substrate sequence fused to the 5' end of Adenylate Kinase from *Thermotoga maritima*.
SEQ ID 38 Protein sequence of Adenylate Kinase from *Thermotoga maritima* fused at the N-terminal with a transglutaminase (Factor XIII) substrate sequence.
SEQ ID 39 DNA sequence of transglutaminase (Factor XIII) substrate sequence fused to the 3' end of Adenylate Kinase from *Thermotoga maritima*.
SEQ ID 40 Protein sequence of Adenylate Kinase from *Thermotoga maritime* fused at the C-terminal with a transglutaminase (Factor XIII) substrate sequence.
SEQ ID 41 DNA sequence of transglutaminase (Factor XIII) substrate sequence fused to both the 5' and 3' ends of Adenylate Kinase from *Thermotoga maritima*.
SEQ ID 42 Protein sequence of Adenylate Kinase from *Thermotoga maritime* fused at the N- and C-terminal with a transglutaminase (Factor XIII) substrate sequence.
SEQ ID 43 DNA sequence of complete Sup35 gene construct from *Saccharomyces cerevisiae*
SEQ ID 44 Protein sequence of complete Sup35 from *Saccharomyces cerevisiae*
SEQ ID 45 DNA sequence of sup35N (N-terminal domain) codon-biased for optimal expression in *E. coli*
SEQ ID 46 Protein sequence of sup35N (N-terminal domain)

SEQ ID 47 DNA sequence of E-coli codon biased Adenylate Kinase from *Sulfolobus acidcaldarius* fused at the N-terminus with Sup35 N-terminal domain from *Saccharomyces cerevisiae*
SEQ ID 48 Protein sequence of Adenylate Kinase from *Sulfolobus acidcaldarius* fused at the N-terminus with Sup35 N-terminal domain from *Saccharomyces cerevisiae*
SEQ ID 49 DNA sequence of *E. coli* codon biased Adenylate Kinase from *Sulfolobus acidcaldarius* fused at the C-terminus with Sup35 N-terminal domain from *Saccharomyces cerevisiae*
SEQ ID 50 Protein sequence of Adenylate Kinase from *Sulfolobus acidcaldarius* fused at the C-terminus with Sup35 N-terminal domain from *Saccharomyces cerevisiae*
SEQ ID 51 DNA sequence of Sup35N fused at the 5' end of Adenylate Kinase from *Thermotoga maritima*.
SEQ ID 52 Protein sequence of Adenylate Kinase from *Thermotoga maritima* fused at the N-terminal with Sup35N.
SEQ ID 53 DNA sequence of Sup35N fused at the 3' end of Adenylate Kinase from *Thermotoga maritima*.
SEQ ID 54 Protein sequence of Adenylate Kinase from *Thermotoga maritima* fused at the C-terminal with Sup35N
SEQ ID 55 DNA sequence encoding a short Sup35 peptide capable of aggregating to form amyloid fibrils; for use as a fusion peptide with tAK genes.
SEQ ID 56 Sup35 derived amyloid peptide SEQ ID 57 DNA sequence encoding a Norovirus capsid protein (58 kDa)

SEQ ID 58 Protein sequence of Norovirus capsid protein (58 kDa)

SEQ ID 59 DNA sequence for a synthetic gene encoding a Norovirus capsid protein (58 kDa) optimised for expression in *E. coli*

SEQ ID 60 DNA sequence for a synthetic gene encoding a Norovirus capsid protein (58 kDa) optimised for expression in *E. coli* fused at the 5' end of a gene encoding the tAK from *Thermotoga maritima.*

SEQ ID 61 Protein sequence of a Norovirus capsid protein (58 kDa) fused at the N-terminus of the Adenylate Kinase from *Thermotoga maritima.*

SEQ ID 62 Protein sequence of a bacteriophage MS2 coat protein

SEQ ID 63 Protein sequence of a bacteriophage PP7 coat protein monomer

SEQ ID 64 Protein sequence of a bacteriophage PP7 coat protein dimer

SEQ ID 65 Protein sequence of *E. coli* CsgA

SEQ ID 66 Protein sequence of *Salmonella* AgfA

SEQ ID 67 Protein sequence of adenylate kinase from *Thermotoga maritima* fused to the N terminus of *E. coli* CsgA SEQ ID 68 Protein sequence of the hydrophobin 3 protein from *Fusarium* species SEQ ID 69 Protein sequence of the hydrophobin 5 protein from *Fusarium* species SEQ ID 70 Protein sequence of cement-like protein from *Balanus albicostatus* (19K)

SEQ ID 71 Protein sequence of cement-like protein from *Megabalanus rosa* (20 k)

SEQ ID 72 Protein sequence of fusion of the barnacle protein from *Balanus albicostatus* with the tAK from *Thermotoga maritima*; N-terminal fusion SEQ ID 73 Protein sequence of fusion of the barnacle protein from *Balanus albicostatus* with the tAK from *Thermotoga maritima*; C-terminal fusion SEQ ID 74 Protein sequence of *Balanus albicostatus* calcite-specific adsorbent SEQ ID 75 Protein sequence of a peptide derived from a barnacle cement protein SEQ ID 76 Protein sequence of a peptide derived from a barnacle cement protein SEQ ID 77 Protein sequence of a peptide derived from a barnacle cement protein SEQ ID 78 Protein sequence of adenylate kinase from *E. coli*

SEQ ID 79 Protein sequence of pyruvate kinase from *E. coli*

SEQ ID 80 Protein sequence of acetate kinase from *E. coli*

SEQ ID 81 Protein sequence of adenylate kinase from *Methanococcus voltae* (MVO)

SEQ ID 82 Protein sequence of adenylate kinase from *Methanococcus thermolithotrophicus* (MTH).

SEQ ID 83 Protein sequence of adenylate kinase from *Bacillus* globisporus

SEQ ID 84 Protein sequence of adenylate kinase from *Bacillus subtilis*

SEQUENCE LISTING

SEQ ID NO: 1

```
Met Lys Ile Gly Ile Val Thr Gly Ile Pro Gly Val Gly Lys Thr Thr Val Leu Ser Phe Ala Asp Lys Ile
Leu Thr Glu Lys Gly Ile Ser Lys Ile Val Asn Tyr Gly Asp Tyr Met Leu Asn Thr Ala Leu Lys Glu Gly
Tyr Val Lys Ser Arg Asp Glu Ile Arg Lys Leu Gln Ile Glu Lys Gln Arg Glu Leu Gln Ala Leu Ala Ala
Arg Arg Ile Val Glu Asp Leu Ser Leu Leu Gly Asp Glu Gly Ile Gly Leu Ile Asp Thr His Ala Ile Arg
Thr Pro Ala Gly Tyr Leu Pro Gly Leu Pro Arg His Val Ile Glu Val Leu Ser Pro Lys Val Ile Phe Leu
Leu Glu Ala Asp Pro Lys Ile Ile Leu Glu Arg Gln Lys Arg Asp Ser Ser Arg Ala Arg Thr Asp Tyr Ser
Asp Thr Ala Val Ile Asn Glu Val Ile Gln Phe Ala Arg Tyr Ser Ala Met Ala Ser Ala Val Leu Val Gly
Ala Ser Val Lys Val Val Val Asn Gln Glu Gly Asp Pro Ser Ile Ala Ala Ser Glu Ile Ile Asn Ser Leu
Met
```

SEQ ID NO: 2

```
Met Lys Ile Gly Ile Val Thr Gly Ile Pro Gly Val Gly Lys Ser Thr Val Leu Ala Lys Val Lys Glu Ile
Leu Asp Asn Gln Gly Ile Asn Asn Lys Ile Ile Asn Tyr Gly Asp Phe Met Leu Ala Thr Ala Leu Lys Leu
Gly Tyr Ala Lys Asp Arg Asp Glu Met Arg Lys Leu Ser Val Glu Lys Gln Lys Lys Leu Gln Ile Asp Ala
Ala Lys Gly Ile Ala Glu Glu Ala Arg Ala Gly Gly Glu Gly Tyr Leu Phe Ile Asp Thr His Ala Val Ile
Arg Thr Pro Ser Gly Tyr Leu Pro Gly Leu Pro Ser Tyr Val Ile Thr Glu Ile Asn Pro Ser Val Ile Phe
Leu Leu Glu Ala Asp Pro Lys Ile Ile Leu Ser Arg Gln Lys Arg Asp Thr Thr Arg Asn Arg Asn Asp Tyr
Ser Asp Glu Ser Val Ile Leu Glu Thr Ile Asn Phe Ala Arg Tyr Ala Ala Thr Ala Ser Ala Val Leu Ala
Gly Ser Thr Val Lys Val Ile Val Asn Val Gln Gly Asp Pro Ser Ile Ala Ala Asn Glu Ile Ile Arg Ser
Met Lys
```

SEQUENCE LISTING

SEQ ID NO: 3
```
Met Ser Lys Met Lys Ile Gly Ile Val Thr Gly Ile Pro Gly Val Gly Lys Thr Thr Val Leu Ser Lys Val
Lys Glu Ile Leu Gln Glu Lys Lys Ile Asn Asn Lys Ile Val Asn Tyr Gly Asp Tyr Met Leu Met Thr Ala
Met Lys Leu Gly Tyr Val Asn Asn Arg Asp Gln Met Arg Lys Leu Pro Val Glu Lys Gln Lys Gln Leu Gln
Ile Glu Ala Ala Arg Gly Ile Ala Asn Glu Ala Lys Gln Gly Gly Asp Gly Leu Leu Phe Ile Asp Thr His
Ala Val Ile Arg Thr Pro Ser Gly Tyr Leu Pro Gly Leu Pro Lys Tyr Val Ile Glu Glu Ile Asn Pro Arg
Val Ile Phe Leu Leu Glu Ala Asp Pro Lys Val Ile Leu Asp Arg Gln Lys Arg Asp Thr Ser Arg Ser Arg
Ser Asp Tyr Ser Asp Glu Arg Ile Ile Ser Glu Thr Ile Asn Phe Ala Arg Tyr Ala Ala Met Ala Ser Ala
Val Leu Val Gly Ala Thr Val Lys Ile Val Ile Asn Val Gln Gly Asp Pro Ala Val Ala Ala Asn Glu Ile
Ile Asn Ser Met Leu
```

SEQ ID NO: 4
```
Met Pro Phe Val Val Ile Ile Thr Gly Ile Pro Gly Val Gly Lys Ser Thr Ile Thr Arg Leu Ala Leu Gln
Arg Thr Lys Ala Lys Phe Arg Leu Ile Asn Phe Gly Asp Leu Met Phe Glu Glu Ala Val Lys Ala Gly Leu
Val Lys His Arg Asp Glu Met Arg Lys Leu Pro Leu Lys Ile Gln Arg Glu Leu Gln Met Lys Ala Ala Lys
Lys Ile Thr Glu Met Ala Lys Glu His Pro Ile Leu Val Asp Thr His Ala Thr Ile Lys Thr Pro His Gly
Tyr Met Leu Gly Leu Pro Tyr Gln Val Val Lys Thr Leu Asn Pro Asn Phe Ile Val Ile Ile Glu Ala Thr
Pro Ser Gln Ile Leu Gly Arg Arg Leu Arg Asp Leu Lys Arg Asp Arg Asp Val Glu Thr Glu Gln Gln Ile
Gln Arg His Gln Asp Leu Asn Arg Ala Ala Ala Ile Ala Tyr Ala Met His Ser Asn Ala Leu Ile Lys Ile
Ile Gln Asn His Gln Asp Lys Gly Leu Glu Gln Ala Val Asn Glu Leu Val Lys Ile Leu Asp Leu Ala Val
Asn Glu Tyr Ala
```

SEQ ID NO: 5
```
Met Pro Phe Val Val Ile Ile Thr Gly Ile Pro Gly Val Gly Lys Ser Thr Ile Thr Lys Leu Ala Leu Gln
Arg Thr Arg Ala Lys Phe Lys Leu Ile Asn Phe Gly Asp Leu Met Phe Glu Glu Ala Leu Lys Leu Lys Leu
Val Lys His Arg Asp Glu Met Arg Lys Leu Pro Leu Gln Val Gln Arg Gln Leu Gln Met Asn Ala Ala Lys
Lys Ile Ala Gln Met Ala Lys Asn Tyr Pro Ile Leu Leu Asp Thr His Ala Thr Ile Lys Thr Pro His Gly
Tyr Leu Leu Gly Leu Pro Tyr Glu Val Ile Lys Leu Leu Asn Pro Asn Phe Ile Val Ile Ile Glu Ala Thr
Pro Ser Glu Ile Leu Gly Arg Arg Leu Arg Asp Leu Lys Arg Asp Arg Asp Val Glu Thr Glu Gln Gln Ile
Gln Arg His Gln Asp Leu Asn Arg Ala Ala Ala Ile Thr Tyr Ala Met His Ser Asn Ala Leu Ile Lys Ile
Ile Glu Asn His Glu Asp Lys Gly Leu Glu Glu Ala Val Asn Glu Leu Val Lys Ile Leu Asp Leu Ala Val
Lys Glu Tyr Ala
```

SEQ ID NO: 6
```
Met Ser Phe Val Val Ile Ile Thr Gly Ile Pro Gly Val Gly Lys Ser Thr Ile Thr Arg Leu Ala Leu Gln
Arg Thr Lys Ala Lys Phe Lys Leu Ile Asn Phe Gly Asp Leu Met Phe Glu Glu Ala Val Lys Ala Gly Leu
Val Asn His Arg Asp Glu Met Arg Lys Leu Pro Leu Glu Ile Gln Arg Asp Leu Gln Met Lys Val Ala Lys
Lys Ile Ser Glu Met Ala Lys Gln Gln Pro Ile Leu Leu Asp Thr His Ala Thr Ile Lys Thr Pro His Gly
Tyr Leu Leu Gly Leu Pro Tyr Glu Val Ile Lys Thr Leu Asn Pro Asn Phe Ile Val Ile Ile Glu Ala Thr
Pro Ser Glu Ile Leu Gly Arg Arg Leu Arg Asp Leu Lys Arg Asp Arg Asp Val Glu Thr Glu Gln Gln Ile
Gln Arg His Gln Asp Leu Asn Arg Ala Ala Ala Ile Ala Tyr Ala Met His Ser Asn Ala Leu Ile Lys Ile
Ile Glu Asn His Glu Asp Lys Gly Leu Glu Glu Ala Val Asn Glu Leu Val Glu Ile Leu Asp Leu Ala Val
Lys Glu Tyr Ala
```

SEQ ID NO: 7
```
Met Lys Asn Lys Leu Val Val Val Thr Gly Val Pro Gly Val Gly Gly Thr Thr Ile Thr Gln Lys Ala Met
Glu Lys Leu Ser Glu Glu Gly Ile Asn Tyr Lys Met Val Asn Phe Gly Thr Val Met Phe Glu Val Ala Gln
Glu Glu Asn Leu Val Glu Asp Arg Asp Gln Met Arg Lys Leu Asp Pro Asp Thr Gln Lys Arg Ile Gln Lys
Leu Ala Gly Arg Lys Ile Ala Glu Met Ala Lys Val Gln Ser Pro Val Val Val Asp Thr His Ile Ser Lys
Thr Pro Lys Gly Tyr Leu Pro Gly Leu Pro Val Trp Val Leu Asn Glu Leu Asn Pro Asp Ile Ile Ile Val
Val Glu Thr Ser Gly Asp Glu Ile Leu Ile Arg Arg Leu Asn Asp Thr Arg Asn Arg Asp Leu Glu Thr
Thr Ala Gly Ile Glu Glu His Gln Ile Met Asn Arg Ala Ala Ala Met Thr Tyr Gly Val Leu Thr Gly Ala
Thr Val Lys Ile Ile Gln Asn Lys Asn Asn Leu Leu Asp Tyr Ala Val Glu Glu Leu Ile Ser Val Leu Arg
```

SEQ ID NO: 8
```
Met Lys Asn Lys Val Val Val Val Thr Gly Val Pro Gly Val Gly Ser Thr Thr Ser Ser Gln Leu Ala Met
Asp Asn Leu Arg Lys Glu Gly Val Asn Tyr Lys Met Val Ser Phe Gly Ser Val Met Phe Glu Val Ala Lys
Glu Glu Asn Leu Val Ser Asp Arg Asp Gln Met Arg Lys Met Asp Pro Glu Thr Gln Lys Arg Ile Gln Lys
Met Ala Gly Arg Lys Ile Ala Glu Met Ala Lys Glu Ser Pro Val Ala Val Asp Thr His Ser Thr Val Ser
Thr Pro Lys Gly Tyr Leu Pro Gly Leu Pro Ser Trp Val Leu Asn Glu Leu Asn Pro Asp Leu Ile Ile Val
Val Glu Thr Thr Gly Asp Glu Ile Leu Met Arg Arg Met Ser Asp Glu Thr Arg Val Arg Asp Leu Asp Thr
Ala Ser Thr Ile Glu Gln His Gln Phe Met Asn Arg Cys Ala Ala Met Ser Tyr Gly Val Leu Thr Gly Ala
Thr Val Lys Ile Val Gln Asn Arg Asn Gly Leu Leu Asp Gln Ala Val Glu Glu Leu Thr Asn Val Leu Arg
```

SEQ ID NO: 9
```
Met Met Met Met Lys Asn Lys Val Val Val Ile Val Gly Val Pro Gly Val Gly Ser Thr Thr Val Thr Asn
Lys Ala Ile Glu Glu Leu Lys Lys Gly Ile Glu Tyr Lys Ile Val Asn Phe Gly Thr Val Met Phe Glu
Ile Ala Lys Glu Glu Gly Leu Val Glu Has Arg Asp Gln Leu Arg Lys Leu Pro Glu Glu Glu Lys Arg
Ile Gln Lys Leu Ala Gly Lys Lys Ile Ala Glu Met Ala Lys Glu Phe Asn Ile Val Val Asp Thr His Ser
Thr Ile Lys Thr Pro Lys Gly Tyr Leu Pro Gly Leu Pro Ala Trp Val Leu Glu Glu Leu Asn Pro Asp Ile
Ile Val Leu Val Glu Ala Glu Asn Asp Glu Ile Leu Met Arg Arg Leu Lys Asp Glu Thr Arg Gln Arg Asp
Phe Glu Ser Thr Glu Asp Ile Gly Glu His Ile Phe Met Asn Arg Cys Ala Ala Met Thr Tyr Ala Val Leu
Thr Gly Ala Thr Val Lys Ile Ile Lys Asn Arg Asp Phe Leu Leu Asp Lys Ala Val Gln Glu Leu Ile Glu
Val Leu Lys
```

SEQUENCE LISTING

SEQ ID NO: 10
Met Gly Tyr Val Ile Val Ala Thr Gly Val Pro Gly Val Gly Ala Thr Thr Val Thr Thr Glu Ala Val Lys
Glu Leu Glu Gly Tyr Glu His Val Asn Tyr Gly Asp Val Met Leu Glu Ile Ala Lys Glu Gly Leu Val
Glu His Arg Asp Glu Ile Arg Lys Leu Pro Ala Glu Lys Gln Arg Glu Ile Gln Arg Leu Ala Ala Arg
Ile Ala Lys Met Ala Glu Glu Lys Glu Gly Ile Ile Val Asp Thr His Cys Thr Ile Lys Thr Pro Ala Gly
Tyr Leu Pro Gly Leu Pro Ile Trp Val Leu Glu Glu Leu Gln Pro Asp Val Ile Val Leu Ile Glu Ala Asp
Pro Asp Glu Ile Met Met Arg Arg Val Lys Asp Ser Glu Glu Ala Gln Arg Asp Tyr Asp Arg Ala His Glu
Ile Glu Glu His Gln Lys Met Asn Arg Met Ala Ala Met Ala Tyr Ala Ala Leu Thr Gly Ala Thr Val Lys
Ile Ile Glu Asn His Asp Arg Leu Glu Glu Ala Val Arg Glu Phe Val Glu Thr Val Arg Ser Leu

SEQ ID NO: 11
Met Lys Asn Lys Val Val Val Val Thr Gly Val Pro Gly Val Gly Gly Thr Thr Leu Thr Gln Lys Thr Ile
Glu Lys Leu Lys Glu Glu Gly Ile Glu Tyr Lys Met Val Asn Phe Gly Thr Val Met Phe Glu Val Ala Lys
Glu Glu Gly Leu Val Glu Asp Arg Asp Gln Met Arg Lys Leu Asp Pro Asp Thr Gln Lys Arg Ile Gln Lys
Leu Ala Gly Arg Lys Ile Ala Glu Met Ala Lys Glu Ser Asn Val Ile Val Asp Thr His Ser Thr Val Lys
Thr Pro Lys Gly Tyr Leu Ala Gly Leu Pro Ile Trp Val Leu Glu Glu Leu Asn Pro Asp Ile Ile Val Ile
Val Glu Thr Ser Ser Asp Glu Ile Leu Met Arg Arg Leu Gly Asp Ala Thr Arg Asn Arg Asp Ile Glu Leu
Thr Ser Asp Ile Asp Glu His Gln Phe Met Asn Arg Cys Ala Ala Met Ala Tyr Gly Val Leu Thr Gly Ala
Thr Val Lys Ile Ile Lys Asn Arg Asp Gly Leu Leu Asp Lys Ala Val Glu Glu Leu Ile Ser Val Leu Lys

SEQ ID NO: 12
Met Lys Ile Val Ile Val Ala Leu Pro Gly Ser Gly Lys Thr Thr Ile Leu Asn Phe Val Lys Gln Lys Leu
Pro Asp Val Lys Ile Val Asn Tyr Gly Asp Val Met Leu Glu Ile Ala Lys Lys Arg Phe Gly Ile Gln His
Arg Asp Glu Met Arg Lys Ile Glu Pro Val Asp Gln Tyr Arg Lys Leu Gln Gln Gly Glu Ala Ala Glu Tyr Ile
Ala Ser Leu Thr Gly Asp Val Ile Ile Asp Thr His Ala Ser Ile Lys Ile Gly Gly Gly Tyr Tyr Pro Gly
Leu Pro Asp Arg Ile Ile Ser Lys Leu Lys Pro Asp Val Ile Leu Leu Leu Glu Tyr Asp Pro Lys Val Ile
Leu Glu Arg Arg Lys Lys Asp Pro Asp Arg Phe Arg Asp Leu Glu Ser Glu Glu Ile Glu Met His Gln
Gln Ala Asn Arg Tyr Tyr Ala Phe Ala Ala Ala Asn Ala Gly Glu Ser Thr Val His Val Leu Asn Phe Arg
Gly Lys Pro Glu Ser Arg Pro Phe Glu His Ala Glu Val Ala Ala Glu Tyr Ile Val Asn Leu Ile Leu Arg
Thr Arg Gln Lys Ser

SEQ ID NO: 13
Met Met Ala Tyr Leu Val Phe Leu Gly Pro Pro Gly Ala Gly Lys Gly Thr Tyr Ala Lys Arg Ile Gln Glu
Lys Thr Gly Ile Pro His Ile Ser Thr Gly Asp Ile Phe Arg Asp Ile Val Lys Lys Glu Asn Asp Glu Leu
Gly Lys Lys Ile Lys Glu Ile Met Glu Lys Gly Glu Leu Val Pro Asp Glu Leu Val Asn Glu Val Val Lys
Arg Arg Leu Ser Glu Lys Lys Asp Cys Glu Lys Gly Phe Ile Leu Asp Gly Tyr Pro Arg Thr Val Ala Gln Ala
Glu Phe Leu Asp Ser Phe Leu Gly Ser Gln Asn Lys Gln Leu Thr Ala Ala Val Leu Glu Val Pro Glu
Asp Val Val Gln Arg Leu Thr Ser Arg Arg Ile Cys Pro Lys Cys Gly Arg Ile Tyr Asn Met Ile Ser
Leu Pro Pro Lys Glu Asp Glu Leu Cys Asp Asp Cys Lys Val Lys Leu Val Gln Arg Asp Asp Asp Lys Glu
Glu Thr Val Arg His Arg Tyr Lys Val Tyr Leu Glu Lys Thr Gln Pro Val Ile Asp Tyr Tyr Gly Lys Lys
Gly Ile Leu Lys Arg Val Asp Gly Thr Ile Gly Ile Asp Asn Val Val Ala Glu Val Leu Lys Ile Ile Gly
Trp Ser Asp Lys

SEQ ID NO: 14
Met Lys Val Arg His Pro Phe Lys Val Val Val Val Thr Gly Val Pro Gly Val Gly Lys Thr Thr Val Ile
Lys Glu Leu Gln Gly Leu Ala Glu Lys Glu Gly Val Lys Leu His Ile Val Asn Phe Gly Ser Phe Met Leu
Asp Thr Ala Val Lys Leu Gly Leu Val Glu Asp Arg Asp Lys Ile Arg Thr Leu Pro Leu Arg Arg Gln Leu
Glu Leu Gln Arg Glu Ala Ala Lys Arg Ile Val Ala Glu Ala Ser Lys Ala Leu Gly Gly Asp Gly Val Leu
Ile Ile Asp Thr His Ala Leu Val Lys Thr Val Ala Gly Tyr Tyr Trp Pro Gly Leu Pro Lys His Val Leu Asp
Glu Leu Lys Pro Asp Met Ile Ala Val Val Glu Ala Ser Pro Glu Glu Ala Ala Arg Gln Ala Arg Asp
Thr Thr Arg Tyr Arg Val Asp Ile Gly Gly Val Glu Gly Val Lys Arg Leu Met Glu Asn Ala Arg Ala
Ser Ile Ala Ser Ala Ile Gln Tyr Ala Ser Thr Val Ala Ile Val Glu Asn Arg Glu Gly Ala Ala Lys
Ala Ala Glu Glu Leu Leu Arg Leu Ile Lys Asn Leu

SEQ ID NO: 15
Met Asn Leu Ile Phe Leu Gly Pro Pro Gly Ala Gly Lys Gly Thr Gln Ala Lys Arg Val Ser Glu Lys Tyr
Gly Ile Pro Gln Ile Ser Thr Gly Asp Met Leu Arg Glu Ala Ile Ala Gly Thr Pro Val Gly Leu Gly Leu Lys Lys
Ala Lys Glu Tyr Met Asp Lys Gly Glu Leu Val Pro Asp Glu Val Val Ile Gly Ile Val Lys Glu Arg Leu
Gln Gln Pro Asp Cys Glu Lys Gly Phe Ile Leu Asp Gly Phe Pro Arg Thr Leu Ala Gln Ala Glu Ala Leu
Asp Glu Met Leu Lys Glu Leu Asn Lys Lys Ile Asp Ala Val Ile Asn Val Val Val Pro Glu Glu Glu Val
Val Lys Arg Ile Thr Tyr Arg Arg Thr Cys Arg Asn Cys Gly Ala Val Tyr His Leu Ile Tyr Ala Pro Pro
Lys Glu Asp Asn Leu Cys Asp Lys Cys Gly Gly Glu Leu Tyr Gln Arg Asp Asp Asp Lys Glu Gln Thr Val Arg
Glu Arg Tyr Arg Val Tyr Lys Gln Asn Thr Glu Pro Leu Ile Asp Tyr Tyr Arg Lys Lys Gly Ile Leu Tyr
Asp Val Asp Gly Thr Lys Asp Ile Glu Gly Val Trp Lys Glu Ile Ala Leu Glu Lys Ile Lys Ser

SEQ ID NO: 16
Met Asn Ile Leu Ile Phe Gly Pro Pro Gly Ser Gly Lys Ser Thr Gln Ala Arg Arg Ile Thr Gln Arg Tyr
Gly Leu Thr Tyr Ile Ala Ser Gly Asp Ile Ile Arg Ala Gln Ile Lys Ala Arg Thr Pro Leu Gly Ile Gln
Met Gln Arg Tyr Leu Ser Arg Gly Asp Leu Ile Pro Asp Thr Val Asn Thr Leu Ile Ile Ser Lys Leu
Arg Arg Val Arg Glu Asn Phe Ile Met Asp Gly Tyr Pro Arg Thr Pro Glu Gln Val Ile Thr Leu Glu Asn
Tyr Leu Tyr Asp His Gly Ile Lys Leu Val Ala Ile Asp Ile Tyr Ile Thr Lys Glu Gly Ser Val Arg
Arg Ile Ser Gly Arg Arg Ile Cys Ser Lys Cys Gly Ala Val Tyr His Val Gln Phe Asn Pro Pro Lys Val
Pro Gly Lys Cys Asp Ile Cys Gly Gly Glu Leu Ile Gln Arg Pro Asp Asp Arg Pro Glu Ile Val Glu Lys
Arg Tyr Asp Ile Tyr Ser Lys Asn Met Glu Pro Ile Lys Phe Tyr Gln Lys Gln Gly Ile Tyr Val Arg
Ile Asp Gly His Gly Ser Ile Asp Glu Val Trp Glu Arg Ile Arg Pro Leu Leu Asp Tyr Ile Tyr Asn Gln
Glu Asn Arg Arg

SEQUENCE LISTING

```
                                                                        SEQ ID NO: 17
Met Pro Phe Val Val Ile Ile Thr Gly Ile Pro Gly Val Gly Lys Ser Thr Ile Thr Arg Leu Ala Leu Gln
Arg Thr Lys Ala Lys Phe Arg Leu Ile Asn Phe Gly Asp Leu Met Phe Glu Glu Ala Val Lys Ala Gly Leu
Val Lys His Arg Asp Glu Met Arg Lys Leu Pro Leu Xaa Ile Gln Arg Glu Leu Gln Met Lys Ala Ala Lys
Lys Ile Xaa Glu Met Ala Lys Glu His Pro Ile Leu Val Asp Thr His Ala Thr Ile Lys Thr Pro His Gly
Tyr Xaa Leu Gly Leu Pro Tyr Glu Val Val Lys Thr Leu Asn Pro Asn Phe Ile Val Ile Glu Ala Thr
Pro Ser Glu Ile Leu Gly Arg Arg Leu Arg Asp Leu Lys Arg Asp Arg Asp Val Glu Thr Glu Glu Gln Ile
Gln Arg His Gln Asp Leu Asn Arg Ala Ala Ala Ile Xaa Tyr Ala Met His Ser Asn Ala Leu Ile Lys Ile
Ile Glu Asn His Glu Asp Lys Gly Leu Glu Glu Ala Val Asn Glu Leu Val Lys Ile Leu Asp Leu Ala Val
Asn Glu Tyr Ala

SEQ ID NO: 18
Met Pro Phe Val Val Ile Ile Thr Gly Ile Pro Gly Val Gly Lys Ser Thr Ile Thr Lys Leu Ala Leu Gln
Arg Thr Arg Ala Lys Phe Lys Leu Ile Asn Phe Gly Asp Leu Met Phe Glu Glu Ala Leu Lys Leu Xaa Leu
Val Lys His Arg Asp Glu Met Arg Lys Leu Pro Leu Glu Val Gln Arg Glu Leu Gln Met Asn Ala Ala Lys
Lys Ile Ala Glu Met Ala Lys Asn Tyr Pro Ile Leu Leu Asp Thr His Ala Thr Ile Lys Thr Pro His Gly
Tyr Leu Leu Gly Leu Pro Tyr Glu Val Ile Lys Leu Asn Pro Asn Phe Ile Val Ile Glu Ala Thr
Pro Ser Glu Ile Leu Gly Arg Arg Leu Arg Asp Leu Lys Arg Asp Arg Asp Val Glu Thr Glu Glu Gln Ile
Gln Arg His Gln Asp Leu Asn Arg Ala Ala Ala Ile Xaa Tyr Ala Met His Ser Asn Ala Leu Ile Lys Ile
Ile Glu Asn His Glu Asp Lys Gly Leu Glu Glu Ala Val Asn Glu Leu Val Lys Ile Leu Asp Leu Ala Val
Lys Glu Tyr Ala

SEQ ID NO: 19
Met Lys Ile Gly Ile Val Thr Gly Ile Pro Gly Val Gly Lys Ser Thr Val Leu Ala Lys Val Lys Glu Ile
Leu Asp Asn Gln Gly Ile Asn Asn Lys Ile Ile Asn Tyr Gly Asp Phe Met Leu Ala Thr Ala Leu Lys Leu
Gly Tyr Ala Lys Asp Arg Asp Glu Met Arg Lys Leu Ser Val Glu Lys Gln Lys Lys Leu Gln Ile Asp Ala
Ala Lys Gly Ile Ala Glu Ile Ala Arg Ala Gly Gly Val Tyr Leu Phe Ile Glu Asp His Ala Val Ile Glu
Arg Thr Pro Ser Gly Tyr Xaa Pro Gly Leu Pro Ser Tyr Val Ile Thr Glu Ile Asn Pro Ser Val Ile Phe
Leu Leu Glu Ala Asp Pro Lys Ile Ile Leu Ser Arg Gln Lys Arg Asp Thr Thr Arg Asn Arg Asn Asp Tyr
Ser Asp Glu Ser Val Ile Leu Glu Thr Ile Asn Phe Ala Arg Tyr Ala Ala Thr Ala Ser Ala Val Leu Ala
Gly Ser Thr Val Lys Val Ile Val Asn Val Glu Gly Asp Pro Ser Ile Ala Ala Asn Glu Ile Ile Arg Ser
Met Lys

SEQ ID NO: 20
Met Arg Val Leu Val Ile Asn Ser Gly Ser Ser Ser Ile Lys Tyr Gln Leu Ile Glu Met Glu Gly Glu Lys
Val Leu Cys Lys Gly Ile Ala Glu Arg Ile Gly Ile Glu Gly Ser Arg Leu Val His Arg Val Gly Asp Glu
Lys His Val Ile Glu Arg Gly Leu Pro Asp His Glu Glu Ala Leu Lys Leu Ile Leu Asn Thr Leu Val Asp
Glu Lys Leu Gly Val Ile Lys Asp Leu Lys Glu Ile Asp Ala Val Gly His Arg Val Val His Gly Gly Glu
Arg Phe Lys Glu Ser Val Leu Val Asp Glu Glu Val Leu Lys Ala Ile Glu Glu Val Ser Pro Leu Ala Pro
Leu His Asn Pro Ala Asn Leu Met Gly Ile Lys Ala Ala Met Lys Leu Leu Pro Gly Val Pro Asn Val Ala
Val Phe Asp Thr Ala Phe His Gln Thr Ile Pro Gln Lys Ala Tyr Leu Tyr Ala Ile Pro Tyr Glu Tyr Tyr
Glu Lys Tyr Lys Ile Arg Arg Tyr Gly Phe His Gly Thr Ser His Arg Tyr Val Ser Lys Arg Ala Ala Glu
Ile Leu Gly Lys Lys Leu Glu Glu Leu Lys Ile Ile Thr Cys His Ile Gly Asn Gly Ala Ser Val Ala Ala
Val Lys Tyr Gly Lys Cys Val Asp Thr Ser Met Gly Phe Thr Pro Leu Glu Gly Leu Val Met Gly Thr Arg
Ser Gly Asp Leu Asp Pro Ala Ile Pro Phe Phe Ile Met Glu Lys Glu Gly Ile Ser Pro Gln Glu Met Tyr
Asp Ile Leu Asn Lys Lys Ser Gly Val Tyr Gly Leu Ser Lys Gly Phe Ser Ser Asp Met Arg Asp Ile Glu
Glu Ala Ala Leu Lys Gly Asp Glu Trp Cys Lys Leu Val Leu Glu Ile Tyr Asp Tyr Arg Ile Ala Lys Tyr
Ile Gly Ala Tyr Ala Ala Ala Met Asn Gly Val Asp Ala Ile Val Phe Thr Ala Gly Val Gly Glu Asn Ser
Pro Ile Thr Arg Glu Asp Val Cys Ser Tyr Leu Glu Phe Leu Gly Val Lys Leu Asp Lys Gln Lys Asn Glu
Glu Thr Ile Arg Gly Lys Glu Gly Ile Ile Ser Thr Pro Asp Ser Arg Val Lys Val Leu Val Val Pro Thr
Asn Glu Glu Leu Met Ile Ala Arg Asp Thr Lys Glu Ile Val Glu Lys Ile Gly Arg

SEQ ID NO: 21
Met Arg Arg Met Lys Leu Pro Ser His Lys Thr Lys Ile Val Ala Thr Ile Gly Pro Ala Thr Asn Ser Lys
Lys Met Ile Lys Lys Leu Ile Glu Ala Gly Met Asn Val Ala Arg Ile Asn Phe Ser His Gly Thr Phe Glu
Glu His Ala Lys Ile Ile Glu Met Val Arg Glu Gln Ser Gln Lys Leu Asp Arg Arg Val Ala Ile Leu Ala
Asp Leu Pro Gly Leu Lys Ile Arg Val Gly Glu Ile Lys Gly Gly Tyr Val Glu Leu Glu Arg Gly Glu Lys
Val Thr Leu Thr Thr Lys Ser Gly Ile Glu Gly Asp Thr Thr Thr Val Pro Val Glu Tyr Lys Asp Phe Pro Lys
Leu Val Ser Lys Gly Asp Val Ile Tyr Leu Ser Asp Gly Tyr Ile Val Leu Arg Val Glu Asp Val Lys Glu
Asn Glu Val Glu Ala Val Val Ile Ser Gly Gly Lys Leu Phe Ser Arg Lys Gly Ile Asn Ile Pro Lys Ala
Tyr Leu Pro Val Glu Ala Ile Thr Pro Arg Asp Ile Glu Ile Met Lys Phe Ala Ile Glu His Gly Val Asp
Ala Ile Gly Leu Ser Phe Val Gly Asn Val Tyr Asp Val Leu Lys Ala Lys Ser Phe Leu Glu Arg Asn Gly
Ala Gly Asp Thr Pro Ile Ile Ala Lys Ile Glu Gly Pro Arg Ala Val Arg Asn Phe Asp Glu Ile Leu Asn
Ala Ala Asp Gly Ile Met Ile Ala Arg Gly Asp Leu Gly Val Glu Met Pro Ile Glu Gln Leu Pro Ile Leu
Gln Lys Arg Leu Ile Arg Lys Ala Asn Met Glu Gly Lys Pro Val Ile Thr Ala Thr Gln Met Leu Val Ser
Met Thr Met Glu Lys Val Pro Thr Arg Ala Glu Val Thr Asp Val Ala Asn Ala Ile Leu Asp Gly Thr Asp
Ala Val Met Leu Ser Glu Glu Thr Ala Val Gly Lys Phe Pro Ile Glu Ala Val Glu Met Met Ala Arg Ile
Ala Lys Val Thr Glu Tyr Arg Glu Ser Phe Gly Ile Thr Arg Met Glu Gly Phe Glu Gly Leu Gly Thr Lys
Arg Gly Ile Thr Lys Glu Ala Ile Thr Arg Ser Ile Ala Ser Ala Ile Cys Thr Ile Gly Ile Lys Phe Ile
Leu Thr Pro Thr Lys Thr Gly Arg Thr Ala Arg Leu Ile Ser Arg Phe Lys Pro Lys Gln Trp Ile Leu Ala
Phe Ser Thr Arg Glu Lys Val Cys Asn Asn Leu Met Phe Ser Tyr Gly Val Tyr Pro Phe Cys Met Glu Glu
Gly Phe Asn Glu Asn Asp Ile Val Arg Leu Ile Lys Gly Leu Gly Leu Val Gly Ser Asp Asp Ile Val Leu
Met Thr Glu Gly Lys Pro Ile Glu Lys Thr Val Gly Thr Asn Ser Ile Lys Ile Phe Gln Ile Ala
```

-continued

SEQUENCE LISTING

SEQ ID NO: 22
Met Arg Lys Thr Lys Ile Val Ala Thr Leu Gly Pro Ser Ser Glu Glu Lys Val Lys Glu Leu Ala Glu Tyr
Val Asp Val Phe Arg Ile Asn Phe Ala His Gly Asp Glu Thr Ser His Arg Lys Tyr Phe Asp Leu Ile Arg
Thr Tyr Ala Pro Glu Ser Ser Ile Ile Val Asp Leu Pro Gly Pro Lys Leu Arg Leu Gly Glu Leu Lys Glu
Pro Ile Glu Val Lys Lys Gly Asp Lys Ile Val Phe Ser Gln Lys Asp Gly Ile Pro Val Asp Asp Glu Leu
Phe Tyr Ser Ala Val Lys Glu Asn Ser Asp Ile Leu Ile Ala Asp Gly Thr Ile Arg Val Arg Val Lys Ser
Lys Ala Lys Asp Arg Val Gly Gly Thr Val Ile Gly Gly Ile Leu Leu Ser Arg Lys Gly Ile Asn Ile
Pro Asn Val Asn Leu Lys Ser Gly Ile Thr Asp Asn Asp Leu Lys Leu Leu Lys Arg Ala Leu Asp Leu Gly
Ala Asp Tyr Ile Gly Leu Ser Phe Val Ile Ser Glu Asn Asp Val Lys Lys Val Lys Glu Phe Val Gly Asp
Glu Ala Trp Val Ile Ala Lys Ile Glu Lys Ser Glu Ala Leu Lys Asn Leu Thr Asn Ile Val Asn Glu Ser
Asp Gly Ile Met Val Ala Arg Gly Asp Leu Gly Val Glu Thr Gly Leu Asn Leu Pro Leu Ile Gln Arg
Arg Ile Val Arg Thr Ser Arg Val Phe Gly Lys Pro Val Ile Leu Ala Thr Gln Val Leu Thr Ser Met Ile
Asn Ser Pro Ile Pro Thr Arg Ala Glu Ile Ile Asp Ile Ser Asn Ser Ile Met Gln Gly Val Asp Ser Ile
Met Leu Ser Asp Glu Thr Ala Ile Gly Asn Tyr Pro Val Glu Ser Val Arg Thr Leu His Asn Ile Ile Ser
Asn Val Glu Lys Ser Val Lys His Arg Pro Ile Gly Pro Leu Asn Ser Glu Ser Asp Ala Ile Ala Leu Ala
Ala Val Asn Ala Ser Lys Val Ser Lys Ala Lys Ala Val Ile Val Val Thr Ser Arg Ser Gly Ala Asn Ser Ile Leu
Arg Val Ser Arg Leu Arg Pro Glu Arg Asn Ile Ile Gly Val Ser Pro Asp Pro Arg Leu Ala Lys Lys Phe
Lys Leu Cys Tyr Gly Val Ile Pro Ile Ser Ile Asn Lys Lys Met Gln Ser Ile Asp Glu Ile Ile Asp Val
Ser Ala Lys Leu Met Gln Glu Lys Ile Lys Asp Leu Lys Phe Lys Lys Ile Val Ile Val Gly Gly Asp Pro
Lys Gln Glu Ala Gly Lys Thr Asn Phe Val Ile Val Lys Thr Leu Glu Gln Gln Lys Lys

SEQ ID NO: 23
Met Arg Ser Thr Lys Ile Val Cys Thr Val Gly Pro Arg Thr Asp Ser Tyr Glu Met Ile Glu Lys Met Ile
Asp Leu Gly Val Asn Val Phe Arg Ile Asn Thr Ser His Gly Asp Trp Asn Glu Glu Gln Gln Lys Ser Ile Leu
Lys Ile Lys Asp Leu Arg Glu Lys Lys Lys Pro Val Ala Ile Leu Ile Asp Leu Ala Gly Pro Lys Ile
Arg Thr Gly Tyr Leu Glu Lys Glu Phe Val Glu Leu Lys Glu Gly Gln Ile Phe Thr Leu Thr Thr Lys Glu
Ile Leu Gly Asn Glu His Ile Val Ser Val Asn Leu Ser Ser Leu Pro Lys Asp Val Lys Lys Gly Asp Thr
Ile Leu Leu Ser Asp Gly Leu Ile Glu Leu Glu Val Ile Asp Thr Asp Thr Glu Val Lys Thr Val Lys Val
Lys Val Gly Gly Lys Ile Thr His Arg Arg Gly Val Asn Val Pro Thr Ala Asp Leu Ser Val Glu Ser Ile
Thr Asp Arg Asp Arg Glu Phe Ile Lys Leu Gly Thr Leu His Asp Val Glu Phe Ala Leu Ser Phe Val
Arg Lys Pro Glu Asp Val Leu Lys Ala Lys Glu Glu Ile Arg Lys His Gly Lys Glu Ile Pro Val Ile Ser
Lys Ile Glu Thr Lys Ala Leu Glu Arg Leu Glu Glu Ile Ile Lys Val Ser Asp Gly Ile Met Val Ala
Arg Gly Asp Leu Gly Val Glu Ile Pro Ile Glu Glu Val Pro Ile Val Gln Lys Glu Ile Ile Lys Leu Ser
Lys Tyr Tyr Ser Lys Pro Val Ile Val Ala Thr Gln Ile Leu Glu Ser Met Ile Glu Asn Pro Phe Pro Thr
Arg Ala Glu Val Thr Asp Ile Ala Asn Ala Ile Phe Asp Gly Ala Asp Ala Leu Leu Leu Thr Ala Glu Thr
Ala Val Gly Lys His Pro Leu Glu Ala Ile Lys Val Leu Ser Val Ala Lys Glu Ala Glu Ala Lys Lys Leu
Glu Phe Phe Arg Thr Ile Glu Tyr Asp Thr Ser Asp Ile Ser Glu Ala Ile Ser His Ala Cys Trp Gln Leu
Ser Glu Ser Leu Asn Ala Lys Leu Ile Ile Thr Pro Thr Ile Ser Gly Ser Thr Ala Val Arg Val Ser Lys
Tyr Asn Val Ser Gln Pro Ile Val Ala Leu Thr Pro Glu Glu Lys Thr Tyr Tyr Arg Leu Ser Leu Val Arg
Lys Val Ile Pro Val Leu Ala Glu Lys Cys Ser Gln Glu Leu Glu Phe Ile Glu Lys Gly Leu Lys Lys Val
Glu Glu Met Gly Leu Ala Glu Lys Gly Asp Leu Val Val Leu Thr Ser Gly Val Pro Gly Lys Val Gly Thr
Thr Asn Thr Ile Arg Val Leu Lys Val Asp

SEQ ID NO: 24
Met Arg Arg Val Lys Leu Pro Ser His Lys Thr Lys Ile Val Ala Thr Ile Gly Pro Ala Thr Asn Ser Arg
Lys Met Ile Lys Gln Leu Ile Lys Ala Gly Met Asn Val Ala Arg Ile Asn Phe Ser His Gly Ser Phe Glu
Glu His Ala Arg Val Ile Glu Ile Ile Arg Glu Glu Ala Gln Lys Leu Asp Arg Arg Val Ala Ile Leu Ala
Asp Leu Pro Gly Leu Lys Ile Arg Val Gly Glu Ile Lys Gly Gly Tyr Val Glu Leu Lys Arg Gly Glu Lys
Val Ile Leu Thr Thr Lys Asp Val Glu Gly Asp Thr Thr Thr Arg Val Asp Tyr Tyr Lys Gly Phe Pro Asn
Leu Val Ser Lys Gly Asp Ile Ile Tyr Leu Asn Asp Gly Tyr Ile Val Leu Lys Val Glu Asn Val Arg Glu
Asn Glu Val Glu Ala Val Leu Ser Gly Gly Lys Leu Phe Ser Arg Lys Gly Val Asn Ile Pro Lys Ala
Tyr Leu Pro Val Glu Ala Ile Thr Pro Lys Asp Phe Glu Ile Met Lys Phe Ala Ile Glu His Gly Val Asp
Ala Ile Gly Leu Ser Phe Val Gly Ser Val Tyr Arg Val Leu Lys Ile Leu Ser Phe Arg Leu Lys Asn Asn
Ala Glu Asp Val Phe Val Ile Ala Lys Ile Glu Arg Pro Asp Ala Val Arg Asn Phe Asp Glu Ile Leu Asn
Ala Ala Asp Gly Ile Met Ile Ala Arg Gly Asp Leu Gly Val Glu Met Pro Ile Glu Gln Leu Pro Ile Leu
Gln Lys Lys Leu Ile Arg Lys Ala Asn Met Glu Gly Lys Pro Val Ile Thr Ala Thr Gln Met Leu Val Ser
Met Thr Thr Glu Pro Thr Pro Thr Arg Ala Glu Val Thr Asp Val Ala Asn Ala Ile Leu Asp Gly Thr Asp
Ala Val Met Leu Ser Glu Glu Thr Ala Ile Gly Lys Phe Pro Ile Glu Thr Val Glu Met Met Gly Lys Ile
Ala Lys Val Thr Glu Glu Tyr Arg Glu Ser Phe Gly Leu Ser Arg Ile Arg Glu Phe Met Glu Ile Lys Lys
Gly Thr Ile Lys Glu Ala Ile Thr Arg Ser Ile Ile Asp Ala Ile Cys Thr Ile Asp Ile Lys Phe Ile Leu
Thr Pro Thr Arg Thr Gly Arg Thr Ala Arg Leu Ile Ser Arg Phe Lys Pro Lys Gln Trp Ile Leu Ala Phe
Ser Thr Arg Asn Gln Arg Val Cys Asn Asn Leu Met Phe Ser Tyr Arg Pro Val Tyr Pro Cys Ser Leu Glu Gly Ser
Phe Asp Glu Asn Asp Ile Val Arg Leu Ile Lys Gly Leu Gly Leu Ile Glu Ser Asp Asp Met Val Leu Met
Thr Glu Gly Lys Pro Ile Glu Lys Thr Val Gly Thr Asn Ser Ile Lys Ile Phe Gln Ile Ala

SEQ ID NO: 25
Met Lys Val Leu Val Ile Asn Ala Gly Ser Ser Ser Leu Lys Tyr Gln Leu Ile Asp Met Thr Asn Glu Ser
Ala Leu Ala Val Gly Leu Cys Glu Arg Ile Gly Ile Asp Asn Ser Ile Ile Thr Gln Lys Lys Phe Asp Gly
Lys Lys Leu Glu Lys Leu Thr Asp Leu Pro Thr His Lys Asp Ala Leu Glu Glu Val Val Lys Ala Leu Thr
Asp Asp Glu Phe Gly Val Ile Lys Asp Met Gly Glu Ile Asn Ala Val Gly His Arg Val Val His Gly Gly
Glu Lys Phe Thr Thr Ser Ala Leu Tyr Asp Gly Val Glu Lys Ala Ile Lys Asp Cys Phe Glu Leu Ala
Pro Leu His Asn Pro Ala Asn Met Met Gly Ile Ser Ala Cys Ala Glu Ile Met Pro Gly Thr Pro Met Val
Ile Val Phe Asp Thr Ala Phe His Gln Thr Met Pro Pro Tyr Ala Tyr Met Tyr Ala Leu Pro Tyr Asp Leu
Tyr Glu Lys His Gly Val Arg Lys Tyr Gly Phe His Gly Thr Ser His Lys Tyr Val Ala Glu Arg Ala Ala
Leu Met Leu Gly Lys Pro Ala Glu Glu Thr Lys Ile Ile Thr Cys His Leu Gly Asn Gly Ser Ser Ile Thr
Ala Val Glu Gly Gly Lys Ser Val Glu Thr Ser Met Gly Phe Thr Pro Leu Glu Gly Leu Ala Met Gly Thr
Arg Cys Gly Ser Ile Asp Pro Ala Ile Val Pro Phe Leu Met Glu Lys Glu Gly Leu Thr Thr Arg Glu Ile

Asp Thr Leu Met Asn Lys Lys Ser Gly Val Leu Gly Val Ser Gly Leu Ser Asn Asp Phe Arg Asp Leu Asp
Glu Ala Ala Ser Lys Gly Asn Arg Lys Ala Glu Leu Ala Leu Glu Ile Phe Ala Tyr Lys Val Lys Lys Phe
Ile Gly Glu Tyr Ser Ala Val Asn Gly Ala Asp Ala Val Val Phe Thr Ala Gly Ile Gly Glu Asn Ser
Ala Ser Ile Arg Lys Arg Ile Leu Thr Gly Leu Asp Gly Ile Gly Ile Lys Ile Asp Asp Glu Lys Asn Lys
Ile Arg Gly Gln Glu Ile Asp Ile Ser Thr Pro Asp Ala Lys Val Arg Val Phe Val Ile Pro Thr Asn Glu
Glu Leu Ala Ile Ala Arg Glu Thr Lys Glu Ile Val Glu Thr Glu Val Lys Leu Arg Ser Ser Ile Pro Val

SEQ ID NO: 26 atgaagattg gtattgtaac tggaattcct ggtgtaggga aaagtactgt cttggctaaa gttaaagaga tattggataa tcaaggtata
aataacaaga tcataaatta tggagatttt atgttagcaa cagcattaaa attaggctat gctaaagata gagacgaaat gagaaaatta
tctgtagaaa agcagaagaa attgcagatt gatgcggcta aaggtatagc tgaagaggca agagcaggtg agaaggata tctgttcata
gatacgcatg ctgtgatacg tacaccctct ggatattacc ctggtttacc gtcatatgta attacagaaa taaatccgtc tgttatcttt
ttactggaag ctgatcctaa gataatatta tcaaggcaaa agagagatac aacaaggaat agaaatgatt atagtgacga atcagttata
ttagaaacca taaacttcgc tagatatgca gctactgctt ctgcagtatt agccggttct actgttaagg taattgtaaa cgtggaagga
gatcctagta tagcagctaa tgagataata aggtctatga agtaa

SEQ ID NO: 27 atgaaaatcg gtatcgttac cggtatcccg ggtgttggta atctaccgt tctggctaaa gttaaagaaa tcctggacaa ccagggtatc
aacaacaaaa tcatcaacta cggtgacttc atgctggcta ccgctctgaa actgggtac gctaaagacc gtgacgaaat gcgtaaactg
tctgttgaaa aacagaaaaa actgcagatc gacgctgcta aaggtatcgc tgaagaagct agagctggtg gtgaaggtta cctgttcatc
gacacccacg ctgttatccg tacccctgtc ggttactgc cggtgctgcc gtcttacgtt atcaccgaaa tcaacccgtc tgttatcttc
ctgctggaag ctgaccccgaa atcatcctg tctcgtcaga acgtgacac cacccgtaac gtaacgact actctgcga atctgttatc
ctggaaacca tcaacttcgc tcgttacgct gctaccgctt ctgctgttct ggctggttct accgttaaag ttatcgttaa cgttgaaggt
gacccgtcta tcgctgctaa cgaaatcatc cgttctatga atag

SEQ ID NO: 28 atgatggcgt accttgtctt tctaggacct ccaggtgcag gaaaaggaac ctacgcaaag agattgcagg aaataacggg gattcctcat
atatccaccg gtgacatttt tcgtgatatt gtcaaaaagg aaaatgacga attaggtaag aaaattaaag aaattatgga agggagaa
ctcgttccgg acgaactcgt gaacgaggtt gtgaaaagaa gactctcaga aaaagattgt gaaagaggat tcatactgga cggctatcca
agaaccgttg ctcaggcgga attcctcgac ggcttttttga aaactcaaaa caaagagctc acggctgctg tactctttga agttcctgag
gaagtggtcg ttcagaggct cacggccaga aggatctgcc cgaaatgtgg aagaatttac aatttgattt cgctccctcc aaaagaagac
gaactgtgcg atgattgtaa agtgaagctc gttcagagag aagacgacaa agaagaaaca gtgagacaca gatacaaggt ttatctcgaa
aagacacagc cagtgattga ttactacgat aaaaagggca ttctcaaacg agtggatggt accataggaa tagacaacgt gatcgctgaa
gtgttaaaga taatagggtg gagtgataaa tga

SEQ ID NO: 29 atgatggcct atctggtttt tcttggtcca ccgggggcag gcaaaggtac atatgcgaaa cgtttacagg aaatcaccgg catcccgcac
attagcacgg gcgacatttt tcgtgatatt gtcaaaaagg aaaatgacga attaggtaag aaaattaaag aaattatgga gcgcggcgag
ttggtgccgg acgaactggt gaatgaagtt gtcaaacgtc ggctgtctga aaggattgc gaacgtggct ttattttgga cggttaccc
cgtacagtag ctcaggcaga gtttctcgac ggcttcctga agactcagaa taaggagtta acggctgcgg tcctgttcga ggtgcctgaa
gaggtggtcg ttcagaggtct gaccgcccgg cgtatctgcc cgaagtgtga tcgtatttac aacctgattt cacttcctcc aaaagaagat
gaactgtgtg atgactgcaa agtaaaactg gtgcaacgcg aagatgtaa agaggaaact gtgcgccatc gctacaaagt atatctgaa
aaacccaac cggttatcga ttattatgat aaaaaaggca ttttgaaacg cgttgatggg accatcggca tcgataacgt gattgccgaa
gttctcaaaa tcattgggtg gagtgataaa

SEQ ID NO: 30 atgaacctga ttttcctggg tccgcctggg gcaggcaaag gcacccaggc gaaacgtgtg tctgaaaagt acggtatccc gcagattagt
accggcgata tgctgcgtga agcggttgct aagggtacgg aactgggaa aaaggcgaaa gaatatatgg acaaagggga acttgttccg
gatgaagtag ttattggaat cgtgaaagaa cgcctccagc aaccggattg tgagaaggc tttattctgg acggttttcc gcgtacgtta
gcacaagccg aagctctgga cgaaattgta aaagaattgc ataagaaaat tgaccgcgta atcaacgtgg tcgtaccgga agaggaagtt
gtcaagcgta ttacctatcg tcgcacttgc cgcaattgcg cgcgccgtgta ccatctcatt tatgcacctc caaaaggaga taataaatgt
gataaatgcg cgcggtgagct ttatcagcgt gatgacgata agaagagac agtccgcgag cgttaccgtg tgtataaaca gaacacagag
ccattgatcg attattaccg taaaaaggga atcctgtatg atgtggatgg tactaaagac atcgaaggag tttggaaaga aattgaggcg
attctggaaa aaattaaaag c

SEQ ID NO: 31

Met Lys Ile Gly Ile Val Thr Gly Ile Pro Gly Val Gly Lys Ser Thr Val Leu Ala Lys Val Lys Glu Ile Leu
Asp Asn Gln Gly Ile Asn Asn Lys Ile Ile Asn Tyr Gly Asp Phe Met Leu Ala Thr Ala Leu Lys Leu Gly Tyr
Ala Lys Asp Arg Asp Glu Met Arg Lys Leu Ser Val Glu Lys Gln Lys Lys Leu Gln Ile Asp Ala Ala Lys Gly
Ile Ala Glu Glu Ala Arg Ala Gly Gly Glu Gly Tyr Leu Phe Ile Asp Thr His Ala Val Ile Arg Thr Pro Ser
Gly Tyr Leu Pro Gly Leu Pro Ser Tyr Val Ile Thr Glu Ile Asn Pro Ser Val Ile Phe Leu Leu Glu Ala Asp
Pro Lys Ile Ile Leu Ser Arg Glu Lys Arg Asp Thr Thr Arg Asn Arg Asn Asp Tyr Ser Asp Glu Ser Val Ile
Leu Glu Thr Ile Asn Phe Ala Arg Tyr Ala Ala Thr Ala Ser Ala Val Leu Ala Gly Ser Thr Val Lys Val Ile
Val Asn Val Glu Gly Asp Pro Ser Ile Ala Ala Asn Glu Ile Ile Arg Ser Met Lys

SEQ ID NO: 32

Met Met Ala Tyr Leu Val Phe Leu Gly Pro Pro Gly Ala Gly Lys Gly Thr Tyr Ala Lys Arg Leu Gln Glu Ile
Thr Gly Ile Pro His Ile Ser Thr Gly Asp Ile Phe Arg Asp Ile Val Lys Glu Asn Asp Glu Leu Gly Lys
Lys Ile Lys Glu Ile Met Glu Arg Gly Glu Leu Val Pro Asp Glu Leu Val Asn Glu Val Val Lys Arg Arg Leu
Ser Glu Lys Asp Cys Gln Arg Gly Phe Ile Leu Asp Gly Tyr Pro Arg Thr Val Ala Gln Ala Glu Phe Leu Asp
Gly Phe Leu Lys Thr Gln Asn Lys Glu Leu Thr Ala Ala Val Leu Phe Glu Val Pro Glu Glu Val Val Val Gln
Arg Leu Thr Ala Arg Arg Ile Cys Pro Lys Cys Gly Arg Ile Tyr Asn Leu Ile Ser Leu Pro Pro Lys Glu Asp
Glu Leu Cys Asp Asp Cys Lys Val Lys Leu Val Gln Arg Glu Asp Asp Lys Glu Glu Thr Val Arg His Arg Tyr
Lys Val Tyr Leu Glu Lys Thr Gln Pro Val Ile Asp Tyr Tyr Asp Lys Lys Gly Ile Leu Lys Arg Val Asp Gly
Thr Ile Gly Ile Asp Asn Val Ile Ala Glu Val Leu Lys Ile Ile Gly Trp Ser Asp Lys

SEQUENCE LISTING

SEQ ID NO: 33
Met Asn Gln Glu Gln Val Ser Pro Leu Gly Gly

SEQ ID NO: 34
Met Asn Gln Glu Gln Val Ser Pro Leu Gly Gly Lys Ile Gly Ile Val Thr Gly Ile Pro Gly Val Gly Lys Ser
Thr Val Leu Ala Lys Val Lys Glu Ile Leu Asp Asn Gln Gly Ile Asn Asn Lys Ile Ile Asn Tyr Gly Asp Phe
Met Leu Ala Thr Ala Leu Lys Leu Gly Tyr Ala Lys Asp Arg Asp Glu Met Arg Lys Leu Ser Val Glu Lys Gln
Lys Lys Leu Gln Ile Asp Ala Ala Lys Gly Ile Ala Gln Glu Ala Arg Ala Gly Gly Glu Gly Tyr Leu Phe Ile
Asp Thr His Ala Val Ile Arg Thr Pro Ser Gly Tyr Leu Pro Gly Leu Pro Ser Tyr Val Ile Thr Glu Ile Asn
Pro Ser Val Ile Phe Leu Leu Glu Ala Asp Pro Lys Ile Ile Leu Ser Arg Gln Lys Arg Asp Thr Thr Arg Asn
Arg Asn Asp Tyr Ser Asp Glu Ser Val Ile Leu Glu Thr Ile Asn Phe Ala Arg Tyr Ala Ala Thr Ala Ser Ala
Val Leu Ala Gly Ser Thr Val Lys Val Ile Val Asn Val Glu Gly Asp Pro Ser Ile Ala Ala Asn Glu Ile Ile
Arg Ser Met Lys

SEQ ID NO: 35
Met Lys Ile Gly Ile Val Thr Gly Ile Pro Gly Val Gly Lys Ser Thr Val Leu Ala Lys Val Lys Glu Ile Leu
Asp Asn Gln Gly Ile Asn Asn Lys Ile Ile Asn Tyr Gly Asp Phe Met Leu Ala Thr Ala Leu Lys Leu Gly Tyr
Ala Lys Asp Arg Asp Glu Met Arg Lys Leu Ser Val Glu Lys Gln Lys Lys Leu Gln Ile Asp Ala Ala Lys Gly
Ile Ala Glu Glu Ala Arg Ala Gly Gly Glu Gly Tyr Leu Phe Ile Asp Thr His Ala Val Ile Arg Thr Pro Ser
Gly Tyr Leu Pro Gly Leu Pro Ser Tyr Val Ile Thr Glu Ile Asn Pro Ser Val Ile Phe Leu Leu Glu Ala Asp
Pro Lys Ile Ile Leu Ser Arg Gln Lys Arg Asp Thr Thr Arg Asn Arg Asn Asp Tyr Ser Asp Glu Ser Val Ile
Leu Glu Thr Ile Asn Phe Ala Arg Tyr Ala Ala Thr Ala Ser Ala Val Leu Ala Gly Ser Thr Val Lys Val Ile
Val Asn Val Glu Gly Asp Pro Ser Ile Ala Ala Asn Glu Ile Ile Arg Ser Met Lys Gly Gly Asn Gln Glu Gln
Val Ser Pro Leu

SEQ ID NO: 36
Met Asn Gln Glu Gln Val Ser Pro Leu Gly Gly Lys Ile Gly Ile Val Thr Gly Ile Pro Gly Val Gly Lys Ser
Thr Val Leu Ala Lys Val Lys Glu Ile Leu Asp Asn Gln Gly Ile Asn Asn Lys Ile Ile Asn Tyr Gly Asp Phe
Met Leu Ala Thr Ala Leu Lys Leu Gly Tyr Ala Lys Asp Arg Asp Glu Met Arg Lys Leu Ser Val Glu Lys Gln
Lys Lys Leu Gln Ile Asp Ala Ala Lys Gly Ile Ala Glu Ala Arg Ala Gly Gly Glu Gly Tyr Leu Phe Ile
Asp Thr His Ala Val Ile Arg Thr Pro Ser Gly Tyr Leu Pro Gly Leu Pro Ser Tyr Val Ile Thr Glu Ile Asn
Pro Ser Val Ile Phe Leu Leu Glu Ala Asp Pro Lys Ile Ile Leu Ser Arg Gln Lys Arg Asp Thr Thr Arg Asn
Arg Asn Asp Tyr Ser Asp Glu Ser Val Ile Leu Glu Thr Ile Asn Phe Ala Arg Tyr Ala Ala Thr Ala Ser Ala
Val Leu Ala Gly Ser Thr Val Lys Val Ile Val Asn Val Glu Gly Asp Pro Ser Ile Ala Ala Asn Glu Ile Ile
Arg Ser Met Lys Gly Gly AsnGln Glu Gln Val Ser Pro Leu

SEQ ID NO: 37
atgaatcaag aacaagtcag cccgctgggc ggcatcatcg cctatctggt ttttcttggt ccaccggggg caggcaaagg tacctatgcg
aaacgtttac aggaaatcac cggcatcccg cacattagca cgggcgacat ttttcgtgat attgtcaaaa aggaaaatga cgaattaggt
aagaaaatta agaaattat ggagcgcggc gagttggtgc cggacgaact ggtgaatgaa gttgtcaaac gtcggctgtc tgaaaaggat
tgcgaacgtg gctttatttt ggacggttac ccgcgtacag tagctcaggc agagtttctc gacggcttcc tgaagactca gaataaggag
ttaacggctg cggtcctgtt cgaggtgcct gaagaggtgg tctgaccgcg cggcgtatct gcccgaagtg tggtcgtatt tacaacctga
tttcacttcc tccaaaagaa gatgaactgt gtgatgactg caaagtaaaa ctggtgcaac gcgaagatga taagaggaa actgtgcgcc
atcgctacaa agtatatctg gaaaaaaccc aaccggttat cgattattat gataaaaaag gcattttgaa acgcgttgat gggaccatcg
gcatcgataa cgtgattgcc gaagttctca aaatcattgg gtggagtgat aaataggtcg acgc SEQ ID NO: 38
Met Asn Gln Glu Gln Val Ser Pro Leu Gly Gly Ile Ile Ala Tyr Leu Val Phe Leu Gly Pro Pro Gly Ala Gly
Lys Gly Thr Tyr Ala Lys Arg Leu Gln Glu Ile Thr Gly Ile Pro His Ile Ser Thr Gly Asp Ile Phe Arg Asp
Ile Val Lys Lys Glu Asn Asp Glu Leu Gly Lys Lys Ile Lys Glu Ile Met Glu Arg Gly Glu Leu Val Pro Asp
Glu Leu Val Asn Glu Val Val Lys Arg Arg Leu Ser Glu Lys Asp Cys Glu Arg Gly Phe Ile Leu Asp Gly Tyr
Pro Arg Thr Val Ala Gln Ala Glu Phe Leu Asp Gly Phe Leu Lys Thr Gln Asn Lys Glu Leu Thr Ala Ala Val
Leu Phe Glu Val Pro Glu Glu Val Val Gln Arg Leu Thr Ala Arg Arg Ile Cys Pro Lys Cys Gly Arg Ile
Tyr Asn Leu Ile Ser Leu Pro Pro Lys Glu Asp Glu Leu Cys Asp Asp Cys Lys Val Lys Leu Val Gln Arg Glu
Asp Asp Lys Glu Glu Thr Val Arg His Arg Tyr Lys Val Tyr Leu Glu Lys Thr Gln Pro Val Ile Asp Tyr Tyr
Asp Lys Lys Gly Ile Leu Lys Arg Val Asp Gly Thr Ile Gly Ile Asp Asn Val Ile Ala Glu Val Leu Lys Ile
Ile Gly Trp Ser Asp Lys SEQ ID NO: 39
atgatggcct atctggtttt tcttggtcca ccgggggcag gcaaaggtac ctatgcgaaa cgtttacagg aaatcaccgg catcccgcac
attagcacgg gcgacatttt tcgtgatatt gtcaaaaagg aaaatgacga attaggtaag aaaattaaag aaattatgga gcgcggcgag
ttggtgccgg acgaactggt gaatgaagtt gtcaaacgtc ggctgtctga aaaggattgc gaacgtggct ttattttgga cggttacccg
cgtacagtag ctcaggcaga gtttctcgac ggcttcctga agactcagaa taaggagtta acggctgcgg tcctgttcga ggtgcctgaa
gaggtggtcg ttcagcgtct gaccgcgcgg cgtatctgcc cgaagtgtgg tcgtatttac aacctgattt cacttcctcc aaaagaagat
gaactgtgtg atgactgcaa agtaaaactg gtgcaacgcg aagatgataa agaggaaact gtgcgccatc gctacaaagt atatctggaa
aaaacccaac cggttatcga ttattatgat aaaaaaggca ttttgaaacg cgttgatggg accatcggca tcgataacgt gattgccgaa
gttctcaaaa tcattgggtg gagtgataaa ctgggcggca tcaagaaca gtcagcccg ctgtaa SEQ ID NO: 40
Met Met Ala Tyr Leu Val Phe Leu Gly Pro Pro Gly Ala Gly Lys Gly Thr Tyr Ala Lys Arg Leu Gln Glu Ile
Thr Gly Ile Pro His Ile Ser Thr Gly Asp Ile Phe Arg Asp Ile Val Lys Lys Glu Asn Asp Glu Leu Gly Lys
Lys Ile Lys Glu Ile Met Glu Arg Gly Glu Leu Val Pro Asp Glu Leu Val Asn Glu Val Val Lys Arg Arg Leu
Ser Glu Lys Asp Cys Glu Arg Gly Phe Ile Leu Asp Gly Tyr Pro Arg Thr Val Ala Gln Ala Glu Phe Leu Asp -continued Gly Phe Leu Lys Thr Gln Asn Lys Glu Leu Thr Ala Ala Val Leu Phe Glu Val Pro Glu Glu Val Val Gln
Arg Leu Thr Ala Arg Arg Ile Cys Pro Lys Cys Gly Arg Ile Tyr Asn Leu Ile Ser Leu Pro Pro Lys Glu Asp
Glu Leu Cys Asp Asp Cys Lys Val Lys Leu Val Gln Arg Glu Asp Lys Glu Glu Thr Val Arg His Arg Tyr
Lys Val Tyr Leu Glu Lys Thr Gln Pro Val Ile Asp Tyr Tyr Asp Lys Lys Gly Ile Leu Lys Arg Val Asp Gly
Thr Ile Gly Ile Asp Asn Val Ile Ala Glu Val Leu Lys Ile Ile Gly Trp Ser Asp Lys Leu Gly Gly Asn Gln
Glu Gln Val Ser Pro Leu

SEQ ID NO: 41 atgaatcaag aacaagtcag cccgctgggc ggcatcatcg cctatctggt ttttcttggt ccaccggggg caggcaaagg tacctatgcg
aaacgtttac aggaaatcac cggcatcccg cacattagca cgggcgacat ttttcgtgat attgtcaaaa aggaaaatga cgaattaggt
aagaaaatta aagaaatttat ggagcgcggc gagttggtgc cggacgaact ggtgaatgaa gttgtcaaac gtcggctgtc tgaaaaggat
tgcgaacgtg gctttatttt ggacggttac ccgcgtacag tagctcaggc agagtttctc gacggcttcc tgaagactca gaataaggag
ttaacggctg cggtcctgtt cgaggtgcct gaagaggtgg tcgttcagcg tctgaccgcg cggcgtatct gcccgaagtg tggtcgtatt
tacaacctga tttcacttcc tccaaaagaa gatgaactgt gtgatgactg caaagtaaaa ctggtgcaac gcgaagatga taaagaggaa
actgtgcgcc atcgctacaa agtatatctg gaaaaaccc aaccggttat cgattattat gataaaaaag cattttgaa acgcgttgat
gggaccatcg gcatcgataa cgtgattgcc gaagttctca aaatcattgg gtggagtgat aaactgggcg gcaatcaaga acaagtcagc
ccgctgtaa

SEQ ID NO: 42

Met Asn Gln Glu Gln Val Ser Pro Leu Gly Gly Ile Ile Ala Tyr Leu Val Phe Leu Gly Pro Pro Gly Ala Gly
Lys Gly Thr Tyr Ala Lys Arg Leu Gln Glu Ile Thr Gly Ile Pro His Ile Ser Thr Gly Asp Ile Phe Arg Asp
Ile Val Lys Lys Glu Asn Asp Glu Leu Gly Lys Lys Ile Lys Glu Ile Met Glu Arg Gly Glu Leu Val Pro Asp
Glu Leu Val Asn Glu Val Val Lys Arg Arg Leu Ser Glu Lys Asp Cys Glu Arg Gly Phe Ile Leu Asp Gly Tyr
Pro Arg Thr Val Ala Gln Ala Glu Phe Leu Asp Gly Phe Leu Lys Thr Gln Asn Lys Glu Leu Thr Ala Ala Val
Leu Phe Glu Val Pro Glu Glu Val Val Gln Arg Leu Thr Ala Arg Arg Ile Cys Pro Lys Cys Gly Arg Ile
Tyr Asn Leu Ile Ser Leu Pro Pro Lys Glu Asp Glu Leu Cys Asp Asp Cys Lys Val Lys Leu Val Gln Arg Glu
Asp Asp Lys Glu Glu Thr Val Arg His Arg Tyr Lys Val Tyr Leu Glu Lys Thr Gln Pro Val Ile Asp Tyr Tyr
Asp Lys Lys Gly Ile Leu Lys Arg Val Asp Gly Thr Ile Gly Ile Asp Asn Val Ile Ala Glu Val Leu Lys Ile
Ile Gly Trp Ser Asp Lys Leu Gly Gly Asn Gln Glu Gln Val Ser Pro Leu

SEQ ID NO: 43 ccaaggttat caagcttaca atgctcaagc ccaacctggg ggtgggtact accaaaatta ccaaggttat tctgggtacc aacaaggtgg
ctatcaacag tacaatcccg acgccggtta ccagcaggta tataatcctc aaggaggcta tcaacagtac aatcctcaag cgcggttatca
gcaccaattc aatccacaag gtggccgtgg aaattacaaa aacttcaact acaataacaa tttgcaagga tatcaagctg gtttccaacc
acagtctcaa ggtatgtctt tgaacgactt caaaagcaa caaagcagg ccgctcccaa accaaagaag actttgaagc ttgtctccag
ttcctgtatc aagttggcca atgctaccaa gaaggttgac acaaaacctg ccgaatctga taagaaagag gaagagaagt ctgctgaaac
caaagaacca actaaagagc caacaaaggt cgaagaacca gttaaaaagg aggaaaaccc agtccgaact gaagaaaaga cggaggaaaa
atcggaactt ccaaaggtag aagaccttaa aatctctgaa tcaacacata taccaacaa tgccaatgtt accagtgctg atgccttgat
caaggaacag gaagaagaag tggatgacga agttgttaac gatatgtttg gtggtaaaga tcacgtttct ttaatttca tgggtcatgt
tgatgccggt aaatcactac tgggtggtaa tctactatac ttgactggct ctgtggataa gagaactatt gagaaatatg ggtaagacta
tcgaagttgg taaggcctac tttgaaactg aaaaaaggcg ttataccata ttggatgctc ctggtcataa aatgtacgtt ccgagatga
tcggtggtgc ttctcaagct gatgttggtg ttttggtcat ttccgccaga aagggtgagt acgaaaccgg ttttgagaga tgacccaacc
gttaactggt ctaaggaacg ttacgaccaa tgtgtgagta atgtcagcaa tttcttga

SEQ ID NO: 44

Asp Ser Asn Gln Gly Asn Asn Gln Gln Asn Tyr Gln Gln Tyr Ser Gln Asn Gly Asn Gln Gln Gly Asn Asn
Arg Tyr Gln Gly Tyr Gln Ala Tyr Asn Ala Gln Ala Gln Pro Gly Gly Gly Tyr Tyr Gln Asn Tyr Gln Gly Tyr
Ser Gly Tyr Gln Gln Gly Gly Tyr Gln Gln Tyr Asn Pro Asp Ala Gly Tyr Gln Gln Tyr Asn Pro Gln Gly
Gly Tyr Gln Gln Tyr Asn Pro Gln Gly Gly Tyr Gln His Gln Phe Asn Pro Gln Gly Gly Arg Gly Asn Tyr Lys
Asn Phe Asn Tyr Asn Asn Asn Leu Gln Gly Tyr Gln Ala Gly Phe Gln Pro Gln Ser Gln Gly Met Ser Leu Asn
Asp Phe Gln Lys Gln Gln Lys Gln Ala Ala Pro Lys Pro Lys Lys Thr Leu Lys Leu Val Ser Ser Ser Cys Ile
Lys Leu Ala Asn Ala Thr Lys Lys Val Asp Thr Lys Pro Ala Glu Ser Asp Lys Lys Glu Glu Glu Lys Ser Ala
Glu Thr Lys Glu Pro Thr Lys Glu Pro Thr Lys Glu Pro Val Lys Lys Glu Glu Lys Pro Val Gln Thr
Glu Glu Lys Thr Glu Glu Lys Ser Glu Leu Pro Lys Val Glu Asp Leu Lys Ile Ser Glu Ser Thr His Asn Thr
Asn Asn Ala Asn Val Thr Ser Ala Asp Ala Leu Ile Lys Glu Gln Glu Glu Glu Val Asp Asp Glu Val Val Asn
Asp Met Phe Gly Gly Lys Asp His Val Ser Leu Ile Phe Met Gly His Val Asp Ala Gly Lys Ser Thr Met Gly
Gly Asn Leu Leu Tyr Leu Thr Gly Ser Val Asp Lys Arg Thr Ile Glu Leu Tyr Glu Glu Ala Leu Lys Ser Asp Ala
Gly Arg Gln Gly Trp Tyr Leu Ser Trp Val Met Asp Thr Asn Lys Glu Glu Arg Asn Asp Gly Lys Thr Ile Glu
Val Gly Lys Ala Tyr Phe Glu Thr Glu Lys Arg Arg Tyr Thr Ile Leu Asp Ala Pro Gly His Lys Met Tyr Val
Ser Glu Met Ile Gly Gly Ala Ser Gln Ala Asp Val Gly Val Leu Val Ile Ser Ala Arg Lys Gly Glu Tyr Glu
Thr Gly Phe Glu Arg Gly Gly Gln Thr Arg Glu His Ala Leu Leu Ala Lys Thr Gln Gly Val Asn Lys Met Val
Val Val Val Asn Lys Met Asp Asp Pro Thr Val Asn Trp Ser Lys Glu Arg Tyr Asp Gln Cys Val Ser Asn Val
Ser Asn Phe Leu

SEQ ID NO: 45 atggactcta accagggtaa caaccagcag aactaccagc agtactctca gaacggtaac cagcagcagg gtaacaaccg ttaccagggt
taccaggctt acaacgctca ggctcagccg gtggtggtt actaccagaa ctaccagggt tactccggat atcaacaggg tggttaccaa
caatataatc cagacgctgg ttaccagcag cagtacaacc cgcagggtgg ttaccagcag tacaacccgc aaggcggata tcaacacag
ttcaatccgc agggtggtcg tggtaactac aaaaacttca actacaacaa caacctgcag ggttaccagg ctggttaa

SEQ ID NO: 46

Met Asp Ser Asn Gln Gly Asn Asn Gln Gln Asn Tyr Gln Gln Tyr Ser Gln Asn Gly Asn Gln Gln Gly Asn
Asn Arg Tyr Gln Gly Tyr Gln Ala Tyr Asn Ala Gln Ala Gln Pro Gly Gly Gly Tyr Tyr Gln Asn Tyr Gln Gly
Tyr Ser Gly Tyr Gln Gln Gly Gly Tyr Gln Gln Tyr Asn Pro Asp Ala Gly Tyr Gln Gln Gln Tyr Asn Pro Gln
Gly Gly Tyr Gln Gln Tyr Asn Pro Gln Gly Gly Tyr Gln His Gln Phe Asn Pro Gln Gly Gly Arg Gly Asn Tyr
Lys Asn Phe Asn Tyr Asn Asn Asn Leu Gln Gly Tyr Gln Ala Gly

SEQUENCE LISTING

SEQ ID NO: 47

```
ttaccagggt taccaggctt acaacgctca ggctcagccg ggtggtggtt actaccagaa ctaccagggt tactccggtt atcagcaagg
tggctaccaa caatataatc cagacgctgg ctatcaacag caatataatc ctcagggtgg ttaccagcag tacaaccgc aaggcggtta
tcaacaccag ttcaatccgc agggtggtcg tggtaactac aaaaacttca actacaacaa caacctgcag ggttaccagg ctggaattat
gaagatcggc attgtgaccg gcattccggg cgttggcaaa agcaccgttc tggcaaaggt gaaggagatc ctggacaacc agggcattaa
taacaaaatt attaattatg gtgatttttat gctggcgacc gcgctgaagc tgggctacgc aaaagatcgt gacgaaatgc gcaaactgag
cgtggaaaaa cagaagaagc tgcagattga tgcggcgaag ggcattgcgg aagaggcacg cgcgggcggc gaaggctacc tgtttatcga
tacccatgcg gtgatccgca ccccgagcgg ttatctgccg ggcctgccgt cttacgtgat tacggaaatc aacccgagcg ttatttttct
gctggaggca gatccgaaga ttattctgag ccgccagaag cgcgatacca cccgcaaccg caacgattat agcgacgaaa gcgttatcct
ggagaccatc aactttgcgc gctatgcgg aaccgcgagc gcggttctgg caggctctac cgttaaagtg atcgtgaacg tgagggtga
tccaagcatc gcggcgaacg aaatcattcg cagcatgaaa taagtcgacg c
```

SEQ ID NO: 48

```
Met Asp Ser Asn Gln Gly Asn Asn Gln Gln Asn Tyr Gln Gln Tyr Ser Gln Asn Gly Asn Gln Gln Gly Asn
Asn Arg Tyr Gln Gly Tyr Gln Ala Tyr Asn Ala Gln Ala Gln Pro Gly Gly Gly Tyr Tyr Gln Asn Tyr Gln Gly
Tyr Ser Gly Tyr Gln Gly Gly Tyr Gln Gly Gly Tyr Gln Asn Pro Asp Ala Gly Tyr Gln Gln Tyr Asn Pro Gln
Gly Gly Tyr Gln Gln Tyr Asn Pro Gln Gly Gly Tyr Gln His Gln Phe Asn Pro Gln Gly Gly Arg Gly Asn Tyr
Lys Asn Phe Asn Tyr Asn Asn Asn Leu Gln Gly Tyr Gln Ala Gly Ile Met Lys Ile Gly Ile Val Thr Gly Ile
Pro Gly Val Gly Lys Ser Thr Val Leu Ala Lys Val Lys Glu Ile Leu Asp Asn Gln Gly Ile Asn Asn Lys Ile
Ile Asn Tyr Gly Asp Phe Met Leu Ala Thr Ala Leu Lys Leu Gly Tyr Ala Lys Asp Arg Asp Glu Met Arg Lys
Leu Ser Val Glu Lys Gln Lys Lys Leu Gln Ile Asp Ala Ala Lys Gly Ile Ala Glu Glu Ala Arg Ala Gly Gly
Glu Gly Tyr Leu Phe Ile Asp Thr His Ala Val Ile Arg Thr Pro Ser Gly Tyr Leu Pro Gly Leu Pro Ser Tyr
Val Ile Thr Glu Ile Asn Pro Ser Val Ile Phe Leu Leu Glu Ala Asp Pro Lys Ile Ile Leu Ser Arg Gln Lys
Arg Asp Thr Thr Arg Asn Arg Asn Asp Tyr Ser Asp Glu Ser Val Ile Leu Glu Thr Ile Asn Phe Ala Arg Tyr
Ala Ala Thr Ala Ser Ala Val Leu Ala Gly Ser Thr Val Lys Val Ile Val Asn Val Glu Gly Asp Pro Ser Ile
Ala Ala Asn Glu Ile Ile Arg Ser Met Lys
```

SEQ ID NO: 49

```
atgaagatcg gcattgtgac cggcattccg ggcgttggca aaagcaccgt tctggcaaag gtgaaggaga tcctggacaa ccagggcatt
aataacaaaa ttattaatta tggtgatttt atgctggcga ccgcgctgaa gctgggctac gcaaaagatc gtgacgaaat gcgcaaactg
agcgtggaaa aacagaagaa gctgcagatt gatgcggcga agggcattgc ggaagaggca cgcgcgggcg gcgaaggcta cctgtttatc
gatacccatg cggtgatccg caccccgagc ggttatctgc cgggcctgcc gtcttacgtg attacggaaa tcaacccgag cgttattttt
ctgctggagg cagatccgaa gattattctg agccgccaga agcgcgatac cacccgcaac cgcaacgatt atagcgacga aagcgttatc
ctggagacca tcaactttgc gcgctatgcg gcaaccgcga gcgcggttct ggcaggctct accgttaaag tgatcgtgaa cgtcgaaggt
gatccatcaa ttgcagcgaa cgaaattatc cgcagcatga aacagagcag catggacagc aaccagggca acaatcagca gaattatcag
cagtataatc ctgagggtgt taccaggaa tacaacccgc aaggcggtt atcaacacca gttcaatccg cagggtggtc
gtggtaacta caaaaacttc aactacaaca caacctgca gggttaccag gctggttaag tcgacgc
```

SEQ ID NO: 50

```
Met Lys Ile Gly Ile Val Thr Gly Ile Pro Gly Val Gly Lys Ser Thr Val Leu Ala Lys Val Lys Glu Ile Leu
Asp Asn Gln Gly Ile Asn Asn Lys Ile Ile Asn Tyr Gly Asp Phe Met Leu Ala Thr Ala Leu Lys Leu Gly Tyr
Ala Lys Asp Arg Asp Glu Met Arg Lys Leu Ser Val Glu Lys Gln Lys Lys Leu Gln Ile Asp Ala Ala Lys Gly
Ile Ala Glu Glu Ala Arg Ala Gly Gly Glu Gly Tyr Leu Phe Ile Asp Thr His Ala Val Ile Arg Thr Pro Ser
Gly Tyr Leu Pro Gly Leu Pro Ser Tyr Val Ile Thr Glu Ile Asn Pro Ser Val Ile Phe Leu Leu Glu Ala Asp
Pro Lys Ile Ile Leu Ser Arg Gln Lys Arg Asp Thr Thr Arg Asn Arg Asn Asp Tyr Ser Asp Glu Ser Val Ile
Leu Glu Thr Ile Asn Phe Ala Arg Tyr Ala Ala Thr Ala Ser Ala Val Leu Ala Gly Ser Thr Val Lys Val Ile
Val Asn Val Glu Gly Asp Pro Ser Ile Ala Ala Asn Glu Ile Ile Arg Ser Met Lys Gln Ser Ser Met Asp Ser
Asn Gln Gly Asn Asn Gln Gln Asn Tyr Gln Gln Tyr Ser Gln Asn Gly Asn Gln Gln Gly Asn Asn Arg Tyr
Gln Gly Tyr Gln Ala Tyr Asn Ala Gln Ala Gln Pro Gly Gly Gly Tyr Tyr Gln Asn Tyr Gln Gly Tyr Ser Gly
Tyr Gln Gly Gly Tyr Gln Gly Gly Tyr Gln Asn Pro Asp Ala Gly Tyr Gln Gln Tyr Asn Pro Gln Gly Gly Tyr
Gln Gln Tyr Asn Pro Gln Gly Gly Tyr Gln His Gln Phe Asn Pro Gln Gly Gly Arg Gly Asn Tyr Lys Asn Phe
Asn Tyr Asn Asn Asn Leu Gln Gly Tyr Gln Ala Gly
```

SEQ ID NO: 51

```
ttaccagggt taccaggctt acaacgctca ggctcagccg ggtggtggtt actaccagaa ctaccagggt tactccggtt atcagcaagg
tggctaccaa caatataatc cagacgctgg ctatcaacag caatataatc ctcagggtgg ttaccagcag tacaaccgc aaggcggtta
tcaacaccag ttcaatccgc agggtggtcg tggtaactac aaaaacttca actacaacaa caacctgcag ggttaccagg ctggaattat
gatggcctat ctggtttttc ttggtccacc gggggcaggc aaaggtacct atgcgaaacg tttacaggaa atcacggga tcccgcacat
tagcacgggc gacatttttc gtgatattgt caaaaaggaa aatgacgaat aggtaagaa aattaaagaa attatggagc gcggcgagtt
ggtgccggac gaactggtga atgaagttgt caaacgtcgg ctgtctgaaa aggattgcga acgtggcttt attttggacg gttaccgcg
tacagtagct caggcagagt ttctcgacgg cttcctgaag actcagaata aggagttaac ggctgcggtc ctgttcgagg tgcctgaaga
ggtggtcgtt cagcgtctga ccgcgcgcat ctatcgcccg aagtgtggtc gtatttacaa cctgatttca cttcctccaa aagaagatga
actgtgtgat gactgcaaag taaaactggt gcaacgcgaa gatgtaaag aggaaactgt gcgccatcgc tacaaagtat atctgggaaaa
aacccaaccg ttatcgatt attatgataa aaaaggcatt tgaaacgcg ttgatgggac tcccggcatc gataacgtga ttgccgaagt
tctcaaaatc attgggtgga gtgataaata g
```

SEQ ID NO: 52

```
Met Asp Ser Asn Gln Gly Asn Asn Gln Gln Asn Tyr Gln Gln Tyr Ser Gln Asn Gly Asn Gln Gln Gly Asn
Asn Arg Tyr Gln Gly Tyr Gln Ala Tyr Asn Ala Gln Ala Gln Pro Gly Gly Gly Tyr Tyr Gln Asn Tyr Gln Gly
Tyr Ser Gly Tyr Gln Gly Gly Tyr Gln Gly Gly Tyr Gln Asn Pro Asp Ala Gly Tyr Gln Gln Tyr Asn Pro Gln
Gly Gly Tyr Gln Gln Tyr Asn Pro Gln Gly Gly Tyr Gln His Gln Phe Asn Pro Gln Gly Gly Arg Gly Asn Tyr
Lys Asn Phe Asn Tyr Asn Asn Asn Leu Gln Gly Tyr Gln Ala Gly Ile Met Met Ala Tyr Leu Val Phe Leu Gly
Pro Pro Gly Ala Gly Lys Gly Thr Tyr Ala Lys Arg Leu Gln Glu Ile Thr Gly Ile Pro His Ile Ser Thr Gly
Asp Ile Phe Arg Asp Ile Val Lys Lys Glu Asn Asp Glu Leu Lys Lys Ile Lys Glu Ile Met Glu Arg Gly
Glu Leu Val Pro Asp Glu Leu Val Asn Glu Val Val Lys Arg Leu Ser Glu Lys Asp Cys Glu Arg Gly Phe
Ile Leu Asp Gly Tyr Pro Arg Thr Val Ala Gln Ala Glu Phe Leu Asp Gly Phe Leu Lys Thr Gln Asn Lys Glu
Leu Thr Ala Ala Val Leu Phe Glu Val Pro Glu Glu Val Val Gln Arg Leu Thr Ala Arg Arg Ile Cys Pro
```

-continued

SEQUENCE LISTING

Lys Cys Gly Arg Ile Tyr Asn Leu Ile Ser Leu Pro Pro Lys Glu Asp Glu Leu Gly Asp Asp Cys Lys Val Lys
Leu Val Gln Arg Glu Asp Asp Lys Glu Thr Val Arg His Arg Tyr Lys Val Tyr Leu Glu Lys Thr Gln Pro
Val Ile Asp Tyr Tyr Asp Lys Lys Gly Ile Leu Lys Arg Val Asp Gly Thr Ile Gly Ile Asp Asn Val Ile Ala
Glu Val Leu Lys Ile Ile Gly Trp Ser Asp Lys

SEQ ID NO: 53
Ala Thr Gly Ala Thr Gly Gly Cys Gly Thr Ala Thr Cys Thr Gly Gly Thr Thr Thr Thr Thr Cys Thr Thr Gly
Gly Thr Cys Cys Ala Cys Cys Gly Gly Gly Gly Cys Ala Gly Gly Cys Ala Ala Ala Gly Gly Thr Ala Cys
Cys Thr Ala Thr Gly Gly Ala Ala Ala Cys Gly Thr Thr Ala Cys Ala Gly Gly Ala Ala Ala Thr Gly
Ala Cys Gly Gly Gly Cys Ala Thr Cys Cys Gly Cys Ala Cys Ala Thr Ala Gly Cys Ala Cys Gly Gly
Gly Cys Gly Ala Cys Ala Thr Thr Thr Thr Cys Gly Gly Thr Ala Thr Ala Thr Gly Thr Cys Ala Ala
Ala Ala Ala Gly Gly Ala Ala Ala Thr Gly Ala Cys Gly Ala Ala Thr Thr Ala Gly Gly Thr Ala Ala
Ala Ala Ala Ala Thr Thr Ala Ala Ala Gly Ala Ala Ala Thr Thr Ala Thr Gly Gly Ala Gly Cys Gly Cys
Gly Cys Gly Ala Gly Thr Thr Gly Gly Thr Gly Gly Cys Gly Ala Cys Gly Ala Ala Cys Thr Gly Gly Thr
Gly Ala Ala Thr Gly Ala Ala Gly Thr Thr Gly Thr Cys Ala Ala Ala Gly Gly Thr Cys Gly Gly Cys Thr
Thr Cys Thr Gly Ala Ala Ala Ala Gly Gly Ala Thr Thr Gly Gly Cys Ala Ala Cys Gly Thr Gly Cys Thr
Thr Thr Ala Thr Thr Thr Gly Gly Ala Cys Gly Gly Thr Ala Cys Cys Gly Cys Gly Gly Thr Ala Cys
Ala Gly Thr Ala Gly Cys Thr Cys Ala Gly Gly Cys Ala Gly Ala Ala Thr Thr Cys Thr Cys Gly Ala Cys
Gly Gly Cys Thr Thr Cys Cys Thr Gly Ala Ala Gly Ala Cys Thr Cys Ala Gly Ala Ala Thr Ala Ala Gly
Ala Gly Thr Thr Ala Cys Gly Gly Thr Gly Thr Cys Gly Gly Thr Gly Thr Thr Cys Gly Ala Gly
Gly Gly Thr Gly Cys Gly Thr Gly Ala Ala Ala Gly Ala Gly Thr Gly Thr Gly Thr Cys Ala Gly
Cys Gly Thr Cys Thr Gly Ala Cys Cys Gly Cys Gly Cys Gly Cys Gly Thr Ala Thr Cys Thr Gly Cys
Cys Gly Ala Ala Gly Thr Gly Thr Gly Gly Thr Cys Gly Thr Ala Thr Thr Ala Cys Ala Ala Cys Cys Thr
Gly Ala Thr Thr Cys Gly Thr Thr Gly Cys Cys Ala Ala Ala Gly Ala Ala Gly Ala Thr Gly Ala Thr
Gly Ala Ala Cys Thr Gly Gly Thr Gly Cys Ala Cys Gly Thr Gly Cys Ala Ala Ala Gly Thr Ala Ala
Ala Ala Cys Thr Gly Gly Thr Gly Cys Ala Ala Cys Gly Cys Gly Ala Ala Gly Ala Thr Gly Ala Thr
Ala Ala Ala Gly Ala Ala Ala Cys Thr Gly Thr Gly Cys Gly Cys Cys Ala Thr Cys Gly Cys Thr Ala Cys
Ala Ala Ala Gly Thr Ala Thr Ala Thr Cys Thr Gly Gly Ala Ala Ala Ala Ala Cys Gly Cys Ala Gly Cys
Cys Gly Gly Thr Thr Ala Thr Cys Gly Ala Thr Thr Ala Thr Thr Ala Thr Gly Ala Thr Ala Ala Ala Ala
Ala Gly Gly Cys Ala Thr Thr Cys Thr Gly Ala Ala Ala Cys Gly Cys Gly Thr Gly Ala Thr Gly Gly Gly
Ala Cys Cys Ala Thr Cys Gly Gly Thr Ala Thr Cys Gly Ala Thr Ala Ala Cys Gly Thr Gly Ala Thr
Thr Gly Cys Cys Gly Ala Gly Gly Thr Gly Cys Thr Gly Ala Ala Ala Ala Thr Cys Ala Thr Cys Gly
Gly Thr Cys Gly Gly Gly Cys Thr Cys Ala Gly Gly Cys Thr Gly Gly Thr Cys Gly Gly Thr Thr Ala
Cys Thr Ala Cys Ala Gly Ala Ala Cys Thr Ala Cys Cys Ala Gly Gly Thr Thr Ala Cys Thr Cys Gly
Gly Gly Thr Thr Ala Thr Cys Ala Gly Ala Ala Gly Gly Thr Gly Gly Cys Thr Ala Cys Cys Ala Ala Cys
Ala Ala Thr Ala Thr Ala Ala Thr Cys Cys Gly Cys Ala Gly Gly Gly Cys Gly Gly Cys Thr Ala Cys Ala
Ala Cys Ala Gly Cys Ala Gly Ala Ala Thr Ala Cys Cys Ala Ala Gly Gly Cys Gly Gly Thr Thr Ala Cys Ala
Thr Ala Cys Cys Ala Gly Cys Ala Ala Thr Ala Thr Ala Ala Thr Cys Cys Thr Cys Ala Gly Gly Gly Thr
Gly Thr Ala Cys Cys Ala Gly Gly Gly Thr Gly Gly Thr Thr Ala Ala Gly Thr Cys Gly Ala Cys Gly Cys

SEQ ID NO: 54
Met Met Ala Tyr Leu Val Phe Leu Gly Pro Pro Gly Ala Gly Lys Gly Thr Tyr Ala Lys Arg Leu Gln Glu Ile
Thr Gly Ile Pro His Ile Ser Thr Gly Asp Ile Phe Arg Asp Ile Val Lys Lys Glu Asn Asp Glu Leu Gly Lys
Lys Ile Lys Glu Ile Met Glu Arg Gly Glu Leu Val Pro Asp Glu Leu Val Asn Glu Val Val Lys Arg Arg Leu
Ser Glu Lys Ser Gly Cys Glu Arg Gly Phe Ile Leu Asp Gly Tyr Pro Arg Thr Val Ala Gln Ala Glu Phe Leu Asp
Gly Phe Leu Lys Thr Gln Asn Lys Glu Leu Thr Ala Ala Val Leu Phe Glu Val Pro Glu Glu Val Val Val Gln
Arg Leu Thr Ala Arg Arg Ile Cys Pro Lys Cys Gly Arg Ile Tyr Asn Leu Ile Ser Leu Pro Pro Lys Glu Asp
Glu Leu Cys Asp Asp Cys Lys Val Lys Leu Val Gln Arg Glu Asp Asp Lys Glu Thr Val Arg His Arg Tyr
Lys Val Tyr Leu Glu Lys Thr Gln Pro Val Ile Asp Tyr Tyr Asp Lys Lys Gly Ile Leu Lys Arg Val Asp Gly
Thr Ile Gly Ile Asp Asn Val Ile Ala Glu Val Leu Lys Ile Ile Gly Trp Ser Asp Lys Leu Ser Ser Met Asp
Ser Asn Gln Gly Asn Asn Gln Gln Asn Tyr Gln Gln Tyr Ser Gln Asn Gly Asn Gln Gln Gly Asn Asn Arg
Tyr Gln Gly Tyr Gln Ala Tyr Asn Ala Gln Ala Gln Pro Gly Gly Gly Tyr Tyr Gln Asn Tyr Gln Gly Tyr Ser
Gly Tyr Gln Gln Gly Gly Tyr Gln Gln Tyr Asn Pro Asp Ala Gly Tyr Gln Gln Tyr Asn Pro Gln Gly Gly
Tyr Gln Gln Tyr Asn Pro Gln Gly Gly Tyr Gln His Gln Phe Asn Pro Gln Gly Gly Arg Gly Asn Tyr Lys Asn
Phe Asn Tyr Asn Asn Asn Leu Gln Gly Tyr Gln Ala Gly

SEQ ID NO: 55
ggtaacaacc agcagaacta c

SEQ ID NO: 56
Gly Asn Asn Gln Gln Asn Tyr

SEQ ID NO: 57
atgatgatgg cgtctaagga cgctacatca agcgtggatg gcgctagtgg cgctggtcag ttggtaccgg aggttaatgc ttctgaccct
cttgcaatgg atcctgtagc aggttcttcg acagcagtcg cgactgctgg acaagttaat cctattgatc cctggataat taataatttt
gtgcaagccc cccaaggtga atttactatt tccccaaata ataccccggg tgatgttttt tttgatttga gtttgggtcc ccatctttaat
cctttcttgc tccatctatc acaaatgtat aatggttggg ttggtaacat gagagtcagg attatgctag ctggtaatgc ctttactgcg
gggagataa tagtttcctg catacccccct ggttttggtt cacataatct tactatagca caagcaactc tctttccaca tgtgattgct
gatgttagga ctctagaccc cattgaggtg ccttgggaag atgttaggaa tgttctcttt cataataatg atagaaatca acaaaccatg

```
cgccttgtgt gcatgctgta caccccctc cgcactggtg gtggtactgg tgattcttt gtagttgcag ggcgagttat gacttgcccc
agtcctgatt ttaatttctt gttttagtc cctcctacgg tggagcagaa aaccaggccc ttcacactcc caaatctgcc attgagttct
ctgtctaact cacgtgcccc tctcccaatc agtagtatgg gcatttcccc agacaatgtc cagagtgtgc agttccaaaa tggtcggtgt
actctggatg gccgcctggt tggcaccacc ccagtttcat tgtcacatgt tgccaagata agagggacct ccaatggcac tgtaatcaac
cttactgaat tggatggcac acctttcac cctttgacgg gccctgcccc cattggttt ccagacctcg gtggttgtga ttggcatatc
aatatgacac agtttggcca ttctagccag acccagtatg atgtagacac caccctgac actttgtcc cccatcttgg ttcaattcag
gcaaatggca ttggcagtgg taattatgtt ggtgttctta gctggatttc cccccatca caccgtctg gctcccaagt tgacctttgg
aagatcccca attatgggtc aagtattacg gaggcaacac atctagcccc ttctgtatac ccccctggtt tcggagaggt attggtcttt
ttcatgtcaa aaatgccagg tcctggtgct tataatttgc cctgtctatt accacaagag tacattcac atcttgctag tgaacaagcc
cctactgtag gtgaggctgc cctgctccac tatgttgacc ctgataccgg tcggaatctt ggggaattca aagcataccc tgatggtttc
ctcacttgtg tccccaatgg ggctagctcg gtccacaac agctgccgat caatgggtc tttgtctttg tttcatgggt gtccagattt
tatcaattaa agcctgtggg aactgccagc tcggcaagag gtaggcttgg tctgcgccga taa
```

SEQ ID NO: 58

```
Met Met Met Ala Ser Lys Asp Ala Thr Ser Ser Val Asp Gly Ala Ser Gly Ala Gly Gln Leu Val Pro Glu Val
Asn Ala Ser Asp Pro Leu Ala Met Asp Pro Val Ala Gly Ser Ser Thr Ala Val Ala Thr Ala Gly Gln Val Asn
Pro Ile Asp Pro Trp Ile Ile Asn Asn Phe Val Gln Ala Pro Gln Gly Glu Phe Thr Ile Ser Pro Asn Asn Thr
Pro Gly Asp Val Leu Phe Asp Leu Ser Leu Gly Pro His Leu Asn Pro Phe Leu Leu His Leu Ser Gln Met Tyr
Asn Gly Trp Val Gly Asn Met Arg Val Arg Ile Met Leu Ala Gly Asn Ala Phe Thr Ala Gly Lys Ile Ile Val
Ser Cys Ile Pro Pro Gly Phe Gly Ser His Asn Leu Thr Ile Ala Gln Ala Thr Leu Phe Pro His Val Ile Ala
Asp Val Arg Thr Leu Asp Pro Ile Glu Val Pro Leu Glu Asp Val Arg Asn Val Leu Phe His Asn Asn Asp Arg
Asn Gln Gln Thr Met Arg Leu Val Cys Met Leu Tyr Thr Pro Leu Arg Thr Gly Gly Gly Thr Gly Asp Ser Phe
Val Val Ala Gly Arg Val Met Thr Cys Pro Ser Pro Asp Phe Asn Phe Leu Phe Leu Val Pro Pro Thr Val Glu
Gln Lys Thr Arg Pro Phe Thr Leu Pro Asn Leu Pro Leu Ser Ser Leu Ser Asn Ser Arg Ala Pro Leu Pro Ile
Ser Ser Met Gly Ile Ser Pro Asp Asn Val Gln Asn Val Gln Phe Gln Asn Gly Arg Cys Thr Leu Asp Gly Arg
Leu Val Gly Thr Thr Pro Val Ser Leu Ser His Val Ala Lys Ile Arg Gly Thr Ser Asn Gly Thr Val Ile Asn
Leu Thr Glu Leu Asp Gly Thr Pro Phe His Pro Phe Gln Gly Pro Ala Pro Ile Gly Phe Pro Asp Leu Gly Gly
Cys Asp Trp His Ile Asn Met Thr Gln Phe Gly His Ser Ser Gln Thr Gln Tyr Asp Val Asp Thr Thr Pro Asp
Thr Phe Val Pro His Leu Gly Ser Ile Gln Ala Asn Gly Ile Gly Ser Gly Asn Tyr Val Gly Val Leu Ser Trp
Ile Ser Pro Pro Ser His Pro Ser Gly Ser Gln Val Asp Leu Trp Lys Ile Pro Asn Tyr Gly Ser Ser Ile Thr
Glu Ala Thr His Leu Ala Pro Ser Val Tyr Pro Pro Gly Phe Gly Gln Val Leu Val Phe Phe Met Ser Lys Met
Pro Gly Pro Gly Ala Tyr Asn Leu Pro Cys Leu Leu Pro Gln Gln Tyr Ile Ser His Leu Ala Ser Gln Gln Ala
Pro Thr Val Gly Glu Ala Ala Leu Leu His Tyr Val Asp Pro Asp Thr Gly Arg Asn Leu Gly Glu Phe Lys Ala
Tyr Pro Asp Gly Phe Leu Thr Cys Val Pro Asn Gly Ala Ser Ser Gly Pro Gln Gln Leu Pro Ile Asn Gly Val
Phe Val Phe Val Ser Trp Val Ser Arg Phe Tyr Gln Leu Lys Pro Val Gly Thr Ala Ser Ser Ala Arg Gly Arg
Leu Gly Leu Arg Arg
```

SEQ ID NO: 59

```
ctggctatgg acccggttgc tggttcttct accgctgttg ctaccgctgg tcaggttaac ccgatcgacc cgtggatcat caacaacttc
gttcaggctc cgcagggtga attcaccatc tctccgaaca caccccggg tgacgttctg ttcgacctgt ctctgggtcc gcacctgaac
ggtaaaatca tcgtttcttg catcccgccg ggtttcggtt ctcacaacct gaccatcgct caggctaccc tgttcccgca cgttatcgct
gacgttcgta ccctggaccc gatcgaagtt ccgctgaag acgttcgtaa cgttctgttc cacaacaacg accgtaacca gcagaccatg
cgtctggttt gcatgctgta caccccgctg cgtaccggtg gtggtaccgg tgactctttc gttgttgctg gtcgtgttat gacctgcccg
tctccggact tcaacttcct gttcctggtt ccgccgaccg ttgaacagaa aaccgtccg ttcaccctgc cgaacctgcc gctgtcttct
ctgtctaact ctcgtgctcc gctgccgatc tcttctatgg gtatctctcc ggacaacgtt cagtctgttc agttccagaa cggtcgttgc
accctgacg tcgtctggt tggtaccacc ccggtttctc tgtctcacgt tgctaaaatc cgtggtacct caacggtac cgttatcaac
ctgaccgaac tggacggtac cccgttccac ccgttcgaag gtccggctcc gatcggtttc ccggacctgg tggttgcga ctggcacatc
aacatgaccc agttcggtca ctcttctcag acccagtacg acgttgacac caccccggac accttcgttc cgcacctggg ttctatccag
gctaacggta tcggttctgg taactacgtt ggtgttctgt cttggatctc tccgccgtct caccgtctg gttctcaggt tgacctgtgg
aaaatcccga actacggttc ttctatcacc gaagctaccc acctggctcc gtctgtttac ccgccgggtt tcggtgaagt tctggttttc
ttcatgtcta aaatgccggg tccgggtgct tacaacctgc cgtgcctgct gccgcaggaa tatatctctc acctggcttc tgaacaggct
ccgaccgttg gtgaagctgc tctgctgcac tacgttgacc cggacaccgg tcgtaacctg ggtgaattca agcttaccc ggacggtttc
ctgacctgcg ttccgaacgg tgcttttct ggtccgcagc agctgccgat caacggtgtt ttcgttttcg ttcttgggt ttctcgtttc
taccagctga aaccggttgg taccgcttct tctgctcgtg gtcgtctggg tctgcgtcgt tag
```

SEQ ID NO: 60

```
ctggctatgg acccggttgc tggttcttct accgctgttg ctaccgctgg tcaggttaac ccgatcgacc cgtggatcat caacaacttc
gttcaggctc cgcagggtga attcaccatc tctccgaaca caccccggg tgacgttctg ttcgacctgt ctctgggtcc gcacctgaac
ggtaaaatca tcgtttcttg catcccgccg ggtttcggtt ctcacaacct gaccatcgct caggctaccc tgttcccgca cgttatcgct
gacgttcgta ccctggaccc gatcgaagtt ccgctgaag acgttcgtaa cgttctgttc cacaacaacg accgtaacca gcagaccatg
cgtctggttt gcatgctgta caccccgctg cgtaccggtg gtggtaccgg tgactctttc gttgttgctg gtcgtgttat gacctgcccg
tctccggact tcaacttcct gttcctggtt ccgccgaccg ttgaacagaa aaccgtccg ttcaccctgc cgaacctgcc gctgtcttct
ctgtctaact ctcgtgctcc gctgccgatc tcttctatgg gtatctctcc ggacaacgtt cagtctgttc agttccagaa cggtcgttgc
accctgacg tcgtctggt tggtaccacc ccggtttctc tgtctcacgt tgctaaaatc cgtggtacct aacggtac cgttatcaac
ctgaccgaac tggacggtac cccgttccac ccgttcgaag gtccggctcc gatcggtttc ccggacctgg tggttgcga ctggcacatc
aacatgaccc agttcggtca ctcttctcag acccagtacg acgttgacac caccccggac accttcgttc gcacctggg ttctatccag
gctaacggta tcggttctgg taactacgtt ggtgttctgt cttggatctc tccgccgtct caccgtctg gttctcaggt tgacctgtgg
tctggttttc ttcatgtcta aatgccggg tccgggtgct tacaacctgc cgtgcctgct gccgcaggaa tatatctctc acctggcttc
tgaacaggct ccgaccgttg gtgaagctgc tctgctgcac tacgttgacc cggacaccgg tcgtaacctg ggtgaattca agcttaccc
ggacggtttc ctgacctgcg ttccgaacgg tgcttttct ggtccgcagc agctgccgat caacggtgtt ttcgttttcg ttcttgggt
ttctcgtttc taccagctga aaccggttgg taccgcttct tctgctcgtg gtcgtctggg tctgcgtcgt atgatggcct atctggtttt
tcttggtcca ccggggcag gcaaaggtac ctatgcgaaa cgtttacagg aaatcaccgg catcccgcac attagcacgg gcgacatttt
tcgtgatatt gtcaaaaagg aaaatgacga attaggtaag aaaattaaag aaattatgga gcgcggcgag ttggtgccgg acgaactggt
```

-continued

SEQUENCE LISTING

```
gaatgaagtt gtcaaacgtc ggctgtctga aaaggattgc gaacgtggct ttatttttgga cggttacccg cgtacagtag ctcaggcaga
gtttctcgac ggcttcctga agactcagaa taaggagtta acggctgcgg tcctgttcga ggtgcctgaa gaggtggtcg ttcagcgtct
gaccgcgcgg cgtatcgcc cgaagtgtgg tcgtatttac aacctgattt cacttcctcc aaaagaagat gaactgtgtg atgactgcaa
agtaaaactg gtgcaacgcg aagatgataa agaggaaact gtgcgccatc gctacaaagt atatctggaa aaaacccaac cggttatcga
ttattatgat aaaaaaggca ttttgaaacg cgttgatggg accatcggca tcgataacgt gattgccgaa gttctcaaaa tcattgggtg
gagtgataaa
```

SEQ ID NO: 61

Met Met Met Ala Ser Lys Asp Ala Thr Ser Ser Val Asp Gly Ala Ser Gly Ala Gly Gln Leu Val Pro Gln Val
Asn Ala Ser Asp Pro Leu Ala Met Asp Pro Val Ala Gly Ser Ser Thr Ala Val Ala Thr Ala Gly Gln Val Asn
Pro Ile Asp Pro Trp Ile Ile Asn Asn Phe Val Gln Ala Pro Gln Gly Glu Phe Thr Ile Ser Pro Asn Asn Thr
Pro Gly Asp Val Leu Phe Asp Leu Ser Leu Gly Pro His Leu Asn Pro Phe Leu Leu His Leu Ser Gln Met Tyr
Asn Gly Trp Val Gly Asn Met Arg Val Arg Ile Met Leu Ala Gly Asn Ala Phe Thr Ala Gly Lys Ile Ile Val
Ser Cys Ile Pro Pro Gly Phe Gly Ser His Asn Leu Thr Ile Ala Gln Ala Thr Leu Phe Pro His Val Ile Ala
Asp Val Arg Thr Leu Asp Pro Ile Glu Val Pro Leu Glu Asp Val Arg Asn Val Leu Phe His Asn Asn Asp Arg
Asn Gln Gln Thr Met Arg Leu Val Cys Met Leu Tyr Thr Pro Leu Arg Thr Gly Gly Gly Thr Gly Asp Ser Phe
Val Val Ala Gly Arg Val Met Thr Cys Pro Ser Pro Asp Phe Asn Phe Leu Phe Leu Val Pro Pro Thr Val Glu
Gln Lys Thr Arg Pro Phe Thr Leu Pro Asn Leu Pro Leu Ser Ser Leu Ser Asn Ser Arg Ala Pro Leu Pro Ile
Ser Ser Met Gly Ile Ser Pro Asp Asn Val Gln Ser Val Gln Phe Gln Asn Gly Arg Cys Thr Leu Asp Gly Arg
Leu Val Gly Thr Thr Pro Val Ser Leu Ser His Val Ala Ile Val Arg Gly Thr Tyr Ser Asn Gly Thr Val Ile Asn
Leu Thr Glu Leu Asp Gly Thr Pro Phe His Pro Phe Gln Gly Pro Ala Pro Ile Gly Phe Pro Asp Leu Gly Gly
Cys Asp Trp His Ile Asn Met Thr Gln Phe Gly His Ser Ser Gln Thr Gln Tyr Asp Val Asp Thr Thr Pro Asp
Thr Phe Val Pro His Leu Gly Ser Ile Gln Ala Asn Gly Ile Gly Ser Gly Asn Tyr Val Gly Val Leu Ser Trp
Ile Ser Pro Pro Ser His Pro Ser Gly Ser Val Gln Val Asp Leu Trp Lys Ile Pro Asn Tyr Gly Ser Ser Ile Thr
Gln Ala Thr His Leu Ala Pro Ser Val Tyr Pro Pro Gly Phe Gly Gln Val Leu Val Phe Phe Met Ser Lys Met
Pro Gly Pro Gly Ala Tyr Asn Leu Pro Cys Leu Leu Pro Gln Gln Tyr Ile Ser His Leu Ala Ser Gln Gln Ala
Pro Thr Val Gly Glu Ala Ala Leu Leu His Tyr Val Asp Pro Asp Thr Gly Arg Asn Leu Gly Gln Phe Lys Ala
Tyr Pro Asp Gly Phe Leu Thr Cys Val Pro Asn Gly Ala Ser Ser Gly Pro Gln Gln Leu Pro Ile Asn Gly Val
Phe Val Phe Val Ser Trp Val Ser Arg Phe Tyr Gln Leu Lys Pro Val Gly Thr Ala Ser Ser Ala Arg Gly Arg
Leu Gly Leu Arg Arg Met Met Ala Tyr Leu Val Phe Leu Gly Pro Pro Gly Ala Gly Lys Gly Thr Tyr Ala Lys
Arg Leu Gln Glu Ile Thr Gly Ile Pro His Ile Ser Thr Gly Asp Ile Phe Arg Asp Ile Val Lys Lys Glu Asn
Asp Glu Leu Gly Lys Lys Leu Glu Ile Met Asp Arg Gly Gln Leu Val Pro Asp Glu Val Val Ile Ser Met Val
Val Lys Arg Leu Ser Gln Lys Asp Cys Glu Arg Gly Phe Ile Leu Asp Gly Tyr Pro Arg Thr Val Ala Gln
Ala Glu Phe Leu Asp Gly Phe Leu Lys Thr Gln Asn Lys Glu Leu Thr Ala Ala Val Leu Phe Glu Val Pro Glu
Glu Val Val Val Gln Arg Leu Thr Ala Arg Arg Ile Cys Pro Lys Cys Gly Arg Ile Tyr Asn Leu Ile Ser Leu
Leu Pro Pro Lys Glu Asp Glu Leu Cys Asp Asp Cys Lys Val Lys Leu Val Gln Arg Glu Asp Asp Lys Glu Glu
Thr Val Arg His Arg Tyr Lys Val Tyr Leu Glu Lys Thr Gln Pro Val Ile Asp Tyr Tyr Asp Lys Lys Gly Ile
Leu Lys Arg Val Asp Gly Thr Ile Gly Ile Asp Asn Val Ile Ala Glu Val Leu Lys Ile Ile Gly Trp Ser Asp
Lys

SEQ ID NO: 62

Met Ala Ser Asn Phe Thr Gln Phe Val Leu Val Asp Asn Gly Gly Thr Gly Asp Val Thr Val Ala Pro Ser Asn
Phe Ala Asn Gly Val Ala Glu Trp Ile Ser Ser Asn Ser Arg Ser Gln Ala Tyr Lys Val Thr Cys Ser Val Arg
Gln Ser Ser Ala Gln Asn Arg Lys Tyr Thr Ile Lys Val Glu Val Pro Lys Val Ala Thr Gln Thr Val Gly Gly
Val Glu Leu Pro Val Ala Ala Trp Arg Ser Tyr Leu Asn Met Glu Leu Thr Ile Pro Ile Phe Ala Thr Asn Ser
Asp Cys Glu Leu Ile Val Lys Ala Met Gln Gly Leu Leu Lys Asp Gly Asn Pro Ile Pro Ser Ala Ile Ala Ala
Asn Ser Gly Ile Tyr

SEQ ID NO: 63

Ser Lys Thr Ile Val Leu Ser Val Gly Glu Ala Thr Arg Thr Leu Thr Glu Ile Gln Ser Thr Ala Asp Arg Gln
Ile Phe Glu Glu Lys Val Gly Pro Leu Val Gly Arg Leu Arg Leu Thr Ala Ser Leu Arg Gln Asn Gly Ala Lys
Thr Ala Tyr Arg Val Asn Leu Lys Leu Asp Gln Ala Asp Val Val Asp Cys Ser Thr Ser Val Cys Gly Glu Leu
Pro Lys Val Arg Tyr Thr Gln Val Trp Ser His Asp Val Thr Ile Val Ala Asn Ser Thr Glu Ala Ser Arg Lys
Ser Leu Tyr Asp Leu Thr Lys Ser Leu Val Val Gln Ala Thr Ser Glu Asp Leu Val Val Asn Leu Val Pro Leu
Gly Arg

SEQ ID NO: 64

Met Ser Lys Thr Ile Val Leu Ser Val Gly Glu Ala Thr Arg Thr Leu Thr Glu Ile Gln Ser Thr Ala Asp Arg
Gln Ile Phe Glu Glu Lys Val Gly Pro Leu Val Gly Arg Leu Arg Leu Thr Ala Ser Leu Arg Gln Asn Gly Ala
Lys Thr Ala Tyr Arg Val Asn Leu Lys Leu Asp Gln Ala Asp Val Val Asp Ser Gly Leu Pro Lys Val Arg Tyr
Thr Gln Val Trp Ser His Asp Val Thr Ile Val Ala Asn Ser Thr Glu Ala Ser Arg Lys Ser Leu Tyr Asp Leu
Thr Lys Ser Leu Val Ala Thr Ser Gln Val Glu Asp Val Val Asn Leu Val Pro Leu Gly Arg Tyr Gly Leu Asp
Lys Thr Ile Val Leu Ser Val Gly Glu Ala Thr Arg Thr Leu Thr Glu Ile Gln Ser Thr Ala Asp Arg Gln Ile
Phe Glu Glu Lys Val Gly Pro Leu Val Gly Arg Leu Arg Leu Thr Ala Ser Leu Arg Gln Asn Gly Ala Lys Thr
Ala Tyr Arg Val Asn Leu Lys Leu Asp Gln Ala Asp Val Val Asp Ser Gly Leu Pro Lys Val Arg Tyr Thr Gln
Val Trp Ser His Asp Val Thr Ile Val Ala Asn Ser Thr Glu Ala Ser Arg Lys Ser Leu Tyr Asp Leu Thr Lys
Ser Leu Val Ala Thr Ser Gln Val Glu Asp Leu Val Val Asn Leu Val Pro Leu Gly Arg

SEQ ID NO: 65

Met Lys Leu Leu Lys Val Ala Ala Ile Ala Ala Ile Val Phe Ser Gly Ser Ala Leu Ala Gly Val Val Pro Gln
Tyr Gly Gly Gly Asn His Gly Gly Gly Gly Asn Asn Ser Gly Pro Asn Ser Glu Leu Asn Ile Tyr Gln Tyr
Gly Gly Gly Asn Ser Ala Leu Ala Leu Gln Thr Asp Ala Arg Asn Ser Asp Ser Leu Thr Phe Ile Thr His Gly
Gly Asn Gly Ala Asp Val Gly Gln Gly Ser Asp Asp Ser Ser Ile Asp Leu Thr Gln Arg Gly Phe Gly Asn Ser
Ala Thr Leu Asp Gln Trp Asn Gly Lys Asn Ser Glu Met Thr Val Lys Gln Phe Gly Gly Gly Asn Gly Ala Ala
Val Asp Gln Thr Ala Ser Asn Ser Ser Val Asn Val Thr Gln Val Gly Phe Gly Asn Asn Ala Thr Ala His Gln
Tyr

SEQUENCE LISTING

SEQ ID NO: 66
Met Lys Leu Leu Lys Val Ala Ala Phe Ala Ala Ile Val Val Ser Gly Ser Ala Leu Ala Gly Val Val Pro Gln
Trp Gly Gly Gly Asn His Asn Gly Gly Asn Ser Ser Gly Pro Asp Ser Thr Leu Ser Ile Tyr Gln Gly
Gly Ser Ala Asn Ala Ala Leu Ala Leu Gln Ser Asp Ala Arg Lys Ser Glu Thr Thr Ile Thr Gln Ser Gly Tyr
Gly Asn Gly Ala Asp Val Gly Gln Gly Ala Asn Ser Thr Ile Glu Leu Thr Gln Asn Gly Phe Arg Asn Asn
Ala Thr Ile Asp Gln Trp Asn Ala Lys Asn Ser Asp Ile Thr Val Gly Gln Tyr Gly Gly Asn Asn Ala Ala Leu
Val Asn Gln Thr Ala Ser Asp Ser Ser Val Met Val Arg Gln Val Gly Phe Gly Asn Asn Ala Thr Ala Asn Gln
Tyr

SEQ ID NO: 67
Met Met Ala Tyr Leu Val Phe Leu Gly Pro Pro Gly Ala Gly Lys Gly Thr Tyr Ala Lys Arg Ile Gln Glu Lys
Thr Gly Ile Pro His Ile Ser Thr Gly Asp Ile Phe Arg Asp Ile Val Lys Lys Glu Asn Asp Glu Leu Gly Lys
Lys Ile Lys Glu Ile Met Glu Lys Gly Glu Leu Val Pro Asp Glu Leu Val Asn Glu Val Val Lys Arg Arg Leu
Ser Glu Lys Asp Cys Glu Lys Gly Phe Ile Leu Asp Gly Tyr Pro Arg Thr Val Ala Gln Ala Glu Phe Leu Asp
Ser Phe Leu Glu Ser Gln Asn Lys Gln Leu Thr Ala Ala Val Leu Phe Asp Val Pro Glu Asp Val Val Val Gln
Arg Leu Thr Ser Arg Arg Ile Cys Pro Lys Cys Gly Arg Ile Tyr Asn Met Ile Ser Leu Pro Pro Lys Glu Asp
Glu Leu Cys Asp Asp Cys Lys Val Lys Leu Val Gln Arg Asp Asp Asp Lys Glu Glu Thr Val Arg His Arg Tyr
Lys Val Tyr Leu Glu Lys Thr Gln Pro Val Ile Asp Tyr Tyr Gly Lys Lys Gly Ile Leu Lys Arg Val Asp Gly
Thr Ile Gly Ile Asp Asn Val Val Ala Glu Val Leu Lys Ile Ile Gly Trp Ser Asp Lys Gly Ser Gly Val Val
Pro Gln Tyr Gly Gly Gly Gly Asn His Gly Gly Gly Gly Asn Asn Ser Gly Pro Asn Ser Gly Leu Asn Ile Tyr
Gln Tyr Gly Gly Gly Asn Ser Ala Leu Ala Leu Gln Thr Asp Ala Arg Asn Ser Asp Leu Thr Ile Thr Gln His
Gly Gly Gly Asn Gly Ala Asp Val Gly Gln Ser Asp Asp Ser Ser Ile Asp Leu Thr Gln Arg Gly Phe Gly
Asn Ser Ala Thr Leu Asp Gln Trp Asn Gly Lys Asn Ser Glu Met Thr Val Lys Gln Phe Gly Gly Gly Asn Gly
Ala Ala Val Asp Gln Thr Ala Ser Asn Ser Ser Val Asn Val Thr Gln Val Gly Phe Gly Asn Asn Ala Thr Ala
His Gln Tyr

SEQ ID NO: 68
Met Gln Phe Ser Thr Leu Thr Thr Val Phe Ala Leu Val Ala Ala Ala Val Ala Ala Pro His Gly Ser Ser Gly
Gly Asn Asn Pro Val Cys Ser Ala Gln Asn Asn Gln Val Cys Cys Asn Gly Leu Leu Ser Cys Ala Val Gln Val
Leu Gly Ser Asn Cys Asn Gly Asn Ala Tyr Cys Cys Asn Thr Glu Ala Pro Thr Gly Thr Leu Ile Asn Val Ala
Leu Leu Asn Cys Val Lys Leu Leu

SEQ ID NO: 69
Met Lys Phe Ser Leu Ala Ala Val Ala Leu Leu Gly Ala Val Ser Ala Leu Pro Ala Asn Glu Lys Arg Gln
Ala Tyr Ile Pro Cys Ser Gly Leu Tyr Gly Thr Ser Gln Cys Cys Ala Thr Asp Val Leu Gly Val Ala Asp Leu
Asp Cys Gly Asn Pro Pro Ser Ser Pro Thr Ala Asp Asn Phe Ser Ala Val Cys Ala Glu Ile Gly Glh Arg
Ala Arg Cyn Cys Val Leu Pro Ile Leu Asp Gln Gly Ile Leu Cys Asn Thr Pro Thr Gly Val Gln Asp

SEQ ID NO: 70
Val Pro Pro Pro Gly Asp Leu Ser Ile Lys Ser Lys Leu Lys Gln Val Gly Ala Thr Ala Gly Asn Ala Ala Val
Thr Thr Thr Gly Thr Ser Gly Ser Gly Val Val Lys Cys Val Val Arg Thr Pro Thr Ser Val Glu Lys Lys
Ala Ala Val Gly Asn Thr Gly Leu Ser Ala Val Ser Ala Ser Ala Ala Asn Gly Phe Phe Lys Asn Leu Gly Lys
Ala Thr Thr Glu Val Lys Thr Thr Lys Asp Gly Thr Val Lys Thr Lys Thr Ala Gly Lys Gly Lys Thr Gly
Gly Thr Ala Thr Thr Ile Gln Ile Ala Asp Ala Asn Gly Gly Val Ser Glu Lys Ser Leu Lys Leu Asp Leu Leu
Thr Asp Gly Leu Lys Phe Val Lys Val Thr Glu Lys Lys Gln Gly Thr Ala Thr Ser Ser Ser Gly His Lys Ala
Ser Gly Val Gly His Ser Val Phe Lys Val Leu Asn Glu Ala Glu Thr Glu Leu Glu Leu Lys Gly Leu

SEQ ID NO: 71
Met Lys Trp Phe Leu Phe Leu Leu Thr Thr Ala Val Leu Ala Ala Val Val Ser Ala His Glu Glu Asp Gly Val
Cys Asn Ser Asn Ala Pro Cys Tyr His Cys Asp Ala Asn Gly Glu Asn Cys Ser Cys Asn Cys Glu Leu Phe Asp
Cys Glu Ala Lys Lys Pro Asp Gly Ser Tyr Ala His Pro Cys Arg Arg Cys Asp Ala Asn Asn Ile Cys Lys Cys
Ser Cys Thr Ala Ile Pro Cys Asn Glu Asp His Pro Cys His His Cys His Glu Glu Asp Asp Gly Asp Thr His
Cys His Cys Ser Gly Val His Ser His His Ala Asp Asp Cys Gly Cys Ser Lys Tyr Lys Ala Pro
Cys Trp Arg Cys Glu Tyr Asn Ala Asp Leu Lys His Asp Val Cys Gly Cys Glu Cys Ser Lys Leu Pro Cys Asn
Asp Glu His Pro Cys Tyr Arg Lys Gly Gly Val Val Ser Cys Ala Cys Lys Thr Ile Thr Cys Asn Glu Asp
His Pro Cys Tyr His Ser Tyr Glu Glu Asp Gly Val Thr Lys Ser Asp Cys Asp Cys Glu His Ser Pro Gly Pro
Ser Glu

SEQ ID NO: 72
Met Arg Val Leu Val Ile Asn Ser Gly Ser Ser Ser Ile Lys Tyr Glh Leu Ile Glu Met Glu Gly Glu Lys Val
Leu Cys Lys Gly Ile Ala Lys Ile Gly Ile Glu Gly Ser Arg Leu Val His Arg Val Gly Asp Glu Lys His
Val Ile Glu Arg Glu Leu Pro Asp His Glu Glu Ala Leu Lys Leu Ile Leu Asn Thr Leu Val Asp Glu Lys Leu
Gly Val Ile Lys Asp Leu Lys Glu Ile Asp Ala Val Gly His Arg Val Val His Gly Gly Glu Arg Phe Lys Glu
Ser Val Leu Val Asp Glu Glu Val Leu Lys Ala Ile Glu Glu Val Ser Pro Leu Ala Pro Leu His Asn Pro Ala
Asn Leu Met Gly Ile Lys Ala Ala Met Lys Leu Leu Pro Gly Val Pro Asn Val Ala Val Phe Asp Thr Ala Phe
His Gln Thr Ile Pro Gln Lys Ala Tyr Leu Tyr Ala Ile Pro Tyr Glu Tyr Tyr Glu Lys Tyr Lys Ile Arg Arg
Tyr Gly Phe His Gly Thr Ser His Arg Tyr Val Ser Lys Arg Ala Ala Glu Ile Leu Gly Lys Lys Leu Glu Glu
Leu Lys Ile Ile Thr Cys His Ile Gly Asn Gly Ala Ser Val Ala Ala Val Lys Tyr Gly Lys Cys Val Asp Thr
Ser Met Gly Phe Thr Pro Leu Glu Gly Leu Val Met Gly Thr Arg Ser Gly Asp Leu Asp Pro Ala Ile Pro Phe
Phe Ile Met Glu Lys Glu Gly Ile Ser Pro Gln Glu Met Tyr Asp Ile Leu Asn Lys Lys Ser Gly Val Tyr Gly
Leu Ser Lys Gly Phe Ser Ser Asp Met Arg Asp Ile Glu Glu Ala Ala Leu Lys Gly Asp Glu Trp Cys Lys Leu
Val Leu Glu Ile Tyr Asp Tyr Arg Ile Ala Lys Tyr Ile Gly Ala Tyr Ala Ala Met Asn Gly Val Asp Ala
Ile Val Phe Thr Ala Gly Val Gly Gln Asn Ser Pro Ile Thr Arg Glu Asp Val Cys Ser Tyr Leu Glu Phe Leu
Gly Val Lys Leu Asp Lys Gln Lys Asn Glu Glu Thr Ile Arg Gly Lys Glu Gly Ile Ile Ser Thr Pro Asp Ser
Arg Val Lys Val Leu Val Val Pro Thr Asn Glu Glu Leu Met Ile Ala Arg Asp Thr Lys Glu Ile Val Gln Lys
Ile Gly Arg Val Pro Pro Pro Cys Asp Leu Ser Ile Lys Ser Lys Leu Lys Gln Val Gly Ala Thr Ala Gly Asn
Ala Ala Val Thr Thr Thr Gly Thr Thr Ser Gly Ser Gly Val Val Lys Cys Val Val Arg Thr Pro Thr Ser Val

SEQUENCE LISTING

```
Gln Lys Lys Ala Ala Val Gly Asn Thr Gly Leu Ser Ala Val Ser Ala Ser Ala Ala Asn Gly Phe Phe Lys Asn
Leu Gly Lys Ala Thr Thr Gln Val Lys Thr Thr Lys Asp Gly Thr Lys Val Lys Thr Lys Thr Ala Gly Lys Gly
Lys Thr Gly Gly Thr Ala Thr Thr Ile Gln Ile Ala Asp Ala Asn Gly Gly Val Ser Glu Lys Ser Leu Lys Leu
Asp Leu Leu Thr Asp Gly Leu Lys Phe Val Lys Val Thr Gln Lys Lys Gln Gly Thr Ala Thr Ser Ser Ser Gly
His Lys Ala Ser Gly Val Gly His Ser Val Phe Lys Val Leu Asn Gln Ala Gln Thr Gln Leu Gln Leu Lys Gly
Leu
```

SEQ ID NO: 73
```
Val Pro Pro Cys Asp Leu Ser Ile Lys Ser Lys Leu Lys Gln Val Gly Ala Thr Ala Gly Asn Ala Ala Val
Thr Thr Thr Gly Thr Thr Ser Gly Ser Gly Val Val Lys Cys Val Val Arg Thr Pro Thr Ser Val Gln Lys Lys
Ala Ala Ala Gly Asn Thr Gly Leu Ser Ala Val Ser Ala Ser Ala Ala Asn Gly Phe Phe Lys Asn Leu Gly Lys
Ala Thr Thr Gln Val Lys Thr Thr Lys Asp Gly Thr Lys Val Lys Thr Lys Thr Ala Gly Lys Gly Lys Thr Gly
Gly Thr Ala Thr Thr Ile Gln Ile Ala Asp Ala Asn Gly Gly Val Ser Gln Lys Ser Leu Lys Leu Asp Leu Leu
Thr Asp Gly Leu Lys Phe Val Lys Val Thr Gln Lys Lys Gln Gly Thr Ala Thr Ser Ser Ser Gly His Lys Ala
Ser Gly Val Gly His Ser Val Phe Lys Val Leu Gln Ala Gln Thr Glu Leu Gln Leu Lys Gly Leu Met Arg Val
Leu Val Ile Asn Ser Gly Ser Ser Ser Ile Lys Tyr Gln Leu Ile Glu Met Gln Gly Gln Val Leu Cys Lys Lys
Gly Ile Ala Gln Arg Ile Gly Ile Gln Gly Ser Arg Leu Val His Arg Val Gly Asp Gln Lys His Val Ile Gln
Arg Gln Leu Pro Asp His Glu Gln Ala Leu Lys Leu Ile Leu Asn Thr Leu Val Asp Gln Lys Leu Gly Val Ile
Lys Asp Leu Lys Gln Ile Asp Ala Val Gly His Arg Val His Gly Gly Gln Arg Phe Lys Gln Ser Val Leu
Val Asp Gln Gln Val Leu Lys Ala Ile Glu Gln Val Ser Gly Pro Leu Ile His Asn Pro Ala Asn Leu Met
Gly Ile Lys Ala Ala Met Lys Leu Leu Pro Gly Val Pro Asn Val Ala Val Phe Asp Thr Ala Phe His Gln Thr
Ile Pro Gln Lys Ala Tyr Leu Tyr Ala Ile Pro Tyr Gln Tyr Tyr Gln Lys Tyr Lys Ile Arg Arg Tyr Gly Phe
His Gly Thr Ser His Arg Tyr Val Ser Lys Arg Ala Ala Gln Ile Leu Gly Lys Lys Leu Gln Gln Leu Lys Ile
Ile Thr Cys His Ile Gly Asn Gly Ala Ser Val Ala Ala Val Lys Tyr Gly Lys Cys Val Asp Thr Ser Met Gly
Phe Thr Pro Leu Gln Gly Leu Val Met Gly Thr Arg Ser Gly Asp Leu Asp Pro Ala Ile Pro Phe Phe Ile Met
Gln Lys Gln Gly Ile Ser Pro Gln Gln Met Tyr Asp Ile Leu Asn Lys Lys Ser Gly Val Tyr Gly Leu Ser Lys
Gly Phe Ser Ser Asp Met Arg Asp Ile Glu Gln Ala Ala Leu Lys Gly Asp Gln Trp Cys Lys Leu Val Leu Gln
Ile Tyr Asp Tyr Arg Ile Lys Tyr Ile Gly Ala Tyr Ala Ala Met Asn Gly Val Asp Ala Ile Val Phe
Thr Ala Gly Val Gly Gln Asn Ser Pro Ile Thr Arg Glu Asp Val Cys Ser Tyr Leu Gln Phe Leu Gly Val Lys
Leu Asp Lys Gln Lys Asn Gln Gln Thr Ile Arg Gly Lys Glu Gly Ile Ile Ser Thr Pro Asp Ser Arg Val Lys
Val Leu Val Val Pro Thr Asn Glu Gln Leu Met Ile Ala Arg Asp Thr Lys Glu Ile Val Glu Lys Ile Gly Arg
```

SEQ ID NO: 74
```
Met Lys Tyr Thr Leu Ala Leu Leu Phe Leu Thr Ala Ile Ile Ala Thr Phe Val Ala Ala His Lys His His Asp
His Gly Lys Ser Cys Ser Lys Ser His Pro Cys Tyr His Gly His Thr Asp Cys Glu Cys Asn His His Asp
Asp Gly Asn Arg Ser His Arg Gly Trp His Lys Val His Gly Val Val Ser Gly Asn Gly Asn Gly Asn Leu Leu
Thr Pro Gly Asn Gln Lys His Pro Gly Trp Arg Arg His Gly Lys Lys His Gly Leu His Arg Lys Phe His Gly
Asn Ala Cys Asn Cys Asp Arg Leu Val Cys Asn Ala Lys His Pro Cys Trp His Lys His Cys Asp Gly Phe
Cys
```

SEQ ID NO: 75
```
Ser Lys Leu Pro Cys Asn Asp Glu His Pro Gly Tyr Arg Lys Glu Gly Gly Val Val Ser Gly Asp Cys Lys
```

SEQ ID NO: 76
```
Ser Lys Leu Pro Ser Asn Asp Glu His Pro Ser Tyr Arg Lys Glu Gly Gly Val Val Ser Asp Ser Lys
```

SEQ ID NO: 77
```
Lys Thr Ile Thr Cys Asn Glu Asp His Pro Cys Tyr His Ser Tyr Glu Glu Asp Gly Val Thr Lys Ser Asp Cys
Asp Cys Glu
```

SEQ ID NO: 78
```
Met Arg Ile Ile Leu Leu Gly Ala Pro Gly Ala Gly Lys Gly Thr Gln Ala Gln Phe Ile Met Glu Lys Tyr Gly
Ile Pro Gln Ile Ser Thr Gly Asp Met Leu Arg Ala Ala Val Lys Ser Gly Ser Glu Leu Gly Lys Gln Ala Lys
Asp Ile Met Asp Ala Gly Lys Leu Val Thr Asp Glu Leu Val Ile Ala Leu Val Lys Glu Arg Ile Ala Gln Glu
Asp Cys Arg Asn Gly Phe Leu Leu Asp Gly Phe Pro Arg Thr Ile Pro Gln Ala Asp Ala Met Lys Glu Ala Gly
Ile Asn Val Asp Tyr Val Leu Glu Phe Asp Val Pro Asp Glu Leu Ile Val Asp Arg Ile Val Gly Arg Arg Val
His Ala Pro Ser Gly Arg Val Tyr His Val Lys Phe Asn Pro Pro Lys Val Glu Gly Lys Asp Asp Val Thr Gly
Glu Glu Leu Thr Thr Arg Lys Asp Asp Gln Glu Glu Thr Val Arg Lys Arg Leu Val Glu Tyr His Gln Met Thr
Ala Pro Leu Ile Gly Tyr Tyr Ser Lys Glu Ala Glu Ala Gly Asn Thr Lys Tyr Ala Lys Val Asp Gly Thr Lys
Pro Val Ala Glu Val Arg Ala Asp Leu Glu Lys Ile Leu Gly
```

SEQ ID NO: 79
```
Met Lys Lys Thr Lys Ile Val Cys Thr Ile Gly Pro Lys Thr Glu Ser Glu Glu Met Leu Ala Lys Met Leu Asp
Ala Gly Met Asn Val Met Arg Leu Asn Phe Ser His Gly Asp Tyr Ala Glu His Gly Gln Arg Ile Gln Asn Leu
Arg Asn Val Met Ser Lys Thr Gly Lys Thr Ala Ala Ile Leu Leu Asp Thr Lys Gly Pro Glu Ile Arg Thr Met
Lys Leu Glu Gly Gly Asn Asp Val Ser Leu Lys Ala Gly Gln Thr Phe Thr Phe Thr Thr Asp Lys Ser Val Ile
Gly Asn Ser Glu Met Val Ala Thr Tyr Glu Gly Phe Thr Thr Asp Leu Ser Val Gly Asn Thr Val Leu Val
Asp Asp Gly Leu Ile Gly Met Glu Val Thr Ala Ile Glu Gly Asn Lys Val Ile Gly Lys Val Leu Asn Asn Gly
Asp Leu Gly Glu Asn Lys Gly Val Asn Leu Pro Gly Val Ser Ile Ala Leu Pro Ala Leu Ala Glu Lys Asp Lys
Gln Asp Leu Ile Phe Gly Cys Glu Gln Gly Val Asp Phe Val Ala Ala Ser Phe Ile Arg Lys Arg Ser Asp Val
Ile Glu Ile Arg Glu His Leu Lys Ala His Gly Gly Gln Asn Ile His Ile Ile Ser Lys Ile Glu Asn Gln Glu
Gly Leu Asn Asn Phe Asp Glu Ile Leu Ala Ala Ser Asp Gly Ile Met Val Ala Arg Gly Asp Leu Gly Val Glu
Ile Pro Val Glu Glu Val Ile Phe Ala Gln Lys Met Met Ile Glu Lys Cys Ile Arg Ala Arg Lys Val Val Ile
Thr Ala Thr Gln Met Leu Asp Ser Met Ile Lys Asn Pro Arg Pro Thr Arg Ala Glu Ala Gly Asp Val Ala Asn
Ala Ile Leu Asp Gly Thr Asp Ala Val Met Leu Ser Gly Glu Ser Ala Lys Gly Lys Tyr Pro Leu Glu Ala Val
Ser Ile Met Ala Thr Ile Cys Glu Arg Thr Asp Arg Val Met Asn Ser Arg Leu Glu Phe Asn Asn Asp Asn Arg
Lys Leu Arg Ile Thr Glu Ala Val Cys Arg Gly Ala Val Glu Thr Ala Glu Lys Leu Asp Ala Pro Leu Ile Val
```

```
Val Ala Thr Gln Gly Gly Lys Ser Ala Arg Ala Val Arg Lys Tyr Phe Pro Asp Ala Thr Ile Leu Ala Leu Thr
Thr Asn Glu Lys Thr Ala His Gln Leu Val Leu Ser Lys Gly Val Val Pro Gln Leu Val Lys Glu Ile Thr Ser
Thr Asp Asp Phe Tyr Arg Leu Gly Lys Glu Leu Ala Leu Gln Ser Gly Leu Ala His Lys Gly Asp Val Val Val
Met Val Ser Gly Ala Leu Val Pro Ser Gly Thr Thr Asn Thr Ala Ser Val His Val Leu
```

SEQ ID NO: 80

```
Met Ser Ser Lys Leu Val Leu Val Leu Asn Cys Gly Ser Ser Leu Lys Phe Ala Ile Ile Asp Ala Val Asn
Gly Glu Glu Tyr Leu Ser Gly Leu Ala Glu Cys Phe His Leu Pro Glu Ala Arg Ile Lys Trp Lys Met Asp Gly
Asn Lys Gln Glu Ala Ala Leu Gly Ala Gly Ala Ala His Ser Glu Ala Leu Asn Phe Ile Val Asn Thr Ile Leu
Ala Gln Lys Pro Gly Leu Ser Ala Gln Leu Thr Ala Ile Gly His Arg Ile Val His Gly Gly Glu Lys Tyr Thr
Ser Ser Val Ile Asp Glu Ser Val Ile Gln Gly Ile Lys Asp Ala Ala Ser Phe Ala Pro Leu His Asn Pro
Ala His Leu Ile Gly Ile Glu Glu Ala Leu Lys Ser Phe Pro Gln Leu Lys Asp Lys Asn Val Ala Val Phe Asp
Thr Ala Phe His Gln Thr Met Pro Glu Glu Ser Tyr Leu Tyr Ala Leu Pro Tyr Asn Leu Tyr Lys Glu His Gly
Ile Arg Arg Tyr Gly Ala His Gly Thr Ser His Phe Tyr Val Thr Gln Glu Ala Ala Lys Met Leu Asn Lys Pro
Val Glu Glu Leu Asn Ile Ile Thr Cys His Leu Gly Asn Gly Gly Ser Val Ser Ala Ile Arg Asn Gly Lys Cys
Val Asp Thr Ser Met Gly Leu Thr Pro Leu Glu Gly Leu Val Met Gly Thr Arg Ser Gly Asp Ile Asp Pro Ala
Ile Ile Phe His Leu His Asp Thr Leu Gly Met Ser Val Asp Ala Ile Asn Lys Leu Leu Thr Lys Glu Ser Gly
Leu Leu Gly Leu Thr Glu Val Thr Ser Asp Cys Arg Tyr Val Glu Asp Asn Tyr Ala Thr Lys Glu Asp Ala Lys
Arg Ala Met Asp Val Tyr Cys His Arg Leu Ala Lys Tyr Ile Gly Ala Tyr Thr Ala Leu Met Asp Gly Arg Leu
Asp Ala Val Val Phe Thr Gly Gly Ile Gly Glu Asn Ala Ala Met Val Arg Glu Leu Ser Leu Gly Lys Leu Gly
Val Leu Gly Phe Glu Val Asp His Glu Arg Asn Leu Ala Ala Arg Phe Gly Lys Ser Gly Phe Ile Asn Lys Glu
Gly Thr Arg Pro Ala Val Val Ile Pro Thr Asn Glu Glu Leu Val Ile Ala Gln Asp Ala Ser Arg Leu Thr Ala
```

SEQ ID NO: 81

```
Met Lys Asn Lys Val Val Val Val Thr Gly Val Pro Gly Val Gly Ser Thr Thr Ser Ser Gln Leu Ala Met Asp
Asn Leu Arg Lys Glu Gly Val Asn Tyr Lys Met Val Ser Phe Gly Ser Val Met Phe Glu Val Ala Lys Glu Glu
Asn Leu Val Ser Asp Arg Asp Gln Met Arg Lys Met Asp Pro Glu Thr Gln Lys Arg Ile Gln Lys Met Ala Gly
Arg Lys Ile Ala Glu Met Ala Lys Glu Ser Pro Val Ala Val Asp Thr His Ser Thr Val Ser Thr Pro Lys Gly
Tyr Leu Pro Gly Leu Pro Ser Trp Val Leu Asn Glu Leu Asn Pro Asp Leu Ile Ile Val Val Glu Thr Thr Gly
Asp Glu Ile Leu Met Arg Arg Met Ser Asp Glu Thr Arg Val Arg Asp Leu Asp Thr Ala Ser Thr Ile Glu Gln
His Gln Phe Met Asn Arg Cys Ala Ala Met Ser Tyr Gly Val Leu Thr Gly Ala Thr Val Lys Ile Val Gln Asn
Arg Asn Gly Leu Leu Asp Gln Ala Val Glu Glu Leu Thr Asn Val Leu Arg
```

SEQ ID NO: 82

```
Met Lys Asn Lys Leu Val Val Val Thr Gly Val Pro Gly Val Gly Gly Thr Thr Ile Thr Gln Lys Ala Met Glu
Lys Leu Ser Glu Glu Gly Ile Asn Tyr Lys Met Val Asn Phe Gly Thr Val Met Phe Glu Val Ala Gln Glu Glu
Asn Leu Val Glu Asp Arg Asp Gln Met Arg Lys Leu Asp Pro Asp Thr Gln Lys Arg Ile Gln Lys Leu Ala Gly
Arg Lys Ile Ala Glu Met Val Lys Glu Ser Pro Val Val Val Asp Thr His Ser Thr Ile Lys Thr Pro Lys Gly
Tyr Leu Pro Gly Leu Pro Val Trp Val Leu Asn Glu Leu Asn Pro Asp Ile Ile Ile Val Val Glu Thr Ser Gly
Asp Glu Ile Leu Ile Arg Arg Leu Asn Asp Glu Thr Arg Asn Arg Asp Leu Glu Thr Thr Ala Gly Ile Glu Glu
His Gln Ile Met Asn Arg Ala Ala Ala Met Thr Tyr Gly Val Leu Thr Gly Ala Thr Val Lys Ile Ile Gln Asn
Lys Asn Asn Leu Leu Asp Tyr Ala Val Glu Glu Leu Ile Ser Val Leu Arg
```

SEQ ID NO: 83

```
Met Asn Ile Val Leu Met Gly Leu Pro Gly Ala Gly Lys Gly Thr Gln Ala Asp Arg Ile Val Glu Lys Tyr Gly
Thr Pro His Ile Ser Thr Gly Asp Met Phe Arg Ala Ala Ile Gln Glu Gly Thr Glu Leu Gly Val Lys Ala Lys
Ser Phe Met Asp Gln Gly Ala Leu Val Pro Asp Glu Val Thr Ile Gly Ile Val Arg Glu Arg Leu Ser Lys Ser
Asp Cys Asp Asn Gly Phe Leu Leu Asp Gly Phe Pro Arg Thr Val Pro Gln Ala Glu Ala Leu Asp Gln Leu Leu
Ala Asp Met Gly Arg Lys Ile Glu His Val Leu Asn Ile Gln Val Glu Lys Glu Leu Ile Ala Arg Leu Thr
Gly Arg Arg Ile Cys Lys Val Cys Gly Thr Ser Tyr His Leu Leu Phe Asn Pro Pro Gln Val Glu Gly Lys Cys
Asp Lys Asp Gly Gly Glu Leu Tyr Gln Arg Ala Asp Asp Asn Pro Asp Thr Val Thr Asn Arg Leu Glu Val Asn
Met Asn Gln Thr Ala Pro Leu Leu Ala Phe Tyr Asp Ser Lys Glu Val Leu Val Asn Ile Asn Gly Lys Asp
Ile Lys Asp Val Phe Lys Asp Leu Asp Val Ile Leu Gln Gly Asn Gly Gln
```

SEQ ID NO: 84

```
Met Asn Leu Val Leu Met Gly Leu Pro Gly Ala Gly Lys Gly Thr Gln Gly Glu Arg Ile Val Glu Asp Tyr Gly
Ile Pro His Ile Ser Thr Gly Asp Met Phe Arg Ala Ala Met Lys Glu Glu Thr Pro Leu Gly Leu Glu Ala Lys
Ser Tyr Ile Asp Lys Gly Glu Leu Val Pro Asp Glu Val Thr Ile Gly Ile Val Lys Glu Arg Leu Gly Lys Asp
Asp Cys Glu Arg Gly Phe Leu Leu Asp Gly Phe Pro Arg Thr Val Ala Gln Ala Glu Ala Leu Glu Glu Ile Leu
Glu Glu Tyr Gly Lys Pro Ile Asp Tyr Val Ile Asn Ile Glu Val Asp Lys Asp Val Leu Met Glu Arg Leu Thr
Gly Arg Arg Ile Cys Ser Val Cys Gly Thr Thr Tyr His Leu Val Phe Asn Pro Pro Lys Thr Pro Gly Ile Cys
Asp Lys Asp Gly Gly Glu Leu Tyr Gln Arg Ala Asp Asp Asn Glu Glu Thr Val Ser Lys Arg Leu Glu Val Asn
Met Lys Gln Thr Gln Pro Leu Leu Asp Phe Tyr Ser Glu Lys Gly Tyr Leu Ala Asn Val Asn Gly Gln Gln Asp
Ile Gln Asp Val Tyr Ala Asp Val Lys Asp Leu Leu Gly Gly Leu Lys Lys
```

EXAMPLES

Example 1

Purification of Native Adenylate Kinase Enzymes

Biomass was produced from twenty-four diverse microorganisms (Table 3).

Eight members of the Archaea were represented along with sixteen diverse aerobic and anaerobic bacteria. AKs from each of these organisms were purified by affinity chromatography using selective absorption and desorption from Cibacron Blue 3A (Blue Sepharose). All enzymes were further characterised and purified by gel filtration (Superdex G200). This enabled identification of the major AK fraction and estimation of molecular mass.

TABLE 3

List of organisms cultured to produce biomass for isolation of AKs.

| | Organism | Domain | Growth | $T_{opt}$ | $pH_{opt}$ |
|---|---|---|---|---|---|
| 1 | *Aeropyrum pernix* | Archaeon | Aerobe | 95° C. | 7.0 |
| 2 | *Alicyclobacillus acidocaldarius* | Bacterium | Aerobe | 65° C. | 3.5 |
| 3 | *Aquifex pyrophilus* | Bacterium | Micro-aerophi leebero-phile | 85° C. | 6.5 |
| 4 | *Bacillus* caldotenax BT1 | Bacterium | Aerobe | 65° C. | 7.0 |
| 5 | *Bacillus* species PS3 | Bacterium | Aerobe | 65° C. | 7.0 |
| 6 | *Bacillus stearothermophilus* 11057 | Bacterium | Aerobe | 65° C. | 7.0 |
| 7 | *Bacillus stearothermophilus* 12001 | Bacterium | Aerobe | 65° C. | 7.0 |
| 8 | *Bacillus thermocatenulatus* | Bacterium | Aerobe | 65° C. | 7.0 |
| 9 | *Clostridium stercocorarium* | Bacterium | Anaerobe | 55° C. | 7.0 |
| 10 | *Meiothermus ruber* | Bacterium | Aerobe | 60° C. | 6.5 |
| 11 | *Pyrococcus furiosus* | Archaeon | Anaerobe | 95° C. | 7.5 |
| 12 | *Pyrococcus horikoshii* | Archaeon | Anaerobe | 95° C. | 7.0 |
| 13 | *Pyrococcus woesei* | Archaeon | Anaerobe | 95° C. | 7.0 |
| 14 | *Rhodothermus marinus* | Bacterium | Aerobe | 70° C. | 6.5 |
| 15 | *Sulfolobus acidocaldarius* 98-3 | Archaeon | Aerobe | 75° C. | 2.5 |
| 16 | *Sulfolobus shibatae* B21 | Archaeon | Aerobe | 75° C. | 2.5 |
| 17 | *Sulfolobus solfataricus* P2 | Archaeon | Aerobe | 75° C. | 2.5 |
| 18 | *Thermoanaerobacter ethanolicus* | Bacterium | Anaerobe | 65° C. | 6.0 |
| 19 | *Thermoanaerobacter thermosulfurogenes* | Bacterium | Anaerobe | 65° C. | 6.5 |
| 20 | *Thermobrachium celere* | Bacterium | Anaerobe | 60° C. | 7.0 |
| 21 | *Thermococcus litoralis* | Archaeon | Anaerobe | 85° C. | 8.5 |
| 22 | *Thermus aquaticus* YT1 | Bacterium | Aerobe | 70° C. | 8.0 |
| 23 | *Thermus caldophilus* GK24 | Bacterium | Aerobe | 70° C. | 8.0 |
| 24 | *Thermus thermophilus* HB8 | Bacterium | Aerobe | 70° C. | 8.0 |

Example 2

Analysis of Stability of Native Adenylate Kinases

Figure 1B:
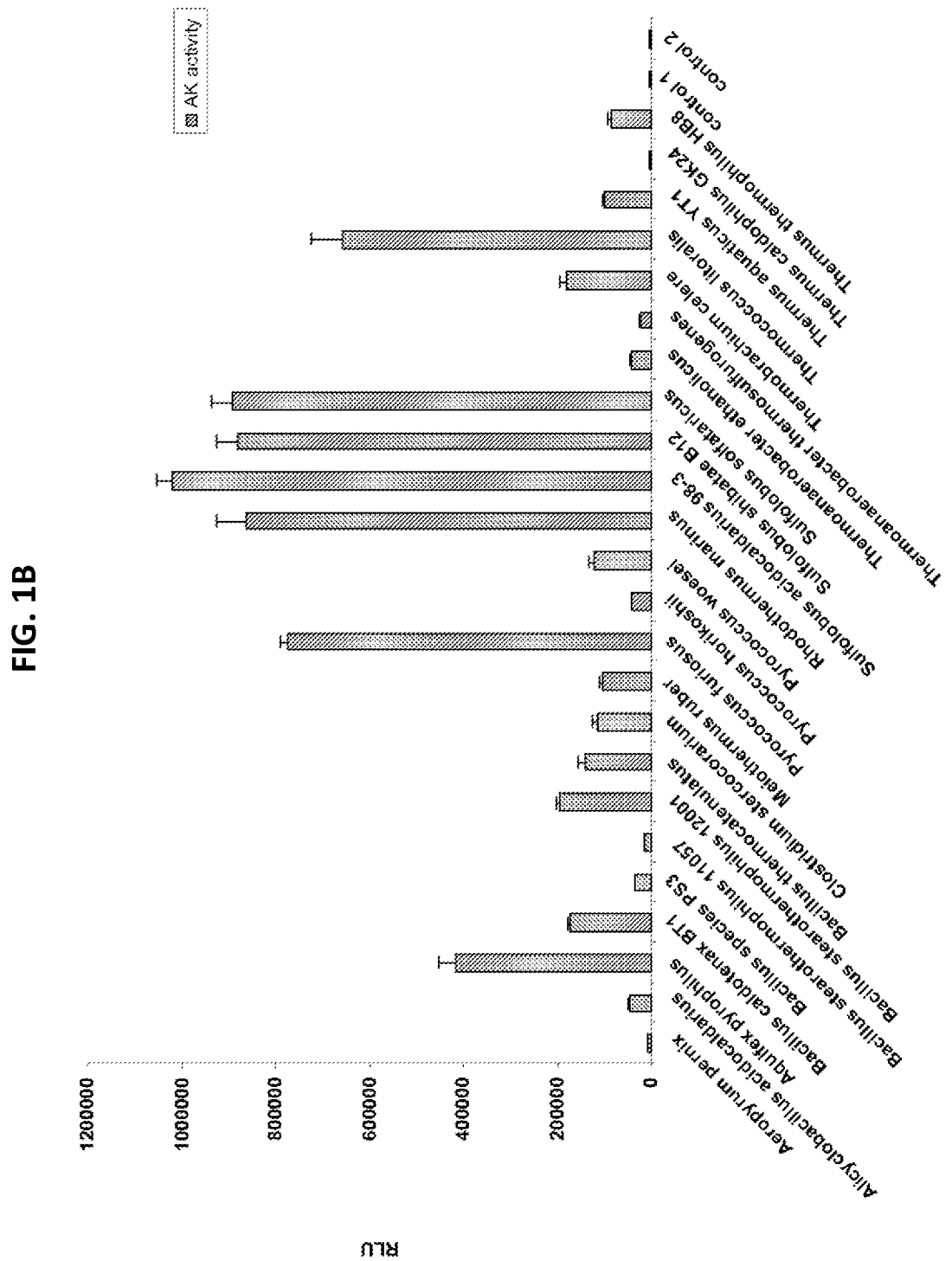
Figure 1C:

The stability at 70, 80 and 90° C. of adenylate kinases isolated from biomass from organisms was assessed, and the results shown in FIG. 1.

The adenylate kinases were isolated from the biomass by affinity chromatography using selective absorption and desorption from Cibacron Blue 3A (Blue Sepharose). The samples eluted from the columns were diluted 1:10 000 and then 10 µl of each added to a microtitre well. 2.5 µl of apyrase was added to each well to destroy the ATP present from the elution buffer, and incubated at 37° C. for 30 minutes. The apyrase was inactivated by heat treatment at 65° C. for 20 minutes.

ADP substrate was added and incubated at either 70 (panel A), 80 (panel B) or 90° C. (panel C) for 30 minutes and cooled to 25° C. before the addition of 10 µl of D-luciferin-luciferase reagent. The ATP produced was measured as RLU on a plate luminometer.

Example 3

Expression and Purification of Recombinant Adenylate Kinases

Clones expressing representative AKs were secured and recombinant AKs from the archaeon *Sulfolobus acidocaldarius* and the bacterium, *Bacillus stearothermophilus* produced. The plasmids were transformed into *E. coli* and the cell extracts shown to contain protein bands on electrophoresis corresponding to the expected molecular masses of the AKs. AK activity was measured after incubation at the appropriate temperature (80° C. for the *Sulfolobus acidocaldarius* AK and 60° C. for the *Bacillus stearothermophilus* AK).

Purification methods for both AKs were established and included an initial heat treatment of incubation for 20 min at 80° C., to inactivate and aggregate proteins derived from *E. coli*, followed by affinity chromatography and gel filtration. The affinity chromatography involved adsorption of the enzyme to Blue Sepharose, followed by specific elution with a low concentration of AK co-factors (AMP+ATP and magnesium ions). The ATP and AMP (Sigma) in the elution buffer were degraded by incubation with mesophile apyrase, which is readily inactivated by subsequent heat treatment. Gel filtration chromatography was scaled up to utilise a preparation grade Superdex column to enable large quantities of both enzymes to be prepared.

Primers were designed for PCR amplification of the AK genes from the organisms identified during the screening of candidate native enzymes.

The microorganisms were grown using individually defined growth conditions and genomic DNA isolated and used as templates for PCR amplification of the adenylate kinase genes from each organism. PCR amplified adenylate kinase genes from the organisms, *Thermotoga maritima*, *Aeropyrum pernix*, *Sulfolobus acidocaldarius* and *Sulfolobus solfataricus* were sub-cloned into the vector, pET28a and transformed into a codon enhanced *E. coli* strain expressing rare tRNAs (Zdanovsky et al, 2000). This *E. coli* strain is suitable for enhancing expression levels of AT-rich genes.

The success of the transformation was assessed by a mini-expression study, and the results analysed by SDS-PAGE of the culture supernatants before and after induction with IPTG. SDS-PAGE was also used to analyse the supernatants after inclusion of a heat treatment step, which consisted of heating the sample to 80° C. for 20 minutes prior to running on the SDS-PAGE gel to remove heat labile proteins present in the sample.

Example 4

Analysis of the Stability of Recombinant Adenylate Kinases

The stability of recombinant tAK enzymes was assessed in crude *E. coli* cell lysates.

Cells were grown essentially as described in Example 3 and lysed by sonication. The AK activity of the crude extract was determined both before and after heat treatment at 80° C. for 30 minutes followed by 10-fold serial dilution.

Figure 2:
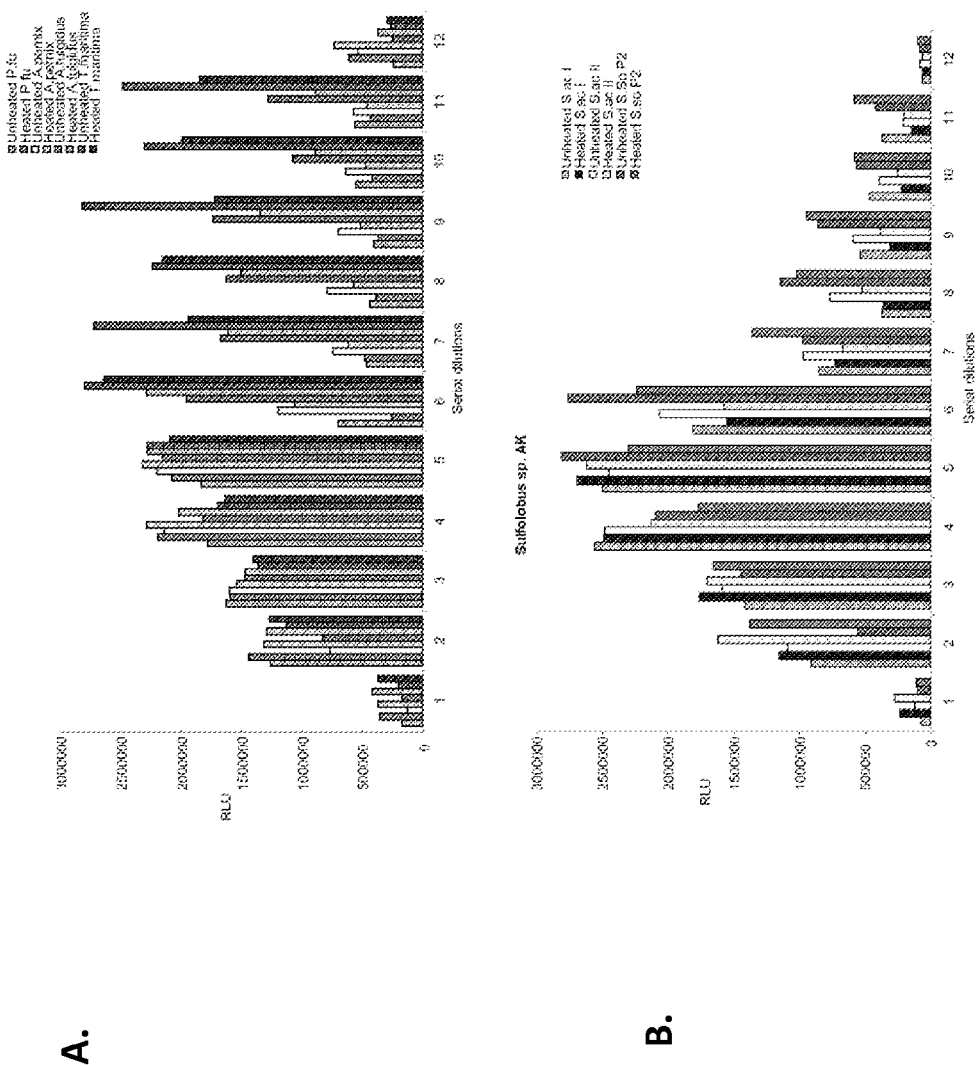
FIG. 2 shows the stability of a range of AK enzymes recombinantly expressed in *E. coli* (A) shows AK enzymes from *Pyrococcus furiosus*, *Aeropyrum pernix*, *Archaeoglobus fulgidus* and *Thermotoga maritime* and (B) shows AK enzymes from *Sulfolobus solfataricus* and *S. acidocaldarius*. Genes encoding AK enzymes were cloned and expressed as described in Example 3. All genes were expressed from the vector pET28a except for *S. acidocaldarius* clone I which was expressed from pET3a as described previously. Expression levels were similar for each clone but a proportion of the *Pyrococcus furiosus* (P. fu) enzyme was in the insoluble fraction and this is likely to have reduced the amount of this enzyme being assayed. The stability of the recombinant enzymes was measured following incubation at 80° C. for 30 minutes in a crude *E. coli* lysate at 10-fold serial dilutions from 1 mg/ml total cellular protein (such that column 12 is equivalent to 1 fg/ml total protein). Enzymes from *Thermotoga maritima* and *Archaeoglobus fulgidus* showed significantly greater stability than the other enzymes tested, although the remaining enzymes (*Sulfolobus solfataricus* (S. so P2), *Aeropyrum pernix* and P. fu) showed similar activity to the *S. acidocaldarius* enzyme used as the basis of previous assays (data labelled as S. ac I).

The results (see FIG. 2) demonstrate that a wide variety of recombinant enzymes are suitable for the use in the method of the invention. Particularly preferred AKs are those from *T. maritima*, *A. fulgidus* and *S. solfataricus*. Such enzymes are likely to provide a greater dynamic range for the bioluminescent assay, if required, to provide still further sensitivity.

Example 5

Genetic Modification of Adenylate Kinases to Improve Stability

Site-directed mutants were constructed in the AK gene from *P. furiosus*, *P. horikoshii* and *S. acidocaldarius* as shown in Examples 6-8 and SEQ IDs 17-19 respectively, using standard methods known to those familiar with the art.

In addition to specific changes identified in each gene, the regions underlined in the *S. acidocaldarius* sequence form the core packing region of the archaeal adenylate kinase trimer structure. Hence amino acid substitutions that disturb the packing of this region are likely to have a major effect in decreasing the thermal and physical stability of the enzyme. Conversely amino acid substitutions that improve the core packing, in particular hydrophobic residues with large side chains, may stabilise the enzyme to heat or other processes. Therefore in addition to the specific mutations already described a number of "selective" approaches were used with localised gene shuffling of related gene sequences in these regions (essentially as described in Stemmer (1994) Nature 370:389-391 and Crameri et al (1996) Nature Biotech. 14:315-319) and random PCR-based mutagenesis using degenerate oligonucleotides or modified nucleotide mixes (e.g. Vartanian et al (1996) Nucleic Acid Res. 24:2627-2633). A number of these modifications show altered stability when assessed by recombinant expression in *E. coli* and rapid assay of adenylate kinase activity in lysed cells at high temperature.

Example 6

Adenylate Kinases from *Pyrococcus Furiosus* Genetically Engineered to Provide Improved Stability (SEQ ID NO. 17)

```
MPFVVIITGI PGVGKSTITR LALQRTKAKF RLINFGDLMF

EEAVKAGLVK HRDEMRKLPL (K TO E) IQRELQMKA AKKI (T TO A) EMAKE HPILVDTHAT IKTPHGY (M TO L) LG

LPYEVVKTLN PNFIVIIEAT PSEILGRRLR DLKRDRDVET

EEQIQRHQDL NRAAAIAYAM HSNALIKIIE NHEDKGLEEA

VNELVKILDL AVNEYA
```

Mutations at one or more or all of the sites indicated modify the stability of the enzyme. In addition to the three defined changes highlighted, modification of the alanine at position 157 to another small hydrophobic residue (such as I, L) or larger hydrophobic residue (such as F) increases the stability of the recombinant protein. Hence, there are 35 variants possible through combination of modifications at these sites. Modification of amino acid 157 to a polar residue such as the T (as observed at the equivalent position in AdkA of *P. horikoshii*), S Y, D, E, K, R results in a decrease in stability.

Example 7

Adenylate Kinases from *Pyrococcus Horikoshii* Genetically Engineered to Provide Improved Stability (SEQ ID NO. 18)

The modification of either or both of the residues shown in bold and underlined increases the stability of the enzyme (3 variants are possible).

```
MPFVVIITGI PGVGKSTITK LALQRTRAKF KLINFGDLMF

EEALKLGLVK HRDEMRKLPL EVQRELQMNA AKKIAEMAKN

YPILLDTHAT IKTPHGYLLG LPYEVIKILN PNFIVIIEAT

PSEILGRRLR DLKRDRDVET EEQIQRHQDL NRAAAIAYAM

HSNALIKIIE NHEDKGLEEA VNELVKILDL AVKEYA
```

Example 8

Adenylate Kinase from *Sulfolobus Acidocaldarius* Genetically Engineered to Provide Improved Stability (SEQ ID NO. 19)

The modification of the underlined residues shown can increase the stability of the enzyme.

```
MKIGIVTGIP GVGKSTVLAK VKEILDNQGI NNKIINYGDF

MLATALKLGY AKDRDEMRKL SVEKQKKLQI DAAKGIAEEA

RAGGEGYLFI DTHAVIRTPS GY (A TO M) PGLPSYV

ITEINPSVIF LLEADPKIIL SRQKRDTTRN RNDYSDESVI

LETINFARYA ATASAVLAGS TVKVIVNVEG DPSIAANEII RSMK
```

Example 9

Expression of Acetate and Pyruvate Kinases

Following the methods of Example 3, we expressed acetate and pyruvate kinases:
SEQ ID No. 20—Acetate kinase from *Thermatoga maritima*
SEQ ID No. 21—Pyruvate kinase from *Pyrococcus horikoshii*
SEQ ID No. 22—Pyruvate kinase from *Sulfolobus solfataricus*
SEQ ID No. 23—Pyruvate kinase from *Thermotoga maritima*
SEQ ID No. 24—Pyruvate kinase from *Pyrococcus furiosus*
SEQ ID No. 25—Acetate kinase from *Methanosarcina thermophila*
SEQ ID No 78—Adenylate kinase from *E. coli*
SEQ ID No 79—Pyruvate kinase from *E. coli*
SEQ ID No 80—Acetate kinase from *E. coli*
SEQ ID No 81—Adenylate kinase from *Methanococcus voltae* (MVO)
SEQ ID No 82—Adenylate kinase from *Methanococcus thermolithotrophicus* (MTH).
SEQ ID No 83—Adenylate kinase from *Bacillus globisporus*
SEQ ID No 84—Adenylate kinase from *Bacillus subtilis*

Example 10

Detection of Hepatitis C in an Oral Fluid Sample

Antibodies are raised against Hepatitis C surface antigens derived from either structural proteins (e.g. E1 and E2) or non-structural proteins (e.g. NS2, NS3, NS4A, NS4B, NS5A, NS5B) using standard methods. In brief, the proteins are expressed as either recombinant proteins in *E. coli*, or synthesized as short immunogenic peptides. Short peptides are conjugated to a suitable carrier, such as HLA, and injected intramuscularly into rabbits or guinea pigs at concentrations of approximately 100 µg/ml. Freund's complete adjuvant is used for the first stage of immunization, with incomplete adjuvant used subsequently.

Polyclonal serum is collected after three monthly challenges over a time-course of 3 months. IgG is purified from the blood and conjugated to Tma tAK using standard coupling chemistry. In brief, the antibody is derivatised using SPDP (Pierce Chemical company) at a molar ratio of 3 SPDP to 1 Tma tAK. The free sulfhydryl in the Tma is released by limited treatment with DTT and the protein reacts with the derivitised antibody. The antibody-tAK conjugate is then separated using gel filtration chromatography.

An oral crevicular fluid sample is collected using a suitable swab device. The device is heated for 1 minute at 90° C. in a dry oven and then mixed with 1 ml of solution containing the anti-HCV polyclonal antibody-tAK conjugate. The swab is then rinsed in cold water to remove any unbound conjugate and inserted into a reagent tube containing a reagent mix comprising Mg-ADP, luciferin and luciferase. The swab is incubated for 2 minutes and then the entire reagent tube is inserted into a hand-held hygiene monitor and the read-out measured immediately.

Example 11

Detection of Immune Status in a Sample of Serum or Whole Blood e.g. Following Immunisation with Measles Vaccine or at an Early Stage Following Exposure to Infectious Measles Virus A fragment of the measles glycoprotein, other measles virus surface components or heat inactivated measles virus, is used to coat a solid support, such as a dipstick. A sample of whole blood, diluted 1:2 with PBS including up to 2M urea to inactivate any non-reporter kinase is applied to the dipstick and antibodies against the measles components are allowed to bind (binding step 1; 5 minutes at 30° C.). Apyrase is added to the blood sample to inactivate any ATP during this phase. After brief rinsing with phosphate buffered saline (PBS; pH7.4), the dipstick is immersed in a solution containing anti-human IgG conjugated to tAK and incubated (binding step 2; 5 minutes at 30° C.). Again the dipstick is rinsed briefly and then placed within a reagent tube. Luciferin/luciferase and ADP were added simultaneously and the reaction measured using a hand held luminometer after 5 minutes.

Example 12

Sample Preparation for Detection of Norovirus in Stool Samples

Norovirus is routinely measured in diarrheal samples (i.e. stool sample) for the purposes of clinical diagnosis.

To reduce the levels of contaminating kinase activity the stool sample is diluted between 1:2 and 1:4 with a buffer designed to inactivate the contaminating kinase. This buffer includes one or more of the following components:

2M urea; 2M guanidine; 1% SDS; 1% deoxycholate; 1% Triton X100

The addition of the above components also makes the norovirus antigen more readily detectable by the antibody conjugates described in the next example, increasing the assay signal as well as reducing assay noise. Optionally, apyrase may also be added to the sample destroy any ATP that may be present.

The same types of additive can also be used as sample processing components for the detection of norovirus in vomitus, a sample which would be useful to test for norovirus but which has not, to date, been suitable for analysis.

Example 13

Lateral Flow Assay for the Detection of Norovirus and/or *C-Difficile* Toxin in a Stool Sample A reporter kinase conjugate is prepared by conjugating the adenylate kinase from *P. abyssi* to norovirus VP1 protein or fragments thereof (e.g. the P-domain (located between amino acids 362 and 703), the P2 domain (amino acids 414-589), or sub-fragments of the P1 domain (aa 362-413 or 590-703). The positions within the norovirus correspond to the numbering as described in Chen R, Neill J D, Estes M K, Prasad B V. X-ray structure of a native calicivirus: structural insights into antigenic diversity and host specificity. Proc Natl Acad Sci USA. (2006) 103 p 8048-53.

Figure 5:
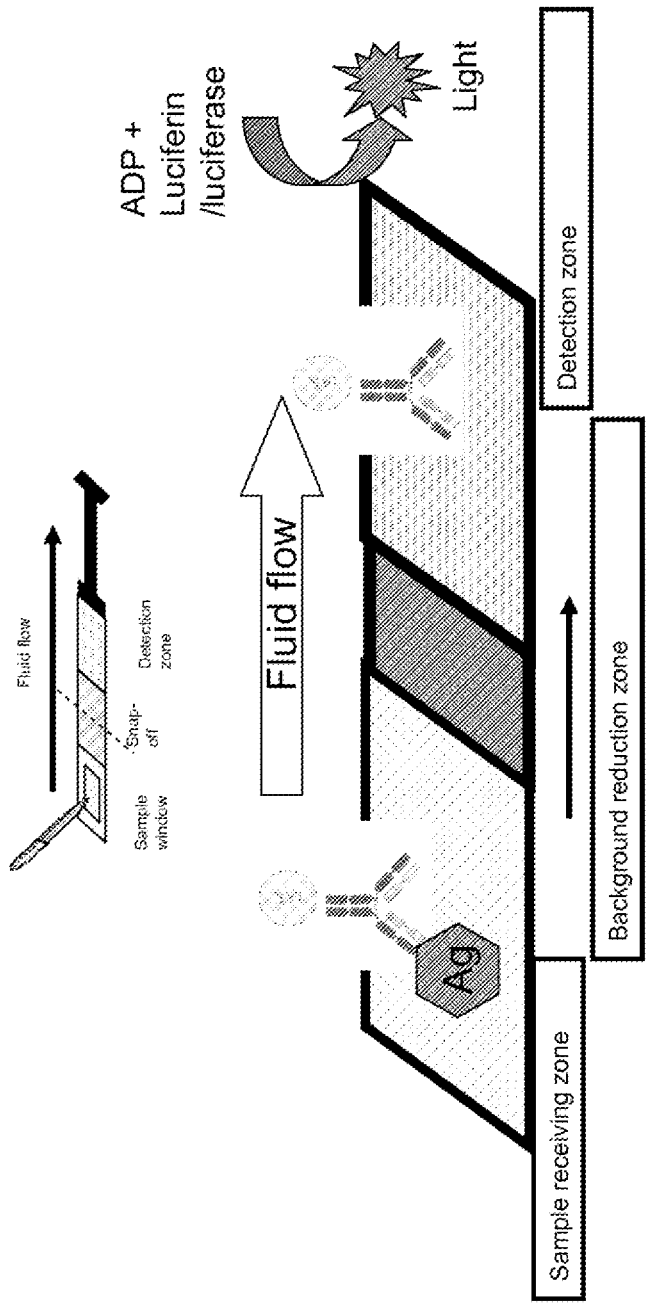
FIG. 5 shows the configuration of a lateral flow device for detection of an analyte in a sample.

A lateral flow device is prepared essentially as shown in FIG. 5. The sample-receiving zone is coated with an anti-norovirus antibody or antibodies (to provide detection of the antigenically diverse range of clinical isolates). The reporter kinase conjugate (described above) is then bound to the sample-receiving zone via the antibodies.

The clinical stool sample is processed as outlined in Example 12 above and applied to the sample-receiving zone of the device. In the presence of norovirus, the reporter kinase conjugate is displaced and migrates to the detection zone, via the background-reduction zone. The background-reduction zone comprises an anion exchange membrane which retains any ATP contained within the original sample. By using a buffer at neutral pH (such as PBS) the ATP is retained on the anion exchange membrane whilst the reporter kinase conjugate passes through as it remain below the isoelectric point and is therefore cationic. Non-reporter kinase has previously been removed in the sample preparation phase (see Example 12).

The lateral flow device is then snapped in two and the detection zone is then placed into a reagent tube containing ADP, luciferin and luciferase. The presence of norovirus in the original sample is determined by measurement of light output with an assay time of 2-5 minutes.

Similarly a lateral flow device may be provided to detect the presence of *C. difficile* toxin A or toxin B in a sample. Antibodies to these targets are well described in the literature and can be conjugated to reporter adenylate kinase(s) as described above. The stool sample is processed as in example 12 and the lateral flow assay carried out as described.

Optionally a device may be provided to detect the presence of either *C. difficile* toxin(s) or norovirus in a sample, enabling differential diagnosis of clinical samples to be carried out. The sample is processed as described in example 12 and mixed with diagnostic reagents for both norovirus and *C. difficile* toxin(s) in the same reaction. The sample may be run on two separate lateral flow devices set up to capture only one of the two targets or preferentially on a single device with two capture windows. These two devices or two windows are then assayed separately to determine the presence of one or more of the target species.

Example 14

Detection of *Legionella* in a Water Sample

Figure 6:
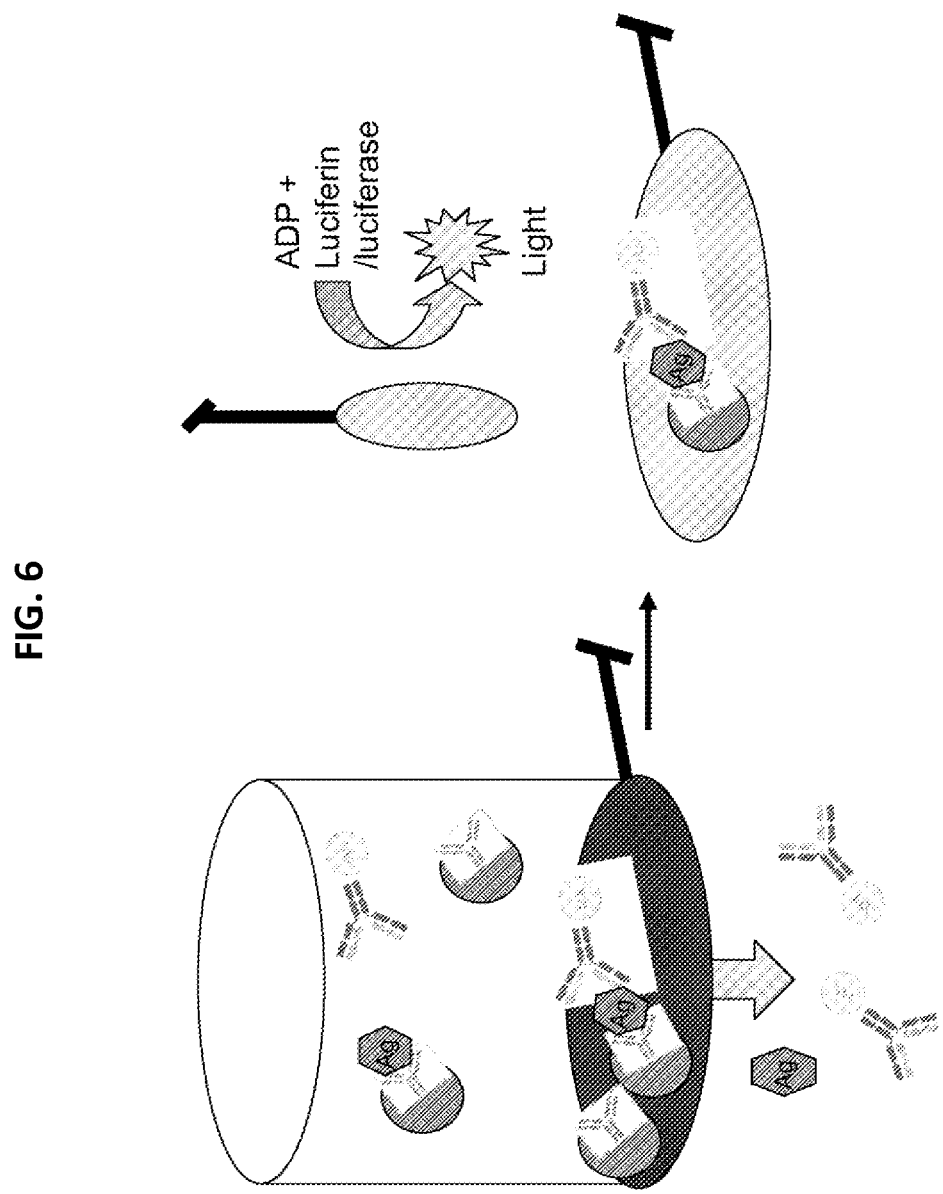
FIG. 6 shows the configuration of a filtration device for the detection of an analyte in a sample.

The assay is carried out using a device as set out in FIG. 6.

A water sample from a cooling tower is sampled at the point of routine maintenance. Typically 50 ml of water is added to a syringe which already contains latex beads coated with anti-*legionella* antibody (antibody A; or fragment thereof) and the reporter kinase from *A. fulgidus* chemically conjugated to a second anti-*legionella* antibody (antibody B). Optionally antibodies A and B may be the same antibody provided there are multiple binding sites on the surface of *legionella*. Preferably they are different antibodies recognising different epitopes of the *legionella*. If *legionella* is present in the water sample, it becomes bound to the latex bead via antibody A. The reporter kinase is bound to the latex bead via the interaction of antibody B with the already-bound *legionella*.

The syringe is shaken continuously for 5 minutes either by hand or optionally within a suitable automated shaker. The syringe is applied to a filtration device which contains a filter designed to allow the free passage of the water, non-reporter kinase, ATP, uncomplexed reporter kinase conjugate, and any uncomplexed microorganisms, but which will retain anything bound to the latex bead. Thus, any reporter kinase bound to the latex bead will be retained on the filter.

The filter is removed from the filter housing and transferred into a reagent tube. The presence of *legionella* is assessed by the addition of ADP, luciferin and luciferase and the measurement of light output using a portable luminometer.

Example 15

Detection of *Chlamydia* in a Swab Sample

A swab device is used to collect a vaginal sample from the test individual. The swab is placed in a reagent tube that contains 1M urea to assist in disrupting the tissue and 2 µM Ap5A final concentration which blocks the activity of any non-reporter kinase. The presence of Ap5A does not have a detrimental effect on the activity of the luciferase (see FIG. 4B), hence even if it is present in the final reaction mixture it does not adversely affect the limits of detection.

A reporter kinase conjugate is prepared by conjugating the adenylate kinase from *S. solfataricus* to a *Chlamydia* antigen. A suitable *Chlamydia* antigen is the major outer membrane protein (MoMP) which is present in high copies on the surface of *Chlamydia*. A series of polymorphic membrane proteins have also been described and may represent suitable target antigens for specific and sensitive detection. Antibodies can be generated to this protein, or peptides derived from it according to conventional protocols.

A lateral flow device is prepared as set out in FIG. 5. The sample-receiving zone of the device is coated with an antibody to a *Chlamydia* antigen. The reporter kinase conjugate is then applied onto the sample-receiving zone of the device, and becomes attached thereto via the interaction between the antigen of the conjugate and the coated antibody.

A small volume of the sample is then spotted onto the sample-receiving zone of the device. Any chlamydia antigen present in the sample displaces the reporter kinase conjugate from the sample-receiving zone and allows flow of the reporter kinase conjugate to the detection zone where it can be measured. The device is then placed in a reagent tube, and with ADP and luciferin/luciferase reagents. The light output signal is measured within 5 minutes.

As an alternative antigen, antibodies raised to the bacterial lipopolysaccharide from *Chlamydia* may be employed and conjugated to the reporter kinase. This multivalent target may provide greater sensitivity and specificity than other targets. Optionally more than one of the target antigens may be combined to amplify the signal detected.

Example 16

Detection of *Listeria* in a Food Sample

A food sample suspected of containing *Listeria* is immobilized onto a microtitre plate by non-specifically binding sample components to the plate, treating the plate to prevent further non-specific binding thereto and washing.

A reporter kinase conjugate is prepared by conjugating an antibody specific to *Listeria* to the pyruvate kinase from *S. solfataricus*.

The reporter kinase conjugate is applied to the plate and allowed to bind, prior to further washing/recovery. The plate is now heated to about 90° C. for about 1 minute in a cell extraction buffer (in a thermal cycler) to denature any non-reporter AK present and release any ATP that may be trapped within the micro-organism. The plate is then cooled to 37° C. and a thermolabile ATPase such as apyrase added. The plate is incubated for about 5 minutes to remove the background ATP, then the temperatures is raised to about 90° C. to denature the thermolabile ATPase.

Next, ADP and a mixture of luciferin and luciferase mixture are added simultaneously to the plate. The kinase acts on the ADP to generate ATP, which subsequently reacts with the luciferin/luciferase to produce light. The light output is measured using a hand-held luminometer and is directly proportional to the concentration of the microorganism present.

Example 17

Detection of *Salmonella* in a Food Sample

A solid phase is prepared by coating magnetic beads with a first anti-salmonella polyclonal antibody raised in Guinea pig.

A reporter kinase conjugate is prepared by conjugating the adenylate kinase from *T. maritima* to a second anti-salmonella polyclonal antibody raised in Guinea pig.

The food sample to be tested is dispersed in a buffer containing 1M urea plus 2 µM Ap5A and mixed for 5 minutes, in the presence of the magnetic beads and the reporter kinase conjugate. This mixing can be carried out at either room temperature or an elevated temperature. If *Salmonella* is present in the food sample, it will bind to the first anti-*salmonella* antibody on the magnetic bead. In turn, the reporter kinase conjugate will bind to the magnetic bead via the interaction between the second anti-salmonella antibody and the already-bound *salmonella*.

The magnetic beads are then collected by attraction to a strong magnet and washed with a neutral buffer. The magnet with beads attached is transferred to a reagent tube and ADP, luciferin and luciferase are added simultaneously. The light output signal is read in a luminometer, preferably hand-held, within 5 minutes.

Example 18

Validation of Processes for Sterilising Bulk Liquids

Preparation of Indicator 1

A first indicator is prepared by covalently attaching 0.1 mg of pyruvate kinase from *Sulfolobus solfataricus* to a polystyrene strip.

Preparation of Indicator 2

A second indicator is prepared by attaching 0.1 mg of the adenylate kinase from *A. fulgidus* to the inner face of a semipermeable membrane such as a dialysis tube. The *A. fulgidus* kinase contains a naturally occurring reactive cysteine residue (i.e. not disulfide-bonded within the native enzyme), which can be reacted with BMPH (Pierce). This generates a group capable of reacting with oxidised carbohydrates, as generated, for example, by the treatment of Visking tubing with a suitable oxidising agent. The enzyme is reacted with the oxidised membrane surface to generate a covalently linked indicator.

Validation

The indicator is then attached within the bulk liquid and the sterilisation process (such as autoclaving, the passage of oxidative gases or other chemical sterilisation) is carried out.

The indicator is removed from the bulk liquid on completion of the process, and the residual activity of the kinase is measured. To achieve the measurement the indicators are first incubated in the presence of apyrase, at a concentration of 10 µg/ml for 2 minutes. The apyrase can be inactivated by addition of Ap5A at a concentration of 5 µM. The two indicators can then be read independently by addition of a combined reagent containing ADP, luciferin and luciferase. The measurement is made within 5 minutes using a hand held luminometer, such as a hygiene monitor.

In this example any non-reporter kinase that might be present is destroyed by the treatment conditions and as such specific kinase-reduction steps are not required. The residual activity is then compared to a defined threshold value.

Example 19

Validation of the Performance of Cloth Washing Cycles Using Biological Detergents Preparation of Indicator 1

A first indicator is prepared by cross-linking a adenylate kinase from *S. solfataricus* onto a flexible polystyrene wand using a method based on disulfide bond formation. In this method, the adenylate kinase is derivitised with a heterobifunctional agent such as Sulfosuccinimidyl 6-(3'-[2-pyridyldithio]-propionamido)hexanoate (SPDP; Pierce chemical company, UK) at a ratio of between 1-3 SPDP:protein. The derivatised kinase is then reduced by reaction with a reducing agent such as dithiothreitol (DTT), or 2-mercaptoethanesulfonic acid (MESNA), the reducing agent removed by dialysis, and the kinase reacted with a maleimide-derivatised polystyrene surface. Typically, 0.1 mg of kinase is present on the indicator.

Preparation of Indicator 2

A second indicator is prepared by the non-specific adherence of an adenylate kinase from *S. acidocaldarius* onto a high-protein binding polystyrene strip. The kinase is prepared at a concentration of 0.5-2 mg/ml in a bicarbonate buffer (pH 9.6), optionally containing the stabilising agent sorbitol at between 0.1 and 2% w/v. The kinase in binding buffer is then incubated with the high protein-binding polystyrene strip for a period of 1-2 hours at 22° C. (or 4° C. overnight). The residual kinase is removed by washing in a phosphate buffered saline. Typically, 0.1 mg of kinase is present on the indicator.

Validation of Wash Cycles

The washer is loaded with the items to be washed, and the indicator is fixed within a suitable holder on the inside of a washer (to facilitate its recovery). The wash cycle is then performed. At completion of the cycle, the indicator is removed and the residual activity of the kinase is assessed. In this example the washing process removes and/or inactivates both any non-reporter kinase and any residual ATP, hence neither interfere with the assay. The presence of the reporter kinase is determined by the addition of ADP, followed within 1 minute by the addition of luciferin and luciferase.

If the measurement of residual kinase activity is equal to or below a predetermined threshold level, then the load is cleared for further processing.

Example 20

Preparation of a Fibrin-Based Indicator Device

Preparation of tAK Fusions for Cross-Linking to Fibrin

A transglutaminase substrate sequence (MNQEQVSPLGG—SEQ ID No: 33) is added on to the N-terminus, the C-terminus, or both N- and C-termini, of the adenylate kinase from *S. acidocaldarius* encoded by a codon optimised gene clone. This construct is transferred as an NdeI-SalI fragment into an in-house expression vector (pMTL 1015; as described in WO 2005/123764). The expression construct is confirmed by DNA sequencing and transferred into expressions hosts BL21 or RV308 for subsequent expression.

Similarly, the resynthesised tAK gene from *Thermatoga maritima* (SEQ ID 29) is fused to the transglutaminase sequence in the three orientations identified above. The cloning and preparation of the expression system is also as described above.

The fusion constructs can also be expressed in other expression vector-host combinations with the addition of affinity tags for subsequent purification. Particularly useful in this context are expression vectors which add 6-histidine tags on either the N- or C-terminus of the fusion proteins, modifications which aid purification and detection but do not interfere with the intrinsic properties of the fusion proteins. Vectors for this type of modification include pET series vectors (Novagen/Merck) and pQE series vectors (Qiagen).

To generate material for the indicator devices the expression strains are grown initially in 8-liter fermenters essentially under static culture conditions. In brief, the strains are prepared as seed stocks and subsequently diluted into the 8-liters of growth media (modified terrific broth containing additional glucose). The cultures are grown under standard fermentation conditions until the cultures reached an optical density (OD at 600 nm) demonstrating that they are entering stationary conditions (typically at around an OD=5). The fermenters are then held under minimally aerated conditions for up to 12 hours prior to harvesting of material by continual centrifugation.

Purification of tAK Fusions

The harvested material is then purified according to the following protocol.

Buffer A: 20 mM Tris-HCl; 900 mM NaCl, pH 7.5
Wash Buffer: 20 mM Tris-HCl; 200 mM NaCl, pH 7.5
Buffer B: 20 mM Tris-HCl; 200 mM NaCl, pH 7.5
  10 mM ATP; 10 mM AMP; 10 mM $MgCl_2$
MgAc buffer: 15 mM MgAc (1M Fluka BioChemika), pH 6.8

1. Weigh frozen cell paste (10 g) and resuspend in 3× (30 ml) volume of Buffer A, pH 7.5.
2. Sonicate on ice (~12,000 khz) using 25 cycles of 30 seconds on/30 seconds off. Take 1 ml sample.
3. Sonicated cell solution is centrifuged at 6,000 rpm for 30 mins at 4 degrees C. Supernatant carefully poured off and 1 ml sample taken.
4. Supernatant is heat treated at 80 degrees C. in a water bath for 20 mins. 1 ml sample taken. (This step is an optional step depending on thermal stability of the fusion proteins).
5. Heat treated solution centrifuged at 6000 rpm for 30 mins at 4 degrees C. Pour off supernatant and take 1 ml sample.
6. Filter the sample with 0.2 μm low binding filter before loading onto column.
7. Equilibrate Blue Sepharose Fast Flow column with 5 Column Volumes (CVs) of Buffer A.
8. Load the sample. Wash column with wash buffer at 0.2 ml/min overnight.
9. Elute protein with 100% buffer B at a flow rate of 1 ml/min collect product in 2.5 ml fractions.
10. Once all proteins have eluted wash column with 100% buffer B at 5 ml/min for 5 CV's.
11. Re-equilibrate column with 5 CV's buffer A.
12. Rinse column with 5 CV's 20% Ethanol for storage at 4° C.

Optionally, additional protein purification methods are applied to yield a higher purity product. Ion exchange chromatography on either SP-Sepharose Fast Flow or Q-Sepharose Fast Flow resins is particularly effective.

The samples are then analysed using a standard assay format to identify fractions containing peak adenylate kinase activity. This is confirmed by SDS-PAGE analysis using standard techniques. In brief, the assay method is carried out using the following protocol:

1. Dilute the purified tAK fusion 1:1000 and 1:10,000 in Mg Ac Buffer. Add 100 μl per well.
2. Treat with Apyrase (50 μl/well at 2.5 units per ml stock concentration; Sigma Grade VI Apyrase from potato) and incubate for 30 mins at 30° C., with shaking, to remove ATP.
3. Incubate plate at 70° C. for 10 mins to denature Apyrase.
4. Add 50 μl/well of ADP (275 μM ADP in MgAc buffer) and seal. Incubate at 70° C. for 20 mins.
5. Remove plate and allow to cool to room temperature for 20 mins, warm Luciferase/Luciferin (L/L) reagent to room temperature for 20 mins.
6. Add 200 μl ATP standard to 1 or 2 empty wells per plate.
7. Set up injectors on luminometer and prime them with L/L reagent (ATP reagent, Biotherma). Inject 30 μl L/L reagent/well.
8. Read light generated immediately using luminometer.

The fractions with peak kinase activity are then dialysed extensively against phosphate buffered saline (PBS pH 7.4) and stored until required. Optionally a fusion can be prepared between tAK and the full length fibrinogen molecule to provide further means to incorporate the enzymatic activity within the fibrin film.

Deposition of tAK Fusions onto a Solid Support

The tAK-fibrin fusion is diluted to around 200 μg/ml in either PBS or bicarbonate buffer (pH 9.6) and applied to a solid support of 316L grade stainless steel, plastic, glass or textiles. The protein is allowed to adhere to the surface for up to 2 hours at room temperature or overnight at 4° C.

Optionally, additional carrier molecules are added at this stage, e.g. sucrose at concentrations up to 1% w/v, albumin at up 1 mg/ml, pig mucin at up to 0.5% w/v. The addition of such carriers may be particularly important for certain types of indicator but the presence of the carrier should not interfere with subsequent interaction and cross-linking to the fibrin film applied in the next stage.

Overlay of Fibrin-Containing Soil and Cross-Linking to Fibrin-tAK Fusion

A solution containing fibrinogen is added to effect the cross-linking of the indicator to the fibrin-containing test soil (biological matrix).

A solution containing up to 3 mg/ml fibrinogen (containing Factor XIII), 2.5 mM $CaCl_2$, and thrombin (up to 5 NIH units per ml) is mixed freshly and added to the coated surface of the solid support. The reaction is allowed to proceed at room temperature for up to 30 minutes, depending on the level of cross-linking required. Optionally, albumin (up to 80 mg/ml) and haemoglobin (up to 80 mg/ml) are added at this stage to provide a tougher and more realistic challenge for cleaning of a blood-like soil. After cross-linking, residual liquid is removed and the indicator device left to dry.

Optionally, the tAK-fibrin peptide fusion is added to the fibrin-containing test soil solution (biological matrix) prior its addition to the solid support surface. Cross-linking of the fibrin peptide to the matrix can be increased by adding more Factor XIII and/or extending the duration of the reaction. Cross-linking can also be enhanced by the use of the tAK fusion protein with fibrin peptides added to both ends of the molecule. Optionally a fibrinogen-tAK fusion could be added directly to this solution to provide further cross linkage of the indicator.

Covalent Chemical Cross-Linking of tAK to Fibrin or Fibrinogen.

tAK may be chemically joined to fibrin, fibrin peptides or fibrinogen by a wide range of methods familiar to those working in the field. For example purified protein preparations for fibrinogen or fibrin are obtained from commercial sources (e.g. Sigma). The tAK from *S. acidocaldarius* is prepared as described above. The tAK is derivatised using the amide reactive reagent SPDP (SPDP(N-Succinimidyl 3-(2-pyridyldithio)-propionate; Pierce chemical company) according to the manufacturer's instructions. The fibrin or fibrinogen is also derivatised using the same protocol. The derivatised tAK is reduced by reaction with mercaptoethanol to yield a reactive sulfhydryl group. This is then mixed with the SPDP-derivatised fibrin causing the formation of covalent bonds between the two molecules. The concentrations of the reaction partners should be determined empirically following the guidelines within the manufacturer's instructions for SPDP. The chemically linked tAK-fibrin or fibrinogen can be used interchangeably or in addition to the fusion protein.

Uses of Fibrin-tAK Indicators

Use in a Washer Disinfector

An indicator is prepared as described above. Preferably the solid support is a rectangular stainless steel strip 55 mm×5 mm×0.75 mm, which may be coated on one or both surfaces. One or preferably several indicator strips are positioned within the chamber of the washer disinfector. Optimally these may be positioned in sites which may be the most difficult to clean, providing the highest degree of certainty that the wash process has been effective. Alternatively they may be positioned to monitor the function of multiple spray arms (i.e. where these may be independent of each other). The indicator strips are clipped to the shelves or other substructure of the washer-disinfector chamber to ensure that they do not move during the wash treatment. The orientation of the surrogate devices can be modified to provide further information about the efficacy of the wash process, for example by positioning them so that the coated surface are at right angles to the direction of water spray.

The instrument load is added and the standard run cycle performed. At the end of the run the devices are removed from the chamber and the presence of residual tAK-fusion assessed, as outlined below, prior to the removal of the instruments and any subsequent processing. Optionally devices can be removed during the wash process either by interrupting the process at carefully defined points or by using a machine that provides a method of withdrawing the indicator during the run.

Use in Endoscope Test Procedure

The indicator device for monitoring an endoscope reprocessing system is essentially similar to that outlined above. A similar size indicator surface, representative of either the stainless steel components within an endoscope, the PTFE tubing or other relevant materials is placed within a tubular chamber. This is attached, via suitable screw, push or bayonet fittings to either the front end of the endoscope or, more preferably the end which makes contact with patient tissues. This is placed within the endoscope reprocessing unit and the ends of the endoscope tubing and indicator device are coupled to the ports in the unit. The process is run as standard and the indicator device removed at the end of the run for analysis, prior to onward processing or the return of the endoscope to use.

Means of Assessing Cleaning Performance

The indicator device is removed at the end of the test process. The indicator strip is then placed into a reagent tube with ADP, luciferin and luciferase, added simultaneously, with signal being read-out on a hand-held luminometer with 2 minutes.

Example 21

Preparation of tAK-Sup35 Fusion

Clones containing the N-terminal domain of Sup35 from *Saccharomyces cerevisae* fused to either the N- or C-terminus, or both termini, of adenylate kinases from either *S. acidocaldarius* or *T. maritima* are generated by standard DNA manipulation techniques. All clones are transferred as NdeI-SalI fragments into the pMTL1015 expression vector and their sequences verified. The expression constructs are used to transform BL21 or RV308 expression strains and the material grown in large scale fermentation conditions, but with minimal aeration.

Expression and purification of a tAK-Sup35 fusion is essentially the same as for the fibrin-peptide fusions described in Example 20, except that the use of the thermal denaturation step (Step 4) is not part of the purification protocol. In brief, cell paste from the fermenter is resuspended in buffer A, and lysed by sonication. The cell debris is removed (no heat treatment is typically used for these type of fusions) and the supernatant used for column purification as outlined in Example 20.

Under certain growth conditions the fusion proteins may be insoluble, being apparent as inclusion bodies within the cells. In this case the cell pellets are prepared and lysed in the same way, but the resulting insoluble fraction, containing the inclusion bodies, is collected by centrifugation. This material is washed in a buffer (e.g. PBS) containing Triton X100 (up to concentrations of 5%). After each wash the pellet containing the fusion proteins is separated by centrifugation. After 5 washes the inclusion bodies are resolubilised in PBS containing 8M urea and agitated gently for up to 30 minutes.

Any residual insoluble material is removed by centrifugation. The urea-solubilised material is dialysed against up to 5×10 volumes of PBS to remove the urea and allow the fusion proteins to refold. Optionally the urea may be removed more rapidly by spraying the urea-solubilised preparation through a fine gauge needle into 100 volumes of rapidly stirred PBS or buffer A as used for purification. The material is allowed to stand at room temperature with stirring for up to 30 minutes prior to subsequent processing.

Subsequent purification of the fusions is carried out essentially as described in Example 20. The supernatant from either lysed cells or solubilised and refolded inclusion bodies is loaded onto a pre-equilibrated Blue Sepharose Fast Flow column. After extensive washing in buffer A and subsequently in wash buffer, the protein is eluted using buffer B. Peak fractions are determined by SDS-PAGE analysis and enzyme assay. Fractions are then pooled and dialysed into PBS.

Conversion of tAK-Sup35 to an Amyloid Form

The Sup35-tAK fusions when assembled into fibrils are more representative of amyloid proteins such as prions which are key molecules against which to assess the efficacy of decontamination processes.

The amyloid form of the Sup35-tAK fusions is generated by either refolding of the purified soluble protein or by modifying the conditions used for dialysis of the urea-resolubilised inclusion body preparations. In the first case, a conformational change is induced by exposure of the fusion proteins to conditions around pH4 (e.g by dialysis into a suitably buffered solution at pH 7.4 optionally containing up to 1M NaCl). In the latter case, the resolubilised fusion proteins in 8M urea/PBS are dialysed for 6-12 hours at room temperature against 2M urea, 300 mM NaCl, in PBS (pH 7.4). Alternatively, the fibrilisation can be induced by dialysis against 20 mM Tris pH8.0 10 mM EDTA under similar incubation conditions. Optionally, the fusion proteins may be incorporated into fibrils containing normal Sup35. This is achieved by mixing the fusions with unfused Sup35 expressed in the same way, at ratios between 1:1 to 1:10 fusion:Sup35.

Deposition of tAK-Sup35 Fusions onto Solid Support.

Deposition of the fibrils onto a solid support is effected by simple protein adsorption in a suitable buffer (e.g. PBS pH 7.4 Bicarbonate buffer pH 9.6) in the presence of high levels of NaCl. The use of charged or precoated surfaces (e.g. plastics coated with Poly-L-lysine) is useful in providing surfaces which can more effectively bind the fusion proteins. Optionally, the fibrils may be deposited in a suitable carrier, such as sucrose (to 1%), pig mucin (up to 0.5%), or albumin (up to 1 mg/ml).

Overlay of Test Soil

A test soil (biological matrix) is then overlaid onto the amyloid preparation adhered onto the surface as described above.

Suitable biological matrices in which the amyloid indicator is embedded include e.g. 0.5% mucin, with or without albumin, a commercial test soil (such as that manufactured by Browne's) or any one of the test soils identified in guidance documents issues by national and international standards committees (e.g. Edinburgh soil as detailed in HTM 01/01 (UK).

Assembly of Amyloid Fibrils within the Test Soil Given the ability of amyloids to self-assemble in complex matrices it is possible for the amyloid-tAK fusion to be mixed with soil components prior to fibril formation and subsequent deposit onto surfaces. This provides further options for indicators in which the amyloid fibrils may be mixed and interchelated with other soil components providing a different type of matrix that may be harder to remove from surfaces.

Use of tAK-Sup35 Indicator for Assessing Prion Removal from Surfaces in a Washing Process An indicator as described above is prepared as fibrils and dried down onto a steel surface in the presence of 0.5% mucin. The indicator is placed within the chamber of a washer disinfector at pre-determined locations. The instrument load is added. The process is started as per the manufacturer's instructions and any process records completed. At the end of the process, and before any instruments are taken from the machine, the indicator devices are removed and assessed as described in Example 20.

Use of tAK-Sup35 Indicator for Assessing Prion Inactivation in a Protease-Based Process Indicators as described above are prepared as fibrils with a high ratio of free Sup35:Sup35-tAK (in excess of 5:1) and deposited onto solid support strips in the presence of Edinburgh soil. The indicator devices are inserted into a pre-soak bath containing freshly made Prionzyme™ (Genencor International) prion inactivation treatment (at 60° C., pH 12). The indicator strips are clipped to the side of the bath such that the ends of the indicators are within the bulk of the liquid. Instruments are added as required and processed for 30 minutes. The indicator devices are removed from the bath at the end of the process, prior to removal of the instruments and assessed as described in Example 20.

Use of tAK-Sup35 Indicator for an Oxidative Process Aimed at Destroying Prions.

An indicator as described above is prepared as fibrils using only Sup35-tAK, and deposited onto a stainless steel surface (optionally in the presence of 0.1% w/v sucrose). The indicator is attached to the inside of the lid of a Genesis™ container in which the instruments are prepared for processing and the lid closed. The container is inserted into the load chamber of a suitable processor for oxidative challenge (e.g. the 125 L ozone steriliser; $TSO_3$ or a vapour phase hydrogen peroxide technology such as that described in published papers by Fichet et al 2004; Lancet) and the process run according to manufacturers' instructions. At the end of the process, the Genesis container is taken out of the chamber and the indicator devices are removed and processed as described in Example 20.

Example 22

Detection of a Reporter Kinase in a Sample Due to an Infection

Use for Rapid Assay of Infection in Patient Sample

A patient presented at the clinic with suspected infection from the obligate intracellular pathogen *Burkholderia pseudomallei*. A blood sample was removed and dispersed in a buffer containing 1M urea plus 5 μM Ap4A. The sample was assayed by addition of ADP and luciferin/luciferase reagent, incubated for 2 minutes and the light output measured in a hand-held luminometer. The signal generated is directly proportional to the amount of *B. pseudomallei* within the blood sample.

Detection of a Reporter Kinase in a Sample Due to an Infection; Use for Rapid Assay of Infection in Cell Models The study of intracellular bacterial pathogens is complicated by the need to grow them in mammalian cell culture systems. Measurement of viable cells the requires subsequent culture or re-infection into mammalian host cells, both of which are very time consuming methods. A rapid assay, such as provided by the invention, is invaluable in providing information that can be used in real-time to determine the results of an experiment.

A suitable isolate of *B. pseudomallei* was incubated with a permissive cell culture model capable of supporting growth of the bacteria within the cell. The culture was grown for an appropriate length of time to establish the infection.

Cells were isolated by centrifugation and lysed by resuspension in a buffer containing 1% Triton X-100, 5 μM Ap4A. A detection reagent containing ADP, luciferin and luciferase was added and incubated for 5 minutes. The light output was read in a 96-well plate luminometer. The amount of signal generated is proportional to the number of viable *B. psudomallei* cells within the cell culture. Optionally this rapid assay method can be extended to measure the effects of vaccines or drugs that reduce the number of viable cells within the cell culture.

For example, antibodies raised in a patient immunised with a prototype *B. pseudomallei* vaccine are mixed with the organisms prior to addition to the permissive cell culture. After an incubation period sufficient to allow uptake of non-neutralised microorganisms, the cells are washed and incubated for a period of time sufficient to establish the infection. Cells are then washed and lysed as described above, again in the presence of inhibitor. The signal measured by simultaneous addition of ADP, luciferin and luciferase is proportional to the number of non-neutralised microorganisms giving a measure of the effectiveness of the vaccine and/or the immune response generated in a vaccinated individual. Such methods are suitable for high-throughput screening.

In a further example, infected cell cultures are set up as described above. After the infection is established, antibiotics are used to treat the infected culture, with the express aim of killing the bacteria within the host cells. After the antibiotics have been applied, the cultures are incubated for sufficient time for the antibiotic to have its effect. The cells are lysed in the presence of inhibitor as described above and the number of viable cells quantified by measurement of the reporter kinase, by addition of ADP, luciferin and luciferase.

The invention claimed is:

1. A lateral flow device for use in an assay for detecting the presence of a known analyte in a sample, comprising:
   a backing strip on which is positioned an elongate flow matrix, wherein said flow matrix comprises:
   (i) a sample-receiving zone containing an exogenous kinase attached to the flow matrix via linker comprising a binding agent specific for the analyte;
   (ii) a detection zone, located downstream of the sample-receiving zone, and containing a mixture of ADP and a bioluminescent reagent; and
   (iii) a background-reduction zone, situated between the sample-receiving zone and the detection zone, that substantially removes or inhibits kinase other than exogenous kinase present in the sample;
   wherein, in use, a sample is applied to the sample-receiving zone and analyte present in the sample displaces exogenous kinase from the flow matrix, said displaced exogenous kinase migrates through the background-reduction zone where kinase other than exogenous kinase is substantially removed or inhibited, and then into the detection zone where ATP generation is detected.

2. The device according to claim 1, wherein any ATP present is substantially removed from the background reduction zone.

3. The device according to claim 1, wherein the background-reduction zone comprises one or more of a substance that substantially inhibits or removes kinase other than exogenous kinase and/or ATP.

4. The device according to claim 1, wherein the device is portable.

5. The device according to claim 3, wherein the one or a substance that substantially inhibits or removes kinase other than exogenous kinase and/or ATP is selected from the group consisting of an immobilised ATPase, an anionic or cationic exchange matrix, a size reduction matrix and a combination thereof.

6. A lateral flow device for use in an assay for detecting the presence of a known analyte in a sample, comprising:
   a backing strip on which is positioned an elongate flow matrix, wherein said flow matrix comprises:
   (i) a sample-receiving zone containing a complex comprising an exogenous kinase linked to a binding agent specific for the analyte and an analyte that is bound to said matrix;
   (ii) a detection zone, located downstream of the sample-receiving zone, and containing a mixture of ADP and a bioluminescent reagent; and
   (iii) a background-reduction zone, situated between the sample-receiving zone and the detection zone, that substantially removes or inhibits kinase other than exogenous kinase present in the sample;
   wherein, in use, a sample is applied to the sample-receiving zone and analyte present in the sample displaces exogenous kinase from the flow matrix, said displaced exogenous kinase migrates through the background-reduction zone where kinase other than exogenous kinase is substantially removed or inhibited, and then into the detection zone where ATP generation is detected.

7. The device according to claim 6, wherein any ATP present is substantially removed from the background reduction zone.

8. The device according to claim 6, wherein the background-reduction zone comprises one or more of a substance that substantially inhibits or removes kinase other than exogenous kinase and/or ATP.

9. The device according to claim 6, wherein the device is portable.

10. The device according to claim 8, wherein the one or more of a substance that substantially inhibits or removes kinase other than exogenous kinase and/or ATP is selected from the group consisting of an immobilised ATPase, an anionic or cationic exchange matrix, a size reduction matrix and a combination thereof.

\* \* \* \* \*

SEQUENCE LISTING

<160> NUMBER OF SEQ ID NOS: 84

<210> SEQ ID NO 1
<211> LENGTH: 195
<212> TYPE: PRT
<213> ORGANISM: Sulfolobus solfataricus

<400> SEQUENCE: 1

Met Lys Ile Gly Ile Val Thr Gly Ile Pro Gly Val Gly Lys Thr Thr
1               5                   10                  15

Val Leu Ser Phe Ala Asp Lys Ile Leu Thr Glu Lys Gly Ile Ser His
            20                  25                  30

Lys Ile Val Asn Tyr Gly Asp Tyr Met Leu Asn Thr Ala Leu Lys Glu
        35                  40                  45

Gly Tyr Val Lys Ser Arg Asp Glu Ile Arg Lys Leu Gln Ile Glu Lys
    50                  55                  60

Gln Arg Glu Leu Gln Ala Leu Ala Arg Arg Ile Val Glu Asp Leu
65              70                  75                  80

Ser Leu Leu Gly Asp Glu Gly Ile Gly Leu Ile Asp Thr His Ala Val
                85                  90                  95

Ile Arg Thr Pro Ala Gly Tyr Leu Pro Gly Leu Pro Arg His Val Ile
            100                 105                 110

Glu Val Leu Ser Pro Lys Val Ile Phe Leu Leu Glu Ala Asp Pro Lys
        115                 120                 125

Ile Ile Leu Glu Arg Gln Lys Arg Asp Ser Ser Arg Ala Arg Thr Asp
    130                 135                 140

Tyr Ser Asp Thr Ala Val Ile Asn Glu Val Ile Gln Phe Ala Arg Tyr
145                 150                 155                 160

Ser Ala Met Ala Ser Ala Val Leu Val Gly Ala Ser Val Lys Val Val
            165                 170                 175

Val Asn Gln Glu Gly Asp Pro Ser Ile Ala Ala Ser Glu Ile Ile Asn
        180                 185                 190

Ser Leu Met
        195

<210> SEQ ID NO 2
<211> LENGTH: 194
<212> TYPE: PRT
<213> ORGANISM: Sulfolobus acidocaldarius

<400> SEQUENCE: 2

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65              70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

```
Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys

<210> SEQ ID NO 3
<211> LENGTH: 197
<212> TYPE: PRT
<213> ORGANISM: Sulfolobus tokodaii

<400> SEQUENCE: 3

Met Ser Lys Met Lys Ile Gly Ile Val Thr Gly Ile Pro Gly Val Gly
1               5                   10                  15

Lys Thr Thr Val Leu Ser Lys Val Lys Glu Ile Leu Glu Glu Lys Lys
                20                  25                  30

Ile Asn Asn Lys Ile Val Asn Tyr Gly Asp Tyr Met Leu Met Thr Ala
            35                  40                  45

Met Lys Leu Gly Tyr Val Asn Asn Arg Asp Glu Met Arg Lys Leu Pro
    50                  55                  60

Val Glu Lys Gln Lys Gln Leu Gln Ile Glu Ala Ala Arg Gly Ile Ala
65                  70                  75                  80

Asn Glu Ala Lys Glu Gly Gly Asp Gly Leu Leu Phe Ile Asp Thr His
                85                  90                  95

Ala Val Ile Arg Thr Pro Ser Gly Tyr Leu Pro Gly Leu Pro Lys Tyr
            100                 105                 110

Val Ile Glu Glu Ile Asn Pro Arg Val Ile Phe Leu Leu Glu Ala Asp
        115                 120                 125

Pro Lys Val Ile Leu Asp Arg Gln Lys Arg Asp Thr Ser Arg Ser Arg
130                 135                 140

Ser Asp Tyr Ser Asp Glu Arg Ile Ile Ser Glu Thr Ile Asn Phe Ala
145                 150                 155                 160

Arg Tyr Ala Ala Met Ala Ser Ala Val Leu Val Gly Ala Thr Val Lys
                165                 170                 175

Ile Val Ile Asn Val Glu Gly Asp Pro Ala Val Ala Asn Glu Ile
            180                 185                 190

Ile Asn Ser Met Leu
        195

<210> SEQ ID NO 4
<211> LENGTH: 196
<212> TYPE: PRT
<213> ORGANISM: Pyrococcus furiosus

<400> SEQUENCE: 4

Met Pro Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Arg Leu
                20                  25                  30

Ile Asn Phe Gly Asp Leu Met Phe Glu Glu Ala Val Lys Ala Gly Leu
            35                  40                  45

Val Lys His Arg Asp Glu Met Arg Lys Leu Pro Leu Lys Ile Gln Arg
    50                  55                  60

Glu Leu Gln Met Lys Ala Ala Lys Lys Ile Thr Glu Met Ala Lys Glu
65                  70                  75                  80

His Pro Ile Leu Val Asp Thr His Ala Thr Ile Lys Thr Pro His Gly
```

```
                        85                  90                  95
Tyr Met Leu Gly Leu Pro Tyr Glu Val Val Lys Thr Leu Asn Pro Asn
                    100                 105                 110

Phe Ile Val Ile Ile Glu Ala Thr Pro Ser Glu Ile Leu Gly Arg Arg
                115                 120                 125

Leu Arg Asp Leu Lys Arg Arg Asp Val Glu Thr Glu Glu Gln Ile
            130                 135                 140

Gln Arg His Gln Asp Leu Asn Arg Ala Ala Ile Ala Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
                180                 185                 190

Asn Glu Tyr Ala
            195

<210> SEQ ID NO 5
<211> LENGTH: 196
<212> TYPE: PRT
<213> ORGANISM: Pyrococcus horikoshii

<400> SEQUENCE: 5

Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Lys Leu
        35                  40                  45

Val Lys His Arg Asp Glu Met Arg Lys Leu Pro Leu Glu Val Gln Arg
    50                  55                  60

Glu Leu Gln Met Asn Ala Ala Lys Lys Ile Ala Glu Met Ala Lys Asn
65                  70                  75                  80

Tyr Pro Ile Leu Leu Asp Thr His Ala Thr Ile Lys Thr Pro His Gly
                85                  90                  95

Tyr Leu Leu Gly Leu Pro Tyr Glu Val Ile Lys Ile Leu Asn Pro Asn
                    100                 105                 110

Phe Ile Val Ile Ile Glu Ala Thr Pro Ser Glu Ile Leu Gly Arg Arg
                115                 120                 125

Leu Arg Asp Leu Lys Arg Asp Arg Asp Val Glu Thr Glu Glu Gln Ile
            130                 135                 140

Gln Arg His Gln Asp Leu Asn Arg Ala Ala Ile Thr Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
                180                 185                 190

Lys Glu Tyr Ala
            195

<210> SEQ ID NO 6
<211> LENGTH: 196
<212> TYPE: PRT
<213> ORGANISM: Pyrococcus abyssi

<400> SEQUENCE: 6

Met Ser Phe Val Val Ile Ile Thr Gly Ile Pro Gly Val Gly Lys Ser
```

```
            1               5                   10                  15
          Thr Ile Thr Arg Leu Ala Leu Gln Arg Thr Lys Ala Lys Phe Lys Leu
                          20                  25                  30
          Ile Asn Phe Gly Asp Leu Met Phe Glu Glu Ala Val Lys Ala Gly Leu
                          35                  40                  45
          Val Asn His Arg Asp Glu Met Arg Lys Leu Pro Leu Glu Ile Gln Arg
                          50                  55                  60
          Asp Leu Gln Met Lys Val Ala Lys Lys Ile Ser Glu Met Ala Arg Gln
          65                  70                  75                  80
          Gln Pro Ile Leu Leu Asp Thr His Ala Thr Ile Lys Thr Pro His Gly
                          85                  90                  95
          Tyr Leu Leu Gly Leu Pro Tyr Glu Val Ile Lys Thr Leu Asn Pro Asn
                          100                 105                 110
          Phe Ile Val Ile Ile Glu Ala Thr Pro Ser Glu Ile Leu Gly Arg Arg
                          115                 120                 125
          Leu Arg Asp Leu Lys Arg Asp Arg Asp Val Glu Thr Glu Glu Gln Ile
                          130                 135                 140
          Gln Arg His Gln Asp Leu Asn Arg Ala Ala Ile Ala Tyr Ala Met
          145                 150                 155                 160
          His Ser Asn Ala Leu Ile Lys Ile Ile Glu Asn His Glu Asp Lys Gly
                          165                 170                 175
          Leu Glu Glu Ala Val Asn Glu Leu Val Glu Ile Leu Asp Leu Ala Val
                          180                 185                 190
          Lys Glu Tyr Ala
                          195

<210> SEQ ID NO 7
<211> LENGTH: 192
<212> TYPE: PRT
<213> ORGANISM: Methanococcus thermolithotrophicus

<400> SEQUENCE: 7

Met Lys Asn Lys Leu Val Val Thr Gly Val Pro Gly Val Gly Gly
          1               5                   10                  15
          Thr Thr Ile Thr Gln Lys Ala Met Glu Lys Leu Ser Glu Glu Gly Ile
                          20                  25                  30
          Asn Tyr Lys Met Val Asn Phe Gly Thr Val Met Phe Glu Val Ala Gln
                          35                  40                  45
          Glu Glu Asn Leu Val Glu Asp Arg Asp Gln Met Arg Lys Leu Asp Pro
                          50                  55                  60
          Asp Thr Gln Lys Arg Ile Gln Lys Leu Ala Gly Arg Lys Ile Ala Glu
          65                  70                  75                  80
          Met Val Lys Glu Ser Pro Val Val Asp Thr His Ser Thr Ile Lys
                          85                  90                  95
          Thr Pro Lys Gly Tyr Leu Pro Gly Leu Pro Val Trp Val Leu Asn Glu
                          100                 105                 110
          Leu Asn Pro Asp Ile Ile Ile Val Glu Thr Ser Gly Asp Glu Ile
                          115                 120                 125
          Leu Ile Arg Arg Leu Asn Asp Glu Thr Arg Asn Arg Asp Leu Glu Thr
                          130                 135                 140
          Thr Ala Gly Ile Glu Glu His Gln Ile Met Asn Arg Ala Ala Met
          145                 150                 155                 160
          Thr Tyr Gly Val Leu Thr Gly Ala Thr Val Lys Ile Ile Gln Asn Lys
                          165                 170                 175
```

Asn Asn Leu Leu Asp Tyr Ala Val Glu Glu Leu Ile Ser Val Leu Arg
            180                 185                 190

<210> SEQ ID NO 8
<211> LENGTH: 192
<212> TYPE: PRT
<213> ORGANISM: Methanococcus voltae

<400> SEQUENCE: 8

Met Lys Asn Lys Val Val Val Thr Gly Val Pro Gly Val Gly Ser
1               5                   10                  15

Thr Thr Ser Ser Gln Leu Ala Met Asp Asn Leu Arg Lys Glu Gly Val
            20                  25                  30

Asn Tyr Lys Met Val Ser Phe Gly Ser Val Met Phe Glu Val Ala Lys
        35                  40                  45

Glu Glu Asn Leu Val Ser Asp Arg Asp Gln Met Arg Lys Met Asp Pro
50                  55                  60

Glu Thr Gln Lys Arg Ile Gln Lys Met Ala Gly Arg Lys Ile Ala Glu
65                  70                  75                  80

Met Ala Lys Glu Ser Pro Val Ala Val Asp Thr His Ser Thr Val Ser
                85                  90                  95

Thr Pro Lys Gly Tyr Leu Pro Gly Leu Pro Ser Trp Val Leu Asn Glu
            100                 105                 110

Leu Asn Pro Asp Leu Ile Ile Val Val Glu Thr Thr Gly Asp Glu Ile
        115                 120                 125

Leu Met Arg Arg Met Ser Asp Glu Thr Arg Val Arg Asp Leu Asp Thr
130                 135                 140

Ala Ser Thr Ile Glu Gln His Gln Phe Met Asn Arg Cys Ala Ala Met
145                 150                 155                 160

Ser Tyr Gly Val Leu Thr Gly Ala Thr Val Lys Ile Val Gln Asn Arg
                165                 170                 175

Asn Gly Leu Leu Asp Gln Ala Val Glu Glu Leu Thr Asn Val Leu Arg
            180                 185                 190

<210> SEQ ID NO 9
<211> LENGTH: 195
<212> TYPE: PRT
<213> ORGANISM: Methanococcus jannaschii

<400> SEQUENCE: 9

Met Met Met Met Lys Asn Lys Val Val Ile Val Gly Val Pro Gly
1               5                   10                  15

Val Gly Ser Thr Thr Val Thr Asn Lys Ala Ile Glu Glu Leu Lys Lys
            20                  25                  30

Glu Gly Ile Glu Tyr Lys Ile Val Asn Phe Gly Thr Val Met Phe Glu
        35                  40                  45

Ile Ala Lys Glu Glu Gly Leu Val His Arg Asp Gln Leu Arg Lys
50                  55                  60

Leu Pro Pro Glu Glu Gln Lys Arg Ile Gln Lys Leu Ala Gly Lys Lys
65                  70                  75                  80

Ile Ala Glu Met Ala Lys Glu Phe Asn Ile Val Val Asp Thr His Ser
                85                  90                  95

Thr Ile Lys Thr Pro Lys Gly Tyr Leu Pro Gly Leu Pro Ala Trp Val
            100                 105                 110

Leu Glu Glu Leu Asn Pro Asp Ile Ile Val Leu Val Glu Ala Glu Asn
        115                 120                 125

```
Asp Glu Ile Leu Met Arg Arg Leu Lys Asp Glu Thr Arg Gln Arg Asp
            130                 135                 140

Phe Glu Ser Thr Glu Asp Ile Gly Glu His Ile Phe Met Asn Arg Cys
145                 150                 155                 160

Ala Ala Met Thr Tyr Ala Val Leu Thr Gly Ala Thr Val Lys Ile Ile
                165                 170                 175

Lys Asn Arg Asp Phe Leu Leu Asp Lys Ala Val Gln Glu Leu Ile Glu
            180                 185                 190

Val Leu Lys
        195

<210> SEQ ID NO 10
<211> LENGTH: 191
<212> TYPE: PRT
<213> ORGANISM: Methanopyrus kandleri

<400> SEQUENCE: 10

Met Gly Tyr Val Ile Val Ala Thr Gly Val Pro Gly Val Gly Ala Thr
1               5                   10                  15

Thr Val Thr Thr Glu Ala Val Lys Glu Leu Glu Gly Tyr Glu His Val
            20                  25                  30

Asn Tyr Gly Asp Val Met Leu Glu Ile Ala Lys Glu Gly Leu Val
        35                  40                  45

Glu His Arg Asp Glu Ile Arg Lys Leu Pro Ala Glu Lys Gln Arg Glu
50                  55                  60

Ile Gln Arg Leu Ala Ala Arg Ile Ala Lys Met Ala Glu Glu Lys
65                  70                  75                  80

Glu Gly Ile Ile Val Asp Thr His Cys Thr Ile Lys Thr Pro Ala Gly
                85                  90                  95

Tyr Leu Pro Gly Leu Pro Ile Trp Val Leu Glu Glu Leu Gln Pro Asp
            100                 105                 110

Val Ile Val Leu Ile Glu Ala Asp Pro Asp Glu Ile Met Met Arg Arg
            115                 120                 125

Val Lys Asp Ser Glu Glu Arg Gln Arg Asp Tyr Asp Arg Ala His Glu
            130                 135                 140

Ile Glu Glu His Gln Lys Met Asn Arg Met Ala Ala Met Ala Tyr Ala
145                 150                 155                 160

Ala Leu Thr Gly Ala Thr Val Lys Ile Ile Glu Asn His Asp Asp Arg
                165                 170                 175

Leu Glu Glu Ala Val Arg Glu Phe Val Glu Thr Val Arg Ser Leu
            180                 185                 190

<210> SEQ ID NO 11
<211> LENGTH: 192
<212> TYPE: PRT
<213> ORGANISM: Methanotorris igneus

<400> SEQUENCE: 11

Met Lys Asn Lys Val Val Val Thr Gly Val Pro Gly Val Gly Gly
1               5                   10                  15

Thr Thr Leu Thr Gln Lys Thr Ile Glu Lys Leu Lys Glu Glu Gly Ile
            20                  25                  30

Glu Tyr Lys Met Val Asn Phe Gly Thr Val Met Phe Glu Val Ala Lys
        35                  40                  45

Glu Glu Gly Leu Val Glu Asp Arg Asp Gln Met Arg Lys Leu Asp Pro
50                  55                  60
```

```
Asp Thr Gln Lys Arg Ile Gln Lys Leu Ala Gly Arg Lys Ile Ala Glu
 65                  70                  75                  80

Met Ala Lys Glu Ser Asn Val Ile Val Asp Thr His Ser Thr Val Lys
                 85                  90                  95

Thr Pro Lys Gly Tyr Leu Ala Gly Leu Pro Ile Trp Val Leu Glu Glu
            100                 105                 110

Leu Asn Pro Asp Ile Ile Val Ile Val Glu Thr Ser Ser Asp Glu Ile
        115                 120                 125

Leu Met Arg Arg Leu Gly Asp Ala Thr Arg Asn Arg Asp Ile Glu Leu
    130                 135                 140

Thr Ser Asp Ile Asp Glu His Gln Phe Met Asn Arg Cys Ala Ala Met
145                 150                 155                 160

Ala Tyr Gly Val Leu Thr Gly Ala Thr Val Lys Ile Ile Lys Asn Arg
                165                 170                 175

Asp Gly Leu Leu Asp Lys Ala Val Glu Glu Leu Ile Ser Val Leu Lys
            180                 185                 190

<210> SEQ ID NO 12
<211> LENGTH: 197
<212> TYPE: PRT
<213> ORGANISM: Pyrobaculum aerophilum

<400> SEQUENCE: 12

Met Lys Ile Val Ile Val Ala Leu Pro Gly Ser Gly Lys Thr Thr Ile
  1               5                  10                  15

Leu Asn Phe Val Lys Gln Lys Leu Pro Asp Val Lys Ile Val Asn Tyr
                 20                  25                  30

Gly Asp Val Met Leu Glu Ile Ala Lys Lys Arg Phe Gly Ile Gln His
            35                  40                  45

Arg Asp Glu Met Arg Lys Lys Ile Pro Val Asp Glu Tyr Arg Lys Val
 50                  55                  60

Gln Glu Glu Ala Ala Glu Tyr Ile Ala Ser Leu Thr Gly Asp Val Ile
 65                  70                  75                  80

Ile Asp Thr His Ala Ser Ile Lys Ile Gly Gly Tyr Tyr Pro Gly
                 85                  90                  95

Leu Pro Asp Arg Ile Ile Ser Lys Leu Lys Pro Asp Val Ile Leu Leu
            100                 105                 110

Leu Glu Tyr Asp Pro Lys Val Ile Leu Glu Arg Arg Lys Lys Asp Pro
        115                 120                 125

Asp Arg Phe Arg Asp Leu Glu Ser Glu Glu Ile Glu Met His Gln
    130                 135                 140

Gln Ala Asn Arg Tyr Tyr Ala Phe Ala Ala Asn Ala Gly Glu Ser
145                 150                 155                 160

Thr Val His Val Leu Asn Phe Arg Gly Lys Pro Glu Ser Arg Pro Phe
                165                 170                 175

Glu His Ala Glu Val Ala Ala Glu Tyr Ile Val Asn Leu Ile Leu Arg
            180                 185                 190

Thr Arg Gln Lys Ser
        195

<210> SEQ ID NO 13
<211> LENGTH: 220
<212> TYPE: PRT
<213> ORGANISM: Thermotoga maritima

<400> SEQUENCE: 13
```

```
Met Met Ala Tyr Leu Val Phe Leu Gly Pro Pro Gly Ala Gly Lys Gly
1               5                   10                  15

Thr Tyr Ala Lys Arg Ile Gln Glu Lys Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Lys Gly Glu Leu Val Pro Asp
    50                  55                  60

Glu Leu Val Asn Glu Val Val Lys Arg Arg Leu Ser Glu Lys Asp Cys
65                  70                  75                  80

Glu Lys Gly Phe Ile Leu Asp Gly Tyr Pro Arg Thr Val Ala Gln Ala
                85                  90                  95

Glu Phe Leu Asp Ser Phe Leu Glu Ser Gln Asn Lys Gln Leu Thr Ala
                100                 105                 110

Ala Val Leu Phe Asp Val Pro Glu Asp Val Val Gln Arg Leu Thr
                115                 120                 125

Ser Arg Arg Ile Cys Pro Lys Cys Gly Arg Ile Tyr Asn Met Ile Ser
    130                 135                 140

Leu Pro Pro Lys Glu Asp Glu Leu Cys Asp Asp Cys Lys Val Lys Leu
145                 150                 155                 160

Val Gln Arg Asp Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
                180                 185                 190

Gly Ile Leu Lys Arg Val Asp Gly Thr Ile Gly Ile Asp Asn Val Val
                195                 200                 205

Ala Glu Val Leu Lys Ile Ile Gly Trp Ser Asp Lys
                210                 215                 220

<210> SEQ ID NO 14
<211> LENGTH: 204
<212> TYPE: PRT
<213> ORGANISM: Aeropyrum pernix

<400> SEQUENCE: 14

Met Lys Val Arg His Pro Phe Lys Val Val Val Thr Gly Val Pro
1               5                   10                  15

Gly Val Gly Lys Thr Thr Val Ile Lys Glu Leu Gln Gly Leu Ala Glu
            20                  25                  30

Lys Glu Gly Val Lys Leu His Ile Val Asn Phe Gly Ser Phe Met Leu
        35                  40                  45

Asp Thr Ala Val Lys Leu Gly Leu Val Glu Asp Arg Asp Lys Ile Arg
    50                  55                  60

Thr Leu Pro Leu Arg Arg Gln Leu Glu Leu Arg Glu Ala Ala Lys
65                  70                  75                  80

Arg Ile Val Ala Glu Ala Ser Lys Ala Leu Gly Gly Asp Gly Val Leu
                85                  90                  95

Ile Ile Asp Thr His Ala Leu Val Lys Thr Val Ala Gly Tyr Trp Pro
                100                 105                 110

Gly Leu Pro Lys His Val Leu Asp Glu Leu Lys Pro Asp Met Ile Ala
                115                 120                 125

Val Val Glu Ala Ser Pro Glu Glu Val Ala Ala Arg Gln Ala Arg Asp
    130                 135                 140

Thr Thr Arg Tyr Arg Val Asp Ile Gly Gly Val Glu Gly Val Lys Arg
145                 150                 155                 160
```

```
Leu Met Glu Asn Ala Arg Ala Ser Ile Ala Ser Ala Ile Gln Tyr
            165                 170                 175

Ala Ser Thr Val Ala Ile Val Glu Asn Arg Glu Gly Glu Ala Lys
        180                 185                 190

Ala Ala Glu Glu Leu Leu Arg Leu Ile Lys Asn Leu
    195                 200

<210> SEQ ID NO 15
<211> LENGTH: 216
<212> TYPE: PRT
<213> ORGANISM: Archaeoglobus fulgidus

<400> SEQUENCE: 15

Met Asn Leu Ile Phe Leu Gly Pro Pro Gly Ala Gly Lys Gly Thr Gln
1               5                   10                  15

Ala Lys Arg Val Ser Glu Lys Tyr Gly Ile Pro Gln Ile Ser Thr Gly
            20                  25                  30

Asp Met Leu Arg Glu Ala Val Ala Lys Gly Thr Glu Leu Gly Lys Lys
        35                  40                  45

Ala Lys Glu Tyr Met Asp Lys Gly Glu Leu Val Pro Asp Glu Val Val
    50                  55                  60

Ile Gly Ile Val Lys Glu Arg Leu Gln Gln Pro Asp Cys Glu Lys Gly
65                  70                  75                  80

Phe Ile Leu Asp Gly Phe Pro Arg Thr Leu Ala Gln Ala Glu Ala Leu
                85                  90                  95

Asp Glu Met Leu Lys Glu Leu Asn Lys Lys Ile Asp Ala Val Ile Asn
            100                 105                 110

Val Val Val Pro Glu Glu Glu Val Val Lys Arg Ile Thr Tyr Arg Arg
        115                 120                 125

Thr Cys Arg Asn Cys Gly Ala Val Tyr His Leu Ile Tyr Ala Pro Pro
    130                 135                 140

Lys Glu Asp Asn Lys Cys Asp Lys Cys Gly Gly Glu Leu Tyr Gln Arg
145                 150                 155                 160

Asp Asp Lys Glu Glu Thr Val Arg Glu Arg Tyr Arg Val Tyr Lys Gln
                165                 170                 175

Asn Thr Glu Pro Leu Ile Asp Tyr Tyr Arg Lys Lys Gly Ile Leu Tyr
            180                 185                 190

Asp Val Asp Gly Thr Lys Asp Ile Glu Gly Val Trp Lys Glu Ile Glu
        195                 200                 205

Ala Ile Leu Glu Lys Ile Lys Ser
    210                 215

<210> SEQ ID NO 16
<211> LENGTH: 220
<212> TYPE: PRT
<213> ORGANISM: Pyrococcus abyssi

<400> SEQUENCE: 16

Met Asn Ile Leu Ile Phe Gly Pro Pro Gly Ser Gly Lys Ser Thr Gln
1               5                   10                  15

Ala Arg Arg Ile Thr Glu Arg Tyr Gly Leu Thr Tyr Ile Ala Ser Gly
            20                  25                  30

Asp Ile Ile Arg Ala Glu Ile Lys Ala Arg Thr Pro Leu Gly Ile Glu
        35                  40                  45

Met Glu Arg Tyr Leu Ser Arg Gly Asp Leu Ile Pro Asp Thr Ile Val
    50                  55                  60
```

```
Asn Thr Leu Ile Ile Ser Lys Leu Arg Arg Val Arg Glu Asn Phe Ile
 65                  70                  75                  80

Met Asp Gly Tyr Pro Arg Thr Pro Glu Gln Val Ile Thr Leu Glu Asn
                 85                  90                  95

Tyr Leu Tyr Asp His Gly Ile Lys Leu Asp Val Ala Ile Asp Ile Tyr
            100                 105                 110

Ile Thr Lys Glu Glu Ser Val Arg Arg Ile Ser Gly Arg Arg Ile Cys
            115                 120                 125

Ser Lys Cys Gly Ala Val Tyr His Val Glu Phe Asn Pro Pro Lys Val
130                 135                 140

Pro Gly Lys Cys Asp Ile Cys Gly Gly Glu Leu Ile Gln Arg Pro Asp
145                 150                 155                 160

Asp Arg Pro Glu Ile Val Glu Lys Arg Tyr Asp Ile Tyr Ser Lys Asn
                165                 170                 175

Met Glu Pro Ile Ile Lys Phe Tyr Gln Lys Gln Gly Ile Tyr Val Arg
            180                 185                 190

Ile Asp Gly His Gly Ser Ile Asp Glu Val Trp Glu Arg Ile Arg Pro
            195                 200                 205

Leu Leu Asp Tyr Ile Tyr Asn Gln Glu Asn Arg Arg
            210                 215                 220

<210> SEQ ID NO 17
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: The amino acid "X" may be K or E.
<220> FEATURE:
<221> NAME/KEY: MISC_FEATURE
<222> LOCATION: (75)..(75)
<223> OTHER INFORMATION: The amino acid "X" may be T or A.
<220> FEATURE:
<221> NAME/KEY: MISC_FEATURE
<222> LOCATION: (98)..(98)
<223> OTHER INFORMATION: The amino acid "X" may be M or L.
<220> FEATURE:
<221> NAME/KEY: MISC_FEATURE
<222> LOCATION: (157)..(157)
<223> OTHER INFORMATION: The amino acid "X" may be A, or a small
      hydrophobic residue (e.g. I or L) or a large hydrophobic residue
      (e.g. F), that increases the thermal stability of the enzyme.

<400> SEQUENCE: 17

Met Pro Phe Val Val Ile Ile Thr Gly Ile Pro Gly Val Gly Lys Ser
 1               5                  10                  15

Thr Ile Thr Arg Leu Ala Leu Gln Arg Thr Lys Ala Lys Phe Arg Leu
             20                  25                  30

Ile Asn Phe Gly Asp Leu Met Phe Glu Glu Ala Val Lys Ala Gly Leu
         35                  40                  45

Val Lys His Arg Asp Glu Met Arg Lys Leu Pro Leu Xaa Ile Gln Arg
 50                  55                  60

Glu Leu Gln Met Lys Ala Ala Lys Lys Ile Xaa Glu Met Ala Lys Glu
 65                  70                  75                  80

His Pro Ile Leu Val Asp Thr His Ala Thr Ile Lys Thr Pro His Gly
             85                  90                  95

Tyr Xaa Leu Gly Leu Pro Tyr Glu Val Val Lys Thr Leu Asn Pro Asn
            100                 105                 110
```

```
Phe Ile Val Ile Ile Glu Ala Thr Pro Ser Glu Ile Leu Gly Arg Arg
            115                 120                 125

Leu Arg Asp Leu Lys Arg Asp Arg Asp Val Glu Thr Glu Glu Gln Ile
130                 135                 140

Gln Arg His Gln Asp Leu Asn Arg Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
                180                 185                 190

Asn Glu Tyr Ala
                195

<210> SEQ ID NO 18
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (47)..(47)
<223> OTHER INFORMATION: The amino acid "X" may be G, or may be any
      other residue that increases the thermal stability of the enzyme.
<220> FEATURE:
<221> NAME/KEY: MISC_FEATURE
<222> LOCATION: (157)..(157)
<223> OTHER INFORMATION: The amino acid "X" may be A, or a small
      hydrophobic residue (e.g. I or L) or a large hydrophobic residue
      (e.g. F), that increases the thermal stability of the enzyme.

<400> SEQUENCE: 18

Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
                20                  25                  30

Ile Asn Phe Gly Asp Leu Met Phe Glu Glu Ala Leu Lys Leu Xaa Leu
            35                  40                  45

Val Lys His Arg Asp Glu Met Arg Lys Leu Pro Leu Glu Val Gln Arg
50                  55                  60

Glu Leu Gln Met Asn Ala Ala Lys Lys Ile Ala Glu Met Ala Lys Asn
65                  70                  75                  80

Tyr Pro Ile Leu Leu Asp Thr His Ala Thr Ile Lys Thr Pro His Gly
                85                  90                  95

Tyr Leu Leu Gly Leu Pro Tyr Glu Val Ile Lys Ile Leu Asn Pro Asn
                100                 105                 110

Phe Ile Val Ile Ile Glu Ala Thr Pro Ser Glu Ile Leu Gly Arg Arg
            115                 120                 125

Leu Arg Asp Leu Lys Arg Asp Arg Asp Val Glu Thr Glu Glu Gln Ile
130                 135                 140

Gln Arg His Gln Asp Leu Asn Arg Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
                180                 185                 190

Lys Glu Tyr Ala
                195
```

```
<210> SEQ ID NO 19
<211> LENGTH: 194
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (103)..(103)
<223> OTHER INFORMATION: The amino acid "X" may be A or M.

<400> SEQUENCE: 19

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Xaa Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys

<210> SEQ ID NO 20
<211> LENGTH: 403
<212> TYPE: PRT
<213> ORGANISM: Thermotoga maritima

<400> SEQUENCE: 20

Met Arg Val Leu Val Ile Asn Ser Gly Ser Ser Ile Lys Tyr Gln
1               5                   10                  15

Leu Ile Glu Met Glu Gly Glu Lys Val Leu Cys Lys Gly Ile Ala Glu
            20                  25                  30

Arg Ile Gly Ile Glu Gly Ser Arg Leu Val His Arg Val Gly Asp Glu
        35                  40                  45

Lys His Val Ile Glu Arg Glu Leu Pro Asp His Glu Glu Ala Leu Lys
50                  55                  60

Leu Ile Leu Asn Thr Leu Val Asp Glu Lys Leu Gly Val Ile Lys Asp
65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Glu Val Leu Lys Ala Ile
```

```
            100                 105                 110
Glu Glu Val Ser Pro Leu Ala Pro Leu His Asn Pro Ala Asn Leu Met
        115                 120                 125

Gly Ile Lys Ala Ala Met Lys Leu Leu Pro Gly Val Pro Asn Val Ala
130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Glu Lys Tyr Lys Ile Arg Arg Tyr
                165                 170                 175

Gly Phe His Gly Thr Ser His Arg Tyr Val Ser Lys Arg Ala Ala Glu
            180                 185                 190

Ile Leu Gly Lys Lys Leu Glu Glu Leu Lys Ile Ile Thr Cys His Ile
        195                 200                 205

Gly Asn Gly Ala Ser Val Ala Ala Val Lys Tyr Gly Lys Cys Val Asp
    210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
                245                 250                 255

Gly Ile Ser Pro Gln Glu Met Tyr Asp Ile Leu Asn Lys Lys Ser Gly
            260                 265                 270

Val Tyr Gly Leu Ser Lys Gly Phe Ser Ser Asp Met Arg Asp Ile Glu
        275                 280                 285

Glu Ala Ala Leu Lys Gly Asp Glu Trp Cys Lys Leu Val Leu Glu Ile
    290                 295                 300

Tyr Asp Tyr Arg Ile Ala Lys Tyr Ile Gly Ala Tyr Ala Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val
            340                 345                 350

Lys Leu Asp Lys Gln Lys Asn Glu Glu Thr Ile Arg Gly Lys Glu Gly
        355                 360                 365

Ile Ile Ser Thr Pro Asp Ser Arg Val Lys Val Leu Val Pro Thr
    370                 375                 380

Asn Glu Glu Leu Met Ile Ala Arg Asp Thr Lys Glu Ile Val Glu Lys
385                 390                 395                 400

Ile Gly Arg
```

<210> SEQ ID NO 21
<211> LENGTH: 478
<212> TYPE: PRT
<213> ORGANISM: Pyrococcus horikoshii

<400> SEQUENCE: 21

```
Met Arg Arg Met Lys Leu Pro Ser His Lys Thr Lys Ile Val Ala Thr
1               5                   10                  15

Ile Gly Pro Ala Thr Asn Ser Lys Lys Met Ile Lys Lys Leu Ile Glu
            20                  25                  30

Ala Gly Met Asn Val Ala Arg Ile Asn Phe Ser His Gly Thr Phe Glu
        35                  40                  45

Glu His Ala Lys Ile Ile Glu Met Val Arg Glu Gln Ser Gln Lys Leu
    50                  55                  60

Asp Arg Arg Val Ala Ile Leu Ala Asp Leu Pro Gly Leu Lys Ile Arg
```

```
            65                  70                  75                  80
Val Gly Glu Ile Lys Gly Gly Tyr Val Glu Leu Glu Arg Gly Glu Lys
                    85                  90                  95
Val Thr Leu Thr Thr Lys Asp Ile Glu Gly Asp Glu Thr Thr Ile Pro
                100                 105                 110
Val Glu Tyr Lys Asp Phe Pro Lys Leu Val Ser Lys Gly Asp Val Ile
                115                 120                 125
Tyr Leu Ser Asp Gly Tyr Ile Val Leu Arg Val Glu Asp Val Lys Glu
            130                 135                 140
Asn Glu Val Glu Ala Val Val Ile Ser Gly Gly Lys Leu Phe Ser Arg
145                 150                 155                 160
Lys Gly Ile Asn Ile Pro Lys Ala Tyr Leu Pro Val Glu Ala Ile Thr
                165                 170                 175
Pro Arg Asp Ile Glu Ile Met Lys Phe Ala Ile Glu His Gly Val Asp
                180                 185                 190
Ala Ile Gly Leu Ser Phe Val Gly Asn Val Tyr Asp Val Leu Lys Ala
            195                 200                 205
Lys Ser Phe Leu Glu Arg Asn Gly Ala Gly Asp Thr Phe Val Ile Ala
        210                 215                 220
Lys Ile Glu Arg Pro Asp Ala Val Arg Asn Phe Asn Glu Ile Leu Asn
225                 230                 235                 240
Ala Ala Asp Gly Ile Met Ile Ala Arg Gly Asp Leu Gly Val Glu Met
                245                 250                 255
Pro Ile Glu Gln Leu Pro Ile Leu Gln Lys Arg Leu Ile Arg Lys Ala
                260                 265                 270
Asn Met Glu Gly Lys Pro Val Ile Thr Ala Thr Gln Met Leu Val Ser
        275                 280                 285
Met Thr Met Glu Lys Val Pro Thr Arg Ala Glu Val Thr Asp Val Ala
    290                 295                 300
Asn Ala Ile Leu Asp Gly Thr Asp Ala Val Met Leu Ser Glu Glu Thr
305                 310                 315                 320
Ala Val Gly Lys Phe Pro Ile Glu Ala Val Glu Met Met Ala Arg Ile
                325                 330                 335
Ala Lys Val Thr Glu Glu Tyr Arg Glu Ser Phe Gly Ile Thr Arg Met
                340                 345                 350
Arg Glu Phe Leu Glu Gly Thr Lys Arg Gly Thr Ile Lys Glu Ala Ile
            355                 360                 365
Thr Arg Ser Ile Ile Asp Ala Ile Cys Thr Ile Gly Ile Lys Phe Ile
        370                 375                 380
Leu Thr Pro Thr Lys Thr Gly Arg Thr Ala Arg Leu Ile Ser Arg Phe
385                 390                 395                 400
Lys Pro Lys Gln Trp Ile Leu Ala Phe Ser Thr Arg Glu Lys Val Cys
                405                 410                 415
Asn Asn Leu Met Phe Ser Tyr Gly Val Tyr Pro Phe Cys Met Glu Glu
                420                 425                 430
Gly Phe Asn Glu Asn Asp Ile Val Arg Leu Ile Lys Gly Leu Gly Leu
            435                 440                 445
Val Gly Ser Asp Asp Ile Val Leu Met Thr Glu Gly Lys Pro Ile Glu
        450                 455                 460
Lys Thr Val Gly Thr Asn Ser Ile Lys Ile Phe Gln Ile Ala
465                 470                 475

<210> SEQ ID NO 22
```

```
<211> LENGTH: 452
<212> TYPE: PRT
<213> ORGANISM: Sulfolobus solfataricus

<400> SEQUENCE: 22
```

| | | | | | | | | | | | | | | | |
|---|---|---|---|---|---|---|---|---|---|---|---|---|---|---|---|
| Met | Arg | Lys | Thr | Lys | Ile | Val | Ala | Thr | Leu | Gly | Pro | Ser | Ser | Glu | Glu |
| 1 | | | | 5 | | | | | 10 | | | | | 15 | |
| Lys | Val | Lys | Glu | Leu | Ala | Glu | Tyr | Val | Asp | Val | Phe | Arg | Ile | Asn | Phe |
| | | | 20 | | | | | 25 | | | | | 30 | | |
| Ala | His | Gly | Asp | Glu | Thr | Ser | His | Arg | Lys | Tyr | Phe | Asp | Leu | Ile | Arg |
| | | | 35 | | | | | 40 | | | | | 45 | | |
| Thr | Tyr | Ala | Pro | Glu | Ser | Ser | Ile | Ile | Val | Asp | Leu | Pro | Gly | Pro | Lys |
| 50 | | | | | 55 | | | | | 60 | | | | | |
| Leu | Arg | Leu | Gly | Glu | Leu | Lys | Glu | Pro | Ile | Glu | Val | Lys | Lys | Gly | Asp |
| 65 | | | | | 70 | | | | | 75 | | | | | 80 |
| Lys | Ile | Val | Phe | Ser | Gln | Lys | Asp | Gly | Ile | Pro | Val | Asp | Asp | Glu | Leu |
| | | | | 85 | | | | | 90 | | | | | 95 | |
| Phe | Tyr | Ser | Ala | Val | Lys | Glu | Asn | Ser | Asp | Ile | Leu | Ile | Ala | Asp | Gly |
| | | | | 100 | | | | | 105 | | | | | 110 | |
| Thr | Ile | Arg | Val | Arg | Val | Lys | Ser | Lys | Ala | Lys | Asp | Arg | Val | Glu | Gly |
| | | | | 115 | | | | | 120 | | | | | 125 | |
| Thr | Val | Ile | Glu | Gly | Gly | Ile | Leu | Leu | Ser | Arg | Lys | Gly | Ile | Asn | Ile |
| | 130 | | | | | 135 | | | | | 140 | | | | |
| Pro | Asn | Val | Asn | Leu | Lys | Ser | Gly | Ile | Thr | Asp | Asn | Asp | Leu | Lys | Leu |
| 145 | | | | | 150 | | | | | 155 | | | | | 160 |
| Leu | Lys | Arg | Ala | Leu | Asp | Leu | Gly | Ala | Asp | Tyr | Ile | Gly | Leu | Ser | Phe |
| | | | | 165 | | | | | 170 | | | | | 175 | |
| Val | Ile | Ser | Glu | Asn | Asp | Val | Lys | Lys | Val | Lys | Glu | Phe | Val | Gly | Asp |
| | | | | 180 | | | | | 185 | | | | | 190 | |
| Glu | Ala | Trp | Val | Ile | Ala | Lys | Ile | Glu | Lys | Ser | Glu | Ala | Leu | Lys | Asn |
| | | | 195 | | | | | 200 | | | | | 205 | | |
| Leu | Thr | Asn | Ile | Val | Asn | Glu | Ser | Asp | Gly | Ile | Met | Val | Ala | Arg | Gly |
| | 210 | | | | | 215 | | | | | 220 | | | | |
| Asp | Leu | Gly | Val | Glu | Thr | Gly | Leu | Glu | Asn | Leu | Pro | Leu | Ile | Gln | Arg |
| 225 | | | | | 230 | | | | | 235 | | | | | 240 |
| Arg | Ile | Val | Arg | Thr | Ser | Arg | Val | Phe | Gly | Lys | Pro | Val | Ile | Leu | Ala |
| | | | | 245 | | | | | 250 | | | | | 255 | |
| Thr | Gln | Val | Leu | Thr | Ser | Met | Ile | Asn | Ser | Pro | Ile | Pro | Thr | Arg | Ala |
| | | | 260 | | | | | 265 | | | | | 270 | | |
| Glu | Ile | Ile | Asp | Ile | Ser | Asn | Ser | Ile | Met | Gln | Gly | Val | Asp | Ser | Ile |
| | | | 275 | | | | | 280 | | | | | 285 | | |
| Met | Leu | Ser | Asp | Glu | Thr | Ala | Ile | Gly | Asn | Tyr | Pro | Val | Glu | Ser | Val |
| | 290 | | | | | 295 | | | | | 300 | | | | |
| Arg | Thr | Leu | His | Asn | Ile | Ile | Ser | Asn | Val | Glu | Lys | Ser | Val | Lys | His |
| 305 | | | | | 310 | | | | | 315 | | | | | 320 |
| Arg | Pro | Ile | Gly | Pro | Leu | Asn | Ser | Glu | Ser | Asp | Ala | Ile | Ala | Leu | Ala |
| | | | | 325 | | | | | 330 | | | | | 335 | |
| Ala | Val | Asn | Ala | Ser | Lys | Val | Ser | Lys | Ala | Asp | Val | Ile | Val | Val | Tyr |
| | | | | 340 | | | | | 345 | | | | | 350 | |
| Ser | Arg | Ser | Gly | Asn | Ser | Ile | Leu | Arg | Val | Ser | Arg | Leu | Arg | Pro | Glu |
| | | | | 355 | | | | | 360 | | | | | 365 | |
| Arg | Asn | Ile | Ile | Gly | Val | Ser | Pro | Asp | Pro | Arg | Leu | Ala | Lys | Lys | Phe |
| | 370 | | | | | 375 | | | | | 380 | | | | |
| Lys | Leu | Cys | Tyr | Gly | Val | Ile | Pro | Ile | Ser | Ile | Asn | Lys | Lys | Met | Gln |

```
                385                 390                 395                 400
Ser Ile Asp Glu Ile Ile Asp Val Ser Ala Lys Leu Met Gln Glu Lys
                        405                 410                 415

Ile Lys Asp Leu Lys Phe Lys Lys Ile Val Ile Val Gly Gly Asp Pro
                420                 425                 430

Lys Gln Glu Ala Gly Lys Thr Asn Phe Val Ile Val Lys Thr Leu Glu
            435                 440                 445

Gln Gln Lys Lys
        450

<210> SEQ ID NO 23
<211> LENGTH: 466
<212> TYPE: PRT
<213> ORGANISM: Thermotoga maritima

<400> SEQUENCE: 23

Met Arg Ser Thr Lys Ile Val Cys Thr Val Gly Pro Arg Thr Asp Ser
1               5                   10                  15

Tyr Glu Met Ile Glu Lys Met Ile Asp Leu Gly Val Asn Val Phe Arg
            20                  25                  30

Ile Asn Thr Ser His Gly Asp Trp Asn Glu Gln Glu Gln Lys Ile Leu
        35                  40                  45

Lys Ile Lys Asp Leu Arg Glu Lys Lys Lys Pro Val Ala Ile Leu
    50                  55                  60

Ile Asp Leu Ala Gly Pro Lys Ile Arg Thr Gly Tyr Leu Glu Lys Glu
65                  70                  75                  80

Phe Val Glu Leu Lys Gly Gln Ile Phe Thr Leu Thr Lys Glu
                85                  90                  95

Ile Leu Gly Asn Glu His Ile Val Ser Val Asn Leu Ser Ser Leu Pro
            100                 105                 110

Lys Asp Val Lys Lys Gly Asp Thr Ile Leu Leu Ser Asp Gly Glu Ile
        115                 120                 125

Val Leu Glu Val Ile Glu Thr Thr Asp Thr Glu Val Lys Thr Val Val
    130                 135                 140

Lys Val Gly Gly Lys Ile Thr His Arg Arg Gly Val Asn Val Pro Thr
145                 150                 155                 160

Ala Asp Leu Ser Val Glu Ser Ile Thr Asp Arg Asp Arg Glu Phe Ile
                165                 170                 175

Lys Leu Gly Thr Leu His Asp Val Glu Phe Phe Ala Leu Ser Phe Val
            180                 185                 190

Arg Lys Pro Glu Asp Val Leu Lys Ala Lys Glu Ile Arg Lys His
        195                 200                 205

Gly Lys Glu Ile Pro Val Ile Ser Lys Ile Glu Thr Lys Lys Ala Leu
    210                 215                 220

Glu Arg Leu Glu Glu Ile Ile Lys Val Ser Asp Gly Ile Met Val Ala
225                 230                 235                 240

Arg Gly Asp Leu Gly Val Glu Ile Pro Ile Glu Glu Val Pro Ile Val
                245                 250                 255

Gln Lys Glu Ile Ile Lys Leu Ser Lys Tyr Tyr Ser Lys Pro Val Ile
            260                 265                 270

Val Ala Thr Gln Ile Leu Glu Ser Met Ile Glu Asn Pro Phe Pro Thr
        275                 280                 285

Arg Ala Glu Val Thr Asp Ile Ala Asn Ala Ile Phe Asp Gly Ala Asp
    290                 295                 300
```

```
Ala Leu Leu Leu Thr Ala Glu Thr Ala Val Gly Lys His Pro Leu Glu
305                 310                 315                 320

Ala Ile Lys Val Leu Ser Lys Val Ala Lys Glu Ala Glu Lys Lys Leu
            325                 330                 335

Glu Phe Phe Arg Thr Ile Glu Tyr Asp Thr Ser Asp Ile Ser Glu Ala
                340                 345                 350

Ile Ser His Ala Cys Trp Gln Leu Ser Glu Ser Leu Asn Ala Lys Leu
            355                 360                 365

Ile Ile Thr Pro Thr Ile Ser Gly Ser Thr Ala Val Arg Val Ser Lys
370                 375                 380

Tyr Asn Val Ser Gln Pro Ile Val Ala Leu Thr Pro Glu Glu Lys Thr
385                 390                 395                 400

Tyr Tyr Arg Leu Ser Leu Val Arg Lys Val Ile Pro Val Leu Ala Glu
                405                 410                 415

Lys Cys Ser Gln Glu Leu Glu Phe Ile Glu Lys Gly Leu Lys Lys Val
                420                 425                 430

Glu Glu Met Gly Leu Ala Glu Lys Gly Asp Leu Val Val Leu Thr Ser
            435                 440                 445

Gly Val Pro Gly Lys Val Gly Thr Thr Asn Thr Ile Arg Val Leu Lys
450                 455                 460

Val Asp
465
```

<210> SEQ ID NO 24
<211> LENGTH: 477
<212> TYPE: PRT
<213> ORGANISM: Pyrococcus furiosus

<400> SEQUENCE: 24

```
Met Arg Arg Val Lys Leu Pro Ser His Lys Thr Lys Ile Val Ala Thr
1               5                   10                  15

Ile Gly Pro Ala Thr Asn Ser Arg Lys Met Ile Lys Gln Leu Ile Lys
            20                  25                  30

Ala Gly Met Asn Val Ala Arg Ile Asn Phe Ser His Gly Ser Phe Glu
        35                  40                  45

Glu His Ala Arg Val Ile Glu Ile Arg Glu Glu Ala Gln Lys Leu
    50                  55                  60

Asp Arg Arg Val Ala Ile Leu Ala Asp Leu Pro Gly Leu Lys Ile Arg
65                  70                  75                  80

Val Gly Glu Ile Lys Gly Gly Tyr Val Glu Leu Lys Arg Gly Glu Lys
                85                  90                  95

Val Ile Leu Thr Thr Lys Asp Val Glu Gly Asp Glu Thr Thr Ile Pro
            100                 105                 110

Val Asp Tyr Lys Gly Phe Pro Asn Leu Val Ser Lys Gly Asp Ile Ile
        115                 120                 125

Tyr Leu Asn Asp Gly Tyr Ile Val Leu Lys Val Glu Asn Val Arg Glu
130                 135                 140

Asn Glu Val Glu Ala Val Val Leu Ser Gly Gly Lys Leu Phe Ser Arg
145                 150                 155                 160

Lys Gly Val Asn Ile Pro Lys Ala Tyr Leu Pro Val Glu Ala Ile Thr
                165                 170                 175

Pro Lys Asp Phe Glu Ile Met Lys Phe Ala Ile Glu His Gly Val Asp
            180                 185                 190

Ala Ile Gly Leu Ser Phe Val Gly Ser Val Tyr Asp Val Leu Lys Ala
        195                 200                 205
```

```
Lys Ser Phe Leu Glu Lys Asn Asn Ala Glu Asp Val Phe Val Ile Ala
    210                 215                 220

Lys Ile Glu Arg Pro Asp Ala Val Arg Asn Phe Asp Glu Ile Leu Asn
225                 230                 235                 240

Ala Ala Asp Gly Ile Met Ile Ala Arg Gly Asp Leu Gly Val Glu Met
                    245                 250                 255

Pro Ile Glu Gln Leu Pro Ile Leu Gln Lys Lys Leu Ile Arg Lys Ala
                260                 265                 270

Asn Met Glu Gly Lys Pro Val Ile Thr Ala Thr Gln Met Leu Val Ser
            275                 280                 285

Met Thr Thr Glu Lys Val Pro Thr Arg Ala Glu Val Thr Asp Val Ala
290                 295                 300

Asn Ala Ile Leu Asp Gly Thr Asp Ala Val Met Leu Ser Glu Thr
305                 310                 315                 320

Ala Ile Gly Lys Phe Pro Ile Glu Thr Val Glu Met Met Gly Lys Ile
                325                 330                 335

Ala Lys Val Thr Glu Glu Tyr Arg Glu Ser Phe Gly Leu Ser Arg Ile
                340                 345                 350

Arg Glu Phe Met Glu Ile Lys Lys Gly Thr Ile Lys Glu Ala Ile Thr
                355                 360                 365

Arg Ser Ile Ile Asp Ala Ile Cys Thr Ile Asp Ile Lys Phe Ile Leu
            370                 375                 380

Thr Pro Thr Arg Thr Gly Arg Thr Ala Arg Leu Ile Ser Arg Phe Lys
385                 390                 395                 400

Pro Lys Gln Trp Ile Leu Ala Phe Ser Thr Asn Glu Arg Val Cys Asn
                405                 410                 415

Asn Leu Met Phe Ser Tyr Gly Val Tyr Pro Phe Cys Leu Glu Glu Gly
                420                 425                 430

Phe Asp Glu Asn Asp Ile Val Arg Leu Ile Lys Gly Leu Gly Leu Val
            435                 440                 445

Glu Ser Asp Asp Met Val Leu Met Thr Glu Gly Lys Pro Ile Glu Lys
    450                 455                 460

Thr Val Gly Thr Asn Ser Ile Lys Ile Phe Gln Ile Ala
465                 470                 475

<210> SEQ ID NO 25
<211> LENGTH: 408
<212> TYPE: PRT
<213> ORGANISM: Methanosarcina thermophila

<400> SEQUENCE: 25

Met Lys Val Leu Val Ile Asn Ala Gly Ser Ser Leu Lys Tyr Gln
1               5                   10                  15

Leu Ile Asp Met Thr Asn Glu Ser Ala Leu Ala Val Gly Leu Cys Glu
                20                  25                  30

Arg Ile Gly Ile Asp Asn Ser Ile Ile Thr Gln Lys Lys Phe Asp Gly
            35                  40                  45

Lys Lys Leu Glu Lys Leu Thr Asp Leu Pro Thr His Lys Asp Ala Leu
    50                  55                  60

Glu Glu Val Val Lys Ala Leu Thr Asp Asp Phe Gly Val Ile Lys
65                  70                  75                  80

Asp Met Gly Glu Ile Asn Ala Val Gly His Arg Val Val His Gly Gly
                85                  90                  95

Glu Lys Phe Thr Thr Ser Ala Leu Tyr Asp Glu Gly Val Glu Lys Ala
```

|  |  |  | 100 |  |  |  | 105 |  |  |  | 110 |  |
|---|---|---|---|---|---|---|---|---|---|---|---|---|

Ile Lys Asp Cys Phe Glu Leu Ala Pro Leu His Asn Pro Pro Asn Met
           115                      120                  125

Met Gly Ile Ser Ala Cys Ala Glu Ile Met Pro Gly Thr Pro Met Val
130                     135                      140

Ile Val Phe Asp Thr Ala Phe His Gln Thr Met Pro Pro Tyr Ala Tyr
145                   150                   155                  160

Met Tyr Ala Leu Pro Tyr Asp Leu Tyr Glu Lys His Gly Val Arg Lys
           165                      170                  175

Tyr Gly Phe His Gly Thr Ser His Lys Tyr Val Ala Glu Arg Ala Ala
           180                      185                  190

Leu Met Leu Gly Lys Pro Ala Glu Glu Thr Lys Ile Ile Thr Cys His
           195                      200                  205

Leu Gly Asn Gly Ser Ser Ile Thr Ala Val Glu Gly Lys Ser Val
           210                      215                  220

Glu Thr Ser Met Gly Phe Thr Pro Leu Glu Gly Leu Ala Met Gly Thr
225                     230                     235                  240

Arg Cys Gly Ser Ile Asp Pro Ala Ile Val Pro Phe Leu Met Glu Lys
           245                      250                  255

Glu Gly Leu Thr Thr Arg Glu Ile Asp Thr Leu Met Asn Lys Lys Ser
           260                      265                  270

Gly Val Leu Gly Val Ser Gly Leu Ser Asn Asp Phe Arg Asp Leu Asp
           275                      280                  285

Glu Ala Ala Ser Lys Gly Asn Arg Lys Ala Glu Leu Ala Leu Glu Ile
290                     295                     300

Phe Ala Tyr Lys Val Lys Lys Phe Ile Gly Glu Tyr Ser Ala Val Leu
305                     310                     315                  320

Asn Gly Ala Asp Ala Val Val Phe Thr Ala Gly Ile Gly Glu Asn Ser
           325                      330                  335

Ala Ser Ile Arg Lys Arg Ile Leu Thr Gly Leu Asp Gly Ile Gly Ile
           340                      345                  350

Lys Ile Asp Asp Glu Lys Asn Lys Ile Arg Gly Gln Glu Ile Asp Ile
           355                      360                  365

Ser Thr Pro Asp Ala Lys Val Arg Val Phe Val Ile Pro Thr Asn Glu
           370                      375                  380

Glu Leu Ala Ile Ala Arg Glu Thr Lys Glu Ile Val Glu Thr Glu Val
385                     390                     395                  400

Lys Leu Arg Ser Ser Ile Pro Val
           405

<210> SEQ ID NO 26
<211> LENGTH: 585
<212> TYPE: DNA
<213> ORGANISM: Sulfolobus acidocaldarius

<400> SEQUENCE: 26

| atgaagattg gtattgtaac tggaattcct ggtgtaggga aaagtactgt cttggctaaa | 60 |
|---|---|
| gttaaagaga tattggataa tcaaggtata aataacaaga tcataaatta tggagatttt | 120 |
| atgttagcaa cagcattaaa aattaggctat gctaaagata gagacgaaat gagaaaatta | 180 |
| tctgtagaaa agcagaagaa attgcagatt gatgcggcta aggtatagc tgaagaggca | 240 |
| agagcaggtg agaaggata tctgttcata gatacgcatg ctgtgatacg tacaccctct | 300 |
| ggatatttac ctggtttacc gtcatatgta attacagaaa taaatccgtc tgttatcttt | 360 |

```
ttactggaag ctgatcctaa gataatatta tcaaggcaaa agagagatac aacaaggaat      420
agaaatgatt atagtgacga atcagttata ttagaaacca taaacttcgc tagatatgca      480
gctactgctt ctgcagtatt agccggttct actgttaagg taattgtaaa cgtggaagga      540
gatcctagta tagcagctaa tgagataata aggtctatga agtaa                     585
```

<210> SEQ ID NO 27
<211> LENGTH: 585
<212> TYPE: DNA
<213> ORGANISM: Artificial Sequence
<220> FEATURE:
<223> OTHER INFORMATION: Synthetic

<400> SEQUENCE: 27

```
atgaaaatcg gtatcgttac cggtatcccg ggtgttggta atctaccgt tctggctaaa       60 gttaaagaaa tcctggacaa ccagggtatc aacaacaaaa tcatcaacta cggtgacttc     120
atgctggcta ccgctctgaa actgggttac gctaaagacc gtgacgaaat gcgtaaactg     180
tctgttgaaa acagaaaaa actgcagatc gacgctgcta aaggtatcgc tgaagaagct     240
cgtgctggtg gtgaaggtta cctgttcatc gacacccacg ctgttatccg taccccgtct     300
ggttacctgc cgggtctgcc gtcttacgtt atcaccgaaa tcaacccgtc tgttatcttc     360
ctgctggaag ctgacccgaa aatcatcctg tctcgtcaga acgtgacac cacccgtaac     420 cgtaacgact actctgacga atcgttatc ctggaaacca tcaacttcgc tcgttacgct     480
gctaccgctt ctgctgttct ggctggttct accgttaaag ttatcgttaa cgttgaaggt     540
gacccgtcta tcgctgctaa cgaaatcatc cgttctatga aatag                     585
```

<210> SEQ ID NO 28
<211> LENGTH: 663
<212> TYPE: DNA
<213> ORGANISM: Thermotoga maritima

<400> SEQUENCE: 28

```
atgatggcgt accttgtctt tctaggacct ccaggtgcag gaaaaggaac ctacgcaaag      60
agattgcagg aaataacggg gattcctcat atatccaccg tgacatttt cagggacatt     120 gtaaaaaaag agaacgacga gcttgggaaa aagataaaag agatcatgga aagggagaa     180 ctcgttccgg acgaactcgt gaacgaggtt gtgaaaagaa gactctcaga aaagattgt     240 gaaagaggat tcatactgga cggctatcca agaaccgttg ctcaggcgga attcctcgac     300 ggcttttga aaactcaaaa caaagagctc acggctgctg tactctttga agttcctgag     360
gaagtggtcg ttcagaggct cacggccaga aggatctgcc cgaaatgtgg aagaatttac     420
aatttgattt cgctccctcc aaaagaagac gaactgtgcg atgattgtaa agtgaagctc     480
gttcagagag aagacgacaa agaagaaaca gtgagacaca gatacaaggt ttatctcgaa     540
aagacacagc cagtgattga ttactacgat aaaaagggca ttctcaaacg agtggatggt     600
accataggaa tagacaacgt gatcgctgaa gtgttaaaga taatagggtg gagtgataaa     660
tga                                                                   663
```

<210> SEQ ID NO 29
<211> LENGTH: 660
<212> TYPE: DNA
<213> ORGANISM: Artificial Sequence
<220> FEATURE:
<223> OTHER INFORMATION: Synthetic

<400> SEQUENCE: 29

```
atgatggcct atctggtttt tcttggtcca ccgggggcag gcaaaggtac atatgcgaaa      60
cgtttacagg aaatcaccgg catcccgcac attagcacgg gcgacatttt tcgtgatatt     120
gtcaaaaagg aaaatgacga attaggtaag aaaattaaag aattatggga gcgcggcgag     180
ttggtgccgg acgaactggt gaatgaagtt gtcaaacgtc ggctgtctga aaaggattgc     240
gaacgtggct ttattttgga cggttacccg cgtacagtag ctcaggcaga gtttctcgac     300
ggcttcctga agactcagaa taaggagtta acggctgcgg tcctgttcga ggtgcctgaa     360
gaggtggtcg ttcagcgtct gaccgcgcgg cgtatctgcc cgaagtgtgg tcgtatttac     420
aacctgattt cacttcctcc aaaagaagat gaactgtgtg atgactgcaa agtaaaactg     480
gtgcaacgcg aagatgataa agaggaaact gtgcgccatc gctacaaagt atatctggaa     540 aaacccaac cggttatcga ttattatgat aaaaaaggca ttttgaaacg cgttgatggg     600
accatcggca tcgataacgt gattgccgaa gttctcaaaa tcattgggtg gagtgataaa     660
```

<210> SEQ ID NO 30
<211> LENGTH: 651
<212> TYPE: DNA
<213> ORGANISM: Artificial Sequence
<220> FEATURE:
<223> OTHER INFORMATION: Synthetic

<400> SEQUENCE: 30

```
atgaacctga ttttcctggg tccgcctggg gcaggcaaag gcacccaggc gaaacgtgtg      60
tctgaaaagt acggtatccc gcagattagt accggcgata tgctgcgtga agcggttgct     120
aagggtacgg aactggggaa aaaggcgaaa gaatatatgg acaaagggga acttgttccg     180
gatgaagtag ttattggaat cgtgaaagaa cgcctccagc aaccggattg tgagaagggc     240
tttattctgg acggttttcc gcgtacgtta gcacaagccg aagctctgga cgaaatgtta     300
aaagaattga ataagaaaat tgacgccgta atcaacgtgg tcgtaccgga agaggaagtt     360
gtcaagcgta ttacctatcg tcgcacttgc cgcaattgcg gcgccgtgta ccatctcatt     420
tatgcacctc caaaagagga taataaatgt gataaatgcg gcggtgagct ttatcagcgt     480
gatgacgata agaagagac agtccgcgag cgttaccgtg tgtataaaca gaacacagag     540
ccattgatcg attattaccg taaaaaggga atcctgtatg atgtggatgg tactaaagac     600
atcgaaggag tttggaaaga aattgaggcg attctggaaa aaattaaaag c              651
```

<210> SEQ ID NO 31
<211> LENGTH: 194
<212> TYPE: PRT
<213> ORGANISM: Sulfolobus acidocaldarius

<400> SEQUENCE: 31

```
Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
```

```
                        85                  90                  95
Arg Thr Pro Ser Gly Tyr Leu Pro Gly Leu Pro Ser Tyr Val Ile Thr
            100                 105                 110
Glu Ile Asn Pro Ser Val Ile Phe Leu Glu Ala Asp Pro Lys Ile
            115                 120                 125
Ile Leu Ser Arg Gln Lys Arg Asp Thr Thr Arg Asn Arg Asn Asp Tyr
            130                 135                 140
Ser Asp Glu Ser Val Ile Leu Glu Thr Ile Asn Phe Ala Arg Tyr Ala
145                 150                 155                 160
Ala Thr Ala Ser Ala Val Leu Ala Gly Ser Thr Val Lys Val Ile Val
                165                 170                 175
Asn Val Glu Gly Asp Pro Ser Ile Ala Ala Asn Glu Ile Ile Arg Ser
            180                 185                 190
Met Lys

<210> SEQ ID NO 32
<211> LENGTH: 220
<212> TYPE: PRT
<213> ORGANISM: Thermotoga maritima

<400> SEQUENCE: 32

Met Met Ala Tyr Leu Val Phe Leu Gly Pro Pro Gly Ala Gly Lys Gly
1               5                   10                  15
Thr Tyr Ala Lys Arg Leu Gln Glu Ile Thr Gly Ile Pro His Ile Ser
                20                  25                  30
Thr Gly Asp Ile Phe Arg Asp Ile Val Lys Lys Glu Asn Asp Glu Leu
            35                  40                  45
Gly Lys Lys Ile Lys Glu Ile Met Glu Arg Gly Glu Leu Val Pro Asp
        50                  55                  60
Glu Leu Val Asn Glu Val Val Lys Arg Arg Leu Ser Glu Lys Asp Cys
65                  70                  75                  80
Glu Arg Gly Phe Ile Leu Asp Gly Tyr Pro Arg Thr Val Ala Gln Ala
                85                  90                  95
Glu Phe Leu Asp Gly Phe Leu Lys Thr Gln Asn Lys Glu Leu Thr Ala
            100                 105                 110
Ala Val Leu Phe Glu Val Pro Glu Glu Val Val Gln Arg Leu Thr
        115                 120                 125
Ala Arg Arg Ile Cys Pro Lys Cys Gly Arg Ile Tyr Asn Leu Ile Ser
        130                 135                 140
Leu Pro Pro Lys Glu Asp Glu Leu Cys Asp Asp Cys Lys Val Lys Leu
145                 150                 155                 160
Val Gln Arg Glu Asp Asp Lys Glu Glu Thr Val Arg His Arg Tyr Lys
                165                 170                 175
Val Tyr Leu Glu Lys Thr Gln Pro Val Ile Asp Tyr Tyr Asp Lys Lys
            180                 185                 190
Gly Ile Leu Lys Arg Val Asp Gly Thr Ile Gly Ile Asp Asn Val Ile
        195                 200                 205
Ala Glu Val Leu Lys Ile Ile Gly Trp Ser Asp Lys
    210                 215                 220

<210> SEQ ID NO 33
<211> LENGTH: 11
<212> TYPE: PRT
<213> ORGANISM: Artificial Sequence
<220> FEATURE:
<223> OTHER INFORMATION: transglutaminase substrate
```

<400> SEQUENCE: 33

Met Asn Gln Glu Gln Val Ser Pro Leu Gly Gly
1               5                   10

<210> SEQ ID NO 34
<211> LENGTH: 204
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the N-terminus with
      a transglutaminase (Factor XIII) substrate sequence

<400> SEQUENCE: 34

Met Asn Gln Glu Gln Val Ser Pro Leu Gly Gly Lys Ile Gly Ile Val
1               5                   10                  15

Thr Gly Ile Pro Gly Val Gly Lys Ser Thr Val Leu Ala Lys Val Lys
            20                  25                  30

Glu Ile Leu Asp Asn Gln Gly Ile Asn Asn Lys Ile Ile Asn Tyr Gly
        35                  40                  45

Asp Phe Met Leu Ala Thr Ala Leu Lys Leu Gly Tyr Ala Lys Asp Arg
50                  55                  60

Asp Glu Met Arg Lys Leu Ser Val Glu Lys Gln Lys Lys Leu Gln Ile
65                  70                  75                  80

Asp Ala Ala Lys Gly Ile Ala Glu Glu Ala Arg Ala Gly Gly Glu Gly
                85                  90                  95

Tyr Leu Phe Ile Asp Thr His Ala Val Ile Arg Thr Pro Ser Gly Tyr
            100                 105                 110

Leu Pro Gly Leu Pro Ser Tyr Val Ile Thr Glu Ile Asn Pro Ser Val
        115                 120                 125

Ile Phe Leu Leu Glu Ala Asp Pro Lys Ile Ile Leu Ser Arg Gln Lys
130                 135                 140

Arg Asp Thr Thr Arg Asn Arg Asn Asp Tyr Ser Asp Glu Ser Val Ile
145                 150                 155                 160

Leu Glu Thr Ile Asn Phe Ala Arg Tyr Ala Ala Thr Ala Ser Ala Val
                165                 170                 175

Leu Ala Gly Ser Thr Val Lys Val Ile Val Asn Val Glu Gly Asp Pro
            180                 185                 190

Ser Ile Ala Ala Asn Glu Ile Ile Arg Ser Met Lys
        195                 200

<210> SEQ ID NO 35
<211> LENGTH: 204
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the C-terminus with
      a transglutaminase (factor VIII) substrate sequence

<400> SEQUENCE: 35

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys

```
            50                  55                  60
Gln Lys Lys Leu Gln Ile Asp Ala Ala Lys Gly Ile Ala Glu Glu Ala
 65                  70                  75                  80

Arg Ala Gly Gly Glu Gly Tyr Leu Phe Ile Asp Thr His Ala Val Ile
                 85                  90                  95

Arg Thr Pro Ser Gly Tyr Leu Pro Gly Leu Pro Ser Tyr Val Ile Thr
                100                 105                 110

Glu Ile Asn Pro Ser Val Ile Phe Leu Leu Glu Ala Asp Pro Lys Ile
                115                 120                 125

Ile Leu Ser Arg Gln Lys Arg Asp Thr Thr Arg Asn Arg Asn Asp Tyr
                130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
                180                 185                 190

Met Lys Gly Gly Asn Gln Glu Gln Val Ser Pro Leu
                195                 200

<210> SEQ ID NO 36
<211> LENGTH: 214
<212> TYPE: PRT
<213> ORGANISM: Artificial Sequence
<220> FEATURE:
<223> OTHER INFORMATION: Protein sequence of thermostable adenylate
      kinase from Sulfolobus acidcaldarius fused at the N-terminus and
      C-terminus with a transglutaminase (Factor XIII) substrate
      sequence

<400> SEQUENCE: 36

Met Asn Gln Glu Gln Val Ser Pro Leu Gly Gly Lys Ile Gly Ile Val
  1               5                  10                  15

Thr Gly Ile Pro Gly Val Gly Lys Ser Thr Val Leu Ala Lys Val Lys
                 20                  25                  30

Glu Ile Leu Asp Asn Gln Gly Ile Asn Asn Lys Ile Ile Asn Tyr Gly
                 35                  40                  45

Asp Phe Met Leu Ala Thr Ala Leu Lys Leu Gly Tyr Ala Lys Asp Arg
 50                  55                  60

Asp Glu Met Arg Lys Leu Ser Val Glu Lys Gln Lys Lys Leu Gln Ile
 65                  70                  75                  80

Asp Ala Ala Lys Gly Ile Ala Glu Glu Ala Arg Ala Gly Gly Glu Gly
                 85                  90                  95

Tyr Leu Phe Ile Asp Thr His Ala Val Ile Arg Thr Pro Ser Gly Tyr
                100                 105                 110

Leu Pro Gly Leu Pro Ser Tyr Val Ile Thr Glu Ile Asn Pro Ser Val
                115                 120                 125

Ile Phe Leu Leu Glu Ala Asp Pro Lys Ile Ile Leu Ser Arg Gln Lys
                130                 135                 140

Arg Asp Thr Thr Arg Asn Arg Asn Asp Tyr Ser Asp Glu Ser Val Ile
145                 150                 155                 160

Leu Glu Thr Ile Asn Phe Ala Arg Tyr Ala Ala Thr Ala Ser Ala Val
                165                 170                 175

Leu Ala Gly Ser Thr Val Lys Val Ile Val Asn Val Glu Gly Asp Pro
                180                 185                 190

Ser Ile Ala Ala Asn Glu Ile Ile Arg Ser Met Lys Gly Gly Asn Gln
```

Glu Gln Val Ser Pro Leu
    210

<210> SEQ ID NO 37
<211> LENGTH: 704
<212> TYPE: DNA
<213> ORGANISM: Artificial Sequence
<220> FEATURE:
<223> OTHER INFORMATION: DNA sequence of transglutaminase (Factor XIII)
      substrate sequence fused to the 5' end of adenylate kinase from
      Thermotoga maritima.

<400> SEQUENCE: 37

```
atgaatcaag aacaagtcag cccgctgggc ggcatcatcg cctatctggt ttttcttggt      60
ccaccggggg caggcaaagg tacctatgcg aaacgtttac aggaaatcac cggcatcccg     120
cacattagca cgggcgacat ttttcgtgat attgtcaaaa aggaaaatga cgaattaggt     180
aagaaaatta agaaaattat ggagcgcggc gagttggtgc cggacgaact ggtgaatgaa     240
gttgtcaaac gtcggctgtc tgaaaaggat tgcgaacgtg gctttatttt ggacggttac     300
ccgcgtacag tagctcaggc agagtttctc gacggcttcc tgaagactca gaataaggag     360
ttaacggctg cggtcctgtt cgaggtgcct gaagaggtgg tcgttcagcg tctgaccgcg     420
cggcgtatct gcccgaagtg tggtcgtatt tacaacctga tttcacttcc tccaaaagaa     480
gatgaactgt gtgatgactg caaagtaaaa ctggtgcaac gcgaagatga taagaggaa     540
actgtgcgcc atcgctacaa agtatatctg gaaaaaaccc aaccggttat cgattattat     600
gataaaaaag gcattttgaa acgcgttgat gggaccatcg gcatcgataa cgtgattgcc     660
gaagttctca aaatcattgg gtggagtgat aaataggtcg acgc                      704
```

<210> SEQ ID NO 38
<211> LENGTH: 231
<212> TYPE: PRT
<213> ORGANISM: Artificial Sequence
<220> FEATURE:
<223> OTHER INFORMATION: Protein sequence of adenylate kinase from
      Thermotoga maritime fused at the N-terminal with a
      transglutaminase (Factor XIII) substrate sequence.

<400> SEQUENCE: 38

Met Asn Gln Glu Gln Val Ser Pro Leu Gly Gly Ile Ile Ala Tyr Leu
1               5                   10                  15

Val Phe Leu Gly Pro Pro Gly Ala Gly Lys Gly Thr Tyr Ala Lys Arg
            20                  25                  30

Leu Gln Glu Ile Thr Gly Ile Pro His Ile Ser Thr Gly Asp Ile Phe
        35                  40                  45

Arg Asp Ile Val Lys Lys Glu Asn Asp Glu Leu Gly Lys Lys Ile Lys
    50                  55                  60

Glu Ile Met Glu Arg Gly Glu Leu Val Pro Asp Glu Leu Val Asn Glu
65                  70                  75                  80

Val Val Lys Arg Arg Leu Ser Glu Lys Asp Cys Glu Arg Gly Phe Ile
                85                  90                  95

Leu Asp Gly Tyr Pro Arg Thr Val Ala Gln Ala Glu Phe Leu Asp Gly
            100                 105                 110

Phe Leu Lys Thr Gln Asn Lys Glu Leu Thr Ala Ala Val Leu Phe Glu
        115                 120                 125

Val Pro Glu Glu Val Val Val Gln Arg Leu Thr Ala Arg Arg Ile Cys
    130                 135                 140

Pro Lys Cys Gly Arg Ile Tyr Asn Leu Ile Ser Leu Pro Pro Lys Glu
145                 150                 155                 160

Asp Glu Leu Cys Asp Asp Cys Lys Val Lys Leu Val Gln Arg Glu Asp
            165                 170                 175

Asp Lys Glu Glu Thr Val Arg His Arg Tyr Lys Val Tyr Leu Glu Lys
        180                 185                 190

Thr Gln Pro Val Ile Asp Tyr Tyr Asp Lys Lys Gly Ile Leu Lys Arg
        195                 200                 205

Val Asp Gly Thr Ile Gly Ile Asp Asn Val Ile Ala Glu Val Leu Lys
        210                 215                 220

Ile Ile Gly Trp Ser Asp Lys
225                 230

<210> SEQ ID NO 39
<211> LENGTH: 696
<212> TYPE: DNA
<213> ORGANISM: Artificial Sequence
<220> FEATURE:
<223> OTHER INFORMATION: DNA sequence of transglutaminase (Factor XIII)
      substrate sequence fused to the 3' end of adenylate kinase from
      Thermotoga maritima.

<400> SEQUENCE: 39
atgatggcct atctggtttt tcttggtcca ccgggggcag gcaaaggtac ctatgcgaaa      60
cgtttacagg aaatcaccgg catcccgcac attagcacgg gcgacatttt tcgtgatatt     120
gtcaaaaagg aaaatgacga attaggtaag aaaattaaag aaattatgga gcgcggcgag     180
ttggtgccgg acgaactggt gaatgaagtt gtcaaacgtc ggctgtctga aaaggattgc     240
gaacgtggct ttatttttgga cggttacccg cgtacagtag ctcaggcaga gtttctcgac     300
ggcttcctga agactcagaa taaggagtta acggctgcgg tcctgttcga ggtgcctgaa     360
gaggtggtcg ttcagcgtct gaccgcgcgg cgtatctgcc cgaagtgtgg tcgtatttac     420
aacctgattt cacttcctcc aaaagaagat gaactgtgtg atgactgcaa agtaaaactg     480
gtgcaacgcg aagatgataa agaggaaact gtgcgccatc gctacaaagt atatctggaa     540
aaaacccaac cggttatcga ttattatgat aaaaaaggca ttttgaaacg cgttgatggg     600
accatcggca tcgataacgt gattgccgaa gttctcaaaa tcattgggtg gagtgataaa     660
ctgggcggca atcaagaaca agtcagcccg ctgtaa                                696

<210> SEQ ID NO 40
<211> LENGTH: 231
<212> TYPE: PRT
<213> ORGANISM: Artificial Sequence
<220> FEATURE:
<223> OTHER INFORMATION: Protein sequence of adenylate kinase from
      Thermotoga maritime fused at the C-terminal with a
      transglutaminase (Factor XIII) substrate sequence.

<400> SEQUENCE: 40

Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Lys Arg Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Glu Val Val Gln Arg Leu Thr
        115                 120                 125

Ala Arg Arg Ile Cys Pro Lys Cys Gly Arg Ile Tyr Asn Leu Ile Ser
130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
            165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
            195                 200                 205

Ala Glu Val Leu Lys Ile Ile Gly Trp Ser Asp Lys Leu Gly Gly Asn
210                 215                 220

Gln Glu Gln Val Ser Pro Leu
225                 230

<210> SEQ ID NO 41
<211> LENGTH: 729
<212> TYPE: DNA
<213> ORGANISM: Artificial Sequence
<220> FEATURE:
<223> OTHER INFORMATION: DNA sequence of transglutaminase (Factor XIII)
      substrate sequence fused to both the 5' and 3' ends of adenylate
      kinase from Thermotoga maritima.

<400> SEQUENCE: 41
atgaatcaag aacaagtcag cccgctgggc ggcatcatcg cctatctggt ttttcttggt      60
ccaccggggg caggcaaagg tacctatgcg aaacgtttac aggaaatcac cggcatcccg     120
cacattagca cgggcgacat ttttcgtgat attgtcaaaa aggaaaatga cgaattaggt     180
aagaaaatta agaaattat ggagcgcggc gagttggtgc ggacgaact ggtgaatgaa       240 gttgtcaaac gtcggctgtc tgaaaaggat tgcgaacgtg gctttatttt ggacggttac     300
ccgcgtacag tagctcaggc agagtttctc gacggcttcc tgaagactca gaataaggag     360
ttaacggctg cggtcctgtt cgaggtgcct gaagaggtgg tcgttcagcg tctgaccgcg     420
cggcgtatct gcccgaagtg tggtcgtatt tacaacctga tttcacttcc tccaaaagaa     480
gatgaactgt gtgatgactg caaagtaaaa ctggtgcaac gcgaagatga taagaggaa      540 actgtgcgcc atcgctacaa agtatatctg gaaaaaccc aaccggttat cgattattat     600
gataaaaaag cattttgaa acgcgttgat gggaccatcg gcatcgataa cgtgattgcc     660
gaagttctca aaatcattgg gtggagtgat aaactgggcg gcaatcaaga acaagtcagc     720
ccgctgtaa                                                             729

<210> SEQ ID NO 42
<211> LENGTH: 242
<212> TYPE: PRT
<213> ORGANISM: Artificial Sequence
<220> FEATURE:
<223> OTHER INFORMATION: Protein sequence of adenylate kinase from
      Thermotoga maritime fused at the N- and C-terminal with a -continued transglutaminase (Factor XIII) substrate sequence.

<400> SEQUENCE: 42

Met Asn Gln Glu Gln Val Ser Pro Leu Gly Gly Ile Ile Ala Tyr Leu
1               5                   10                  15

Val Phe Leu Gly Pro Pro Gly Ala Gly Lys Gly Thr Tyr Ala Lys Arg
            20                  25                  30

Leu Gln Glu Ile Thr Gly Ile Pro His Ile Ser Thr Gly Asp Ile Phe
        35                  40                  45

Arg Asp Ile Val Lys Lys Glu Asn Asp Glu Leu Gly Lys Lys Ile Lys
    50                  55                  60

Glu Ile Met Glu Arg Gly Glu Leu Val Pro Asp Glu Leu Val Asn Glu
65                  70                  75                  80

Val Val Lys Arg Arg Leu Ser Glu Lys Asp Cys Glu Arg Gly Phe Ile
                85                  90                  95

Leu Asp Gly Tyr Pro Arg Thr Val Ala Gln Ala Glu Phe Leu Asp Gly
            100                 105                 110

Phe Leu Lys Thr Gln Asn Lys Glu Leu Thr Ala Ala Val Leu Phe Glu
        115                 120                 125

Val Pro Glu Glu Val Val Gln Arg Leu Thr Ala Arg Arg Ile Cys
    130                 135                 140

Pro Lys Cys Gly Arg Ile Tyr Asn Leu Ile Ser Leu Pro Pro Lys Glu
145                 150                 155                 160

Asp Glu Leu Cys Asp Asp Cys Lys Val Lys Leu Val Gln Arg Glu Asp
                165                 170                 175

Asp Lys Glu Glu Thr Val Arg His Arg Tyr Lys Val Tyr Leu Glu Lys
            180                 185                 190

Thr Gln Pro Val Ile Asp Tyr Tyr Asp Lys Lys Gly Ile Leu Lys Arg
        195                 200                 205

Val Asp Gly Thr Ile Gly Ile Asp Asn Val Ile Ala Glu Val Leu Lys
    210                 215                 220

Ile Ile Gly Trp Ser Asp Lys Leu Gly Gly Asn Gln Glu Gln Val Ser
225                 230                 235                 240

Pro Leu

<210> SEQ ID NO 43
<211> LENGTH: 1288
<212> TYPE: DNA
<213> ORGANISM: Artificial Sequence
<220> FEATURE:
<223> OTHER INFORMATION: DNA sequence of complete Sup35 gene construct
      from Saccharomyces cerevisiae

<400> SEQUENCE: 43
gattcaaacc aaggcaacaa tcagcaaaac taccagcaat acagccagaa cggtaaccaa       60
caacaaggta acaacagata ccaaggttat caagcttaca atgctcaagc ccaacctggg      120
ggtgggtact accaaaatta ccaaggttat tctgggtacc aacaaggtgg ctatcaacag      180
tacaatcccg acgccggtta ccagcaacag tataatcctc aaggaggcta tcaacagtac      240
aatcctcaag gcggttatca gcaccaattc aatccacaag gtggccgtgg aaattacaaa      300
aacttcaact acaataacaa tttgcaagga tatcaagctg gtttccaacc acagtctcaa      360
ggtatgtctt tgaacgactt tcaaaagcaa caaaagcagg ccgctcccaa accaaagaag      420
actttgaagc ttgtctccag ttcctgtatc aagttggcca atgctaccaa gaaggttgac      480
acaaaacctg ccgaatctga taagaaagag gaagagaagt ctgctgaaac caaagaacca      540

```
actaaagagc caacaaaggt cgaagaacca gttaaaaagg aggagaaacc agtccagact     600
gaagaaaaga cggaggaaaa atcggaactt ccaaaggtag aagaccttaa aatctctgaa     660
tcaacacata ataccaacaa tgccaatgtt accagtgctg atgccttgat caaggaacag     720
gaagaagaag tggatgacga agttgttaac gatatgtttg gtggtaaaga tcacgtttct     780
ttaattttca tgggtcatgt tgatgccggt aaatctacta tgggtggtaa tctactatac     840
ttgactggct ctgtggataa agaactatt gagaaatatg aaagagaagc caaggatgca     900
ggcagacaag gttggtactt gtcatgggtc atggatacca acaagaaga agaaatgat     960 ggtaagacta tcgaagttgg taaggcctac tttgaaactg aaaaaaggcg ttataccata    1020
ttggatgctc ctggtcataa aatgtacgtt tccgagatga tcggtggtgc ttctcaagct    1080
gatgttggtg ttttggtcat ttccgccaga aagggtgagt acgaaaccgg ttttgagaga    1140
ggtggtcaaa ctcgtgaaca cgccctattg gccaagaccc aaggtgttaa taagatggtt    1200
gtcgtcgtaa ataagatgga tgacccaacc gttaactggt ctaaggaacg ttacgaccaa    1260
tgtgtgagta atgtcagcaa tttcttga                                       1288
```

<210> SEQ ID NO 44
<211> LENGTH: 429
<212> TYPE: PRT
<213> ORGANISM: Artificial Sequence
<220> FEATURE:
<223> OTHER INFORMATION: Protein sequence of complete Sup35 from
      Saccharomyces cerevisiae

<400> SEQUENCE: 44

```
Asp Ser Asn Gln Gly Asn Asn Gln Gln Asn Tyr Gln Gln Tyr Ser Gln
1               5                   10                  15

Asn Gly Asn Gln Gln Gln Gly Asn Asn Arg Tyr Gln Gly Tyr Gln Ala
            20                  25                  30

Tyr Asn Ala Gln Ala Gln Pro Gly Gly Tyr Tyr Gln Asn Tyr Gln
        35                  40                  45

Gly Tyr Ser Gly Tyr Gln Gln Gly Gly Tyr Gln Gln Tyr Asn Pro Asp
    50                  55                  60

Ala Gly Tyr Gln Gln Gln Tyr Asn Pro Gln Gly Gly Tyr Gln Gln Tyr
65                  70                  75                  80

Asn Pro Gln Gly Gly Tyr Gln His Gln Phe Asn Pro Gln Gly Gly Arg
                85                  90                  95

Gly Asn Tyr Lys Asn Phe Asn Tyr Asn Asn Asn Leu Gln Gly Tyr Gln
            100                 105                 110

Ala Gly Phe Gln Pro Gln Ser Gln Gly Met Ser Leu Asn Asp Phe Gln
        115                 120                 125

Lys Gln Gln Lys Gln Ala Ala Pro Lys Pro Lys Lys Thr Leu Lys Leu
    130                 135                 140

Val Ser Ser Ser Cys Ile Lys Leu Ala Asn Ala Thr Lys Lys Val Asp
145                 150                 155                 160

Thr Lys Pro Ala Glu Ser Asp Lys Lys Glu Glu Lys Ser Ala Glu
                165                 170                 175

Thr Lys Glu Pro Thr Lys Glu Pro Thr Lys Val Glu Glu Pro Val Lys
            180                 185                 190

Lys Glu Glu Lys Pro Val Gln Thr Glu Glu Lys Thr Glu Glu Lys Ser
        195                 200                 205

Glu Leu Pro Lys Val Glu Asp Leu Lys Ile Ser Glu Ser Thr His Asn
    210                 215                 220
```

```
Thr Asn Asn Ala Asn Val Thr Ser Ala Asp Ala Leu Ile Lys Glu Gln
225                 230                 235                 240

Glu Glu Glu Val Asp Glu Val Val Asn Asp Met Phe Gly Gly Lys
            245                 250                 255

Asp His Val Ser Leu Ile Phe Met Gly His Val Asp Ala Gly Lys Ser
            260                 265                 270

Thr Met Gly Gly Asn Leu Leu Tyr Leu Thr Gly Ser Val Asp Lys Arg
            275                 280                 285

Thr Ile Glu Lys Tyr Glu Arg Glu Ala Lys Asp Ala Gly Arg Gln Gly
            290                 295                 300

Trp Tyr Leu Ser Trp Val Met Asp Thr Asn Lys Glu Glu Arg Asn Asp
305                 310                 315                 320

Gly Lys Thr Ile Glu Val Gly Lys Ala Tyr Phe Glu Thr Glu Lys Arg
            325                 330                 335

Arg Tyr Thr Ile Leu Asp Ala Pro Gly His Lys Met Tyr Val Ser Glu
            340                 345                 350

Met Ile Gly Gly Ala Ser Gln Ala Asp Val Gly Val Leu Val Ile Ser
            355                 360                 365

Ala Arg Lys Gly Glu Tyr Glu Thr Gly Phe Glu Arg Gly Gly Gln Thr
370                 375                 380

Arg Glu His Ala Leu Leu Ala Lys Thr Gln Gly Val Asn Lys Met Val
385                 390                 395                 400

Val Val Val Asn Lys Met Asp Asp Pro Thr Val Asn Trp Ser Lys Glu
            405                 410                 415

Arg Tyr Asp Gln Cys Val Ser Asn Val Ser Asn Phe Leu
            420                 425

<210> SEQ ID NO 45
<211> LENGTH: 348
<212> TYPE: DNA
<213> ORGANISM: Artificial Sequence
<220> FEATURE:
<223> OTHER INFORMATION: DNA sequence of sup35N (N-terminal domain)
      codon-biased for optimal expression in E. coli

<400> SEQUENCE: 45
atggactcta accagggtaa caaccagcag aactaccagc agtactctca gaacggtaac      60
cagcagcagg gtaacaaccg ttaccagggt taccaggctt acaacgctca ggctcagccg     120
ggtggtggtt actaccagaa ctaccagggt tactccggat atcaacaggg tggttaccaa     180
caatataatc agacgctggg ttaccagcag cagtacaacc cgcagggtgg ttaccagcag     240
tacaacccgc aaggcggata tcaacaccag ttcaatccgc agggtggtcg tggtaactac     300
aaaaacttca actacaacaa caacctgcag ggttaccagg ctggttaa                  348

<210> SEQ ID NO 46
<211> LENGTH: 115
<212> TYPE: PRT
<213> ORGANISM: Artificial Sequence
<220> FEATURE:
<223> OTHER INFORMATION: Protein sequence of sup35N (N-terminal domain)

<400> SEQUENCE: 46

Met Asp Ser Asn Gln Gly Asn Asn Gln Gln Asn Tyr Gln Gln Tyr Ser
1               5                   10                  15

Gln Asn Gly Asn Gln Gln Gly Asn Asn Arg Tyr Gln Gly Tyr Gln
            20                  25                  30
```

```
Ala Tyr Asn Ala Gln Ala Gln Pro Gly Gly Gly Tyr Tyr Gln Asn Tyr
            35                  40                  45

Gly Gly Tyr Ser Gly Tyr Gln Gln Gly Gly Tyr Gln Gln Tyr Asn Pro
 50                  55                  60

Asp Ala Gly Tyr Gln Gln Tyr Asn Pro Gln Gly Tyr Gln Gln
 65                  70                  75                  80

Tyr Asn Pro Gln Gly Tyr Gln His Gln Phe Asn Pro Gln Gly Gly
                85                  90                  95

Arg Gly Asn Tyr Lys Asn Phe Asn Tyr Asn Asn Asn Leu Gln Gly Tyr
            100                 105                 110

Gln Ala Gly
        115

<210> SEQ ID NO 47
<211> LENGTH: 941
<212> TYPE: DNA
<213> ORGANISM: Artificial Sequence
<220> FEATURE:
<223> OTHER INFORMATION: DNA sequence of E-coli codon biased Adenylate
      kinase from Sulfolobus acidcaldarius fused at the N-terminus with
      Sup35 N-terminal domain from Saccharomyces cerevisiae

<400> SEQUENCE: 47
atggactcta accagggtaa caaccagcag aactaccagc agtactctca gaacggtaac      60
cagcagcagg gtaacaaccg ttaccagggt taccaggctt acaacgctca ggctcagccg     120
ggtggtggtt actaccagaa ctaccagggt tactccggtt atcagcaagg tggctaccaa     180
caatataatc cagacgctgg ctatcaacag caatataatc ctcagggtgg ttaccagcag     240
tacaacccgc aaggcggtta tcaacaccag ttcaatccgc agggtggtcg tggtaactac     300
aaaaacttca actacaacaa caacctgcag ggttaccagg ctggaattat gaagatcggc     360
attgtgaccg gcattccggg cgttggcaaa agcaccgttc tggcaaaggt gaaggagatc     420
ctggacaacc aggcattaa taacaaaatt attaattatg gtgattttat gctggcgacc     480
gcgctgaagc tgggctacgc aaaagatcgt gacgaaatgc gcaaactgag cgtggaaaaa     540
cagaagaagc tgcagattga tgcggcgaag ggcattgcgg aagaggcacg cgcgggcggc     600
gaaggctacc tgtttatcga tacccatgcg gtgatccgca ccccgagcgg ttatctgccg     660
ggcctgccgt cttacgtgat tacggaaatc aacccgagcg ttattttct gctggaggca     720 gatccgaaga ttattctgag ccgccagaag cgcgatacca cccgcaaccg caacgattat     780
agcgacgaaa gcgttatcct ggagaccatc aactttgcgc gctatgcggc aaccgcgagc     840
gcggttctgg caggctctac cgttaaagtg atcgtgaacg tggagggtga tccaagcatc     900
gcggcgaacg aaatcattcg cagcatgaaa taagtcgacg c                         941

<210> SEQ ID NO 48
<211> LENGTH: 310
<212> TYPE: PRT
<213> ORGANISM: Artificial Sequence
<220> FEATURE:
<223> OTHER INFORMATION: Protein sequence of Adenylate kinase from
      Sulfolobus acidcaldarius fused at the N-terminus with Sup35
      N-terminal domain from Saccharomyces cerevisiae

<400> SEQUENCE: 48

Met Asp Ser Asn Gln Gly Asn Asn Gln Gln Asn Tyr Gln Gln Tyr Ser
1               5                   10                  15

Gln Asn Gly Asn Gln Gln Gln Gly Asn Asn Arg Tyr Gln Gly Tyr Gln
            20                  25                  30
```

```
Ala Tyr Asn Ala Gln Ala Gln Pro Gly Gly Gly Tyr Tyr Gln Asn Tyr
            35                  40                  45

Gln Gly Tyr Ser Gly Tyr Gln Gln Gly Gly Tyr Gln Gln Tyr Asn Pro
    50                  55                  60

Asp Ala Gly Tyr Gln Gln Gln Tyr Asn Pro Gln Gly Tyr Gln Gln
65                  70                  75                  80

Tyr Asn Pro Gln Gly Gly Tyr Gln His Gln Phe Asn Pro Gln Gly Gly
                85                  90                  95

Arg Gly Asn Tyr Lys Asn Phe Asn Tyr Asn Asn Leu Gln Gly Tyr
                100                 105                 110

Gln Ala Gly Ile Met Lys Ile Gly Ile Val Thr Gly Ile Pro Gly Val
                115                 120                 125

Gly Lys Ser Thr Val Leu Ala Lys Val Lys Glu Ile Leu Asp Asn Gln
            130                 135                 140

Gly Ile Asn Asn Lys Ile Ile Asn Tyr Gly Asp Phe Met Leu Ala Thr
145                 150                 155                 160

Ala Leu Lys Leu Gly Tyr Ala Lys Asp Arg Asp Glu Met Arg Lys Leu
                165                 170                 175

Ser Val Glu Lys Gln Lys Lys Leu Gln Ile Asp Ala Ala Lys Gly Ile
            180                 185                 190

Ala Glu Glu Ala Arg Ala Gly Gly Gly Tyr Leu Phe Ile Asp Thr
            195                 200                 205

His Ala Val Ile Arg Thr Pro Ser Gly Tyr Leu Pro Gly Leu Pro Ser
    210                 215                 220

Tyr Val Ile Thr Glu Ile Asn Pro Ser Val Ile Phe Leu Leu Glu Ala
225                 230                 235                 240

Asp Pro Lys Ile Ile Leu Ser Arg Gln Lys Arg Asp Thr Thr Arg Asn
                245                 250                 255

Arg Asn Asp Tyr Ser Asp Glu Ser Val Ile Leu Glu Thr Ile Asn Phe
                260                 265                 270

Ala Arg Tyr Ala Ala Thr Ala Ser Ala Val Leu Ala Gly Ser Thr Val
            275                 280                 285

Lys Val Ile Val Asn Val Glu Gly Asp Pro Ser Ile Ala Ala Asn Glu
            290                 295                 300

Ile Ile Arg Ser Met Lys
305                 310
```

<210> SEQ ID NO 49
<211> LENGTH: 947
<212> TYPE: DNA
<213> ORGANISM: Artificial Sequence
<220> FEATURE:
<223> OTHER INFORMATION: DNA sequence of E. coli codon biased Adenylate
      kinase from Sulfolobus acidcaldarius fused at the C-terminus with
      Sup35 N-terminal domain from Saccharomyces cerevisiae

<400> SEQUENCE: 49

```
atgaagatcg gcattgtgac cggcattccg ggcgttggca aaagcaccgt tctggcaaag      60
gtgaaggaga tcctggacaa ccagggcatt aataacaaaa ttattaatta tggtgatttt     120
atgctggcga ccgcgctgaa gctgggctac gcaaaagatc gtgacgaaat gcgcaaactg     180
agcgtggaaa aacagaagaa gctgcagatt gatgcggcga agggcattgc ggaagaggca     240
cgcgcgggcg gcgaaggcta cctgtttatc gataccatg cggtgatccg cacccccgagc     300 ggttatctgc cgggcctgcc gtcttacgtg attacggaaa tcaacccgag cgttatttt     360
```

```
ctgctggagg cagatccgaa gattattctg agccgccaga agcgcgatac cacccgcaac    420
cgcaacgatt atagcgacga aagcgttatc ctggagacca tcaactttgc gcgctatgcg    480
gcaaccgcga gcgcggttct ggcaggctct accgttaaag tgatcgtgaa cgtggagggt    540
gatccaagca tcgcggcgaa cgaaatcatt cgcagcatga acagtcgag tatggactct     600
aaccagggta caaccagca gaactaccag cagtactctc agaacggtaa ccagcagcag     660
ggtaacaacc gttaccaggg ttaccaggct tacaacgctc aggctcagcc gggtggtggt    720
tactaccaga actaccaggg ttactccggt tatcagcaag gtggctacca acaatataat    780
ccagacgctg gctatcaaca gcaatataat cctcagggtg gttaccagca gtacaacccg    840
caaggcggtt atcaacacca gttcaatccg cagggtggtc gtggtaacta caaaaacttc    900
aactacaaca caacctgca gggttaccag gctggttaag tcgacgc                   947
```

<210> SEQ ID NO 50
<211> LENGTH: 312
<212> TYPE: PRT
<213> ORGANISM: Artificial Sequence
<220> FEATURE:
<223> OTHER INFORMATION: Protein sequence of Adenylate kinase from
       Sulfolobus acidcaldarius fused at the C-terminus with Sup35
       N-terminal domain from Saccharomyces cerevisiae

<400> SEQUENCE: 50

```
Met Lys Ile Gly Ile Val Thr Gly Ile Pro Gly Val Gly Lys Ser Thr
 1               5                  10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys Gln Ser Ser Met Asp Ser Asn Gln Gly Asn Asn Gln Gln Asn
        195                 200                 205

Tyr Gln Gln Tyr Ser Gln Asn Gly Asn Gln Gln Gly Asn Asn Arg
    210                 215                 220

Tyr Gln Gly Tyr Gln Ala Tyr Asn Ala Gln Ala Gln Pro Gly Gly Gly
225                 230                 235                 240

Tyr Tyr Gln Asn Tyr Gln Gly Tyr Ser Gly Tyr Gln Gln Gly Gly Tyr
                245                 250                 255
```

Gln Gln Tyr Asn Pro Asp Ala Gly Tyr Gln Gln Tyr Asn Pro Gln
                260                 265                 270

Gly Gly Tyr Gln Gln Tyr Asn Pro Gln Gly Gly Tyr Gln His Gln Phe
        275                 280                 285

Asn Pro Gln Gly Gly Arg Gly Asn Tyr Lys Phe Asn Tyr Asn Asn
    290                 295                 300

Asn Leu Gln Gly Tyr Gln Ala Gly
305                 310

<210> SEQ ID NO 51
<211> LENGTH: 1011
<212> TYPE: DNA
<213> ORGANISM: Artificial Sequence
<220> FEATURE:
<223> OTHER INFORMATION: DNA sequence of Sup35N fused at the 5' end of
      adenylate kinase from Thermotoga maritima.

<400> SEQUENCE: 51
atggactcta accagggtaa caaccagcag aactaccagc agtactctca gaacggtaac         60
cagcagcagg gtaacaaccg ttaccagggt taccaggctt acaacgctca ggctcagccg        120
ggtggtggtt actaccagaa ctaccagggt tactccggtt atcagcaagg tggctaccaa        180
caatataatc cagacgctgg ctatcaacag caatataatc ctcagggtgg ttaccagcag        240
tacaacccgc aaggcggtta tcaacaccag ttcaatccgc agggtggtcg tggtaactac        300
aaaaacttca actacaacaa caacctgcag ggttaccagg ctggaattat gatggcctat        360
ctggtttttc ttggtccacc ggggcaggc aaaggtacct atgcgaaacg tttacaggaa        420
atcaccggca tcccgcacat tagcacgggc gacttttttc gtgatattgt caaaaaggaa        480
aatgacgaat taggtaagaa aattaaagaa attatgagc gcggcgagtt ggtgccggac        540
gaactggtga atgaagttgt caaacgtcgg ctgtctgaaa aggattgcga acgtggcttt        600
attttggacg gttacccgcg tacagtagct caggcagagt ttctcgacgg cttcctgaag        660
actcagaata aggagttaac ggctgcggtc ctgttcgagg tgcctgaaga ggtggtcgtt        720
cagcgtctga ccgcgcggcg tatctgcccg aagtgtggtc gtatttacaa cctgatttca        780
cttcctccaa agaagatga actgtgtgat gactgcaaag taaaactggt gcaacgcgaa        840
gatgataaag aggaaactgt gcgccatcgc tacaaagtat atctggaaaa acccaaccg        900 gttatcgatt attatgataa aaaaggcatt ttgaaacgcg ttgatgggac catcggcatc        960
gataacgtga ttgccgaagt tctcaaaatc attgggtgga gtgataaata g               1011

<210> SEQ ID NO 52
<211> LENGTH: 336
<212> TYPE: PRT
<213> ORGANISM: Artificial Sequence
<220> FEATURE:
<223> OTHER INFORMATION: Protein sequence of adenylate kinase from
      Thermotoga maritima fused at the N-terminal with Sup35N.

<400> SEQUENCE: 52

Met Asp Ser Asn Gln Gly Asn Asn Gln Gln Asn Tyr Gln Gln Tyr Ser
1               5                   10                  15

Gln Asn Gly Asn Gln Gln Gln Gly Asn Asn Arg Tyr Gln Gly Tyr Gln
            20                  25                  30

Ala Tyr Asn Ala Gln Ala Gln Pro Gly Gly Gly Tyr Tyr Gln Asn Tyr
        35                  40                  45

Gln Gly Tyr Ser Gly Tyr Gln Gln Gly Gly Tyr Gln Gln Tyr Asn Pro

```
        50                  55                  60
Asp Ala Gly Tyr Gln Gln Tyr Asn Pro Gln Gly Tyr Gln Gln
 65                  70                  75                  80

Tyr Asn Pro Gln Gly Tyr Gln His Gln Phe Asn Pro Gln Gly Gly
                 85                  90                  95

Arg Gly Asn Tyr Lys Asn Phe Asn Tyr Asn Asn Asn Leu Gln Gly Tyr
                100                 105                 110

Gln Ala Gly Ile Met Met Ala Tyr Leu Val Phe Leu Gly Pro Pro Gly
                115                 120                 125

Ala Gly Lys Gly Thr Tyr Ala Lys Arg Leu Gln Glu Ile Thr Gly Ile
130                 135                 140

Pro His Ile Ser Thr Gly Asp Ile Phe Arg Asp Ile Val Lys Lys Glu
145                 150                 155                 160

Asn Asp Glu Leu Gly Lys Lys Ile Lys Glu Ile Met Glu Arg Gly Glu
                165                 170                 175

Leu Val Pro Asp Glu Leu Val Asn Glu Val Val Lys Arg Arg Leu Ser
                180                 185                 190

Glu Lys Asp Cys Glu Arg Gly Phe Ile Leu Asp Gly Tyr Pro Arg Thr
                195                 200                 205

Val Ala Gln Ala Glu Phe Leu Asp Gly Phe Leu Lys Thr Gln Asn Lys
210                 215                 220

Glu Leu Thr Ala Ala Val Leu Phe Glu Val Pro Glu Glu Val Val Val
225                 230                 235                 240

Gln Arg Leu Thr Ala Arg Arg Ile Cys Pro Lys Cys Gly Arg Ile Tyr
                245                 250                 255

Asn Leu Ile Ser Leu Pro Pro Lys Glu Asp Glu Leu Cys Asp Asp Cys
                260                 265                 270

Lys Val Lys Leu Val Gln Arg Glu Asp Asp Lys Glu Thr Val Arg
                275                 280                 285

His Arg Tyr Lys Val Tyr Leu Glu Lys Thr Gln Pro Val Ile Asp Tyr
                290                 295                 300

Tyr Asp Lys Lys Gly Ile Leu Lys Arg Val Asp Gly Thr Ile Gly Ile
305                 310                 315                 320

Asp Asn Val Ile Ala Glu Val Leu Lys Ile Ile Gly Trp Ser Asp Lys
                325                 330                 335

<210> SEQ ID NO 53
<211> LENGTH: 1025
<212> TYPE: PRT
<213> ORGANISM: Artificial Sequence
<220> FEATURE:
<223> OTHER INFORMATION: DNA sequence of Sup35N fused at the 3' end of
      adenylate kinase from Thermotoga maritima.

<400> SEQUENCE: 53

Ala Thr Gly Ala Thr Gly Gly Cys Cys Thr Ala Thr Cys Thr Gly Gly
 1               5                  10                  15

Thr Thr Thr Thr Thr Cys Thr Thr Gly Gly Thr Cys Cys Ala Cys Cys
                20                  25                  30

Gly Gly Gly Gly Gly Cys Ala Gly Gly Cys Ala Ala Ala Gly Gly Thr
                35                  40                  45

Ala Cys Cys Thr Ala Thr Gly Cys Gly Ala Ala Ala Cys Gly Thr Thr
                50                  55                  60

Thr Ala Cys Ala Gly Gly Ala Ala Ala Thr Cys Ala Cys Cys Gly Gly
 65                  70                  75                  80
```

-continued

```
Cys Ala Thr Cys Cys Cys Gly Cys Ala Cys Ala Thr Thr Ala Gly Cys
                85                  90                  95

Ala Cys Gly Gly Gly Cys Gly Ala Cys Ala Thr Thr Thr Thr Thr Cys
            100                 105                 110

Gly Thr Gly Ala Thr Ala Thr Thr Gly Thr Cys Ala Ala Ala Ala Ala
        115                 120                 125

Gly Gly Ala Ala Ala Ala Thr Gly Ala Cys Gly Ala Ala Thr Thr Ala
    130                 135                 140

Gly Gly Thr Ala Ala Gly Ala Ala Ala Ala Thr Thr Ala Ala Ala Gly
145                 150                 155                 160

Ala Ala Ala Thr Thr Ala Thr Gly Gly Ala Gly Cys Gly Cys Gly Gly
                165                 170                 175

Cys Gly Ala Gly Thr Thr Gly Gly Thr Gly Cys Cys Gly Gly Ala Cys
            180                 185                 190

Gly Ala Ala Cys Thr Gly Gly Thr Gly Ala Ala Thr Gly Ala Ala Gly
        195                 200                 205

Thr Thr Gly Thr Cys Ala Ala Ala Cys Gly Thr Cys Gly Gly Cys Thr
    210                 215                 220

Gly Thr Cys Thr Gly Ala Ala Ala Ala Gly Gly Ala Thr Thr Gly Cys
225                 230                 235                 240

Gly Ala Ala Cys Gly Thr Gly Gly Cys Thr Thr Thr Ala Thr Thr Thr
                245                 250                 255

Thr Gly Gly Ala Cys Gly Gly Thr Thr Ala Cys Cys Cys Gly Cys Gly
            260                 265                 270

Thr Ala Cys Ala Gly Thr Ala Gly Cys Thr Cys Ala Gly Gly Cys Ala
        275                 280                 285

Gly Ala Gly Thr Thr Thr Cys Thr Cys Gly Ala Cys Gly Gly Cys Thr
    290                 295                 300

Thr Cys Cys Thr Gly Ala Ala Gly Ala Cys Thr Cys Ala Gly Ala Ala
305                 310                 315                 320

Thr Ala Ala Gly Gly Ala Gly Thr Thr Ala Ala Cys Gly Gly Cys Thr
                325                 330                 335

Gly Cys Gly Gly Thr Cys Cys Thr Gly Thr Thr Cys Gly Ala Gly Gly
            340                 345                 350

Thr Gly Cys Cys Thr Gly Ala Ala Gly Ala Gly Gly Thr Gly Gly Thr
        355                 360                 365

Cys Gly Thr Thr Cys Ala Gly Cys Gly Thr Cys Thr Gly Ala Cys Cys
    370                 375                 380

Gly Cys Gly Cys Gly Gly Cys Gly Thr Ala Thr Cys Thr Gly Cys Cys
385                 390                 395                 400

Cys Gly Ala Ala Gly Thr Gly Thr Gly Gly Thr Cys Gly Thr Ala Thr
                405                 410                 415

Thr Thr Ala Cys Ala Ala Cys Cys Thr Gly Ala Thr Thr Thr Cys Ala
            420                 425                 430

Cys Thr Thr Cys Cys Thr Cys Cys Ala Ala Ala Ala Gly Ala Ala Gly
        435                 440                 445

Ala Thr Gly Ala Ala Cys Thr Gly Thr Gly Thr Gly Ala Thr Gly Ala
    450                 455                 460

Cys Thr Gly Cys Ala Ala Ala Gly Thr Ala Ala Ala Ala Cys Thr Gly
465                 470                 475                 480

Gly Thr Gly Cys Ala Ala Cys Gly Cys Gly Ala Ala Gly Ala Thr Gly
                485                 490                 495

Ala Thr Ala Ala Ala Gly Ala Gly Gly Ala Ala Ala Cys Thr Gly Thr
```

-continued

```
                500                 505                 510
Gly Cys Gly Cys Cys Ala Thr Cys Gly Cys Thr Ala Cys Ala Ala Ala
            515                 520                 525

Gly Thr Ala Thr Ala Thr Cys Thr Gly Gly Ala Ala Ala Ala Ala Ala
            530                 535                 540

Cys Cys Cys Ala Ala Cys Gly Gly Thr Thr Ala Thr Cys Gly Ala
545                 550                 555                 560

Thr Thr Ala Thr Ala Thr Gly Ala Thr Ala Ala Ala Ala Ala
                565                 570                 575

Gly Gly Cys Ala Thr Thr Thr Gly Ala Ala Cys Gly Cys Gly
            580                 585                 590

Thr Thr Gly Ala Thr Gly Gly Ala Cys Cys Ala Thr Cys Gly Gly
            595                 600                 605

Cys Ala Thr Cys Gly Ala Thr Ala Ala Cys Gly Thr Gly Ala Thr Thr
            610                 615                 620

Gly Cys Cys Gly Ala Ala Gly Thr Thr Cys Thr Cys Ala Ala Ala Ala
625                 630                 635                 640

Thr Cys Ala Thr Thr Gly Gly Thr Gly Gly Ala Gly Thr Gly Ala
            645                 650                 655

Thr Ala Ala Ala Cys Thr Gly Thr Cys Gly Ala Gly Thr Ala Thr Gly
            660                 665                 670

Gly Ala Cys Thr Cys Thr Ala Ala Cys Cys Ala Gly Gly Thr Ala
            675                 680                 685

Ala Cys Ala Ala Cys Cys Ala Gly Cys Ala Gly Ala Ala Cys Thr Ala
            690                 695                 700

Cys Cys Ala Gly Cys Ala Gly Thr Ala Cys Thr Cys Thr Cys Ala Gly
705                 710                 715                 720

Ala Ala Cys Gly Gly Thr Ala Ala Cys Cys Ala Gly Cys Ala Gly Cys
            725                 730                 735

Ala Gly Gly Gly Thr Ala Ala Cys Ala Ala Cys Cys Gly Thr Thr Ala
            740                 745                 750

Cys Cys Ala Gly Gly Gly Thr Thr Ala Cys Cys Ala Gly Gly Cys Thr
755                 760                 765

Thr Ala Cys Ala Ala Cys Gly Cys Thr Cys Ala Gly Gly Cys Thr Cys
            770                 775                 780

Ala Gly Cys Cys Gly Gly Gly Thr Gly Gly Thr Gly Thr Thr Ala
785                 790                 795                 800

Cys Thr Ala Cys Cys Ala Gly Ala Ala Cys Thr Ala Cys Cys Ala Gly
                805                 810                 815

Gly Gly Thr Thr Ala Cys Thr Cys Cys Gly Gly Thr Ala Thr Cys
            820                 825                 830

Ala Gly Cys Ala Ala Gly Gly Thr Gly Gly Cys Thr Ala Cys Cys Ala
            835                 840                 845

Ala Cys Ala Ala Thr Ala Thr Ala Ala Thr Cys Cys Ala Gly Ala Cys
            850                 855                 860

Gly Cys Thr Gly Gly Cys Thr Ala Thr Cys Ala Ala Cys Ala Gly Cys
865                 870                 875                 880

Ala Ala Thr Ala Thr Ala Ala Thr Cys Cys Thr Cys Ala Gly Gly Gly
                885                 890                 895

Thr Gly Gly Thr Thr Ala Cys Cys Ala Gly Cys Ala Gly Thr Ala Cys
            900                 905                 910

Ala Ala Cys Cys Cys Gly Cys Ala Ala Gly Gly Cys Gly Gly Thr Thr
            915                 920                 925
```

```
Ala Thr Cys Ala Ala Cys Ala Cys Cys Ala Gly Thr Thr Cys Ala Ala
            930                 935                 940

Thr Cys Cys Gly Cys Ala Gly Gly Gly Thr Gly Gly Thr Cys Gly Thr
945                 950                 955                 960

Gly Gly Thr Ala Ala Cys Thr Ala Cys Ala Ala Ala Ala Cys Thr
                965                 970                 975

Thr Cys Ala Ala Cys Thr Ala Cys Ala Ala Cys Ala Cys Ala Ala
            980                 985                 990

Cys Cys Thr Gly Cys Ala Gly Gly  Gly Thr Thr Ala Cys  Cys Ala Gly
            995             1000                1005

Gly Cys  Thr Gly Gly Thr Thr  Ala Ala Gly Thr Cys  Gly Ala Cys
    1010                1015                1020

Gly Cys
    1025
```

<210> SEQ ID NO 54
<211> LENGTH: 338
<212> TYPE: PRT
<213> ORGANISM: Artificial Sequence
<220> FEATURE:
<223> OTHER INFORMATION: Protein sequence of adenylate kinase from
      Thermotoga maritima fused at the C-terminal fusion with Sup35N

<400> SEQUENCE: 54

```
Met Met Ala Tyr Leu Val Phe Leu Gly Pro Pro Gly Ala Gly Lys Gly
1               5                   10                  15

Thr Tyr Ala Lys Arg Leu Gln Glu Ile Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Arg Gly Glu Leu Val Pro Asp
    50                  55                  60

Glu Leu Val Asn Glu Val Val Lys Arg Leu Ser Glu Lys Asp Cys
65                  70                  75                  80

Glu Arg Gly Phe Ile Leu Asp Gly Tyr Pro Arg Thr Val Ala Gln Ala
                85                  90                  95

Glu Phe Leu Asp Gly Phe Leu Lys Thr Gln Asn Lys Glu Leu Thr Ala
            100                 105                 110

Ala Val Leu Phe Glu Val Pro Glu Glu Val Val Gln Arg Leu Thr
        115                 120                 125

Ala Arg Arg Ile Cys Pro Lys Cys Gly Arg Ile Tyr Asn Leu Ile Ser
    130                 135                 140

Leu Pro Pro Lys Glu Asp Glu Leu Cys Asp Asp Cys Lys Val Lys Leu
145                 150                 155                 160

Val Gln Arg Glu Asp Asp Lys Glu Glu Thr Val Arg His Arg Tyr Lys
                165                 170                 175

Val Tyr Leu Glu Lys Thr Gln Pro Val Ile Asp Tyr Tyr Asp Lys Lys
            180                 185                 190

Gly Ile Leu Lys Arg Val Asp Gly Thr Ile Gly Ile Asp Asn Val Ile
        195                 200                 205

Ala Glu Val Leu Lys Ile Ile Gly Trp Ser Asp Lys Leu Ser Ser Met
    210                 215                 220

Asp Ser Asn Gln Gly Asn Asn Gln Gln Asn Tyr Gln Gln Tyr Ser Gln
225                 230                 235                 240

Asn Gly Asn Gln Gln Gln Gly Asn Asn Arg Tyr Gln Gly Tyr Gln Ala
```

```
                    245                 250                 255
Tyr Asn Ala Gln Ala Gln Pro Gly Gly Gly Tyr Tyr Gln Asn Tyr Gln
                260                 265                 270

Gly Tyr Ser Gly Tyr Gln Gln Gly Gly Tyr Gln Gln Tyr Asn Pro Asp
            275                 280                 285

Ala Gly Tyr Gln Gln Gln Tyr Asn Pro Gln Gly Tyr Gln Gln Gln Tyr
    290                 295                 300

Asn Pro Gln Gly Tyr Gln His Gln Phe Asn Pro Gln Gly Gly Arg
305                 310                 315                 320

Gly Asn Tyr Lys Asn Phe Asn Tyr Asn Asn Asn Leu Gln Gly Tyr Gln
                325                 330                 335

Ala Gly

<210> SEQ ID NO 55
<211> LENGTH: 21
<212> TYPE: DNA
<213> ORGANISM: Artificial Sequence
<220> FEATURE:
<223> OTHER INFORMATION: DNA sequence encoding a short Sup35 peptide
      capable of aggregating to form amyloid fibrils; for use as a
      fusion peptide with tAK genes.

<400> SEQUENCE: 55
ggtaacaacc agcagaacta c                                            21

<210> SEQ ID NO 56
<211> LENGTH: 7
<212> TYPE: PRT
<213> ORGANISM: Artificial Sequence
<220> FEATURE:
<223> OTHER INFORMATION: Sup35 derived amyloid peptide

<400> SEQUENCE: 56

Gly Asn Asn Gln Gln Asn Tyr
1               5

<210> SEQ ID NO 57
<211> LENGTH: 1593
<212> TYPE: DNA
<213> ORGANISM: Artificial Sequence
<220> FEATURE:
<223> OTHER INFORMATION: DNA sequence encoding a Norovirus capsid
      protein (58kDa)

<400> SEQUENCE: 57
atgatgatgg cgtctaagga cgctacatca agcgtggatg gcgctagtgg cgctggtcag      60
ttggtaccgg aggttaatgc ttctgaccct cttgcaatgg atcctgtagc aggttcttcg     120
acagcagtcg cgactgctgg acaagttaat cctattgatc cctggataat taataatttt     180
gtgcaagccc cccaaggtga atttactatt tccccaaata taccccggg tgatgttttg     240 tttgatttga gtttgggtcc ccatcttaat cctttcttgc tccatctatc acaaatgtat     300
aatggttggg ttggtaacat gagagtcagg attatgctag ctggtaatgc ctttactgcg     360
gggaagataa tagtttcctg cataccccct ggttttggtt cacataatct tactatagca     420
caagcaactc tctttccaca tgtgattgct gatgttagga ctctagaccc cattgaggtg     480 ccttttggaag atgttaggaa tgttctcttt cataataatg atagaaatca acaaaccatg     540
cgccttgtgt gcatgctgta cacccccctc gcactggtg tggtactgg tgattctttt     600 gtagttgcag ggcgagttat gacttgcccc agtcctgatt ttaatttctt gttttttagtc     660
```

-continued

```
cctcctacgg tggagcagaa aaccaggccc ttcacactcc caaatctgcc attgagttct    720
ctgtctaact cacgtgcccc tctcccaatc agtagtatgg gcatttcccc agacaatgtc    780
cagagtgtgc agttccaaaa tggtcggtgt actctggatg gccgcctggt tggcaccacc    840
ccagtttcat tgtcacatgt tgccaagata agagggacct ccaatggcac tgtaatcaac    900
cttactgaat tggatggcac acccttcac cctttgagg gccctgcccc cattgggttt    960
ccagacctcg gtggttgtga ttggcatatc aatatgacac agtttggcca ttctagccag   1020
acccagtatg atgtagacac cacccctgac acttttgtcc cccatcttgg ttcaattcag   1080
gcaaatggca ttggcagtgg taattatgtt ggtgttctta gctggatttc ccccccatca   1140
cacccgtctg gctcccaagt tgacctttgg aagatcccca attatgggtc aagtattacg   1200
gaggcaacac atctagcccc ttctgtatac ccccctggtt tcggagaggt attggtcttt   1260
ttcatgtcaa aaatgccagg tcctggtgct tataatttgc cctgtctatt accacaagag   1320
tacatttcac atcttgctag tgaacaagcc cctactgtag gtgaggctgc cctgctccac   1380
tatgttgacc ctgataccgg tcggaatctt ggggaattca aagcataccc tgatggtttc   1440
ctcacttgtg tccccaatgg ggctagctcg ggtccacaac agctgccgat caatggggtc   1500
tttgtctttg tttcatgggt gtccagattt tatcaattaa agcctgtggg aactgccagc   1560
tcggcaagag gtaggcttgg tctgcgccga taa                                1593
```

```

<210> SEQ ID NO 58
<211> LENGTH: 530
<212> TYPE: PRT
<213> ORGANISM: Artificial Sequence
<220> FEATURE:
<223> OTHER INFORMATION: Protein sequence of Norovirus capsid protein
      (58kDa)

<400> SEQUENCE: 58

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190
```

-continued

```
Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240
Leu Ser Asn Ser Arg Ala Pro Leu Pro Ile Ser Ser Met Gly Ile Ser
                245                 250                 255
Pro Asp Asn Val Gln Ser Val Gln Phe Gln Asn Gly Arg Cys Thr Leu
            260                 265                 270
Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320
Pro Asp Leu Gly Gly Cys Asp Trp His Ile Asn Met Thr Gln Phe Gly
                325                 330                 335
His Ser Ser Gln Thr Gln Tyr Asp Val Asp Thr Thr Pro Asp Thr Phe
            340                 345                 350
Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400
Glu Ala Thr His Leu Ala Pro Ser Val Tyr Pro Pro Gly Phe Gly Glu
                405                 410                 415
Val Leu Val Phe Phe Met Ser Lys Met Pro Gly Pro Gly Ala Tyr Asn
            420                 425                 430
Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480
Leu Thr Cys Val Pro Asn Gly Ala Ser Ser Gly Pro Gln Gln Leu Pro
                485                 490                 495
Ile Asn Gly Val Phe Val Phe Val Ser Trp Val Ser Arg Phe Tyr Gln
            500                 505                 510
Leu Lys Pro Val Gly Thr Ala Ser Ser Ala Arg Gly Arg Leu Gly Leu
        515                 520                 525

Arg Arg
    530
```

<210> SEQ ID NO 59
<211> LENGTH: 1593
<212> TYPE: DNA
<213> ORGANISM: Artificial Sequence
<220> FEATURE:
<223> OTHER INFORMATION: DNA sequence for a synthetic gene encoding a Norovirus capsid protein (58kDa) optimised for expression in E.coli

<400> SEQUENCE: 59

```
atgatgatgg cttctaaaga cgctacctct tctgttgacg gtgcttctgg tgctggtcag     60
```

-continued

```
ctggttccgg aagttaacgc ttctgacccg ctggctatgg acccggttgc tggttcttct      120
accgctgttg ctaccgctgg tcaggttaac ccgatcgacc cgtggatcat caacaacttc      180
gttcaggctc cgcagggtga attcaccatc tctccgaaca caccccggg tgacgttctg       240 ttcgacctgt ctctgggtcc gcacctgaac ccgttcctgc tgcacctgtc tcagatgtac      300
aacggttggg ttggtaacat gcgtgttcgt atcatgctgg ctggtaacgc tttcaccgct      360
ggtaaaatca tcgtttcttg catcccgccg ggtttcggtt ctcacaacct gaccatcgct      420
caggctaccc tgttcccgca cgttatcgct gacgttcgta ccctggaccc gatcgaagtt      480
ccgctggaag acgttcgtaa cgttctgttc cacaacaacg accgtaacca gcagaccatg      540
cgtctggttt gcatgctgta caccccgctg cgtaccggtg gtggtaccgg tgactctttc      600
gttgttgctg gtcgtgttat gacctgcccg ctctccggact tcaacttcct gttcctggtt      660
ccgccgaccg ttgaacagaa aacccgtccg ttcacctgc cgaacctgcc gctgtcttct       720
ctgtctaact ctcgtgctcc gctgccgatc tcttctatgg gtatctctcc ggacaacgtt      780
cagtctgttc agttccagaa cggtcgttgc accctggacg gtcgtctggt tggtaccacc      840
ccggtttctc tgtctcacgt tgctaaaatc cgtggtacct ctaacggtac cgttatcaac      900
ctgaccgaac tggacggtac cccgttccac ccgttcgaag gtccggctcc gatcggtttc      960
ccggacctgg gtggttgcga ctggcacatc aacatgaccc agttcggtca ctcttctcag     1020
acccagtacg acgttgacac caccccggac accttcgttc cgcacctggg ttctatccag     1080
gctaacggta tcggttctgg taactacgtt ggtgttctgt cttggatctc tccgccgtct    1140
cacccgtctg gttctcaggt tgacctgtgg aaaatcccga actacggttc ttctatcacc     1200
gaagctaccc acctggctcc gtctgtttac ccgccgggtt tcggtgaagt tctggttttc     1260
ttcatgtcta aaatgccggg tccgggtgct tacaacctgc cgtgcctgct gccgcaggaa     1320
tacatctctc acctggcttc tgaacaggct ccgaccgttg gtgaagctgc tctgctgcac     1380
tacgttgacc cggacaccgg tcgtaacctg ggtgaattca aagcttaccc ggacggtttc     1440
ctgacctgcg ttccgaacgg tgcttcttct ggtccgcagc agctgccgat caacggtgtt     1500
ttcgttttcg tttcttgggt ttctcgtttc taccagctga aaccggttgg taccgcttct     1560
tctgctcgtg gtcgtctggg tctgcgtcgt tag                                  1593
```

<210> SEQ ID NO 60
<211> LENGTH: 2250
<212> TYPE: DNA
<213> ORGANISM: Artificial Sequence
<220> FEATURE:
<223> OTHER INFORMATION: DNA sequence for a synthetic gene encoding a
      Norovirus capsid protein (58kDa) optimised for expression in E.coli fused at the 5' end of a gene encoding the tAK from Thermotoga maritima.

<400> SEQUENCE: 60

```
atgatgatgg cttctaaaga cgctacctct tctgttgacg gtgcttctgg tgctggtcag     60
ctggttccgg aagttaacgc ttctgacccg ctggctatgg acccggttgc tggttcttct    120
accgctgttg ctaccgctgg tcaggttaac ccgatcgacc cgtggatcat caacaacttc    180
gttcaggctc cgcagggtga attcaccatc tctccgaaca acaccccggg tgacgttctg    240
ttcgacctgt ctctgggtcc gcacctgaac ccgttcctgc tgcacctgtc tcagatgtac    300
aacggttggg ttggtaacat gcgtgttcgt atcatgctgg ctggtaacgc tttcaccgct    360
ggtaaaatca tcgtttcttg catcccgccg ggtttcggtt ctcacaacct gaccatcgct    420
```

-continued

```
caggctaccc tgttcccgca cgttatcgct gacgttcgta ccctggaccc gatcgaagtt      480
ccgctggaag acgttcgtaa cgttctgttc cacaacaacg accgtaacca gcagaccatg      540
cgtctggttt gcatgctgta caccccgctg cgtaccggtg gtggtaccgg tgactctttc      600
gttgttgctg gtcgtgttat gacctgcccg tctccggact tcaacttcct gttcctggtt      660
ccgccgaccg ttgaacagaa aaccgtccg ttcaccctgc cgaacctgcc gctgtcttct       720
ctgtctaact ctcgtgctcc gctgccgatc tcttctatgg gtatctctcc ggacaacgtt      780
cagtctgttc agttccagaa cggtcgttgc accctggacg tcgtctggt tggtaccacc       840 ccggtttctc tgtctcacgt tgctaaaatc cgtggtacct taacggtac cgttatcaac       900 ctgaccgaac tggacggtac cccgttccac ccgttcgaag gtccggctcc gatcggtttc      960
ccggacctgg gtggttgcga ctggcacatc aacatgaccc agttcggtca ctcttctcag     1020
acccagtacg acgttgacac caccccggac accttcgttc cgcacctggg ttctatccag     1080
gctaacggta tcggttctgg taactacgtt ggtgttctgt cttggatctc tccgccgtct     1140
cacccgtctg gttctcaggt tgacctgtgg aaaatcccga actacggttc ttctatcacc     1200
gaagctaccc ccctggctcc gtctgtttac ccgccgggtt tcggtgaagt tctggttttc     1260
ttcatgtcta aaatgccggg tccgggtgct acaacctgc cgtgcctgct gccgcaggaa      1320
tacatctctc acctggcttc tgaacaggct ccgaccgttg gtgaagctgc tctgctgcac     1380
tacgttgacc cggacaccgg tcgtaacctg ggtgaattca agcttacccc ggacggttc     1440 ctgacctgcg ttccgaacgg tgcttcttct ggtccgcagc agctgccgat caacggtgtt     1500
ttcgttttcg tttcttgggt ttctcgttc taccagctga accggttgg taccgcttct      1560 tctgctcgtg gtcgtctggg tctgcgtcgt atgatggcct atctggtttt tcttggtcca     1620 ccggggcag gcaaaggtac ctatgcgaaa cgtttacagg aaatcaccgg catcccgcac      1680
attagcacgg gcgacatttt tcgtgatatt gtcaaaaagg aaaatgacga attaggtaag     1740
aaaattaaag aaattatgga gcgcggcgag ttggtgccgg acgaactggt gaatgaagtt     1800
gtcaaacgtc ggctgtctga aaaggattgc gaacgtggct ttattttgga cggttacccg     1860
cgtacagtag ctcaggcaga gttctcgac ggcttcctga agactcagaa taaggagtta      1920
acggctgcgg tcctgttcga ggtgcctgaa gaggtggtcg ttcagcgtct gaccgcgcgg     1980
cgtatctgcc cgaagtgtgg tcgtatttac aacctgattt cacttcctcc aaaagaagat     2040
gaactgtgtg atgactgcaa agtaaaactg gtgcaacgcg aagatgataa agaggaaact     2100
gtgcgccatc gctacaaagt atatctggaa aaacccaac cggttatcga ttattatgat      2160
aaaaaaggca ttttgaaacg cgttgatggg accatcggca tcgataacgt gattgccgaa     2220
gttctcaaaa tcattgggtg gagtgataaa                                      2250
```

<210> SEQ ID NO 61
<211> LENGTH: 750
<212> TYPE: PRT
<213> ORGANISM: Artificial Sequence
<220> FEATURE:
<223> OTHER INFORMATION: Protein sequence of a Norovirus capsid protein (58kDa) fused at the N-terminus of the adenylate kinase from Thermotoga maritima

<400> SEQUENCE: 61

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
```

```
            20                  25                  30
Met Asp Pro Val Ala Gly Ser Ser Thr Ala Val Ala Thr Ala Gly Gln
            35                  40                  45
Val Asn Pro Ile Asp Pro Trp Ile Ile Asn Asn Phe Val Gln Ala Pro
 50                  55                  60
Gln Gly Glu Phe Thr Ile Ser Pro Asn Asn Thr Pro Gly Asp Val Leu
 65                  70                  75                  80
Phe Asp Leu Ser Leu Gly Pro His Leu Asn Pro Phe Leu Leu His Leu
                85                  90                  95
Ser Gln Met Tyr Asn Gly Trp Val Gly Asn Met Arg Val Arg Ile Met
            100                 105                 110
Leu Ala Gly Asn Ala Phe Thr Ala Gly Lys Ile Ile Val Ser Cys Ile
            115                 120                 125
Pro Pro Gly Phe Gly Ser His Asn Leu Thr Ile Ala Gln Ala Thr Leu
            130                 135                 140
Phe Pro His Val Ile Ala Asp Val Arg Thr Leu Asp Pro Ile Glu Val
145                 150                 155                 160
Pro Leu Glu Asp Val Arg Asn Val Leu Phe His Asn Asn Asp Arg Asn
                165                 170                 175
Gln Gln Thr Met Arg Leu Val Cys Met Leu Tyr Thr Pro Leu Arg Thr
            180                 185                 190
Gly Gly Gly Thr Gly Asp Ser Phe Val Val Ala Gly Arg Val Met Thr
            195                 200                 205
Cys Pro Ser Pro Asp Phe Asn Phe Leu Phe Leu Val Pro Pro Thr Val
            210                 215                 220
Glu Gln Lys Thr Arg Pro Phe Thr Leu Pro Asn Leu Pro Leu Ser Ser
225                 230                 235                 240
Leu Ser Asn Ser Arg Ala Pro Leu Pro Ile Ser Ser Met Gly Ile Ser
                245                 250                 255
Pro Asp Asn Val Gln Ser Val Gln Phe Gln Asn Gly Arg Cys Thr Leu
            260                 265                 270
Asp Gly Arg Leu Val Gly Thr Thr Pro Val Ser Leu Ser His Val Ala
            275                 280                 285
Lys Ile Arg Gly Thr Ser Asn Gly Thr Val Ile Asn Leu Thr Glu Leu
            290                 295                 300
Asp Gly Thr Pro Phe His Pro Phe Glu Gly Pro Ala Pro Ile Gly Phe
305                 310                 315                 320
Pro Asp Leu Gly Gly Cys Asp Trp His Ile Asn Met Thr Gln Phe Gly
                325                 330                 335
His Ser Ser Gln Thr Gln Tyr Asp Val Asp Thr Thr Pro Asp Thr Phe
            340                 345                 350
Val Pro His Leu Gly Ser Ile Gln Ala Asn Gly Ile Gly Ser Gly Asn
            355                 360                 365
Tyr Val Gly Val Leu Ser Trp Ile Ser Pro Pro Ser His Pro Ser Gly
            370                 375                 380
Ser Gln Val Asp Leu Trp Lys Ile Pro Asn Tyr Gly Ser Ser Ile Thr
385                 390                 395                 400
Glu Ala Thr His Leu Ala Pro Ser Val Tyr Pro Pro Gly Phe Gly Glu
                405                 410                 415
Val Leu Val Phe Phe Met Ser Lys Met Pro Gly Pro Gly Ala Tyr Asn
            420                 425                 430
Leu Pro Cys Leu Leu Pro Gln Glu Tyr Ile Ser His Leu Ala Ser Glu
            435                 440                 445
```

```
Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
                500                 505                 510

Leu Lys Pro Val Gly Thr Ala Ser Ser Ala Arg Gly Arg Leu Gly Leu
            515                 520                 525

Arg Arg Met Met Ala Tyr Leu Val Phe Leu Gly Pro Pro Gly Ala Gly
530                 535                 540

Lys Gly Thr Tyr Ala Lys Arg Leu Gln Glu Ile Thr Gly Ile Pro His
545                 550                 555                 560

Ile Ser Thr Gly Asp Ile Phe Arg Asp Ile Val Lys Lys Glu Asn Asp
                565                 570                 575

Glu Leu Gly Lys Lys Ile Lys Glu Ile Met Glu Arg Gly Glu Leu Val
            580                 585                 590

Pro Asp Glu Leu Val Asn Glu Val Val Lys Arg Arg Leu Ser Glu Lys
        595                 600                 605

Asp Cys Glu Arg Gly Phe Ile Leu Asp Gly Tyr Pro Arg Thr Val Ala
610                 615                 620

Gln Ala Glu Phe Leu Asp Gly Phe Leu Lys Thr Gln Asn Lys Glu Leu
625                 630                 635                 640

Thr Ala Ala Val Leu Phe Glu Val Pro Glu Glu Val Val Val Gln Arg
                645                 650                 655

Leu Thr Ala Arg Arg Ile Cys Pro Lys Cys Gly Arg Ile Tyr Asn Leu
            660                 665                 670

Ile Ser Leu Pro Pro Lys Glu Asp Glu Leu Cys Asp Asp Cys Lys Val
        675                 680                 685

Lys Leu Val Gln Arg Glu Asp Asp Lys Glu Glu Thr Val Arg His Arg
690                 695                 700

Tyr Lys Val Tyr Leu Glu Lys Thr Gln Pro Val Ile Asp Tyr Tyr Asp
705                 710                 715                 720

Lys Lys Gly Ile Leu Lys Arg Val Asp Gly Thr Ile Gly Ile Asp Asn
                725                 730                 735

Val Ile Ala Glu Val Leu Lys Ile Ile Gly Trp Ser Asp Lys
            740                 745                 750

<210> SEQ ID NO 62
<211> LENGTH: 130
<212> TYPE: PRT
<213> ORGANISM: Bacteriophage MS2

<400> SEQUENCE: 62

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
```

```
                65                  70                  75                  80
Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
               100                 105                 110

Leu Lys Asp Gly Asn Pro Ile Pro Ser Ala Ile Ala Ala Asn Ser Gly
               115                 120                 125

Ile Tyr
   130

<210> SEQ ID NO 63
<211> LENGTH: 127
<212> TYPE: PRT
<213> ORGANISM: Bacteriophage PP7

<400> SEQUENCE: 63

Ser Lys Thr Ile Val Leu Ser Val Gly Glu Ala Thr Arg Thr Leu Thr
1               5                   10                  15

Glu Ile Gln Ser Thr Ala Asp Arg Gln Ile Phe Glu Glu Lys Val Gly
                20                  25                  30

Pro Leu Val Gly Arg Leu Arg Leu Thr Ala Ser Leu Arg Gln Asn Gly
            35                  40                  45

Ala Lys Thr Ala Tyr Arg Val Asn Leu Lys Leu Asp Gln Ala Asp Val
        50                  55                  60

Val Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Val Gln
               100                 105                 110

Ala Thr Ser Glu Asp Leu Val Val Asn Leu Val Pro Leu Gly Arg
           115                 120                 125

<210> SEQ ID NO 64
<211> LENGTH: 245
<212> TYPE: PRT
<213> ORGANISM: Bacteriophage PP7

<400> SEQUENCE: 64

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
                20                  25                  30

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
        50                  55                  60

Val Val Asp Ser Gly Leu Pro Lys Val Arg Tyr Thr Gln Val Trp Ser
65                  70                  75                  80

His Asp Val Thr Ile Val Ala Asn Ser Thr Glu Ala Ser Arg Lys Ser
                85                  90                  95

Leu Tyr Asp Leu Thr Lys Ser Leu Val Ala Thr Ser Gln Val Glu Asp
               100                 105                 110

Leu Val Val Asn Leu Val Pro Leu Gly Arg Tyr Gly Ser Lys Thr Ile
           115                 120                 125

Val Leu Ser Val Gly Glu Ala Thr Arg Thr Leu Thr Glu Ile Gln Ser
```

```
                    130                 135                 140
Thr Ala Asp Arg Gln Ile Phe Glu Glu Lys Val Gly Pro Leu Val Gly
145                 150                 155                 160

Arg Leu Arg Leu Thr Ala Ser Leu Arg Gln Asn Gly Ala Lys Thr Ala
                165                 170                 175

Tyr Arg Val Asn Leu Lys Leu Asp Gln Ala Asp Val Val Asp Ser Gly
            180                 185                 190

Leu Pro Lys Val Arg Tyr Thr Gln Val Trp Ser His Asp Val Thr Ile
        195                 200                 205

Val Ala Asn Ser Thr Glu Ala Ser Arg Lys Ser Leu Tyr Asp Leu Thr
    210                 215                 220

Lys Ser Leu Val Ala Thr Ser Gln Val Glu Asp Leu Val Val Asn Leu
225                 230                 235                 240

Val Pro Leu Gly Arg
                245

<210> SEQ ID NO 65
<211> LENGTH: 151
<212> TYPE: PRT
<213> ORGANISM: Escherichia coli

<400> SEQUENCE: 65

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
        50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150

<210> SEQ ID NO 66
<211> LENGTH: 151
<212> TYPE: PRT
<213> ORGANISM: Artificial Sequence
<220> FEATURE:
<223> OTHER INFORMATION: Protein sequence of AgfA protein from
      Salmonella

<400> SEQUENCE: 66

Met Lys Leu Leu Lys Val Ala Ala Phe Ala Ala Ile Val Val Ser Gly
1               5                   10                  15

Ser Ala Leu Ala Gly Val Val Pro Gln Trp Gly Gly Gly Gly Asn His
                20                  25                  30

Asn Gly Gly Gly Asn Ser Ser Gly Pro Asp Ser Thr Leu Ser Ile Tyr
```

```
                35                  40                  45
Gln Tyr Gly Ser Ala Asn Ala Ala Leu Ala Leu Gln Ser Asp Ala Arg
 50                  55                  60

Lys Ser Glu Thr Thr Ile Thr Gln Ser Gly Tyr Gly Asn Gly Ala Asp
 65                  70                  75                  80

Val Gly Gln Gly Ala Asp Asn Ser Thr Ile Glu Leu Thr Gln Asn Gly
                 85                  90                  95

Phe Arg Asn Asn Ala Thr Ile Asp Gln Trp Asn Ala Lys Asn Ser Asp
                100                 105                 110

Ile Thr Val Gly Gln Tyr Gly Gly Asn Asn Ala Ala Leu Val Asn Gln
                115                 120                 125

Thr Ala Ser Asp Ser Ser Val Met Val Arg Gln Val Gly Phe Gly Asn
                130                 135                 140

Asn Ala Thr Ala Asn Gln Tyr
145                 150

<210> SEQ ID NO 67
<211> LENGTH: 353
<212> TYPE: PRT
<213> ORGANISM: Artificial Sequence
<220> FEATURE:
<223> OTHER INFORMATION: Protein sequence of adenylate kinase from
      Thermotoga maritima fused to the N terminus of E.coli CsgA

<400> SEQUENCE: 67

Met Met Ala Tyr Leu Val Phe Leu Gly Pro Pro Gly Ala Gly Lys Gly
  1               5                  10                  15

Thr Tyr Ala Lys Arg Ile Gln Glu Lys Thr Gly Ile Pro His Ile Ser
                 20                  25                  30

Thr Gly Asp Ile Phe Arg Asp Ile Val Lys Lys Glu Asn Asp Glu Leu
                 35                  40                  45

Gly Lys Lys Ile Lys Glu Ile Met Glu Lys Gly Glu Leu Val Pro Asp
 50                  55                  60

Glu Leu Val Asn Glu Val Val Lys Arg Arg Leu Ser Glu Lys Asp Cys
 65                  70                  75                  80

Glu Lys Gly Phe Ile Leu Asp Gly Tyr Pro Arg Thr Val Ala Gln Ala
                 85                  90                  95

Glu Phe Leu Asp Ser Phe Leu Glu Ser Gln Asn Lys Gln Leu Thr Ala
                100                 105                 110

Ala Val Leu Phe Asp Val Pro Glu Asp Val Val Gln Arg Leu Thr
                115                 120                 125

Ser Arg Arg Ile Cys Pro Lys Cys Gly Arg Ile Tyr Asn Met Ile Ser
130                 135                 140

Leu Pro Pro Lys Glu Asp Glu Leu Cys Asp Asp Cys Lys Val Lys Leu
145                 150                 155                 160

Val Gln Arg Asp Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
                180                 185                 190

Gly Ile Leu Lys Arg Val Asp Gly Thr Ile Gly Ile Asp Asn Val Val
                195                 200                 205

Ala Glu Val Leu Lys Ile Ile Gly Trp Ser Asp Lys Gly Ser Gly Val
                210                 215                 220

Val Pro Gln Tyr Gly Gly Gly Gly Asn His Gly Gly Gly Gly Asn Asn
225                 230                 235                 240
```

```
Ser Gly Pro Asn Ser Glu Leu Asn Ile Tyr Gln Tyr Gly Gly Gly Asn
                245                 250                 255

Ser Ala Leu Ala Leu Gln Thr Asp Ala Arg Asn Ser Asp Leu Thr Ile
            260                 265                 270

Thr Gln His Gly Gly Asn Gly Ala Asp Val Gly Gln Gly Ser Asp
        275                 280                 285

Asp Ser Ser Ile Asp Leu Thr Gln Arg Gly Phe Gly Asn Ser Ala Thr
    290                 295                 300

Leu Asp Gln Trp Asn Gly Lys Asn Ser Glu Met Thr Val Lys Gln Phe
305                 310                 315                 320

Gly Gly Gly Asn Gly Ala Ala Val Asp Gln Thr Ala Ser Asn Ser Ser
                325                 330                 335

Val Asn Val Thr Gln Val Gly Phe Gly Asn Asn Ala Thr Ala His Gln
                340                 345                 350

Tyr

<210> SEQ ID NO 68
<211> LENGTH: 83
<212> TYPE: PRT
<213> ORGANISM: Artificial Sequence
<220> FEATURE:
<223> OTHER INFORMATION: Protein sequence of hydrophobin 3 protein from
      Fusarium species

<400> SEQUENCE: 68

Met Gln Phe Ser Thr Leu Thr Thr Val Phe Ala Leu Val Ala Ala Ala
1               5                   10                  15

Val Ala Ala Pro His Gly Ser Ser Gly Gly Asn Asn Pro Val Cys Ser
                20                  25                  30

Ala Gln Asn Asn Gln Val Cys Cys Asn Gly Leu Leu Ser Cys Ala Val
            35                  40                  45

Gln Val Leu Gly Ser Asn Cys Asn Gly Asn Ala Tyr Cys Cys Asn Thr
        50                  55                  60

Glu Ala Pro Thr Gly Thr Leu Ile Asn Val Ala Leu Leu Asn Cys Val
65                  70                  75                  80

Lys Leu Leu

<210> SEQ ID NO 69
<211> LENGTH: 98
<212> TYPE: PRT
<213> ORGANISM: Artificial Sequence
<220> FEATURE:
<223> OTHER INFORMATION: Protein sequence of hydrophobin 5 protein from
      Fusarium species

<400> SEQUENCE: 69

Met Lys Phe Ser Leu Ala Ala Val Ala Leu Leu Gly Ala Val Val Ser
1               5                   10                  15

Ala Leu Pro Ala Asn Glu Lys Arg Gln Ala Tyr Ile Pro Cys Ser Gly
                20                  25                  30

Leu Tyr Gly Thr Ser Gln Cys Cys Ala Thr Asp Val Leu Gly Val Ala
            35                  40                  45

Asp Leu Asp Cys Gly Asn Pro Pro Ser Ser Pro Thr Ala Asp Asn
        50                  55                  60

Phe Ser Ala Val Cys Ala Glu Ile Gly Gln Arg Ala Arg Cys Val
65                  70                  75                  80

Leu Pro Ile Leu Asp Gln Gly Ile Leu Cys Asn Thr Pro Thr Gly Val
                85                  90                  95
```

Gln Asp

<210> SEQ ID NO 70
<211> LENGTH: 173
<212> TYPE: PRT
<213> ORGANISM: Balanus albicostatus

<400> SEQUENCE: 70

Val Pro Pro Pro Cys Asp Leu Ser Ile Lys Ser Lys Leu Lys Gln Val
1               5                   10                  15

Gly Ala Thr Ala Gly Asn Ala Ala Val Thr Thr Gly Thr Thr Ser
            20                  25                  30

Gly Ser Gly Val Val Lys Cys Val Arg Thr Pro Thr Ser Val Glu
        35                  40                  45

Lys Lys Ala Ala Val Gly Asn Thr Gly Leu Ser Ala Val Ser Ala Ser
50                  55                  60

Ala Ala Asn Gly Phe Phe Lys Asn Leu Gly Lys Ala Thr Thr Glu Val
65                  70                  75                  80

Lys Thr Thr Lys Asp Gly Thr Lys Val Lys Thr Lys Thr Ala Gly Lys
                85                  90                  95

Gly Lys Thr Gly Gly Thr Ala Thr Thr Ile Gln Ile Ala Asp Ala Asn
            100                 105                 110

Gly Gly Val Ser Glu Lys Ser Leu Lys Leu Asp Leu Leu Thr Asp Gly
        115                 120                 125

Leu Lys Phe Val Lys Val Thr Glu Lys Lys Gln Gly Thr Ala Thr Ser
130                 135                 140

Ser Ser Gly His Lys Ala Ser Gly Val Gly His Ser Val Phe Lys Val
145                 150                 155                 160

Leu Asn Glu Ala Glu Thr Glu Leu Glu Leu Lys Gly Leu
                165                 170

<210> SEQ ID NO 71
<211> LENGTH: 202
<212> TYPE: PRT
<213> ORGANISM: Megabalanus rosa

<400> SEQUENCE: 71

Met Lys Trp Phe Leu Phe Leu Leu Thr Thr Ala Val Leu Ala Ala Val
1               5                   10                  15

Val Ser Ala His Glu Glu Asp Gly Val Cys Asn Ser Asn Ala Pro Cys
            20                  25                  30

Tyr His Cys Asp Ala Asn Gly Glu Asn Cys Ser Cys Asn Cys Glu Leu
        35                  40                  45

Phe Asp Cys Glu Ala Lys Lys Pro Asp Gly Ser Tyr Ala His Pro Cys
50                  55                  60

Arg Arg Cys Asp Ala Asn Asn Ile Cys Lys Cys Ser Cys Thr Ala Ile
65                  70                  75                  80

Pro Cys Asn Glu Asp His Pro Cys His His Cys His Glu Glu Asp Asp
                85                  90                  95

Gly Asp Thr His Cys His Cys Ser Cys Glu His Ser His Asp His His
            100                 105                 110

Asp Asp Asp Thr His Gly Glu Cys Thr Lys Lys Ala Pro Cys Trp Arg
        115                 120                 125

Cys Glu Tyr Asn Ala Asp Leu Lys His Asp Val Cys Gly Cys Glu Cys
130                 135                 140

```
Ser Lys Leu Pro Cys Asn Asp Glu His Pro Cys Tyr Arg Lys Glu Gly
145                 150                 155                 160

Gly Val Val Ser Cys Asp Cys Lys Thr Ile Thr Cys Asn Glu Asp His
                165                 170                 175

Pro Cys Tyr His Ser Tyr Glu Glu Asp Gly Val Thr Lys Ser Asp Cys
            180                 185                 190

Asp Cys Glu His Ser Pro Gly Pro Ser Glu
            195                 200
```

<210> SEQ ID NO 72
<211> LENGTH: 576
<212> TYPE: PRT
<213> ORGANISM: Artificial Sequence
<220> FEATURE:
<223> OTHER INFORMATION: Protein sequence of fusion of the barnacle
      protein from Balanus albicostatus with the adenylate kinase from
      Thermotgoa maritima; N-terminal fusion

<400> SEQUENCE: 72

```
Met Arg Val Leu Val Ile Asn Ser Gly Ser Ser Ile Lys Tyr Gln
1               5                   10                  15

Leu Ile Glu Met Glu Gly Glu Lys Val Leu Cys Lys Gly Ile Ala Glu
                20                  25                  30

Arg Ile Gly Ile Glu Gly Ser Arg Leu Val His Arg Val Gly Asp Glu
            35                  40                  45

Lys His Val Ile Glu Arg Glu Leu Pro Asp His Glu Glu Ala Leu Lys
        50                  55                  60

Leu Ile Leu Asn Thr Leu Val Asp Glu Lys Leu Gly Val Ile Lys Asp
65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Glu Val Leu Lys Ala Ile
            100                 105                 110

Glu Glu Val Ser Pro Leu Ala Pro Leu His Asn Pro Ala Asn Leu Met
        115                 120                 125

Gly Ile Lys Ala Ala Met Lys Leu Leu Pro Gly Val Pro Asn Val Ala
    130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Glu Lys Tyr Lys Ile Arg Arg Tyr
                165                 170                 175

Gly Phe His Gly Thr Ser His Arg Tyr Val Ser Lys Arg Ala Ala Glu
            180                 185                 190

Ile Leu Gly Lys Lys Leu Glu Glu Leu Lys Ile Ile Thr Cys His Ile
        195                 200                 205

Gly Asn Gly Ala Ser Val Ala Ala Val Lys Tyr Gly Lys Cys Val Asp
    210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
                245                 250                 255

Gly Ile Ser Pro Gln Glu Met Tyr Asp Ile Leu Asn Lys Lys Ser Gly
            260                 265                 270

Val Tyr Gly Leu Ser Lys Gly Phe Ser Ser Asp Met Arg Asp Ile Glu
        275                 280                 285

Glu Ala Ala Leu Lys Gly Asp Glu Trp Cys Lys Leu Val Leu Glu Ile
```

```
            290                 295                 300
Tyr Asp Tyr Arg Ile Ala Lys Tyr Ile Gly Ala Tyr Ala Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val
            340                 345                 350

Lys Leu Asp Lys Gln Lys Asn Glu Glu Thr Ile Arg Gly Lys Glu Gly
        355                 360                 365

Ile Ile Ser Thr Pro Asp Ser Arg Val Lys Val Leu Val Pro Thr
370                 375                 380

Asn Glu Glu Leu Met Ile Ala Arg Asp Thr Lys Glu Ile Val Glu Lys
385                 390                 395                 400

Ile Gly Arg Val Pro Pro Cys Asp Leu Ser Ile Lys Ser Lys Leu
                405                 410                 415

Lys Gln Val Gly Ala Thr Ala Gly Asn Ala Ala Val Thr Thr Thr Gly
                420                 425                 430

Thr Thr Ser Gly Ser Gly Val Val Lys Cys Val Val Arg Thr Pro Thr
            435                 440                 445

Ser Val Glu Lys Lys Ala Ala Val Gly Asn Thr Gly Leu Ser Ala Val
    450                 455                 460

Ser Ala Ser Ala Ala Asn Gly Phe Phe Lys Asn Leu Gly Lys Ala Thr
465                 470                 475                 480

Thr Glu Val Lys Thr Thr Lys Asp Gly Thr Lys Val Lys Thr Lys Thr
                485                 490                 495

Ala Gly Lys Gly Lys Thr Gly Gly Thr Ala Thr Thr Ile Gln Ile Ala
                500                 505                 510

Asp Ala Asn Gly Gly Val Ser Glu Lys Ser Leu Lys Leu Asp Leu Leu
            515                 520                 525

Thr Asp Gly Leu Lys Phe Val Lys Val Thr Glu Lys Lys Gln Gly Thr
        530                 535                 540

Ala Thr Ser Ser Ser Gly His Lys Ala Ser Gly Val Gly His Ser Val
545                 550                 555                 560

Phe Lys Val Leu Asn Glu Ala Glu Thr Glu Leu Glu Leu Lys Gly Leu
                565                 570                 575

<210> SEQ ID NO 73
<211> LENGTH: 575
<212> TYPE: PRT
<213> ORGANISM: Artificial Sequence
<220> FEATURE:
<223> OTHER INFORMATION: Protein sequence of fusion of barnacle protein
      from Balanus albicostatus with the adenylate kinase from
      Thermotoga maritima; C-terminal fusion

<400> SEQUENCE: 73

Val Pro Pro Pro Cys Asp Leu Ser Ile Lys Ser Lys Leu Lys Gln Val
1               5                   10                  15

Gly Ala Thr Ala Gly Asn Ala Ala Val Thr Thr Thr Gly Thr Thr Ser
                20                  25                  30

Gly Ser Gly Val Val Lys Cys Val Val Arg Thr Pro Thr Ser Val Glu
            35                  40                  45

Lys Lys Ala Ala Val Gly Asn Thr Gly Leu Ser Ala Val Ser Ala Ser
        50                  55                  60

Ala Ala Asn Gly Phe Phe Lys Asn Leu Gly Lys Ala Thr Thr Glu Val
65                  70                  75                  80
```

-continued

```
Lys Thr Thr Lys Asp Gly Thr Lys Val Lys Thr Lys Thr Ala Gly Lys
                 85                  90                  95
Gly Lys Thr Gly Gly Thr Ala Thr Thr Ile Gln Ile Ala Asp Ala Asn
            100                 105                 110
Gly Gly Val Ser Glu Lys Ser Leu Lys Leu Asp Leu Leu Thr Asp Gly
            115                 120                 125
Leu Lys Phe Val Lys Val Thr Glu Lys Lys Gln Gly Thr Ala Thr Ser
130             135                 140
Ser Ser Gly His Lys Ala Ser Gly Val Gly His Ser Val Phe Lys Val
145             150                 155                 160
Leu Glu Ala Glu Thr Glu Leu Glu Leu Lys Gly Leu Met Arg Val Leu
                165                 170                 175
Val Ile Asn Ser Gly Ser Ser Ile Lys Tyr Gln Leu Ile Glu Met
            180                 185                 190
Glu Gly Glu Lys Val Leu Cys Lys Gly Ile Ala Glu Arg Ile Gly Ile
            195                 200                 205
Glu Gly Ser Arg Leu Val His Arg Val Gly Asp Glu Lys His Val Ile
            210                 215                 220
Glu Arg Glu Leu Pro Asp His Glu Glu Ala Leu Lys Leu Ile Leu Asn
225             230                 235                 240
Thr Leu Val Asp Glu Lys Leu Gly Val Ile Lys Asp Leu Lys Glu Ile
                245                 250                 255
Asp Ala Val Gly His Arg Val Val His Gly Gly Glu Arg Phe Lys Glu
                260                 265                 270
Ser Val Leu Val Asp Glu Glu Val Leu Lys Ala Ile Glu Glu Val Ser
            275                 280                 285
Pro Leu Ala Pro Leu His Asn Pro Ala Asn Leu Met Gly Ile Lys Ala
290             295                 300
Ala Met Lys Leu Leu Pro Gly Val Pro Asn Val Ala Val Phe Asp Thr
305             310                 315                 320
Ala Phe His Gln Thr Ile Pro Gln Lys Ala Tyr Leu Tyr Ala Ile Pro
                325                 330                 335
Tyr Glu Tyr Tyr Glu Lys Tyr Lys Ile Arg Arg Tyr Gly Phe His Gly
                340                 345                 350
Thr Ser His Arg Tyr Val Ser Lys Arg Ala Ala Glu Ile Leu Gly Lys
                355                 360                 365
Lys Leu Glu Glu Leu Lys Ile Ile Thr Cys His Ile Gly Asn Gly Ala
370                 375                 380
Ser Val Ala Ala Val Lys Tyr Gly Lys Cys Val Asp Thr Ser Met Gly
385                 390                 395                 400
Phe Thr Pro Leu Glu Gly Leu Val Met Gly Thr Arg Ser Gly Asp Leu
                405                 410                 415
Asp Pro Ala Ile Pro Phe Phe Ile Met Glu Lys Glu Gly Ile Ser Pro
                420                 425                 430
Gln Glu Met Tyr Asp Ile Leu Asn Lys Lys Ser Gly Val Tyr Gly Leu
                435                 440                 445
Ser Lys Gly Phe Ser Ser Asp Met Arg Asp Ile Glu Glu Ala Ala Leu
450                 455                 460
Lys Gly Asp Glu Trp Cys Lys Leu Val Leu Glu Ile Tyr Asp Tyr Arg
465                 470                 475                 480
Ile Ala Lys Tyr Ile Gly Ala Tyr Ala Ala Ala Met Asn Gly Val Asp
                485                 490                 495
```

```
Ala Ile Val Phe Thr Ala Gly Val Gly Glu Asn Ser Pro Ile Thr Arg
                500                 505                 510

Glu Asp Val Cys Ser Tyr Leu Glu Phe Leu Gly Val Lys Leu Asp Lys
            515                 520                 525

Gln Lys Asn Glu Glu Thr Ile Arg Gly Lys Glu Gly Ile Ile Ser Thr
        530                 535                 540

Pro Asp Ser Arg Val Lys Val Leu Val Val Pro Thr Asn Glu Glu Leu
545                 550                 555                 560

Met Ile Ala Arg Asp Thr Lys Glu Ile Val Glu Lys Ile Gly Arg
                565                 570                 575

<210> SEQ ID NO 74
<211> LENGTH: 125
<212> TYPE: PRT
<213> ORGANISM: Balanus albicostatus

<400> SEQUENCE: 74

Met Lys Tyr Thr Leu Ala Leu Leu Phe Leu Thr Ala Ile Ile Ala Thr
1               5                   10                  15

Phe Val Ala Ala His Lys His His Asp His Gly Lys Ser Cys Ser Lys
            20                  25                  30

Ser His Pro Cys Tyr His Cys Thr Asp Cys Glu Cys Asn His His
        35                  40                  45

His Asp Asp Cys Asn Arg Ser His Arg Cys Trp His Lys Val His Gly
    50                  55                  60

Val Val Ser Gly Asn Cys Asn Cys Asn Leu Leu Thr Pro Cys Asn Gln
65                  70                  75                  80

Lys His Pro Cys Trp Arg Arg His Gly Lys Lys His Gly Leu His Arg
                85                  90                  95

Lys Phe His Gly Asn Ala Cys Asn Cys Asp Arg Leu Val Cys Asn Ala
            100                 105                 110

Lys His Pro Cys Trp His Lys His Cys Asp Cys Phe Cys
        115                 120                 125

<210> SEQ ID NO 75
<211> LENGTH: 24
<212> TYPE: PRT
<213> ORGANISM: Artificial Sequence
<220> FEATURE:
<223> OTHER INFORMATION: Protein sequence of a peptide derived from a
      barnacle cement protein

<400> SEQUENCE: 75

Ser Lys Leu Pro Cys Asn Asp Glu His Pro Cys Tyr Arg Lys Glu Gly
1               5                   10                  15

Gly Val Val Ser Cys Asp Cys Lys
            20

<210> SEQ ID NO 76
<211> LENGTH: 24
<212> TYPE: PRT
<213> ORGANISM: Artificial Sequence
<220> FEATURE:
<223> OTHER INFORMATION: Protein sequence of a peptide derived from a
      barnacle cement protein

<400> SEQUENCE: 76

Ser Lys Leu Pro Ser Asn Asp Glu His Pro Ser Tyr Arg Lys Glu Gly
1               5                   10                  15

Gly Val Val Ser Ser Asp Ser Lys
            20
```

-continued

20

<210> SEQ ID NO 77
<211> LENGTH: 28
<212> TYPE: PRT
<213> ORGANISM: Artificial Sequence
<220> FEATURE:
<223> OTHER INFORMATION: Protein sequence of a peptide derived from a
      barnacle cement protein

<400> SEQUENCE: 77

Lys Thr Ile Thr Cys Asn Glu Asp His Pro Cys Tyr His Ser Tyr Glu
1               5                   10                  15

Glu Asp Gly Val Thr Lys Ser Asp Cys Asp Cys Glu
            20                  25

<210> SEQ ID NO 78
<211> LENGTH: 214
<212> TYPE: PRT
<213> ORGANISM: Escherichia coli

<400> SEQUENCE: 78

Met Arg Ile Ile Leu Leu Gly Ala Pro Gly Ala Gly Lys Gly Thr Gln
1               5                   10                  15

Ala Gln Phe Ile Met Glu Lys Tyr Gly Ile Pro Gln Ile Ser Thr Gly
            20                  25                  30

Asp Met Leu Arg Ala Ala Val Lys Ser Gly Ser Glu Leu Gly Lys Gln
        35                  40                  45

Ala Lys Asp Ile Met Asp Ala Gly Lys Leu Val Thr Asp Glu Leu Val
    50                  55                  60

Ile Ala Leu Val Lys Glu Arg Ile Ala Gln Glu Asp Cys Arg Asn Gly
65                  70                  75                  80

Phe Leu Leu Asp Gly Phe Pro Arg Thr Ile Pro Gln Ala Asp Ala Met
                85                  90                  95

Lys Glu Ala Gly Ile Asn Val Asp Tyr Val Leu Glu Phe Asp Val Pro
            100                 105                 110

Asp Glu Leu Ile Val Asp Arg Ile Val Gly Arg Arg Val His Ala Pro
        115                 120                 125

Ser Gly Arg Val Tyr His Val Lys Phe Asn Pro Pro Lys Val Glu Gly
    130                 135                 140

Lys Asp Asp Val Thr Gly Glu Glu Leu Thr Thr Arg Lys Asp Asp Gln
145                 150                 155                 160

Glu Glu Thr Val Arg Lys Arg Leu Val Glu Tyr His Gln Met Thr Ala
                165                 170                 175

Pro Leu Ile Gly Tyr Tyr Ser Lys Glu Ala Glu Ala Gly Asn Thr Lys
            180                 185                 190

Tyr Ala Lys Val Asp Gly Thr Lys Pro Val Ala Glu Val Arg Ala Asp
        195                 200                 205

Leu Glu Lys Ile Leu Gly
    210

<210> SEQ ID NO 79
<211> LENGTH: 470
<212> TYPE: PRT
<213> ORGANISM: Escherichia coli

<400> SEQUENCE: 79

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
            35                  40                  45

Asn Leu Arg Asn Val Met Ser Lys Thr Gly Lys Thr Ala Ala Ile Leu
50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
                100                 105                 110

Phe Thr Thr Asp Leu Ser Val Gly Asn Thr Val Leu Val Asp Asp Gly
            115                 120                 125

Leu Ile Gly Met Glu Val Thr Ala Ile Glu Gly Asn Lys Val Ile Cys
130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Ile Glu Ile Arg Glu His Leu Lys
            195                 200                 205

Ala His Gly Gly Glu Asn Ile His Ile Ile Ser Lys Ile Glu Asn Gln
            210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
            260                 265                 270

Val Val Ile Thr Ala Thr Gln Met Leu Asp Ser Met Ile Lys Asn Pro
            275                 280                 285

Arg Pro Thr Arg Ala Glu Ala Gly Asp Val Ala Asn Ala Ile Leu Asp
290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
            340                 345                 350

Arg Ile Thr Glu Ala Val Cys Arg Gly Ala Val Glu Thr Ala Glu Lys
            355                 360                 365

Leu Asp Ala Pro Leu Ile Val Val Ala Thr Gln Gly Gly Lys Ser Ala
            370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
            420                 425                 430

```
Gly Lys Glu Leu Ala Leu Gln Ser Gly Leu Ala His Lys Gly Asp Val
            435                 440                 445

Val Val Met Val Ser Gly Ala Leu Val Pro Ser Gly Thr Thr Asn Thr
    450                 455                 460

Ala Ser Val His Val Leu
465             470

<210> SEQ ID NO 80
<211> LENGTH: 400
<212> TYPE: PRT
<213> ORGANISM: Escherichia coli

<400> SEQUENCE: 80

Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
    290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335
```

-continued

Asn Ala Ala Met Val Arg Glu Leu Ser Leu Gly Lys Leu Gly Val Leu
                340                 345                 350

Gly Phe Glu Val Asp His Glu Arg Asn Leu Ala Ala Arg Phe Gly Lys
                355                 360                 365

Ser Gly Phe Ile Asn Lys Glu Gly Thr Arg Pro Ala Val Val Ile Pro
        370                 375                 380

Thr Asn Glu Glu Leu Val Ile Ala Gln Asp Ala Ser Arg Leu Thr Ala
385                 390                 395                 400

<210> SEQ ID NO 81
<211> LENGTH: 192
<212> TYPE: PRT
<213> ORGANISM: Methanococcus voltae

<400> SEQUENCE: 81

Met Lys Asn Lys Val Val Val Thr Gly Val Pro Gly Val Gly Val Ser
1               5                   10                  15

Thr Thr Ser Ser Gln Leu Ala Met Asp Asn Leu Arg Lys Glu Gly Val
                20                  25                  30

Asn Tyr Lys Met Val Ser Phe Gly Ser Val Met Phe Glu Val Ala Lys
            35                  40                  45

Glu Glu Asn Leu Val Ser Asp Arg Asp Gln Met Arg Lys Met Asp Pro
        50                  55                  60

Glu Thr Gln Lys Arg Ile Gln Lys Met Ala Gly Arg Lys Ile Ala Glu
65                  70                  75                  80

Met Ala Lys Glu Ser Pro Val Ala Val Asp Thr His Ser Thr Val Ser
                85                  90                  95

Thr Pro Lys Gly Tyr Leu Pro Gly Leu Pro Ser Trp Val Leu Asn Glu
                100                 105                 110

Leu Asn Pro Asp Leu Ile Ile Val Glu Thr Thr Gly Asp Glu Ile
            115                 120                 125

Leu Met Arg Arg Met Ser Asp Glu Thr Arg Val Arg Asp Leu Asp Thr
        130                 135                 140

Ala Ser Thr Ile Glu Gln His Gln Phe Met Asn Arg Cys Ala Ala Met
145                 150                 155                 160

Ser Tyr Gly Val Leu Thr Gly Ala Thr Val Lys Ile Val Gln Asn Arg
                165                 170                 175

Asn Gly Leu Leu Asp Gln Ala Val Glu Glu Leu Thr Asn Val Leu Arg
            180                 185                 190

<210> SEQ ID NO 82
<211> LENGTH: 192
<212> TYPE: PRT
<213> ORGANISM: Methanococcus thermolithotrophicus

<400> SEQUENCE: 82

Met Lys Asn Lys Leu Val Val Thr Gly Val Pro Gly Val Gly Gly
1               5                   10                  15

Thr Thr Ile Thr Gln Lys Ala Met Glu Lys Leu Ser Glu Glu Gly Ile
                20                  25                  30

Asn Tyr Lys Met Val Asn Phe Gly Thr Val Met Phe Glu Val Ala Gln
            35                  40                  45

Glu Glu Asn Leu Val Glu Asp Arg Asp Gln Met Arg Lys Leu Asp Pro
        50                  55                  60

Asp Thr Gln Lys Arg Ile Gln Lys Leu Ala Gly Arg Lys Ile Ala Glu
65                  70                  75                  80

```
Met Val Lys Glu Ser Pro Val Val Asp Thr His Ser Thr Ile Lys
                85                  90                  95

Thr Pro Lys Gly Tyr Leu Pro Gly Leu Pro Val Trp Val Leu Asn Glu
            100                 105                 110

Leu Asn Pro Asp Ile Ile Val Val Glu Thr Ser Gly Asp Glu Ile
        115                 120                 125

Leu Ile Arg Arg Leu Asn Asp Glu Thr Arg Asn Arg Asp Leu Glu Thr
130                 135                 140

Thr Ala Gly Ile Glu Glu His Gln Ile Met Asn Arg Ala Ala Ala Met
145                 150                 155                 160

Thr Tyr Gly Val Leu Thr Gly Ala Thr Val Lys Ile Ile Gln Asn Lys
                165                 170                 175

Asn Asn Leu Leu Asp Tyr Ala Val Glu Glu Leu Ile Ser Val Leu Arg
            180                 185                 190
```

<210> SEQ ID NO 83
<211> LENGTH: 217
<212> TYPE: PRT
<213> ORGANISM: Bacillus globisporus

<400> SEQUENCE: 83

```
Met Asn Ile Val Leu Met Gly Leu Pro Gly Ala Gly Lys Gly Thr Gln
1               5                   10                  15

Ala Asp Arg Ile Val Glu Lys Tyr Gly Thr Pro His Ile Ser Thr Gly
                20                  25                  30

Asp Met Phe Arg Ala Ala Ile Gln Glu Gly Thr Glu Leu Gly Val Lys
            35                  40                  45

Ala Lys Ser Phe Met Asp Gln Gly Ala Leu Val Pro Asp Glu Val Thr
50                  55                  60

Ile Gly Ile Val Arg Glu Arg Leu Ser Lys Ser Asp Cys Asp Asn Gly
65                  70                  75                  80

Phe Leu Leu Asp Gly Phe Pro Arg Thr Val Pro Gln Ala Glu Ala Leu
                85                  90                  95

Asp Gln Leu Leu Ala Asp Met Gly Arg Lys Ile Glu His Val Leu Asn
            100                 105                 110

Ile Gln Val Glu Lys Glu Glu Leu Ile Ala Arg Leu Thr Gly Arg Arg
        115                 120                 125

Ile Cys Lys Val Cys Gly Thr Ser Tyr His Leu Leu Phe Asn Pro Pro
130                 135                 140

Gln Val Glu Gly Lys Cys Asp Lys Asp Gly Gly Glu Leu Tyr Gln Arg
145                 150                 155                 160

Ala Asp Asp Asn Pro Asp Thr Val Thr Asn Arg Leu Glu Val Asn Met
                165                 170                 175

Asn Gln Thr Ala Pro Leu Leu Ala Phe Tyr Asp Ser Lys Glu Val Leu
            180                 185                 190

Val Asn Ile Asn Gly Gln Lys Asp Ile Lys Asp Val Phe Lys Asp Leu
        195                 200                 205

Asp Val Ile Leu Gln Gly Asn Gly Gln
    210                 215
```

<210> SEQ ID NO 84
<211> LENGTH: 217
<212> TYPE: PRT
<213> ORGANISM: Bacillus subtilis

<400> SEQUENCE: 84

```
Met Asn Leu Val Leu Met Gly Leu Pro Gly Ala Gly Lys Gly Thr Gln
1               5                   10                  15

Gly Glu Arg Ile Val Glu Asp Tyr Gly Ile Pro His Ile Ser Thr Gly
                20                  25                  30

Asp Met Phe Arg Ala Ala Met Lys Glu Glu Thr Pro Leu Gly Leu Glu
            35                  40                  45

Ala Lys Ser Tyr Ile Asp Lys Gly Glu Leu Val Pro Asp Glu Val Thr
        50                  55                  60

Ile Gly Ile Val Lys Glu Arg Leu Gly Lys Asp Asp Cys Glu Arg Gly
65                      70                  75                  80

Phe Leu Leu Asp Gly Phe Pro Arg Thr Val Ala Gln Ala Glu Ala Leu
                85                  90                  95

Glu Glu Ile Leu Glu Glu Tyr Gly Lys Pro Ile Asp Tyr Val Ile Asn
            100                 105                 110

Ile Glu Val Asp Lys Asp Val Leu Met Glu Arg Leu Thr Gly Arg Arg
            115                 120                 125

Ile Cys Ser Val Cys Gly Thr Thr Tyr His Leu Val Phe Asn Pro Pro
        130                 135                 140

Lys Thr Pro Gly Ile Cys Asp Lys Asp Gly Gly Glu Leu Tyr Gln Arg
145                 150                 155                 160

Ala Asp Asp Asn Glu Glu Thr Val Ser Lys Arg Leu Glu Val Asn Met
                165                 170                 175

Lys Gln Thr Gln Pro Leu Leu Asp Phe Tyr Ser Glu Lys Gly Tyr Leu
            180                 185                 190

Ala Asn Val Asn Gly Gln Gln Asp Ile Gln Asp Val Tyr Ala Asp Val
            195                 200                 205

Lys Asp Leu Leu Gly Gly Leu Lys Lys
    210                 215
```